United States Patent
Harb et al.

(10) Patent No.: US 11,992,506 B2
(45) Date of Patent: May 28, 2024

(54) STEM CELL DERIVED PANCREATIC ISLET DIFFERENTIATION

(71) Applicant: Vertex Pharmaceuticals Incorporated, Boston, MA (US)

(72) Inventors: George Harb, Boston, MA (US); Chunhui Xie, Belmont, MA (US); Bryce W. Carey, Boston, MA (US); Aleksander Szymaniak, Boston, MA (US); Christopher Thanos, Cumberland, RI (US); Evrett Thompson, Boston, MA (US); Rebecca Chinn, Boston, MA (US); Suyash Raj, Boston, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 18/051,721

(22) Filed: Nov. 1, 2022

(65) Prior Publication Data
US 2023/0218676 A1 Jul. 13, 2023

Related U.S. Application Data

(60) Provisional application No. 63/274,402, filed on Nov. 1, 2021, provisional application No. 63/274,391, filed on Nov. 1, 2021.

(51) Int. Cl.
*A61K 9/00* (2006.01)
*A61K 35/39* (2015.01)
(Continued)

(52) U.S. Cl.
CPC .............. *A61K 35/39* (2013.01); *A61K 38/28* (2013.01); *A61P 3/10* (2018.01); *C12N 5/0676* (2013.01);
(Continued)

(58) Field of Classification Search
CPC ...................................................... A61K 35/39
See application file for complete search history.

(56) References Cited

U.S. PATENT DOCUMENTS

| 9,062,290 B2 | 6/2015 | Rezania |
| 9,096,832 B2 | 8/2015 | Xu |

(Continued)

FOREIGN PATENT DOCUMENTS

| WO | WO 2009/132083 A2 | 10/2009 |
| WO | WO 2010/002846 A1 | 1/2010 |

(Continued)

OTHER PUBLICATIONS

Nishimura T. et al., "Use of Polyvinyl Alcohol for CAR T Cell Expansion", Exp Hematol 80:16-20 (Dec. 2019).

(Continued)

*Primary Examiner* — Paul W Dickinson
(74) *Attorney, Agent, or Firm* — Scully, Scott, Murphy & Presser, P.C.

(57) ABSTRACT

Disclosed herein are compositions and methods related to differentiation of stem cells into pancreatic islet cells. In some aspects, the methods provided herein relate to generation of pancreatic β cell, α cell, δ cells, and EC cells in vitro. In some aspects, the disclosure provides pharmaceutical compositions including the cells generated according to the methods disclosed herein, as well as methods of treatment making use thereof.

30 Claims, 70 Drawing Sheets
Specification includes a Sequence Listing.

(51) Int. Cl.
  *A61K 38/28* (2006.01)
  *A61P 3/10* (2006.01)
  *C12N 5/071* (2010.01)
(52) U.S. Cl.
  CPC .. *C12N 2501/115* (2013.01); *C12N 2501/117* (2013.01); *C12N 2501/16* (2013.01); *C12N 2506/45* (2013.01)

(56) References Cited

U.S. PATENT DOCUMENTS

| | | | |
|---|---|---|---|
| 9,585,917 | B2 | 3/2017 | Martinson et al. |
| 9,744,195 | B2 | 8/2017 | Xu |
| 10,030,229 | B2 | 7/2018 | Peterson et al. |
| 10,358,628 | B2 | 7/2019 | Rezania |
| 10,370,645 | B2 | 8/2019 | D'Amour et al. |
| 10,443,042 | B2 | 10/2019 | Melton et al. |
| 10,494,609 | B2 | 12/2019 | Rezania |
| 10,947,511 | B2 | 3/2021 | Rezania |
| 11,085,027 | B2 | 8/2021 | Melton et al. |
| 11,466,256 | B2 | 10/2022 | Pagliuca et al. |
| 11,525,120 | B2 | 12/2022 | Pagliuca et al. |
| 2007/0259421 | A1 | 11/2007 | D'Amour et al. |
| 2008/0267926 | A1 | 10/2008 | Martinson et al. |
| 2011/0008819 | A1 | 1/2011 | Chipperfield et al. |
| 2015/0240212 | A1 | 8/2015 | Peterson et al. |
| 2017/0029778 | A1 | 2/2017 | Peterson et al. |
| 2017/0157110 | A1 | 6/2017 | Herrera et al. |
| 2019/0112572 | A1 | 4/2019 | Figueroa et al. |
| 2020/0332262 | A1 | 10/2020 | Poh et al. |
| 2021/0017157 | A1 | 1/2021 | Thiel et al. |
| 2021/0198632 | A1 | 7/2021 | Pagliuca et al. |
| 2021/0198633 | A1 | 7/2021 | Nostro et al. |
| 2021/0214690 | A1 | 7/2021 | Melton et al. |
| 2021/0238553 | A1 | 8/2021 | Pagliuca et al. |
| 2021/0353686 | A1 | 11/2021 | Ito et al. |
| 2021/0403876 | A1 | 12/2021 | Pagliuca et al. |
| 2022/0090020 | A1* | 3/2022 | Harb ............... C12N 5/0676 |
| 2022/0162562 | A1 | 5/2022 | Peterson et al. |
| 2022/0186188 | A1 | 6/2022 | Jiang et al. |
| 2022/0233646 | A1 | 7/2022 | Carey |
| 2023/0075375 | A1 | 3/2023 | Pagliuca et al. |

FOREIGN PATENT DOCUMENTS

| | | | |
|---|---|---|---|
| WO | 2017/177163 A1 | 10/2017 | |
| WO | 2017/222879 A1 | 12/2017 | |
| WO | WO 2019/018818 A1 | 1/2019 | |
| WO | WO 2019/169351 A1 | 9/2019 | |
| WO | WO 2019/217487 A1 | 11/2019 | |
| WO | WO 2020/033879 A1 | 2/2020 | |
| WO | WO-2020033879 A1 * | 2/2020 | ............. A61K 35/39 |
| WO | 2020/142646 A1 | 7/2020 | |
| WO | 2020/198351 A1 | 10/2020 | |
| WO | WO 2020/264072 A1 | 12/2020 | |
| WO | 2021/126841 A1 | 6/2021 | |
| WO | WO 2022/026932 A2 | 2/2022 | |
| WO | WO 2022/026933 A2 | 2/2022 | |
| WO | WO 2022/147056 A1 | 7/2022 | |
| WO | WO 2022/192300 A1 | 9/2022 | |

OTHER PUBLICATIONS

Co-pending U.S. Appl. No. 18/055,327, inventors Felicia J. Pagliuca et al., filed Nov. 14, 2022.
Co-pending U.S. Appl. No. 18/054,860, inventors Felicia Pagliuca et al., filed Nov. 11, 2022.
Co-pending U.S. Appl. No. 17/988,257, inventors George Harb et al., filed Nov. 16, 2022.
Co-pending U.S. Appl. No. 17/985,746, inventors Felicia J. Pagliuca et al., filed Nov. 11, 2022.
Al-Masri et al., Effect of forkhead box 01 (FOXO1) on beta cell development in the human fetal pancreas. Diabetologia. Apr. 2010;53(4):699-711.
Apelqvist et al., Notch signalling controls pancreatic cell differentiation. Nature. Aug. 26, 1999;400(6747):877-81. doi: 10.1038/23716.
Balboa et al., Functional, metabolic and transcriptional maturation of human pancreatic islets derived from stem cells. Nat Biotechnol. Jul. 2022;40(7):1042-1055. doi: 10.1038/s41587-022-01219-z. Epub Mar. 3, 2022.
Bouchi et al., FOXO1 inhibition yields functional insulin-producing cells in human gut organoid cultures. Nat Commun. Jun. 30, 2014;5:4242. doi: 10.1038/ncomms5242. Author Manuscript, 24 pages.
Chen et al., A small molecule that directs differentiation of human ESCs into the pancreatic lineage. Nat Chem Biol. Apr. 2009;5(4):258-65. doi: 10.1038/nchembio.154. Epub Mar. 15, 2009.
D'Amour et al., Production of pancreatic hormone-expressing endocrine cells from human embryonic stem cells. Nat Biotechnol. Nov. 2006;24(11):1392-401. doi: 10.1038/nbt1259. Epub Oct. 19, 2006.
Hering et al., Phase 3 Trial of Transplantation of Human Islets in Type 1 Diabetes Complicated by Severe Hypoglycemia. Diabetes Care. Jul. 2016;39(7):1230-40. doi: 10.2337/dc15-1988. Epub Apr. 18, 2016.
Kimura et al., Small molecule AT7867 proliferates PDX1-expressing pancreatic progenitor cells derived from human pluripotent stem cells. Stem Cell Res. Oct. 2017;24:61-68.
Nagashima et al., Discovery of novel forkhead box O1 inhibitors for treating type 2 diabetes: improvement of fasting glycemia in diabetic db/db mice. Mol Pharmacol. Nov. 2010;78(5):961-70. doi: 10.1124/mol.110.065714. Epub Aug. 24, 2010.
Sasaki et al., Transient FOXO1 inhibition in pancreatic endoderm promotes the generation of NGN3+ endocrine precursors from human iPSCs. Stem Cell Res. Apr. 2020;44:101754.
Segerstolpe et al., Single-Cell Transcriptome Profiling of Human Pancreatic Islets in Health and Type 2 Diabetes. Cell Metab. Oct. 11, 2016;24(4):593-607. doi: 10.1016/j.cmet.2016.08.020. Epub Sep. 22, 2016.
Sharon et al., Wnt Signaling Separates the Progenitor and Endocrine Compartments during Pancreas Development. Cell Rep. May 21, 2019;27(8):2281-2291.e5. doi: 10.1016/j.celrep.2019.04.083.
Talchai et al., Legacy Effect of Foxo1 in Pancreatic Endocrine Progenitors on Adult B-Cell Mass and Function. Diabetes. Aug. 2015;64(8):2868-79. doi: 10.2337/db14-1696. Epub Mar. 17, 2015.
Yu et al., FoxO1 inhibition promotes differentiation of human embryonic stem cells into insulin producing cells. Exp Cell Res. Jan. 1, 2018;362(1):227-234.
Peterson Q.P. et al., "A Method for the Generation of Human Stem Cell-Derived Alpha Cells", Nature Communications 11(2241):1-14 (2020).
Schweicher J. et al., "Membrances to Achieve Immunoprotection of Transplanted Islets", Front Biosci 29:49-76 (2014).
Street C.N. et al., "Islet Graft Assessment in the Edmonton Protocol", Diabetes 53:3107-3114 (2004).
Street C.N. et al., "Stem Cell-Based Approaches to Solving the Problem of Tissue Supply for Islet Transplantation In Type 1 Diabetes", The International Journal of Biochemistry & Cell Biology 36:667-683 (2004).
Du W. et al., "Triple Notch/Tgfβ/FoxO1 Blockade Converts Multiple Intestinal Sub-Lineages into β-Like Cells and Lowers Glycemia in Diabetic Animals", bioRxiv, Retrieved from the Internet: URL:https://doi. org/10.1101/2022.03.21.484748 (Mar. 21, 2022).
Kitamoto T. et al., "Chemical Induction of Gut β-Like-Cells by Combined FoxO1/Notch Inhibition as a Glucose-Lowering Treatment for Diabetes", bioRxiv, Retrieved from the Internet: URL:https://www.biorxiv.org/content/10.1101/2021.12.07.471572v1.full.pdf(Dec. 7, 2021).
Pandey A. et al., "FoxO1 Inhibitors: The Future Medicine for Metabolic Disorders?", Current Diabetes Reviews 12:223-230 (2016).
Langlet F. et al., "Selective Inhibition of FOXO1 Activator/Repressor Balance Modulates Hepatic Glucose Handling", Cell 171:824-835 (Nov. 2, 2017).
Mariotti L. et al., "Regulation of Wnt/Beta-Catenin Signalling by Tankyrase-Dependent Poly(ADP-Ribosyl)ation and Scaffolding", British Journal of Pharmacology 174(24):4611-4636 (2017).

(56) References Cited

OTHER PUBLICATIONS

Wilkinson A C et al., "Long-Term Ex Vivo Hematopoietic Stem Cell Expansion Affords Nonconditional Transplantation", Nature 571(7763):117-121 (Jul. 2019).
Vertex Press Release, "Vertex to Acquire ViaCyte, With the Goal of Accelerating its Potentially Curative VX-880 Programs in Type 1 Diabetes", (Jul. 11, 2022).
Xin Y. et al., "Pseudotime Ordering of Single Human Beta-Cells Reveals States of Insulin Production and Unfolded Protein Response", Diabetes 67:1783-1794 (Sep. 2018) (including single-cell sequencing data stored in the Gene Expression Omnibus database under accession No. GSE114297; https://www.ncbi.nlm.nih.gov/geo/query/acc.cgi?acc=GSE114297).
Co-pending U.S. Appl. No. 18/391,867, inventors Yeh-Chuin Poh et al., filed on Dec. 21, 2023.
Co-pending U.S. Appl. No. 18/391,831, inventors Yeh-Chuin Poh et al., filed on Dec. 21, 2023.
Co-pending U.S. Appl. No. 18/391,799, inventors George Harb et al., filed on Dec. 21, 2023.

* cited by examiner

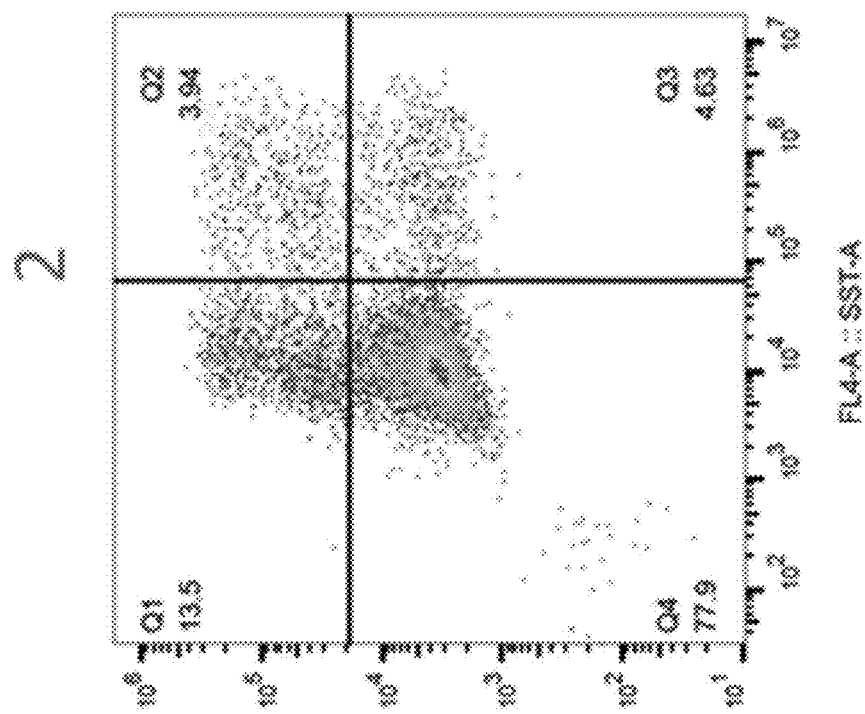
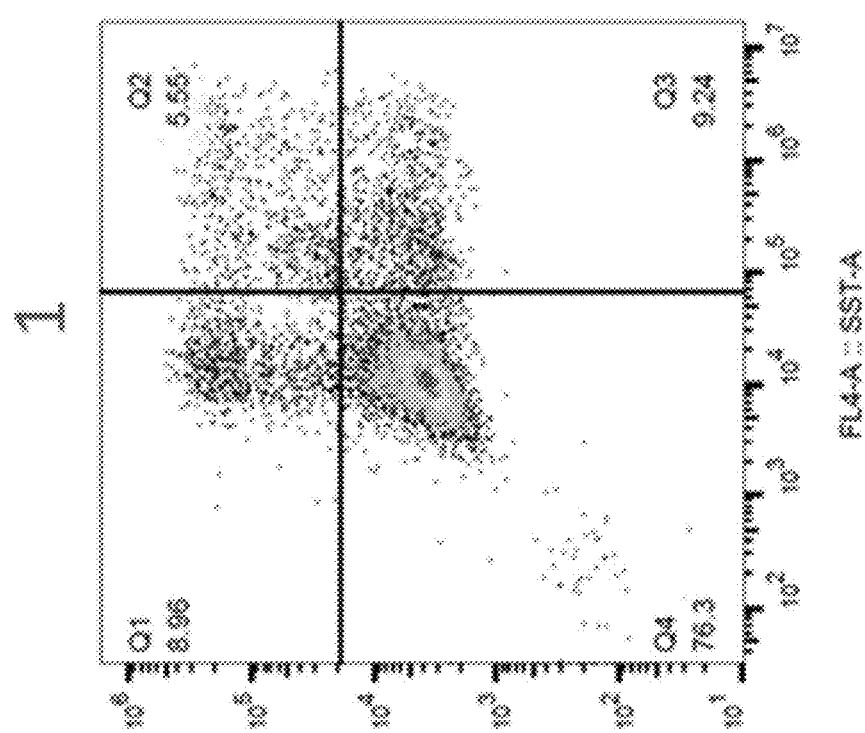
FIG. 24B
FIG. 24A

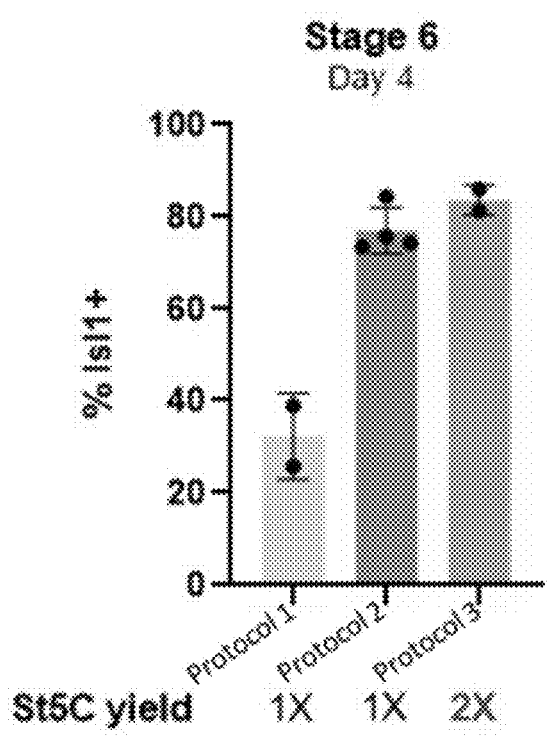 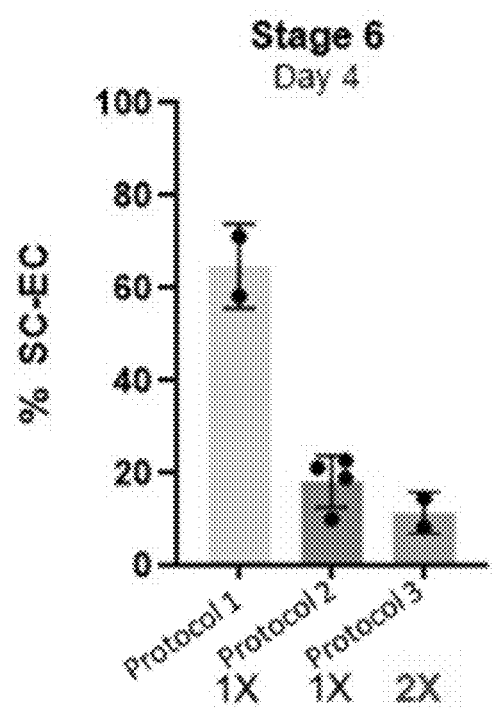
FIG. 25A                              FIG. 25B

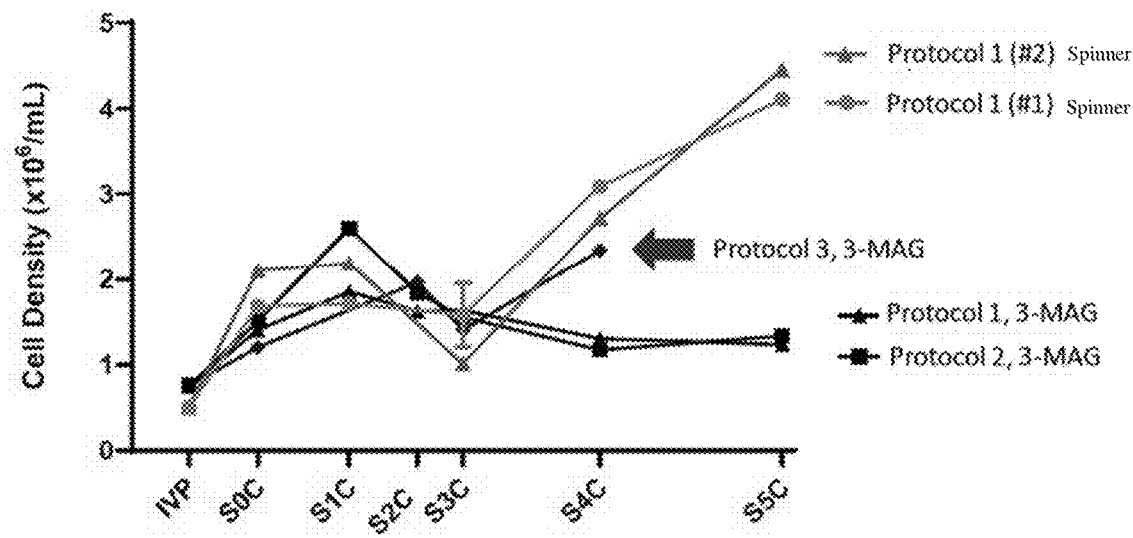
FIG. 27
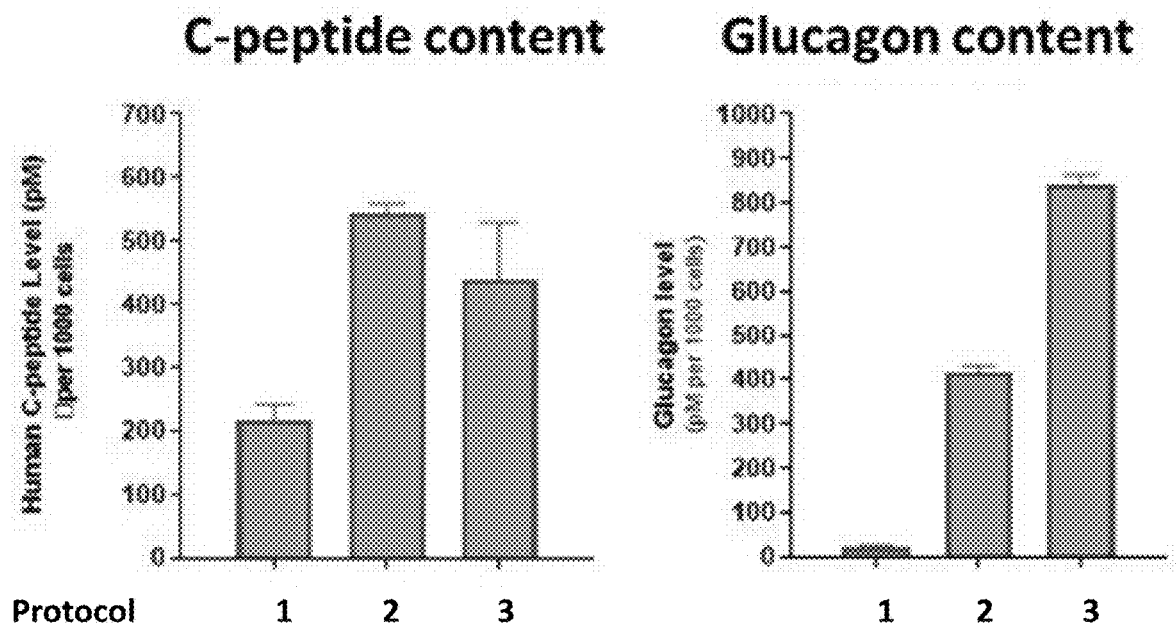
FIG. 28A
FIG. 28B

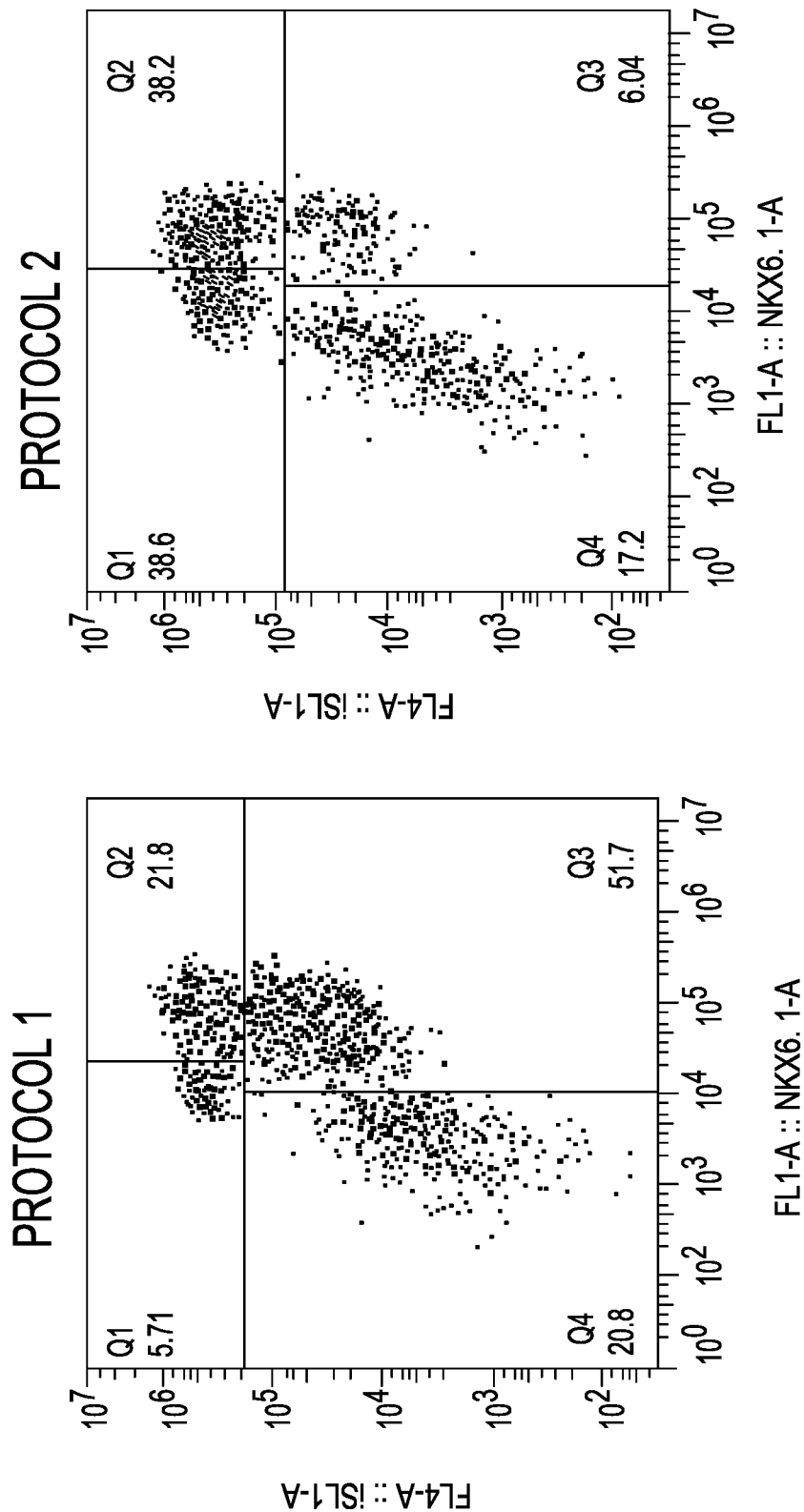

STEM CELL DERIVED PANCREATIC ISLET DIFFERENTIATION

RELATED APPLICATIONS

This application claims the benefit under 35 U.S.C. § 119(e) to U.S. Provisional Application No. 63/274,402, filed on Nov. 1, 2021, entitled "STEM CELL DERIVED PANCREATIC ISLET DIFFERENTIATION," and U.S. Provisional Application No. 63/274,391, filed on Nov. 1, 2021, entitled "ENHANCED DIFFERENTIATION OF PANCREATIC ISLET CELLS," the entire contents of each of which are incorporated herein by reference.

REFERENCE TO AN ELECTRONIC SEQUENCE LISTING

The contents of the electronic sequence listing (V013870082US01-SEQ-ZJG.xml; Size: 40,337 bytes; and Date of Creation: Oct. 31, 2022) is herein incorporated by reference in its entirety.

BACKGROUND

Transplantation of pancreas or pancreatic islets has been used for treating diabetes, such as type I diabetes. Pancreatic islet transplantation does not need major surgery and the function of the islet grafts can be maintained for years in a recipient. However, a shortage of pancreatic islets donors prevents this therapy from being effectively implemented. Artificial pancreas or pancreatic islets provide an alternative source of transplantable islets. Thus, there is a need for methods of in vitro restitution of pancreatic islets whose function and characteristics resemble endogenous pancreatic islets.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties.

SUMMARY

Provided herein, in some aspects, are compositions and methods for producing pancreatic islet cells (e.g., stem cell-derived pancreatic islet cells). In some embodiments, a method described herein comprises contacting pancreatic progenitor cells (e.g., pancreatic progenitor cells that are PDX1-positive and NKX6.1-negative) with a medium comprising a Forkhead Box O1 (FoxO1) inhibitor and a notch signaling pathway inhibitor, and optionally a notch signaling pathway inhibitor. In some embodiments, a method described herein comprises contacting pancreatic progenitor cells (e.g., pancreatic progenitor cells that are PDX1-positive and NKX6.1-positive) with a medium comprising a Wnt signaling pathway inhibitor and a PKC activator. In some embodiments, a method described herein comprises contacting pancreatic progenitor cells (e.g., pancreatic progenitor cells that are PDX1-positive and NKX6.1-negative) with a medium comprising a Forkhead Box O1 (FoxO1) inhibitor and a notch signaling pathway inhibitor, and contacting resulting cells with a medium comprising a comprising a Wnt signaling pathway inhibitor and a PKC activator. In some aspects, a population of in vitro differentiated cells (e.g., stem cell-derived pancreatic islet cells) produced using the compositions and methods described herein are also provided. In some embodiments, the population of in vitro differentiated cells (e.g., stem cell-derived pancreatic islet cells) comprises NKX6.1-positive, ISL1-positive cells and NKX6.1-negative, ISL1-positive cells. In some embodiments, the population comprises more NKX6.1-positive, ISL1-positive cells than NKX6.1-negative, ISL-positive cells. In some embodiments, at least 15% of the cells in the population are NKX6.1-negative, ISL1-positive cells; and wherein less than 12% of the cells in the population are NKX6.1-negative, ISL1-negative cells. In some aspects, methods of using the population of in vitro differentiated cells (e.g., stem cell-derived pancreatic islet cells) described herein to treat diseases (e.g., diabetes) are provided.

Some aspects of the present disclosure provide in vitro compositions comprising a population of pancreatic progenitor cells and a medium comprising a Forkhead Box O1 (FoxO1) inhibitor and a notch signaling pathway inhibitor, wherein the population of pancreatic progenitor cells comprises cells that are PDX1-positive and NKX6.1-negative and cells that are PDX1-positive and NKX6.1-positive.

In some embodiments, the medium further comprises a PKC activator. In some embodiments, the notch signaling pathway inhibitor is a γ-secretase inhibitor. In some embodiments, the γ-secretase inhibitor is XXI, DAPT or derivatives thereof. In some embodiments, the γ-secretase inhibitor is XXI. In some embodiments, the FOXO1 inhibitor is of formula (I-B):

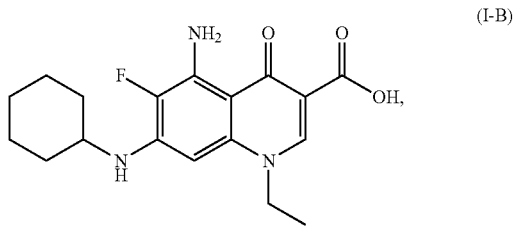 [SMILES: CCn1cc(C(=O)O)c(=O)c2c(N)c(F)c(NC3CCCCC3)cc21]

or a pharmaceutically acceptable salt, solvate, hydrate, polymorph, co-crystal, tautomer, stereoisomer, isotopically labeled derivative, prodrug, composition, or mixture thereof. In some embodiments, the FoxO1 inhibitor is present in the medium at a concentration of 0.1-10 μM. In some embodiments, the FoxO1 inhibitor is present in the medium at a concentration of 1 μM. In some embodiments, the PKC activator is phorbol 12,13-dibutyrate (PdBU), TPB, phorbol 12-myristate 13-acetate, bryostatin 1, or derivatives thereof. In some embodiments, the PKC activator is PdBU. In some embodiments, the medium further comprises one or more agents selected from: a fibroblast growth factor, a sonic hedgehog (SHH) signaling pathway inhibitor, retinoic acid, a Rho-associated, coiled-coil containing protein kinase (ROCK) inhibitor, and a TGF-β ligand, optionally wherein the medium further comprises a fibroblast growth factor, a sonic hedgehog (SHH) signaling pathway inhibitor, retinoic acid, a Rho-associated, coiled-coil containing protein kinase (ROCK) inhibitor, and a TGF-β ligand. In some embodiments, the medium further comprises keratinocyte growth factor (KGF), SANT-1, RA, triazovivin, and activin A. In some embodiments, the medium further comprises a water-soluble synthetic polymer. In some embodiments, the water-soluble synthetic polymer is polyvinyl alcohol, poloxamer, polyvinylpyrrolidone, polyethylene glycol (PEG), PEG copolymers, poly(N-isopropylacrylamide), or polyacrylamide. In some embodiments, the water-soluble synthetic polymer is polyvinyl alcohol (PVA). In some embodiments, the water-soluble synthetic polymer has a concentration of 0.005% to 0.5% (w/v), 0.01% to 0.2% (w/v), 0.02% to 0.1% (w/v), or 0.03% to 0.08% (w/v) of the medium. In some embodiments, the PVA is at most 85% hydrolyzed. In some embodiments, the PVA is about 80% hydrolyzed.

In some embodiments, at least 50% of the population of pancreatic progenitor cells are PDX1-positive and NKX6.1-negative, and/or no more than 50% of the population of pancreatic progenitor cells are PDX1-positive and NKX6.1-positive. In some embodiments, no more than 50% of the population of pancreatic progenitor cells are PDX1-positive and NKX6.1-negative, and/or at least 50% of the population of pancreatic progenitor cells are PDX1-positive and NKX6.1-positive. In some embodiments, medium does not comprise a Wnt inhibitor.

Other aspects of the present disclosure provide in vitro compositions comprising a population of pancreatic progenitor cells comprising cells that are PDX1-positive, NKX6.1-positive, and insulin-negative; and a medium comprising a protein kinase C (PKC) activator and a Wnt signaling pathway inhibitor, wherein the medium does not comprise a FOXO1 inhibitor, and wherein the population of pancreatic progenitor cells had been previously cultured in a medium comprising a FOXO1 inhibitor. In some embodiments, the PKC activator is phorbol 12,13-dibutyrate (PdBU), phorbol 12-myristate 13-acetate, bryostatin 1, or derivatives thereof. In some embodiments, the PKC activator is PdBU. In some embodiments, the Wnt signaling pathway inhibitor is a tankyrase inhibitor. In some embodiments, the tankyrase inhibitor is NVP-TNKS656. In some embodiments, the medium further comprises one or more agents selected from: a sonic hedgehog (SHH) signaling pathway inhibitor, an epidermal growth factor, a notch signaling pathway inhibitor, a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, and retinoic acid. In some embodiments, the medium further comprises a sonic hedgehog (SHH) signaling pathway inhibitor, an epidermal growth factor, a notch signaling pathway inhibitor, a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, and retinoic acid. In some embodiments, the medium further comprises SANT-1, betacellulin, XXI, Alk5i, GC-1, LDN-193189, thiazovivin, staurosporine, DZNEP, and retinoic acid. In some embodiments, the medium further comprises one or more agents selected from an acetyl CoA related metabolite, an HDAC inhibitor, a redox homeostasis regulator, and a one carbon metabolism pathway intermediate. In some embodiments, the medium further comprises an acetyl CoA related metabolite, an HDAC inhibitor, a redox homeostasis regulator, and a one carbon metabolism pathway intermediate. In some embodiments, the medium further comprises acetate, β-hydroxybutyrate, taurine, and formate. In some embodiments, the medium further comprises a vitamin. In some embodiments, the vitamin is biotin. In some embodiments, the medium further comprises glutamine. In some embodiments, the medium comprises PDBU, NVP-TNKS656, SANT-1, beta- cellulin, XXI, Alk5i, GC-1, LDN-193189, thiazovivin, staurosporine, DZNEP, retinoic acid, acetate, β-hydroxybutyrate, taurine, formate, biotin, and glutamine. In some embodiments, the medium further comprises a water-soluble synthetic polymer. In some embodiments, the water-soluble synthetic polymer is polyvinyl alcohol, poloxamer, polyvinylpyrrolidone, polyethylene glycol (PEG), PEG copolymers, poly(N-isopropylacrylamide), or polyacrylamide. In some embodiments, the water-soluble synthetic polymer is polyvinyl alcohol (PVA). In some embodiments, the water-soluble synthetic polymer has a concentration of 0.005% to 0.5% (w/v), 0.01% to 0.2% (w/v), 0.02% to 0.1% (w/v), or 0.03% to 0.08% (w/v) of the medium. In some embodiments, the PVA is at most 90% hydrolyzed. In some embodiments, the PVA is about 87%-89% hydrolyzed.

In some embodiments, at least 50% of the population of pancreatic progenitor cells are PDX1-positive, NKX6.1-positive, and insulin-negative.

In some embodiments, the in vitro composition further comprises=pancreatic endocrine cells that are PDX1-positive, NKX6.1-positive, and insulin-positive.

In some embodiments, the Wnt signaling pathway inhibitor is present in the medium at a concentration of 0.2 μM-2 μM. In some embodiments, the Wnt signaling pathway inhibitor is present in the medium at a concentration of about 2 μM.

Further provided herein are methods comprising culturing a first population of cells in a first medium, wherein the first population of cells comprises pancreatic progenitor cells that are PDX1-positive and NKX6.1 negative, and pancreatic progenitor cells that are PDX1-positive and NKX6.1 positive; and the first medium comprises a Forkhead Box O1 (FoxO1) inhibitor and a notch signaling pathway inhibitor.

In some embodiments, the first medium further comprises a PKC activator. In some embodiments, the notch signaling pathway inhibitor is a γ-secretase inhibitor. In some embodiments, the γ-secretase inhibitor is XXI, DAPT or derivatives thereof. In some embodiments, the γ-secretase inhibitor is XXI. In some embodiments, the FoxO1 inhibitor is of formula (I-B):

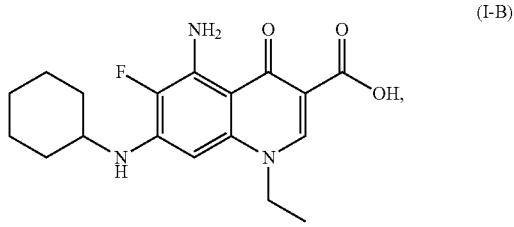 [SMILES: CCn1cc(C(=O)O)c(=O)c2c(N)c(F)c(NC3CCCCC3)cc21]

or a pharmaceutically acceptable salt, solvate, hydrate, polymorph, co-crystal, tautomer, stereoisomer, isotopically labeled derivative, prodrug, composition, or mixture thereof. In some embodiments, the FoxO1 inhibitor is present in the first medium at a concentration of 0.1-10 μM. In some embodiments, the FoxO1 inhibitor is present in the first medium at a concentration of 1 μM. In some embodiments, the PKC activator is phorbol 12,13-dibutyrate (PdBU), TPB, phorbol 12-myristate 13-acetate, bryostatin 1, or derivatives thereof. In some embodiments, the PKC activator is PdBU. In some embodiments, the first medium further comprises one or more agents selected from: a fibroblast growth factor, a sonic hedgehog (SHH) signaling pathway inhibitor, retinoic acid, a Rho-associated, coiled-coil containing protein kinase (ROCK) inhibitor, and a TGF-β ligand. In some embodiments, the first medium further comprises a fibroblast growth factor, a sonic hedgehog (SHH) signaling pathway inhibitor, retinoic acid, a Rho-associated, coiled-coil containing protein kinase (ROCK) inhibitor, and a TGF-β ligand. In some embodiments, rein the first medium further comprises keratinocyte growth factor (KGF), SANT-1, RA, triazovivin, and activin A. In some embodiments, the first medium does not comprise a Wnt signaling pathway inhibitor. In some embodiments, the first medium further comprises a water soluble synthetic polymer. In some embodiments, the water-soluble synthetic polymer is PVA, further optionally wherein the PVA is at most 85% hydrolyzed (e.g., 80% hydrolyzed). In some embodiments, the first population of cells are cultured in the first medium for about 20-80, 20-60, 20-50, 30-50, 30-55, 24-72 hours, resulting in a second population of cells. In some embodiments, the first population of cells are cultured in the first medium for a period of 24-48 hours, resulting in a second population of cells.

In some embodiments, the method further comprises culturing the second population of cells with a second medium comprising a Wnt signaling pathway inhibitor and a PKC activator. In some embodiments, the Wnt signaling pathway inhibitor is a tankyrase inhibitor. In some embodiments, the tankyrase inhibitor is NVP-TNKS656. In some embodiments, the PKC activator is phorbol 12,13-dibutyrate (PdBU), TPB, phorbol 12-myristate 13-acetate, bryostatin 1, or derivatives thereof. In some embodiments, the PKC activator is PdBU. In some embodiments, the second medium further comprises one or more agents selected from: an epidermal growth factor, a thyroid hormone, a TGFβ-R1 kinase inhibitor, a notch signaling pathway inhibitor, a sonic hedgehog (SHH) signaling pathway inhibitor, retinoic acid, a Rho-associated, coiled-coil containing protein kinase (ROCK) inhibitor, a protein kinase inhibitor, a bone morphogenetic (BMP) signaling pathway inhibitor, and a histone methyltransferase EZH2 inhibitor. In some embodiments, the second medium further comprises an epidermal growth factor, a thyroid hormone, a TGFβ-R1 kinase inhibitor, a notch signaling pathway inhibitor, a sonic hedgehog (SHH) signaling pathway inhibitor, retinoic acid, a Rho-associated, coiled-coil containing protein kinase (ROCK) inhibitor, a protein kinase inhibitor, a bone morphogenetic (BMP) signaling pathway inhibitor, and a histone methyltransferase EZH2 inhibitor. In some embodiments, the second medium further comprises SANT-1, betacellulin, XXI, Alk5i, GC-1, LDN-193189, thiazovivin, staurosporine, DZNEP, and retinoic acid. In some embodiments, the second medium further comprises one or more agents selected from an acetyl CoA related metabolite, an HDAC inhibitor, a redox homeostasis regulator, and a one carbon metabolism pathway intermediate. In some embodiments, the second medium further comprises an acetyl CoA related metabolite, an HDAC inhibitor, a redox homeostasis regulator, and a one carbon metabolism pathway intermediate. In some embodiments, the second medium further comprises acetate, β-hydroxybutyrate, taurine, and formate. In some embodiments, the second medium further comprises a vitamin. In some embodiments, the vitamin is biotin. In some embodiments, wherein the second medium further comprises glutamine. In some embodiments, the second medium comprises: PDBU, NVP-TNKS656, SANT-1, betacellulin, XXI, Alk5i, GC-1, LDN-193189, thiazovivin, staurosporine, DZNEP, retinoic acid, acetate, β-hydroxybutyrate, taurine, formate, biotin, and glutamine. In some embodiments, the second medium does not comprise a FOXO1 inhibitor. In some embodiments, wherein the second medium further comprises a water-soluble synthetic polymer. In some embodiments, the water-soluble synthetic polymer is polyvinyl alcohol, poloxamer, polyvinylpyrrolidone, polyethylene glycol (PEG), PEG copolymers, poly(N-isopropylacrylamide), or polyacrylamide. In some embodiments, wherein the water-soluble synthetic polymer is polyvinyl alcohol (PVA). In some embodiments, the water-soluble synthetic polymer has a concentration of 0.005% to 0.5% (w/v), 0.01% to 0.2% (w/v), 0.02% to 0.1% (w/v), or 0.03% to 0.08% (w/v) of the medium. In some embodiments, the PVA is at most 90% hydrolyzed, optionally wherein the PVA is about 87%-89% hydrolyzed. In some embodiments, the Wnt signaling pathway inhibitor is present in the second medium at a concentration of 0.2 µM-2 µM. In some embodiments, the Wnt signaling pathway inhibitor is present in the second medium at a concentration of about 2 µM. In some embodiments, the second population of cells are cultured in the second medium for about 20-80, 20-60, 20-50, 30-50, 30-55, 40-120, 40-100, 60-110, 70-110, 80-110, 80-100, 90-100, or 24-72 hours, resulting in a third population of cells. In some embodiments, the second population of cells are cultured in the second medium for about 24-72 hours, resulting in a third population of cells. In some embodiments, the second population of cells are cultured in the second medium for about 72-120 hours, resulting in a third population of cells.

In some embodiments, the method further comprises culturing the third population of cells in a third medium comprising: a thyroid hormone, a TGFβ-R1 kinase inhibitor, a notch signaling pathway inhibitor a Rho-associated, coiled-coil containing protein kinase (ROCK) inhibitor, a protein kinase inhibitor, a bone morphogenetic (BMP) signaling pathway inhibitor, a histone methyltransferase EZH2 inhibitor, an acetyl CoA related metabolite, an HDAC inhibitor, a redox homeostasis regulator, a one carbon metabolism pathway intermediate, a vitamin, glutamine, and a water-soluble synthetic polymer. In some embodiments, the third medium comprises GC-1, ALK5i II, XXI, triazovivin, staurosporine (SSP), LDN193189, DZNep, acetate, β-hydroxybutyrate, taurine, formate, biotin, glutamine, and PVA, optionally wherein the PVA is at most 90% hydrolyzed. In some embodiments, the third population of cells are cultured in the third medium for about 20-80, 20-60, 20-50, 30-50, 30-55, 40-120, 40-100, 60-110, 70-110, 80-110, 90-110, 70-120, 80-100, 90-100, or 24-72 hours, resulting in a fourth population of cells. In some embodiments, the third population of cells are cultured in the third medium for about 48-96 hours, resulting in a fourth population of cells.

In some embodiments, the method further comprises culturing the fourth population of cells in a fourth medium comprising a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, an acetyl CoA related metabolite, an HDAC inhibitor, a redox homeostasis regulator, an one carbon metabolism pathway intermediate, a vitamin, glutamine, glutamate, carnitine, albumin, and ZnSO4. In some embodiments, the fourth medium comprises ALK5i, GC-1, LDN-193189, thiazovivin, staurosporine (SSP), DZBEP, acetate, β-hydroxybutyrate, taurine, formate, biotin, glutamine, glutamate, carnitine, HSA, and $ZnSO_4$. In some embodiments, the fourth population of cells are cultured in the fourth medium for about 20-80, 20-60, 20-50, 30-50, 30-55, 40-120, 40-100, 60-110, 70-110, 80-110, 90-110, 70-120, 80-100, 90-100, or 24-72 hours, resulting in a fifth population of cells. In some embodiments, the fourth population of cells are cultured in the fourth medium for about 48-96 hours, resulting in a fifth population of cells.

In some embodiments, the method further comprises culturing the fifth population of cells in a fifth medium comprising glutamine, HSA and ZnSO4, optionally wherein the fifth medium further comprises acetate, β-hydroxybutyrate, taurine, formate, biotin, glutamate, and carnitine. In some embodiments, the fifth population of cells are culture in the fifth medium for at least 72 hours, resulting in a sixth population of cells. In some embodiments, at least 15% of the cells of the sixth population of cells are NKX6.1-negative, ISL1-positive; and wherein less than 12% of the fifth population of cells are NKX6.1-negative, ISL1-negative.

Further provided herein are methods comprising:
(i) culturing a first population of cells in a first medium to obtain a second population of cells, wherein the first population of cells comprises pancreatic progenitor cells that are PDX1-positive and NKX6.1 negative, and pancreatic progenitor cells that are PDX1-positive and NKX6.1 positive; and the first medium comprises: a FoxO1 inhibitor, a notch signaling pathway inhibitor, a PKC activator, a fibroblast growth factor, a sonic hedgehog (SHH) signaling pathway inhibitor, retinoic acid, a Rho-associated, coiled-coil containing protein kinase (ROCK) inhibitor, a TGF-β ligand, and a water-soluble synthetic polymer;
(ii) culturing the second population of cells obtained in (i) with a second medium to obtain a third population of cells, wherein the second medium comprises: a Wnt signaling pathway inhibitor, a PKC activator, an epidermal growth factor, a thyroid hormone, a TGFβ-R1 kinase inhibitor, a notch signaling pathway inhibitor, a sonic hedgehog (SHH) signaling pathway inhibitor, retinoic acid, a Rho-associated, coiled-coil containing protein kinase (ROCK) inhibitor, a protein kinase inhibitor, a bone morphogenetic (BMP) signaling pathway inhibitor, a histone methyltransferase EZH2 inhibitor, an acetyl CoA related metabolite, an HDAC inhibitor, a redox homeostasis regulator, a one carbon metabolism pathway intermediate, a vitamin, glutamine and a water soluble synthetic polymer (e.g., PVA), and wherein the second medium does not comprise a FOXO1 inhibitor;
(iii) culturing the third population of cells obtained in (ii) with a third medium to obtain a fourth population of cells, wherein the third medium comprises: a notch signaling pathway inhibitor, a TGFβ-R1 kinase inhibitor, a thyroid hormone, a bone morphogenetic (BMP) signaling pathway, a Rho-associated, coiled-coil containing protein kinase (ROCK) inhibitor, a protein kinase inhibitor, and a histone methyltransferase EZH2 inhibitor, an acetyl CoA related metabolite, an HDAC inhibitor, a redox homeostasis regulator, an one carbon metabolism pathway intermediate, a vitamin, glutamine and a water soluble synthetic polymer, and wherein the third medium does not comprise a Wnt signaling pathway inhibitor and a PKC activator;
(iv) culturing the fourth population of cells obtained in (iii) with a fourth medium to obtain a fifth population of cells, wherein the fourth medium comprises a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, an acetyl CoA related metabolite, an HDAC inhibitor, a redox homeostasis regulator, an one carbon metabolism pathway intermediate, a vitamin, glutamine, glutamate, carnitine, albumin, and ZnSO4, and wherein the fourth medium does not comprise a Wnt signaling pathway inhibitor and a PKC activator; and
(v) culturing the fifth population of cells obtained in (iv) with a fifth medium to obtain a sixth population of cells, wherein the fifth medium comprises albumin and ZnSO4.

In some embodiments, the first population of cells are obtained by differentiation of human embryonic stem cells.

Other aspects of the present disclosure provide population of in vitro differentiated cells comprising NKX6.1-positive, ISL1-positive cells and NKX6.1-negative, ISL1-positive cells; ISL1-positive cells; wherein at least 15% of the cells in the population are NKX6.1-negative, ISL1-positive cells; and wherein less than 12% of the cells in the population are NKX6.1-negative, ISL1-negative cells. In some embodiments, the population of in vitro differentiated cells comprises at least 60%, at least 70%, at least 75%, at least 80%, about 50-90%, or about 70-85% ISL1-positive cells. In some embodiments, at least 20% of the ISL1-positive cells are NKX6.1-negative. In some embodiments, at least 25%, at least 30%, at least 40%, about 30-50%, or about 40-50% of the ISL1-positive cells are NKX6.1-negative. In some embodiments, the population of in vitro differentiated cells comprises up to 20%, up to 30%, up to 40% or up to 50% of NK6.1-positive, ISL1-positive cells. In some embodiments, the population of in vitro differentiated cells comprises less than 25% or less than 20% of NKX6.1-positive, ISL1-negative cells. In some embodiments, the population of in vitro differentiated cells comprises less than 10% or less than 5% of NKX6.1-negative, ISL1-negative cells.

In some embodiments, the C-peptide content per 1,000 of the in vitro differentiated cells is at least 300 μM, optionally wherein the C-peptide content per 1,000 of the in vitro differentiated cells is at least 400 μM. In some embodiments, the glucagon content per 1,000 of the in vitro differentiated cells is at least 100 μM. In some embodiments, the glucagon content per 1,000 of the in vitro differentiated cells is at least 200 μM, at least 300 μM, at least 500 μM, at least 600 μM, at least 700 μM, or at least 800 μM. In some embodiments, at least 10% of the in vitro differentiated cells are stem cell-derived alpha cells. In some embodiments, at least 20%, at least 25%, at least 30%, at least 35%, about 20-40%, or about 30-40% of the in vitro differentiated cells are stem cell-derived alpha cells. In some embodiments, at least 35% of the in vitro differentiated cells are stem cell-derived beta cells/In some embodiments, at least 40%, at least 45%, or about 35-50% of the in vitro differentiated cells are stem cell-derived beta cells. In some embodiments, at least 5% of the in vitro differentiated cells are stem cell-derived delta cells. In some embodiments, about 5-10% of the in vitro differentiated cells are stem cell derived delta cells. In some embodiments, at least 5% of the in vitro differentiated cells are glucagon-positive and somatostatin-negative. In some embodiments, at least 5% of the in vitro differentiated cells are glucagon-negative and somatostatin-positive. In some embodiments, less than 10% of the in vitro differentiated cells are both ISL1-1 negative and NKX6.1-negative. In some embodiments, about 5-10% of the in vitro differentiated cells are both ISL1-1 negative and NKX6.1-negative. In some embodiments, less than 20% of the in vitro differentiated cells are both ISL1-negative and NKX6.1-positive. In some embodiments, about 10-20% of the in vitro differentiated cells are both ISL1-negative and NKX6.1-positive.

Further provided herein are populations of in vitro differentiated cells comprising NKX6.1-positive, ISL1-positive cells and NKX6.1-negative, ISL1-positive cells; wherein at least 15% of the cells in the population are NKX6.1-positive, ISL1-positive cells; wherein at least 10% of the cells in the population are NKX6.1-negative, ISL1-positive cells; and wherein less than 12% of the cells in the population are NKX6.1-negative, ISL1-negative cells.

Further provided herein are populations of in vitro differentiated cells comprising NKX6.1-positive, ISL1-positive cells and NKX6.1-negative, ISL1-positive cells; wherein at least 15% of the cells in the population are NKX6.1-positive, ISL1-positive cells; wherein at least 10% of the cells in the population are NKX6.1-negative, ISL1-positive cells; and wherein between 5-25% of the cells in the population are NKX6.1-positive, ISL1-negative cells.

In some embodiments, at least 30% of the cells in the population are NKX6.1-positive, ISL1-positive cells. In some embodiments, 30-60% of the cells in the population are NKX6.1-positive, ISL1-positive cells. In some embodiments, 35-50% of the cells in the population are NKX6.1-positive, ISL1-positive cells.

In some embodiments, at least 25% of the cells in the population are NKX6.1-negative, ISL1-positive cells. In some embodiments, 25-50% of the cells in the population are NKX6.1-negative, ISL1-positive cells. In some embodiments, 30-45% of the cells in the population are NKX6.1-negative, ISL1-positive cells.

In some embodiments, 1-12% of the cells in the population are NKX6.1-negative, ISL1-negative cells. In some embodiments, 2-12% of the cells in the population are NKX6.1-negative, ISL1-negative cells.

In some embodiments, between 5-25% of the cells in the population are NKX6.1-positive, ISL1-negative cells. In some embodiments, between 9-25% of the cells in the population are NKX6.1-positive, ISL1-negative cells.

In some embodiments, there are more NKX6.1-positive, ISL1-positive cells than NKX6.1-negative, ISL1-positive cells in the population.

In some embodiments, the population of in vitro differentiated cells further comprises a medium. In some embodiments, the medium comprises a sugar. In some embodiments, the sugar is sucrose or glucose. In some embodiments, the medium comprises the sugar at a concentration of between about 0.05% and about 1.5%. In some embodiments, the medium is a CMRL medium or wherein the medium is HypoThermosol® FRS Preservation Media.

In some embodiments, the population of cells are in a cell cluster. In some embodiments, wherein the cell cluster is between 125-225 microns, 130-160, 170-225, 140-200, 140-170, 160-220, 170-215, and 170-200 microns in diameter.

In some embodiments, the population comprises one or more NKX6.1-positive, ISL1-positive cells that express CHGA, MAFB, and/or ESRRG at a higher level (e.g., at least 10%, 30%, 50%, 70%, 100%, 125%, 150%, or 200% higher) than a NKX6.1-positive, ISL1-positive cell from the pancreas of a healthy control adult subject. In some embodiments, at least 30%, 40%, 50%, 60%, 70%, 80%, 90%, 95%, or 100% of the NKX6.1-positive, ISL1-positive cells in a population of cells express CHGA, MAFB, and/or ESRRG at a higher level than at least 30%, 40%, 50%, 60%, 70%, 80%, 90%, 95%, or 100% of the NKX6.1-positive, ISL1-positive cells from the pancreas of a healthy control adult subject. In some embodiments, the population comprises one or more NKX6.1-positive, ISL1-positive cells that express SIX3, MAFA, CHGB, RBP4 and/or FXYD2 at a lower level (e.g., at least 10%, 20%, 30%, 40%, 50%, 60%, 70%, 80%, 90% or 100% lower) than a NKX6.1-positive, ISL1-positive cell from the pancreas of a healthy control adult subject. In some embodiments, at least 30%, 40%, 50%, 60%, 70%, 80%, 90%, 95%, or 100% of the NKX6.1-positive, ISL1-positive cells in a population of cells express SIX3, MAFA, CHGB, RBP4 and/or FXYD2 at a lower level than at least 30%, 40%, 50%, 60%, 70%, 80%, 90%, 95%, or 100% of the NKX6.1-positive, ISL1-positive cells from the pancreas of a healthy control adult subject. In some embodiments, the population comprises NKX6.1-positive, ISL1-positive cells that express lower levels of MAFA than NKX6.1-positive, ISL1-positive cells from the pancreas of a healthy control adult subject. In some embodiments, the population comprises NKX6.1-positive, ISL1-positive cells that express lower levels of SIX3 than NKX6.1-positive, ISL1-positive cells from the pancreas of a healthy control adult subject. In some embodiments, the population comprises NKX6.1-positive, ISL1-positive cells that express lower levels of CHGB than NKX6.1-positive, ISL1-positive cells from the pancreas of a healthy control adult subject. In some embodiments, the population comprises NKX6.1-positive, ISL1-positive cells that express lower levels of RBP4 than NKX6.1-positive, ISL1-positive cells from the pancreas of a healthy control adult subject. In some embodiments, the population comprises NKX6.1-positive, ISL1-positive cells that express lower levels of FXYD2 than NKX6.1-positive, ISL1-positive cells from the pancreas of a healthy control adult subject. In some embodiments, the population comprises NKX6.1-positive, ISL1-positive cells that express higher levels of MAFB than NKX6.1-positive, ISL1-positive cells from the pancreas of a healthy control adult subject. In some embodiments, the population comprises NKX6.1-positive, ISL1-positive cells that express higher levels of SIX2, HOPX, IAPP and/or UCN3 than NKX6.1-positive, ISL1-positive cells from the pancreas of a healthy control adult subject. In some embodiments, the population comprises NKX6.1-positive, ISL1-positive cells that do not express MAFA. In some embodiments, the population comprises NKX6.1-positive, ISL1-positive cells that express MAFB.

In some embodiments, as an alternative to comparing gene expression to the cells of a healthy adult pancreas, the comparison could be to the expression of genes in one or more cadaveric islets (e.g., cadaveric islets suitable for transplantation in a diabetic patient-see, e.g., Hering et al., 2016, Diabetes Care, 39(7):1230-1240) and/or primary human islet cells (e.g., primary adult human islet cells, such as those obtainable from Nordic Network for Islet Transplantation (Uppsala University) and University of Alberta IsletCore (Canada)—see, e.g., Balboa et al., 2022, Nature Biotechnology, 40:1042-1055).

In some embodiments, the population comprises one or more NKX6.1-positive, ISL1-positive cells that express CHGA, MAFB, and/or ESRRG at a higher level (e.g., at least 10%, 30%, 50%, 70%, 100%, 125%, 150%, or 200% higher) than a NKX6.1-positive, ISL1-positive cell of cadaveric islets or primary human islet cells. In some embodiments, at least 30%, 40%, 50%, 60%, 70%, 80%, 90%, 95%, or 100% of the NKX6.1-positive, ISL1-positive cells in a population of cells express CHGA, MAFB, and/or ESRRG at a higher level than at least 30%, 40%, 50%, 60%, 70%, 80%, 90%, 95%, or 100% of the NKX6.1-positive, ISL1-positive cells of cadaveric islets or primary human islet cells. In some embodiments, the population comprises one or more NKX6.1-positive, ISL1-positive cells that express SIX3, MAFA, CHGB, RBP4 and/or FXYD2 at a lower level (e.g., at least 10%, 20%, 30%, 40%, 50%, 60%, 70%, 80%, 90% or 100% lower) than a NKX6.1-positive, ISL1-positive cell of cadaveric islets or primary human islet cells. In some embodiments, at least 30%, 40%, 50%, 60%, 70%, 80%, 90%, 95%, or 100% of the NKX6.1-positive, ISL1-positive cells in a population of cells express SIX3, MAFA, CHGB, RBP4 and/or FXYD2 at a lower level than at least 30%, 40%, 50%, 60%, 70%, 80%, 90%, 95%, or 100% of the NKX6.1-positive, ISL1-positive cells of cadaveric islets or primary human islet cells. In some embodiments, the population comprises NKX6.1-positive, ISL1-positive cells that express lower levels of MAFA than NKX6.1-positive, ISL1-positive cells of cadaveric islets or primary human islet cells. In some embodiments, the population comprises NKX6.1-positive, ISL1-positive cells that express lower levels of SIX3 than NKX6.1-positive, ISL1-positive cells of cadaveric islets or primary human islet cells. In some embodiments, the population comprises NKX6.1-positive, ISL1-positive cells that express lower levels of CHGB than NKX6.1-positive, ISL1-positive cells of cadaveric islets or primary human islet cells. In some embodiments, the population comprises NKX6.1-positive, ISL1-positive cells that express lower levels of RBP4 than NKX6.1-positive, ISL1-positive cells of cadaveric islets or primary human islet cells. In some embodiments, the population comprises NKX6.1-positive, ISL1-positive cells that express lower levels of FXYD2 than NKX6.1-positive, ISL1-positive cells of cadaveric islets or primary human islet cells. In some embodiments, the population comprises NKX6.1-positive, ISL1-positive cells that express higher levels of MAFB than NKX6.1-positive, ISL1-positive cells of cadaveric islets or primary human islet cells. In some embodiments, the population comprises NKX6.1-positive, ISL1-positive cells that express higher levels of SIX2, HOPX, IAPP and/or UCN3 than NKX6.1-positive, ISL1-positive cells of cadaveric islets or primary human islet cells.

In some embodiments, any of the NKX6.1-positive, ISL1-positive cells disclosed herein also expresses any one or more of the following genes: PC2, MNX1, or ABCC8.

In some embodiments, any of the compositions or cell populations described herein comprise less than 40% VMAT1-positive cells. In some embodiments, less than 40%, 35%, 30%, 25%, 20%, 15%, or 10% of the cells in any of the compositions or cell populations disclosed herein are VMAT1-positive cells. In some embodiments, the composition or cell population comprises 1-40%, 1-35%, 1-30%, 1-25%, 1-20%, 1-15%, 1-10%, 5-40%, 5-35%, 5-30%, 5-25%, 5-20%, 5-15%, 5-10%, 10-40%, 10-35%, 10-30%, 10-25%, 15-25%, 10-20%, 10-15%, 20-40%, 20-35%, 20-30%, 20-25%, 30-40% VMAT1-positive cells.

In some embodiments, the population of cells is derived from stem cells in vitro. In some embodiments, the stem cells are genetically modified. In some embodiments, the stem cells have reduced expression of one or more of beta-2 microglobulin, CXCL10, renalase, CIITA, HLA-A, HLA-B, HLA-C, HLA-DP, HLA-DQ, and/or HLADR, relative to stem cells that are not genetically modified. In some embodiments, the stem cells have increased expression of one or more of CD47, PDL1, HLA-G, CD46, CD55, CD59 and/or CTLA, relative to stem cells that are not genetically modified.

In some embodiments, the population of in vitro differentiated cells are contained in a device for implantation into a subject.

Further provided herein are in vitro compositions comprising the population of in vitro differentiated cells described herein a medium. In some embodiments, the medium comprises human serum albumin. In some embodiments, the medium comprises glutamine. In some embodiments, the medium comprises any one or more of the following: an inorganic compound, an Alk5 inhibitor, a thyroid hormone receptor beta-specific agonist, a BMP type I receptor inhibitor, a RHO/ROCK pathway inhibitor, a protein kinase inhibitor, or a S-adenosylhomocysteine hydrolase inhibitor. In some embodiments, the medium comprises any one or more of the following: ZnSO4, Alk5i, GC-1, LDN-193189, thiazovivin, staurosporine, or DZNEP. In some embodiments, the medium comprises any one or more of L-glutamate, L-carnitine, taurine, acetate, beta-hydroxybutarate, biotin or formate.

Further provided herein are implantable encapsulation device comprising the population of in vitro differentiated cells described herein. In some embodiments, the device comprises a first membrane having a first surface comprising a plurality of channels, and a plurality of second surfaces opposing the first surface; and a second membrane opposite and attached to the plurality of the second surfaces of the first membrane. In some embodiments, the first membrane and the second membrane comprise PVDF, PTFE, ePTFE, PCL, PE/PES, PP, PS, PMMA, PLGA, PLLA, or any combination thereof.

Further provided herein are implantable encapsulation devices including an internal volume comprising the composition described herein disposed therein. In some embodiments, the implantable encapsulation device comprises at least one membrane that at least partially defines the internal volume. In some embodiments, the at least one membrane includes a first membrane and a second membrane, wherein the first membrane and the second membrane are bonded together to form a seal extending at least partially around the internal volume disposed between the first membrane and the second membrane. In some embodiments, the at least one membrane comprises at least one selected from PVDF, PTFE, ePTFE, PCL, PE/PES, PP, PS, PMMA, PLGA, and PLLA. In some embodiments, the at least one membrane comprises ePTFE.

In some embodiments, the device has been implanted in a subject having diabetes. In some embodiments, the subject has Type I Diabetes.

Methods of treating a subject are provided, the method comprising administering to the subject a composition comprising the population of in vitro differentiated cells described herein. In some embodiments, the method comprises administering to the subject a composition comprising a population in vitro differentiated cells comprising NKX6.1-positive, ISL1-positive cells and NKX6.1-negative, ISL1-positive cells; wherein the population comprises more NKX6.1-positive, ISL1-positive cells than NKX6.1-negative, ISL1-positive cells; wherein at least 15% of the cells in the population are NKX6.1-negative, ISL1-positive cells; and wherein less than 12% of the cells in the population are NKX6.1-negative, ISL1-negative cells. In some embodiments, the method comprises implanting into the subject a implantable encapsulation device comprising a population in vitro differentiated cells comprising NKX6.1-positive, ISL1-positive cells and NKX6.1-negative, ISL1-positive cells; wherein the population comprises more NKX6.1-positive, ISL1-positive cells than NKX6.1-negative, ISL1-positive cells; wherein at least 15% of the cells in the population are NKX6.1-negative, ISL1-positive cells; and wherein less than 12% of the cells in the population are NKX6.1-negative, ISL1-negative cells.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A shows glucose levels up to 180 minutes post-glucose administration. FIG. 2B shows Area Under the Curve (AUC) derived from the oral glucose tolerance test (OGTT).

FIGS. 24A-24H are flow cytometry graphs showing Glucagon (GCG)/Somatostatin (SST) expression on S6D12 in SC-islet cells differentiated using the methods described in Table 6.

FIGS. 25A-25B are graphs showing the percentage of ISL1+ cells (FIG. 25A) and percentage of SC-EC cells (FIG. 25B) in SC-islets differentiated using Protocol 1, Protocol 2, or Protocol 3. SC-islets differentiated using Protocol 2 or Protocol 3 show increased total ISL1+ cells and reduced ISL1− cells (SC-EC cells).

FIG. 27 shows a graph of cell density throughout differentiation using Protocol 1, Protocol 2, or Protocol 3. "Spinner" indicates the cells were cultured in spinner flasks, while "3-MAG" indicates the cells were cultured in a 3-liter reactor.

FIGS. 28A-28B. is a graph showing the C-peptide (FIG. 28A) and glucagon (FIG. 28B) content of SC-islet cells differentiated using Protocol 1 (Table 2), Protocol 2 (Table 2), or Protocol 3 (Table 9).

FIGS. 34A-34D are flow cytometry graphs showing ISL1/Nkx6.1 expression on S6D11 in SC-islet cells differentiated using Protocol 1 (FIG. 34A), Protocol 2 (FIG. 34B), Protocol 3 (FIG. 34C), or Protocol 3 with the addition of FGF2 (at 100 ng/ml) in stage 6 media (Media A shown in Table 7A) (FIG. 34D).

DETAILED DESCRIPTION

Figure 1:
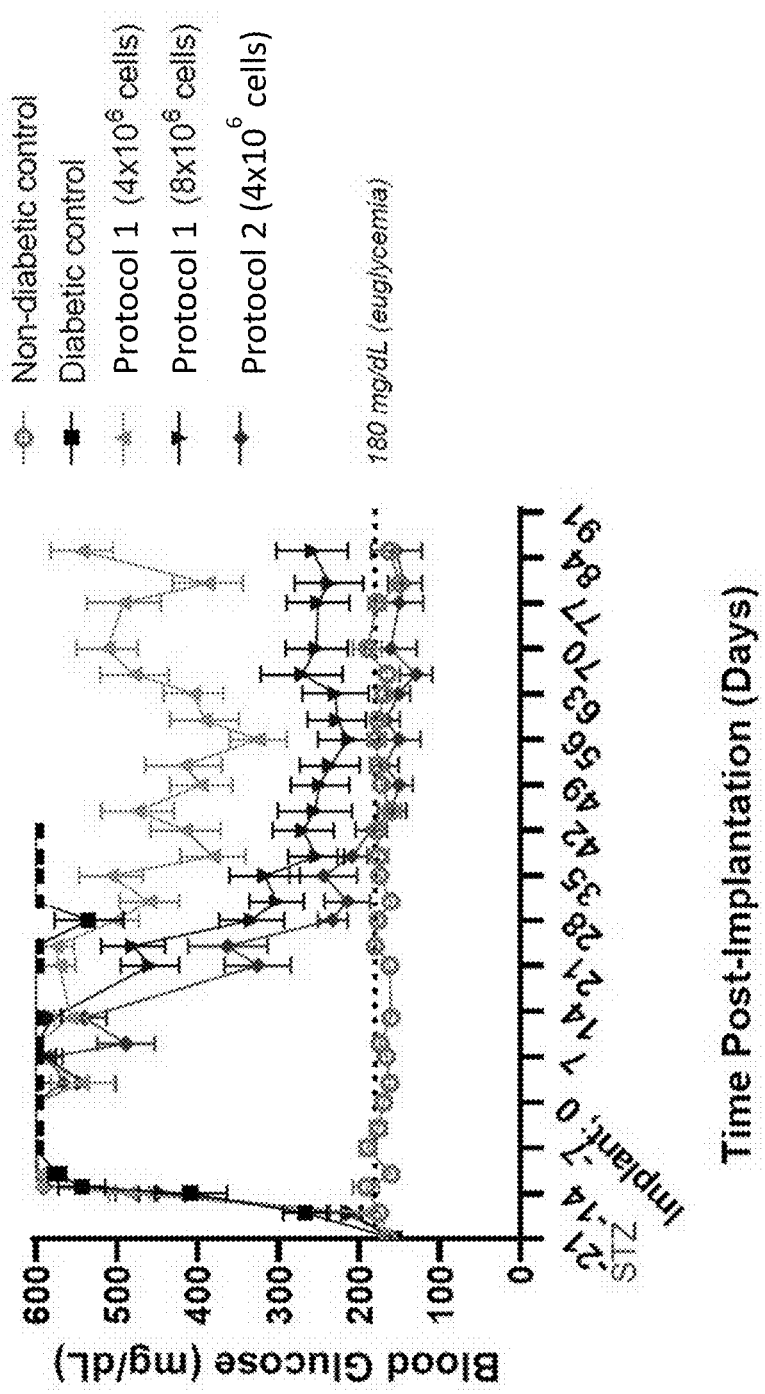
FIG. 1 is a graph showing the blood glucose level of mice implanted with SC-islet cells differentiated using Protocol 1 or Protocol 2. SC-islet cells differentiated using Protocol 2 lowered blood glucose level in diabetic mice to a level achieved using twice the dose of SC-islet cells differentiated using Protocol 1.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some embodiments, diabetes can be a form of hereditary diabetes. In some embodiments, diabetes can be an autoimmune form of diabetes.

The term "endocrine cell(s)," if not particularly specified, can refer to hormone-producing cells present in the pancreas of an organism, such as "islet", "islet cells", "islet equivalent", "islet-like cells", "pancreatic islets" and their grammatical equivalents. In an embodiment, the endocrine cells can be differentiated from pancreatic progenitor cells or precursors. Islet cells can comprise different types of cells, including, but not limited to, pancreatic α cells, pancreatic β cells, pancreatic δ cells, pancreatic F cells, and/or pancreatic F cells. Islet cells can also refer to a group of cells, cell clusters, or the like.

The terms "progenitor" and "precursor" cell are used interchangeably herein and refer to cells that have a cellular phenotype that is more primitive (e.g., is at an earlier step along a developmental pathway or progression than is a fully differentiated cell) relative to a cell which it can give rise to by differentiation. Often, progenitor cells can also have significant or very high proliferative potential. Progenitor cells can give rise to multiple distinct differentiated cell types or to a single differentiated cell type, depending on the developmental pathway and on the environment in which the cells develop and differentiate.

A "precursor thereof" as the term related to an insulin-positive endocrine cell can refer to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, that if cultured under suitable conditions will differentiate the precursor cell into the insulin-positive endocrine cell.

The terms "stem cell-derived β cell," "SC-β cell," "functional β cell," "functional pancreatic β cell," "mature SC-β cell," "β-like cell" and their grammatical equivalents can refer to cells (e.g., non-native pancreatic β cells) that display at least one marker indicative of a pancreatic β cell (e.g., PDX-1 or NKX6.1), expresses insulin, and display a glucose stimulated insulin secretion (GSIS) response similar or superior to that of an endogenous mature β cell (e.g., a mature R from a healthy functioning pancreas from a healthy adult non-diabetic patient). For simplicity, SC-β cells may be referred to as simply "β cells" in this disclosure. In some embodiments, the terms "SC-β cell" and "non-native β cell" as used herein are interchangeable. In some embodiments, the "SC-β cell" expresses lower levels of MAFA than a pancreatic β cell from a healthy adult human patient. In some embodiments, the "SC-β cell" expresses higher levels of MAFB than a pancreatic β cell from a healthy adult human patient. In some embodiments, the "SC-β cell" expresses higher levels of SIX2, HOPX, IAPP and/or UCN3 than a pancreatic β cell from a healthy adult human patient. In some embodiments, the "SC-β cell" comprises a mature pancreatic cell. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells such as definitive endoderm cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc., as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous R cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. In some embodiments, the GSIS response of the SC-β cell can be observed within two weeks of transplantation of the SC-β cell into a host (e.g., a human or animal). In some embodiments, the GSIS response of the SC-β cell can be observed within three weeks of transplantation of the SC-β cell into a host (e.g., a human or animal). In some embodiments, the GSIS response of the SC-β cell can be observed within four weeks of transplantation of the SC-β cell into a host (e.g., a human or animal). In some embodiments, the GSIS response of the SC-β cell can be observed between one month and three months of transplantation of the SC-β cell into a host (e.g., a human or animal). In some embodiments, the SC-β cells package insulin into secretory granules. In some embodiments, the SC-β cells exhibit encapsulated crystalline insulin granules when viewed using electron microscopy. In some embodiments, the SC-β cells exhibit a stimulation index of greater than 1.

In some embodiments, the SC-β cells exhibit a stimulation index of greater than 1.1. In some embodiments, the SC-β cells exhibit a stimulation index of greater than 2. In some embodiments, the stimulation index of the cell is characterized by the ratio of insulin secreted in response to high glucose concentrations (e.g., 15 mM) compared to low glucose concentrations (e.g., 2.5 mM).

In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular $Ca2+$ in response to glucose.

The terms "stem cell-derived α cell," "SC-α cell," "functional α cell," "functional pancreatic α cell," "mature SC-α cell," "α-like cell" and their grammatical equivalents can refer to cells (e.g., non-native pancreatic α cells) that display at least one marker indicative of a pancreatic α cell (e.g., glucagon, expressing ISL1 but not NKX6.1), expresses glucagon, and is capable of secreting functional glucagon in response to a stimulus that induces an endogenous pancreatic α cell to secrete functional glucagon. In some embodiments, the "SC-α cell" does not express somatostatin. In some embodiments, the "SC-α cell" does not express insulin. In some embodiments, the terms "SC-α cell" and "non-native α cell" as used herein are interchangeable. In some embodiments, the "SC-α cell" comprises a mature pancreatic cell. For short, these cells may be referred to as simply "α cells" in this disclosure.

The terms "stem cell-derived δ cell," "SC-δ cell," "functional δ cell," "functional pancreatic δ cell," "mature SC-δ cell," "δ-like cell" and their grammatical equivalents can refer to cells (e.g., non-native pancreatic δ cells) that display at least one marker indicative of a pancreatic δ cell (e.g., somatostatin), expresses and is capable of secreting somatostatin in response to a stimulus that induces an endogenous pancreatic δ cell to secrete functional glucagon. For simplicity, SC-δ cells may be referred to as simply "δ cells" in this disclosure. In some embodiments, "SC-δ cell" does not express glucagon. In some embodiments, "SC-δ cell" does not express insulin. In some embodiments, the terms "SC-δ cell" and "non-native δ cell" as used herein are interchangeable. In some embodiments, the "SC-δ cell" comprises a mature pancreatic cell.

The terms "stem cell-derived enterochromaffin (EC) cell," "SC-EC cell," and their grammatical equivalents can refer to cells (e.g., non-native pancreatic EC cells) that display at least one marker indicative of a pancreatic EC cell (e.g., VMAT1 (vesicular monoamine transporter 1), expressing NKX6.1 but not ISL1). In some embodiments, the terms "SC-EC cell" and "non-native EC cell" as used herein are interchangeable.

Similar to SC-β cells, it is to be understood that the SC-α, SC-δ cells, and SC-EC cells need not be derived (e.g., directly) from stem cells, as the methods of the disclosure are capable of deriving SC-α cells from other precursor cells generated during in vitro differentiation of SC-β cells as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc., as the invention is not intended to be limited in this manner).

As used herein, the term "insulin producing cell" and its grammatical equivalent refer to a cell differentiated from a pancreatic progenitor, or precursor thereof, which secretes insulin. An insulin-producing cell can include pancreatic β cell as that term is described herein, as well as pancreatic β-like cells (e.g., insulin-positive, endocrine cells) that synthesize (e.g., transcribe the insulin gene, translate the proinsulin mRNA, and modify the proinsulin mRNA into the insulin protein), express (e.g., manifest the phenotypic trait carried by the insulin gene), or secrete (release insulin into the extracellular space) insulin in a constitutive or inducible manner. A population of insulin producing cells e.g., produced by differentiating insulin-positive endocrine cells or a precursor thereof into SC-β cells according to the methods of the present disclosure can be pancreatic β cells or β-like cells (e.g., cells that have at least one, or at least two least characteristics of an endogenous β cell and exhibit a glucose stimulated insulin secretion (GSIS) response that resembles an endogenous adult β cell). The population of insulin-producing cells, e.g., produced by the methods as disclosed herein can comprise mature pancreatic β cell or SC-β cells, and can also contain non-insulin-producing cells (e.g., cells of cell like phenotype with the exception they do not produce or secrete insulin).

The terms "insulin-positive β-like cell," "insulin-positive endocrine cell," and their grammatical equivalents can refer to cells (e.g., pancreatic endocrine cells) that display at least one marker indicative of a pancreatic β cell and also expresses insulin but, unless specified otherwise, lack a glucose stimulated insulin secretion (GSIS) response characteristic of an endogenous β cell. Exemplary markers of "insulin-positive endocrine cell" include, but are not limited to, NKX6.1 (NK6 homeobox 1), ISL1 (Islet1), and insulin.

The term "β cell marker" refers to, without limitation, proteins, peptides, nucleic acids, polymorphism of proteins and nucleic acids, splice variants, fragments of proteins or nucleic acids, elements, and other analyte which are expressed or present in pancreatic β cells. Exemplary β cell markers include, but are not limited to, pancreatic and duodenal homeobox 1 (PDX1) polypeptide, insulin, c-peptide, amylin, E-cadherin, Hnf3β, PCI/3, B2, Nkx2.2, GLUT2, PC2, ZnT-8, ISL1, Pax6, Pax4, NeuroD, 1 Inf1b, Hnf-6, Hnf-3beta, VMAT2, NKX6.1, and MafA, and those described in Zhang et al., Diabetes. 50(10):2231-6 (2001). In some embodiments, the β cell marker is a nuclear β-cell marker. In some embodiments, the R cell marker is PDX1 or PH3.

The term "pancreatic endocrine marker" can refer to without limitation, proteins, peptides, nucleic acids, polymorphism of proteins and nucleic acids, splice variants, fragments of proteins or nucleic acids, elements, and other analytes which are expressed or present in pancreatic endocrine cells. Exemplary pancreatic endocrine cell markers include, but are not limited to, Ngn-3, NeuroD and Islet-1.

The term "pancreatic progenitor," "pancreatic endocrine progenitor," "pancreatic precursor," "pancreatic endocrine precursor" and their grammatical equivalents are used interchangeably herein and can refer to a stem cell which is capable of becoming a pancreatic hormone expressing cell capable of forming pancreatic endocrine cells, pancreatic exocrine cells or pancreatic duct cells. These cells are committed to differentiating towards at least one type of pancreatic cell, e.g. β cells that produce insulin; α cells that produce glucagon; δ cells (or D cells) that produce somatostatin; and/or F cells that produce pancreatic polypeptide. Such cells can express at least one of the following markers: NGN3, NKX2.2, NeuroD, ISL-1, Pax4, Pax6, or ARX.

The term "PDX1-positive pancreatic progenitor" as used herein can refer to a cell which is a pancreatic endoderm (PE) cell which has the capacity to differentiate into SC-β cells, such as pancreatic β cells. A PDX1-positive pancreatic progenitor expresses the marker PDX1. Other markers include, but are not limited to Cdcp1, or Ptf1a, or HNF6 or NRx2.2. The expression of PDX1 may be assessed by any method known by the skilled person such as immunochemistry using an anti-PDX1 antibody or quantitative RT-PCR. In some embodiments, a PDX1-positive pancreatic progenitor cell lacks expression of NKX6.1. In some embodiments, a PDX1-positive pancreatic progenitor cell can also be referred to as PDX1-positive, NKX6.1-negative pancreatic progenitor cell due to its lack of expression of NKX6.1. In some embodiments, the PDX1-positive pancreatic progenitor cells can also be termed as "pancreatic foregut endoderm cells."

The terms "PDX1-positive, NKX6.1-positive pancreatic progenitor," and "NKX6.1-positive pancreatic progenitor" are used interchangeably herein and can refer to a cell which is a pancreatic endoderm (PE) cell which has the capacity to differentiate into insulin-producing cells, such as pancreatic β cells. A PDX1-positive, NKX6.1-positive pancreatic progenitor expresses the markers PDX1 and NKX6-1. Other markers may include, but are not limited to Cdcp1, or Ptf1a, or HNF6 or NRx2.2. The expression of NKX6-1 may be assessed by any method known by the skilled person such as immunochemistry using an anti-NKX6-1 antibody or quantitative RT-PCR. As used herein, the terms "NKX6.1" and "NKX6-1" are equivalent and interchangeable. In some embodiments, the PDX1-positive, NKX6.1-positive pancreatic progenitor cells can also be termed as "pancreatic foregut precursor cells."

The terms "NeuroD" and "NeuroD1" are used interchangeably and identify a protein expressed in pancreatic endocrine progenitor cells and the gene encoding it.

The term "differentiated cell" or its grammatical equivalents means any primary cell that is not, in its native form, pluripotent as that term is defined herein. Stated another way, the term "differentiated cell" can refer to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell may lead to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiated into other cells of endodermal origin, e.g. lung, liver, intestine, thymus etc.

As used herein, the term "somatic cell" can refer to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" can refer to a cell found throughout the body after embryonic development.

The term "endoderm cell" as used herein can refer to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g., the intestine), the liver and the pancreas.

The term "a cell of endoderm origin" as used herein can refer to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are developed from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein can refer to a cell differentiated from an endoderm cell and which can be differentiated into a SC-β cell (e.g., a pancreatic β cell). A definitive endoderm cell expresses the marker Sox17. Other markers characteristic of definitive endoderm cells may include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker PDX1 (e.g. they are PDX1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" can refer to a cell of endoderm origin which is capable of differentiating into multiple pancreatic lineages, including pancreatic β cells, but no longer has the capacity to differentiate into non-pancreatic lineages.

The term "pancreatic islet cells" refers to a population of cells that include different types of pancreatic endocrine cells (β-cells, α-cells, δ-cells, ε-cells) and enterochromaffin (EC) cells, e.g., as described in Xavier et al. (J Clin Med. 2018 March; 7(3): 54), incorporated herein by reference.

The term "primitive gut tube cell" or "gut tube cell" as used herein can refer to a cell differentiated from an endoderm cell and which can be differentiated into a SC-β cell (e.g., a pancreatic 1 cell). A primitive gut tube cell expresses at least one of the following markers: HNP1-β, HNF3-β or HNF4-α. In some embodiments, a primitive gut tube cell is FOXA2-positive and SOX2-positive, i.e., expresses both FOXA2 (also known as HNF3-β) and SOX2. In some embodiments, a primitive gut tube cell is FOXA2-positive and PDX1-negative, i.e., expresses FOXA2 but not PDX1. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "phenotype" can refer to one or a number of total biological characteristics that define the cell or organism under a particular set of environmental conditions and factors, regardless of the actual genotype.

The terms "patient," "subject," and "individual" may be used interchangeably and refer to either a human or a non-human animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g., dog, cat, horse, and the like, or production mammal, e.g. cow, sheep, pig, and the like. "Patient in need thereof" or "subject in need thereof" is referred to herein as a patient diagnosed with or suspected of having a disease or disorder, for instance, but not restricted to diabetes.

"Administering" as used herein can refer to providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise the cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The ranges disclosed throughout are sometimes referred to as, for example, "X is administered on or on about day 1 to 2; or 2 to 3 [or any numerical range]." This range includes the numbers themselves (e.g., the endpoints of the range) and any individual numbers present in this range. All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

Differentiation Stages

Pancreatic differentiation as disclosed herein may be carried out in a step-wise manner. In an exemplary embodiment of the step-wise progression, "Stage 1" or "S1" or "St1" refers to the first step in the differentiation process, the differentiation of pluripotent stem cells into cells expressing markers characteristic of definitive endoderm cells ("DE", "Stage 1 cells" or "St1 cells" or "S1 cells"). "Stage 2" or "S2" or "St2" refers to the second step, the differentiation of cells expressing markers characteristic of definitive endoderm cells into cells expressing markers characteristic of gut tube cells ("GT", "Stage 2 cells" or "St2 cells" or "S2 cells"). "Stage 3" or "S3" or "St3" refers to the third step, the differentiation of cells expressing markers characteristic of gut tube cells into cells expressing markers characteristic of pancreatic progenitor 1 cells ("PP1", "Stage 3 cells" or "St3 cells" or "S3 cells"). "Stage 4" or "S4" or "St4" refers to the fourth step, the differentiation of cells expressing markers characteristic of pancreatic progenitor 1 cells into cells expressing markers characteristic of pancreatic progenitor 2 cells ("PP2", "Stage 4 cells" or "St4 cells" or "S4 cells"). "Stage 5" or "S5" or "St5" refers to the fifth step, the differentiation of cells expressing markers characteristic of pancreatic progenitor 2 cells (e.g., PDX.1+, NKX6.1+) into cells expressing markers characteristic of pancreatic endoderm cells and/or pancreatic endocrine progenitor cells (e.g., insulin+) ("EN", "Stage 5 cells" or "St5 cells" or "S5 cells"). "Stage 6" or "S6" or "St6" refers to the differentiation of cells expressing markers characteristic of pancreatic endocrine progenitor cells (e.g., insulin) into cells expressing markers characteristic of pancreatic endocrine β cells ("SC-β cells") or pancreatic endocrine α cells ("SC-α cells"). It should be appreciated, however, that not all cells in a particular population progress through these stages at the same rate, i.e., some cells may have progressed less, or more, down the differentiation pathway than the majority of cells present in the population. For example, in some embodiments, SC-β cells can be identified during stage 5, at the conclusion of stage 5, at the beginning of stage 6, etc. Examples of methods of making cells of any one of stages 1-6 are provided in, for example, U.S. Pat. Nos. 10,030,229; 10,443,042; published application US 20200332262; and published application US 20210198632, published application US 20220090020, and published application WO2022147056, each of which is incorporated by reference in its entirety.

Compositions and Methods for Producing Pancreatic Islet Cells

In aspects, the present disclosure provides compositions and methods of differentiating pancreatic islet cells (e.g., differentiating from stem cells such as human embryonic stem cells or human pluripotent stem cells). The compositions and methods provided herein can, in some embodiments, offer pancreatic SC-islet cells, cell populations, or cell clusters containing pancreatic SC-β cells and pancreatic SC-α cells. In some embodiments, such pancreatic SC-islet cells, cell populations or cell clusters exhibit, high insulin content, superior glucose-dependent insulin secretion response, as well as a percentage of pancreatic SC-α, SC-β, and SC-δ cells and enterochromaffin (EC) cells, which can resemble native pancreatic islets both structurally and functionally. In some embodiments, a population of pancreatic islet cells (e.g., stem cell derived pancreatic islet cells) produced using the compositions and methods described herein comprises about 30%-45% pancreatic SC-β cells, 40%-50% pancreatic α cells, 3-10% pancreatic SC-δ cells, and/or less than 20% SC-EC cells. In some embodiments, a population of pancreatic islet cells (e.g., stem cell derived pancreatic islet cells) produced using the compositions and methods described herein has improved glucose-stimulated insulin secretion (GSIS) response as compared to cell compositions generated according to conventional methods. In some embodiments, a population of pancreatic islet cells (e.g., stem cell derived pancreatic islet cells) produced using the compositions and methods described herein has dynamic GSIS response similar to native pancreatic islets (e.g., pancreatic islets from a healthy functioning pancreas from a healthy adult non-diabetic subject).

In some embodiments, a method of producing pancreatic islet cells (e.g., SC-beta cells, SC-alpha cells, SC-delta cells) described herein comprises contacting pancreatic progenitor cells (e.g., pancreatic progenitor cells that are PDX1-positive and NKX6.1-negative) with a medium comprising a comprising a Forkhead Box O1 (FoxO1) inhibitor and/or a notch signaling pathway inhibitor (e.g., a γ-secretase inhibitor). In some embodiments, a method described herein comprises contacting pancreatic progenitor cells in a culture with a FOXO1 inhibitor and/or a notch signaling pathway inhibitor (e.g., a γ-secretase inhibitor), wherein the culture comprises pancreatic progenitor cells that are PDX1-positive and NKX6.1-negative and pancreatic progenitor cells that are PDX1-positive and NKX6.1-positive. In some embodiments, a method described herein comprises contacting pancreatic progenitor cells (e.g., pancreatic progenitor cells that are PDX1-positive and NKX6.1-positive) with a medium comprising a comprising a Wnt signaling pathway inhibitor and/or a PKC activator. In some embodiments, a method described herein comprises contacting pancreatic progenitor cells (e.g., pancreatic progenitor cells that are PDX1-positive and NKX6.1-negative) with a medium comprising a comprising a Forkhead Box O1 (FoxO1) inhibitor and/or a notch signaling pathway inhibitor (e.g., a γ-secretase inhibitor), and contacting resulting cells with a medium comprising a comprising a Wnt signaling pathway inhibitor and/or a PKC activator. In some embodiments, the method does not comprise the step of contacting cells with a Wnt signaling pathway inhibitor and a FoxO1 inhibitor at the same time.

Composition Comprising FoxO1 Inhibitor and Optionally a Notch Signaling Inhibitor In some aspects, the present disclosure provides in vitro compositions comprising a population of pancreatic progenitor cells and a medium comprising a Forkhead Box O1 (FoxO1) inhibitor. In some embodiments, the medium further comprises a notch signaling pathway inhibitor (e.g., a γ-secretase inhibitor). In some embodiments, the medium further comprises a PKC activator. In some embodiments, the medium further comprises one or more (e.g., 1, 2, 3, 4, 5) agents selected from: a fibroblast growth factor, a sonic hedgehog (SHH) signaling pathway inhibitor, retinoic acid, a Rho-associated, coiled-coil containing protein kinase (ROCK) inhibitor, and a TGF-β ligand. In some embodiments, the medium further comprises a fibroblast growth factor, a sonic hedgehog (SHH) signaling pathway inhibitor, retinoic acid, a Rho-associated, coiled-coil containing protein kinase (ROCK) inhibitor, and a TGF-3 ligand.

In some embodiments, the medium comprises a FoxO1 inhibitor, a notch signaling pathway inhibitor (e.g., a γ-secretase inhibitor), a PKC activator, a fibroblast growth factor, a sonic hedgehog (SHH) signaling pathway inhibitor, retinoic acid, a Rho-associated, coiled-coil containing protein kinase (ROCK) inhibitor, and a TGF-β ligand. In some embodiments, the medium comprises FoxO1 inhibitor AS1842856 (e.g., Catalog #344355 as Sigma-Aldrich), XXI, PdBu, keratinocyte growth factor (KGF), SANT-1, RA, triazovivin, and activin A. In some embodiments, the medium does not comprise a Wnt signaling pathway inhibitor.

In some embodiments, a FoxO1 inhibitor (e.g., AS1842856) is present in the medium at a concentration of 0.1 μM-10 μM. In some embodiments, a FoxO1 inhibitor (AS1842856) is present in the medium at a concentration of 0.1 μM-10 μM, 0.1 μM-9 μM, 0.1 μM-8 μM, 0.1 μM-7 μM, 0.1 μM-6 μM, 0.1 μM-5 μM, 0.1 μM-4 μM, 0.1 μM-3 μM, 0.1 μM-2 μM, 0.1 μM-1 μM, 0.1 μM-0.5 μM, 0.5 μM-10 μM, 0.5 μM-9 μM, 0.5 μM-8 μM, 0.5 μM-7 μM, 0.5 μM-6 μM, 0.5 μM-5 μM, 0.5 μM-4 μM, 0.5 μM-3 μM, 0.5 μM-2 μM, 0.5 μM-1 μM, 1 μM-10 μM, 1 μM-9 μM, 1 μM-8 μM, 1 μM-7 μM, 1 μM-6 μM, 1 μM-5 μM, 1 μM-4 μM, 1 μM-3 μM, 1 μM-2 μM, 2 μM-10 μM, 2 μM-9 μM, 2 μM-8 μM, 2 μM-7 μM, 2 μM-6 μM, 2 μM-5 μM, 2 μM-4 μM, 2 μM-3 μM, 3 μM-10 μM, 3 μM-9 μM, 3 μM-8 μM, 3 μM-7 μM, 3 μM-6 μM, 3 μM-5 μM, 3 μM-4 μM, 4 μM-10 μM, 4 μM-9 μM, 4 μM-8 μM, 4 μM-7 μM, 4 μM-6 μM, 4 μM-5 μM, 5 μM-10 μM, 5 μM-9 μM, 5 μM-8 μM, 5 μM-7 μM, 5 μM-6 μM, 6 μM-10 μM, 6 μM-9 μM, 6 μM-8 μM, 6 μM-7 μM, 7 μM-10 μM, 7 μM-9 μM, 7 μM-8 μM, 8 μM-10 μM, 8 μM-9 μM, or 9 μM-10 μM. In some embodiments, a FoxO1 inhibitor (e.g., AS1842856) is present in the medium at a concentration of 0.5 μM-5 μM (e.g., 0.5 μM, 1 μM, 1.5 μM, 2 μM, 2.5 μM, 3 μM, 3.5 μM, 4 μM, 4.5 μM, or 5 μM). In some embodiments, a FoxO1 inhibitor (e.g., AS1842856) is present in the medium at a concentration of 0.7-1.3 μM, 0.8-1.2 μM, or 0.9-1.1 μM. In some embodiments, a FoxO1 inhibitor (e.g., AS1842856) is present in the medium at a concentration of 1 μM.

In some embodiments, a notch signaling pathway inhibitor (e.g., γ-secretase inhibitor such as XXI) is present in the medium at a concentration of 0.1 μM-10 μM. In some embodiments, a notch signaling pathway inhibitor (e.g., γ-secretase inhibitor such as XXI) is present in the medium at a concentration of 0.1 μM-10 μM, 0.1 μM-9 μM, 0.1 μM-8 μM, 0.1 μM-7 μM, 0.1 μM-6 μM, 0.1 μM-5 μM, 0.1 μM-4 μM, 0.1 μM-3 μM, 0.1 μM-2 μM, 0.1 μM-1 μM, 0.1 μM-0.5 μM, 0.5 μM-10 μM, 0.5 μM-9 μM, 0.5 μM-8 μM, 0.5 μM-7 μM, 0.5 μM-6 μM, 0.5 μM-5 μM, 0.5 μM-4 μM, 0.5 μM-3 μM, 0.5 μM-2 μM, 0.5 μM-1 μM, 1 μM-10 μM, 1 μM-9 μM, 1 μM-8 μM, 1 μM-7 μM, 1 μM-6 μM, 1 μM-5 μM, 1 μM-4 μM, 1 μM-3 μM, 1 μM-2 μM, 2 μM-10 μM, 2 μM-9 μM, 2 μM-8 μM, 2 μM-7 μM, 2 μM-6 μM, 2 μM-5 μM, 2 μM-4 μM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a notch signaling pathway inhibitor (e.g., γ-secretase inhibitor such as XXI) is present in the medium at a concentration of 0.5 µM-5 µM (e.g., 0.5 µM, 1 µM, 1.5 µM, 2 µM, 2.5 µM, 3 µM, 3.5 µM, 4 µM, 4.5 µM, or 5 µM). In some embodiments, a notch signaling pathway inhibitor (e.g., γ-secretase inhibitor such as XXI) is present in the medium at a concentration of 1.5 µM-2.5 µM or 1.8 µM-2.2 µM. In some embodiments, a notch signaling pathway inhibitor (e.g., γ-secretase inhibitor such as XXI) is present in the medium at a concentration of 2 µM.

In some embodiments, a PKC activator (e.g., PdBu) is present in the medium at a concentration of 0.1 µM-10 µM. In some embodiments, a PKC activator (e.g., PdBu) is present in the medium at a concentration of 0.1 µM-10 µM, 0.1 µM-9 µM, 0.1 µM-8 µM, 0.1 µM-7 µM, 0.1 µM-6 µM, 0.1 µM-5 µM, 0.1 µM-4 µM, 0.1 µM-3 µM, 0.1 µM-2 µM, 0.1 µM-1 µM, 0.1 µM-0.5 µM, 0.5 µM-10 µM, 0.5 µM-9 µM, 0.5 µM-8 µM, 0.5 µM-7 µM, 0.5 µM-6 µM, 0.5 µM-5 µM, 0.5 µM-4 µM, 0.5 µM-3 µM, 0.5 µM-2 µM, 0.5 µM-1 µM, 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a PKC activator (e.g., PdBu) is present in the medium at a concentration of 0.2 µM-1 µM (e.g., 0.2 µM, 0.3 µM, 0.4 µM, 0.5 µM, 0.6 µM, 0.7 µM, 0.8 µM, 0.9 µM, or 1 µM). In some embodiments, a PKC activator (e.g., PdBu) is present in the medium at a concentration of 0.3 µM-0.7 µM or 0.4 µM-0.6 µM. In some embodiments, a PKC activator (e.g., PdBu) is present in the medium at a concentration of 0.5 µM.

In some embodiments, a sonic hedgehog (SHH) signaling pathway inhibitor (e.g., SANT-1) is present in the medium at a concentration of 0.1 µM-10 µM. In some embodiments, a sonic hedgehog (SHH) signaling pathway inhibitor (e.g., SANT-1) is present in the medium at a concentration of 0.1 µM-10 µM, 0.1 µM-9 µM, 0.1 µM-8 µM, 0.1 µM-7 µM, 0.1 µM-6 µM, 0.1 µM-5 µM, 0.1 µM-4 µM, 0.1 µM-3 µM, 0.1 µM-2 µM, 0.1 µM-1 µM, 0.1 µM-0.5 µM, 0.5 µM-10 µM, 0.5 µM-9 µM, 0.5 µM-8 µM, 0.5 µM-7 µM, 0.5 µM-6 µM, 0.5 µM-5 µM, 0.5 µM-4 µM, 0.5 µM-3 µM, 0.5 µM-2 µM, 0.5 µM-1 µM, 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a sonic hedgehog (SHH) signaling pathway inhibitor (e.g., SANT-1) is present in the medium at a concentration of 0.1 µM-0.5 µM (e.g., 0.1 µM, 0.15 µM, 0.2 µM, 0.25 µM, 0.3 µM, 0.35 µM, 0.4 µM, 0.45 µM, or 0.5 µM). In some embodiments, a sonic hedgehog (SHH) signaling pathway inhibitor (e.g., SANT-1) is present in the medium at a concentration of 0.25 µM.

In some embodiments, a Rho-associated, coiled-coil containing protein kinase (ROCK) inhibitor (e.g., thiazovivin) is present in the medium at a concentration of 1 µM-10 µM. In some embodiments, a Rho-associated, coiled-coil containing protein kinase (ROCK) inhibitor (e.g., thiazovivin) is present in the medium at a concentration of 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a Rho-associated, coiled-coil containing protein kinase (ROCK) inhibitor (e.g., thiazovivin) is present in the medium at a concentration of 1 µM-5 µM (e.g., 1 µM, 1.5 µM, 2 µM, 2.5 µM, 3 µM, 3.5 µM, 4 µM, 4.5 µM, or 5 µM). In some embodiments, a Rho-associated, coiled-coil containing protein kinase (ROCK) inhibitor (e.g., thiazovivin) is present in the medium at a concentration of 2.5 µM.

In some embodiments, retinoic acid is present in the medium at a concentration of 0.05 µM-0.5 µM. In some embodiments, retinoic acid is present in the medium at a concentration of 0.05 µM-0.5 µM, 0.1 µM-0.5 µM, 0.15 µM-0.5 µM, 0.2 µM-0.5 µM, 0.25 µM-0.5 µM, 0.3 µM-0.5 µM, 0.35 µM-0.5 µM, 0.4 µM-0.5 µM, 0.45 µM-0.5 µM, 0.05 µM-0.4 µM, 0.1 µM-0.4 µM, 0.15 µM-0.4 µM, 0.2 µM-0.4 µM, 0.25 µM-0.4 µM, 0.3 µM-0.4 µM, 0.35 µM-0.4 µM, 0.05 µM-0.3 µM, 0.1 µM-0.3 µM, 0.15 µM-0.3 µM, 0.2 µM-0.3 µM, 0.25 µM-0.3 µM, 0.05 µM-0.2 µM, 0.1 µM-0.2 µM, 0.15 µM-0.2 µM, or 0.05 µM-0.1 µM. In some embodiments, retinoic acid is present in the medium at a concentration of 0.05 µM-0.2 µM (e.g., 0.05 µM, 0.1 µM, 0.15 µM, or 0.2 µM). In some embodiments, retinoic acid is present in the medium at a concentration of 0.1 µM.

In some embodiments, a TGF-β ligand (e.g., activin A) is present in the medium at a concentration of 1 ng/ml-10 ng/ml. In some embodiments, a TGF-β ligand (e.g., activin A) is present in the medium at a concentration of 1 ng/ml-10 ng/ml, 1 ng/ml-9 ng/ml, 1 ng/ml-8 ng/ml, 1 ng/ml-7 ng/ml, 1 ng/ml-6 ng/ml, 1 ng/ml-5 ng/ml, 1 ng/ml-4 ng/ml, 1 ng/ml-3 ng/ml, 1 ng/ml-2 ng/ml, 2 ng/ml-10 ng/ml, 2 ng/ml-9 ng/ml, 2 ng/ml-8 ng/ml, 2 ng/ml-7 ng/ml, 2 ng/ml-6 ng/ml, 2 ng/ml-5 ng/ml, 2 ng/ml-4 ng/ml, 2 ng/ml-3 ng/ml, 3 ng/ml-10 ng/ml, 3 ng/ml-9 ng/ml, 3 ng/ml-8 ng/ml, 3 ng/ml-7 ng/ml, 3 ng/ml-6 ng/ml, 3 ng/ml-5 ng/ml, 3 ng/ml-4 ng/ml, 4 ng/ml-10 ng/ml, 4 ng/ml-9 ng/ml, 4 ng/ml-8 ng/ml, 4 ng/ml-7 ng/ml, 4 ng/ml-6 ng/ml, 4 ng/ml-5 ng/ml, 5 ng/ml-10 ng/ml, 5 ng/ml-9 ng/ml, 5 ng/ml-8 ng/ml, 5 ng/ml-7 ng/ml, 5 ng/ml-6 ng/ml, 6 ng/ml-10 ng/ml, 6 ng/ml-9 ng/ml, 6 ng/ml-8 ng/ml, 6 ng/ml-7 ng/ml, 7 ng/ml-10 ng/ml, 7 ng/ml-9 ng/ml, 7 ng/ml-8 ng/ml, 8 ng/ml-10 ng/ml, 8 ng/ml-9 ng/ml, or 9 ng/ml-10 ng/ml. In some embodiments, a TGF-β ligand (e.g., activin A) is present in the medium at a concentration of 2 ng/ml-8 ng/ml (e.g., 2 ng/ml, 3 ng/ml, 4 ng/ml, 5 ng/ml, 6 ng/ml, 7 ng/ml, 8 ng/ml). In some embodiments, a TGF-β ligand (e.g., activin A) is present in the medium at a concentration of 5 ng/ml.

In some embodiments, a fibroblast growth factor (e.g., keratinocyte growth factor (KGF)) is present in the medium at a concentration of 10 ng/ml-100 ng/ml. In some embodiments, a fibroblast growth factor (e.g., keratinocyte growth factor (KGF)) is present in the medium at a concentration of 10 ng/ml-100 ng/ml, 10 ng/ml-90 ng/ml, 10 ng/ml-80 ng/ml, 10 ng/ml-70 ng/ml, 10 ng/ml-60 ng/ml, 10 ng/ml-50 ng/ml, 10 ng/ml-40 ng/ml, 10 ng/ml-30 ng/ml, 10 ng/ml-20 ng/ml, 20 ng/ml-100 ng/ml, 20 ng/ml-90 ng/ml, 20 ng/ml-80 ng/ml, 20 ng/ml-70 ng/ml, 20 ng/ml-60 ng/ml, 20 ng/ml-50 ng/ml, 20 ng/ml-40 ng/ml, 20 ng/ml-30 ng/ml, 30 ng/ml-100 ng/ml, 30 ng/ml-90 ng/ml, 30 ng/ml-80 ng/ml, 30 ng/ml-70 ng/ml, 30 ng/ml-60 ng/ml, 30 ng/ml-50 ng/ml, 30 ng/ml-40 ng/ml, 40 ng/ml-100 ng/ml, 40 ng/ml-90 ng/ml, 40 ng/ml-80 ng/ml, 40 ng/ml-70 ng/ml, 40 ng/ml-60 ng/ml, 40 ng/ml-50 ng/ml, 50 ng/ml-100 ng/ml, 50 ng/ml-90 ng/ml, 50 ng/ml-80 ng/ml, 50 ng/ml-70 ng/ml, 50 ng/ml-60 ng/ml, 60 ng/ml-100 ng/ml, 60 ng/ml-90 ng/ml, 60 ng/ml-80 ng/ml, 60 ng/ml-70 ng/ml, 70 ng/ml-100 ng/ml, 70 ng/ml-90 ng/ml, 70 ng/ml-80 ng/ml, 80 ng/ml-100 ng/ml, 80 ng/ml-90 ng/ml, or 90 ng/ml-100 ng/ml. In some embodiments, a fibroblast growth factor (e.g., keratinocyte growth factor (KGF)) is present in the medium at a concentration of 20 ng/ml-80 ng/ml (e.g., 20 ng/ml, 30 ng/ml, 40 ng/ml, 50 ng/ml, 60 ng/ml, 70 ng/ml, 80 ng/ml). In some embodiments, a fibroblast growth factor (e.g., keratinocyte growth factor (KGF)) is present in the medium at a concentration of 50 ng/ml.

In some embodiments, the medium comprises a FoxO1 inhibitor (e.g., AS1842856) at a concentration of 0.5 µM-5 µM, a notch signaling pathway inhibitor (e.g., a γ-secretase inhibitor such as XXI) at a concentration of 0.5 µM-5 µM, a PKC activator (e.g., PdBu) at a concentration of 0.2 µM-1 µM, a fibroblast growth factor (e.g., KGF) at a concentration of 20 ng/ml-80 ng/ml, a sonic hedgehog (SHH) signaling pathway inhibitor (e.g., SANT-1) at a concentration of 0.1 µM-0.5 µM, retinoic acid at a concentration of 0.05 µM-0.2 µM, a Rho-associated, coiled-coil containing protein kinase (ROCK) inhibitor (e.g., thiazovivin) at a concentration of 1 µM-5 µM, and a TGF-β ligand (e.g., activin A) at a concentration of 2 ng/ml-8 ng/ml.

In some embodiments, the medium comprises a FoxO1 inhibitor (e.g., AS1842856) at a concentration of 1 µM, a notch signaling pathway inhibitor (e.g., a γ-secretase inhibitor such as XXI) at a concentration of 2 µM, a PKC activator (e.g., PdBu) at a concentration of 0.5 µM, a fibroblast growth factor (e.g., KGF) at a concentration of 50 ng/ml, a sonic hedgehog (SHH) signaling pathway inhibitor (e.g., SANT-1) at a concentration of 0.25 µM, retinoic acid at a concentration of 0.1 µM, a Rho-associated, coiled-coil containing protein kinase (ROCK) inhibitor (e.g., thiazovivin) at a concentration of 2.5 µM, and a TGF-β ligand (e.g., activin A) at a concentration of 5 ng/ml.

In some embodiments, an in vitro composition described herein further comprises a water-soluble synthetic polymer. In some embodiments, the water-soluble synthetic polymer is polyvinyl alcohol (PVA), poloxamer, polyvinylpyrrolidone, polyethylene glycol (PEG), PEG copolymers, poly(N-isopropylacrylamide), or polyacrylamide, optionally wherein the water-soluble synthetic polymer is polyvinyl alcohol. In some embodiments, the water-soluble synthetic polymer is polyvinyl alcohol (PVA). In some embodiments, the water-soluble synthetic polymer has a concentration of 0.005% to 0.5% (w/v), 0.01% to 0.2% (w/v), 0.02% to 0.1% (w/v), or 0.03% to 0.08% (w/v) of the culture medium. In some embodiments, the water-soluble synthetic polymer has a concentration of 0.005% (w/v), 0.01% (w/v), 0.05% (w/v), 0.1% (w/v), 0.15% (w/v), 0.2% (w/v), 0.25% (w/v), 0.3% (w/v), 0.35% (w/v), to 0.4% (w/v), 0.45% (w/v), or 0.5% (w/v) of the medium. In some embodiments, the water-soluble synthetic polymer is polyvinyl alcohol (PVA), and the PVA is at most 85% (e.g., 75%-80%) hydrolyzed.

In some embodiments, an in vitro composition comprises a population of pancreatic progenitor cells comprising cells that are PDX1-positive and NKX6.1-negative. In some embodiments, an in vitro composition comprising described herein comprises a population of pancreatic progenitor cells comprising cells that are PDX1-positive and NKX6.1-positive. In some embodiments, an in vitro composition comprising described herein comprises a population of pancreatic progenitor cells comprising cells that are PDX1-positive and NKX6.1-negative and cells that are PDX1-positive and NKX6.1-positive. In some embodiments, the PDX1-positive and NKX6.1-positive cells are insulin-negative.

In some embodiments, the population of pancreatic progenitor cells comprises more cells that are PDX1-positive and NKX6.1-negative than cells that are PDX1-positive and NKX6.1-positive. In some embodiments, at least 50% (e.g., at least 50%, at least 60%, at least 70%, at least 80%, or at least 90%) of the population of pancreatic progenitor cells are PDX1-positive and NKX6.1-negative. In some embodiments, no more than 50% (e.g., no more than 50%, no more than 40%, no more than 30%, no more than 20%, or no more than 10%) of the population of pancreatic progenitor cells are pancreatic progenitor cells that are PDX1-positive and NKX6.1-positive. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive and NKX6.1-negative. In some embodiments, 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive and NKX6.1-positive. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive and NKX6.1-negative and 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive and NKX6.1-positive. In some embodiments, at least 50% of the population of pancreatic progenitor cells are PDX1-positive and NKX6.1-negative, and no more than 50% of the population of pancreatic progenitor cells are pancreatic progenitor cells that are PDX1-positive and NKX6.1-positive.

In some embodiments, the population of pancreatic progenitor cells comprises more cells that are PDX1-positive and NKX6.1-positive than cells that are PDX1-positive and NKX6.1-negative. In some embodiments, at least 50% (e.g., at least 50%, at least 60%, at least 70%, at least 80%, or at least 90%) of the population of pancreatic progenitor cells are PDX1-positive and NKX6.1-positive. In some embodiments, no more than 50% (e.g., no more than 50%, no more than 40%, no more than 30%, no more than 20%, or no more than 10%) of the population of pancreatic progenitor cells are pancreatic progenitor cells that are PDX1-positive and NKX6.1-negative. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive and NKX6.1-positive. In some embodiments, 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive and NKX6.1-negative. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive and NKX6.1-positive and 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive and NKX6.1-negative. In some embodiments, at least 50% of the population of pancreatic progenitor cells are PDX1-positive and NKX6.1-positive, and no more than 50% of the population of pancreatic progenitor cells are pancreatic progenitor cells that are PDX1-positive and NKX6.1-negative.

Composition Comprising Wnt Inhibitor and Optionally a PKC Activator

The present disclosure, in other aspects, provides in vitro compositions comprising a population of pancreatic progenitor cells comprising cells that are PDX1-positive, NKX6.1-positive, and insulin-negative; and a medium comprising a Wnt signaling pathway inhibitor (e.g., a tankyrase inhibitor). In some embodiments, the medium further comprises a protein kinase C (PKC) activator. In some embodiments, the medium does not comprise a FOXO1 inhibitor. In some embodiments, the population of pancreatic progenitor cells had been previously cultured in a medium comprising a FOXO1 inhibitor. In some embodiments, the medium further comprises one or more (e.g., 1, 2, 3, 4, 5, 6, 7, 8, 9, or 10) agents selected from: a sonic hedgehog (SHH) signaling pathway inhibitor, an epidermal growth factor, a notch signaling pathway inhibitor (e.g., a γ-secretase inhibitor), a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, and retinoic acid. In some embodiments, the medium further comprises a sonic hedgehog (SHH) signaling pathway inhibitor, an epidermal growth factor, a notch signaling pathway inhibitor (e.g., a γ-secretase inhibitor), a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, and retinoic acid.

In some embodiments, the medium further comprises one or more (e.g., 1, 2, 3, or 4) agents selected from an acetyl CoA related metabolite, an HDAC inhibitor, a redox homeostasis regulator, and a one carbon metabolism pathway intermediate. In some embodiments, the medium further comprises acetyl CoA related metabolite, an HDAC inhibitor, a redox homeostasis regulator, and a one carbon metabolism pathway intermediate.

In some embodiments, the medium further comprises a vitamin. In some embodiments, the medium further comprises glutamine.

In some embodiments, the medium comprises a PKC activator, Wnt signaling pathway inhibitor (e.g., a tankyrase inhibitor), a sonic hedgehog (SHH) signaling pathway inhibitor, an epidermal growth factor, a notch signaling pathway inhibitor (e.g., a γ-secretase inhibitor), a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, retinoic acid, an acetyl CoA related metabolite, an HDAC inhibitor, a redox homeostasis regulator, a one carbon metabolism pathway intermediate, a vitamin, and glutamine. In some embodiments, the medium comprises PdBu, NVP-TNKS656, SANT-1, betacellulin, XXI, Alk5i, GC-1, LDN-193189, thiazovivin, staurosporine, DZNEP, retinoic acid, acetate, β-hydroxybutyrate, taurine, formate, biotin, and glutamine.

In some embodiments, a PKC activator (e.g., PdBu) is present in the medium at a concentration of 0.1 μM-10 μM. In some embodiments, a PKC activator (e.g., PdBu) is present in the medium at a concentration of 0.1 μM-10 μM, 0.1 μM-9 μM, 0.1 μM-8 μM, 0.1 μM-7 μM, 0.1 μM-6 μM, 0.1 μM-5 μM, 0.1 μM-4 μM, 0.1 μM-3 μM, 0.1 μM-2 μM, 0.1 μM-1 μM, 0.1 μM-0.5 μM, 0.5 μM-10 μM, 0.5 μM-9 μM, 0.5 μM-8 μM, 0.5 μM-7 μM, 0.5 μM-6 μM, 0.5 μM-5 μM, 0.5 μM-4 μM, 0.5 μM-3 μM, 0.5 μM-2 μM, 0.5 μM-1 μM, 1 μM-10 μM, 1 μM-9 μM, 1 μM-8 μM, 1 μM-7 μM, 1 μM-6 μM, 1 μM-5 μM, 1 μM-4 μM, 1 μM-3 μM, 1 μM-2 μM, 2 μM-10 μM, 2 μM-9 μM, 2 μM-8 μM, 2 μM-7 μM, 2 μM-6 μM, 2 μM-5 μM, 2 μM-4 μM, 2 μM-3 μM, 3 μM-10 μM, 3 μM-9 μM, 3 μM-8 μM, 3 μM-7 μM, 3 μM-6 μM, 3 μM-5 μM, 3 μM-4 μM, 4 μM-10 μM, 4 μM-9 μM, 4 μM-8 μM, 4 μM-7 μM, 4 μM-6 μM, 4 μM-5 μM, 5 μM-10 μM, 5 μM-9 μM, 5 μM-8 μM, 5 μM-7 μM, 5 μM-6 μM, 6 μM-10 μM, 6 μM-9 μM, 6 μM-8 μM, 6 μM-7 μM, 7 μM-10 μM, 7 μM-9 μM, 7 μM-8 μM, 8 μM-10 μM, 8 μM-9 μM, or 9 μM-10 μM. In some embodiments, a PKC activator (e.g., PdBu) is present in the medium at a concentration of 0.2 μM-1 μM (e.g., 0.2 μM, 0.3 μM, 0.4 μM, 0.5 μM, 0.6 μM, 0.7 μM, 0.8 μM, 0.9 μM, or 1 μM). In some embodiments, a PKC activator (e.g., PdBu) is present in the medium at a concentration of 0.3 μM-0.7 μM or 0.4 μM-0.6 μM. In some embodiments, a PKC activator (e.g., PdBu) is present in the medium at a concentration of 0.5 μM.

In some embodiments, a Wnt signaling pathway inhibitor (e.g., a tankyrase inhibitor such as NVP-TNKS656) is present in the medium at a concentration of 0.1 μM-10 μM. In some embodiments, a Wnt signaling pathway inhibitor (e.g., a tankyrase inhibitor such as NVP-TNKS656) is present in the medium at a concentration of 0.1 μM-10 μM, 0.1 μM-9 μM, 0.1 μM-8 μM, 0.1 μM-7 μM, 0.1 μM-6 μM, 0.1 μM-5 μM, 0.1 μM-4 μM, 0.1 μM-3 μM, 0.1 μM-2 μM, 0.1 μM-1 μM, 0.1 μM-0.5 μM, 0.1 μM-0.2 μM, 0.2 μM-10 μM, 0.2 μM-9 μM, 0.2 μM-8 μM, 0.2 μM-7 μM, 0.2 μM-6 μM, 0.2 μM-5 μM, 0.2 μM-4 μM, 0.2 μM-3 μM, 0.2 μM-2 μM, 0.2 μM-1 μM, 0.2 μM-0.5 μM, 0.5 μM-10 μM, 0.5 μM-9 μM, 0.5 μM-8 μM, 0.5 μM-7 μM, 0.5 μM-6 μM, 0.5 μM-5 μM, 0.5 μM-4 μM, 0.5 μM-3 μM, 0.5 μM-2 μM, 0.5 μM-1 μM, 1 μM-10 μM, 1 μM-9 μM, 1 μM-8 μM, 1 μM-7 μM, 1 μM-6 μM, 1 μM-5 μM, 1 μM-4 μM, 1 μM-3 μM, 1 μM-2 μM, 2 μM-10 μM, 2 μM-9 μM, 2 μM-8 μM, 2 μM-7 μM, 2 μM-6 μM, 2 μM-5 μM, 2 μM-4 μM, 2 μM-3 μM, 3 μM-10 μM, 3 μM-9 μM, 3 μM-8 μM, 3 μM-7 μM, 3 μM-6 μM, 3 μM-5 μM, 3 μM-4 μM, 4 μM-10 μM, 4 μM-9 μM, 4 μM-8 μM, 4 μM-7 μM, 4 μM-6 μM, 4 μM-5 μM, 5 μM-10 μM, 5 μM-9 μM, 5 μM-8 μM, 5 μM-7 μM, 5 μM-6 μM, 6 μM-10 μM, 6 μM-9 μM, 6 μM-8 μM, 6 μM-7 μM, 7 μM-10 μM, 7 μM-9 μM, 7 μM-8 μM, 8 μM-10 μM, 8 μM-9 μM, or 9 μM-10 μM. In some embodiments, a Wnt signaling pathway inhibitor (e.g., a tankyrase inhibitor such as NVP-TNKS656) is present in the medium at a concentration of 0.5 μM-5 μM (e.g., 0.5 μM, 1 μM, 1.5 μM, 2 μM, 2.5 μM, 3 μM, 3.5 μM, 4 μM, 4.5 μM, or 5 μM). In some embodiments, a Wnt signaling pathway inhibitor (e.g., a tankyrase inhibitor such as NVP-TNKS656) is present in the medium at a concentration of 1.5 μM-2.5 μM or 1.8 μM-2.2 μM. In some embodiments, a Wnt signaling pathway inhibitor (e.g., a tankyrase inhibitor such as NVP-TNKS656) is present in the medium at a concentration of 2 µM.

In some embodiments, a sonic hedgehog (SHH) signaling pathway inhibitor (e.g., SANT-1) is present in the medium at a concentration of 0.1 µM-10 µM. In some embodiments, a sonic hedgehog (SHH) signaling pathway inhibitor (e.g., SANT-1) is present in the medium at a concentration of 0.1 µM-10 µM, 0.1 µM-9 µM, 0.1 µM-8 µM, 0.1 µM-7 µM, 0.1 µM-6 µM, 0.1 µM-5 µM, 0.1 µM-4 µM, 0.1 µM-3 µM, 0.1 µM-2 µM, 0.1 µM-1 µM, 0.1 µM-0.5 µM, 0.5 µM-10 µM, 0.5 µM-9 µM, 0.5 µM-8 µM, 0.5 µM-7 µM, 0.5 µM-6 µM, 0.5 µM-5 µM, 0.5 µM-4 µM, 0.5 µM-3 µM, 0.5 µM-2 µM, 0.5 µM-1 µM, 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a sonic hedgehog (SHH) signaling pathway inhibitor (e.g., SANT-1) is present in the medium at a concentration of 0.1 µM-0.5 µM (e.g., 0.1 µM, 0.15 µM, 0.2 µM, 0.25 µM, 0.3 µM, 0.35 µM, 0.4 µM, 0.45 µM, or 0.5 µM). In some embodiments, a sonic hedgehog (SHH) signaling pathway inhibitor (e.g., SANT-1) is present in the medium at a concentration of 0.25 µM.

In some embodiments, an epidermal growth factor (e.g., betacellulin) is present in the medium at a concentration of 10 ng/ml-50 ng/ml. In some embodiments, an epidermal growth factor (e.g., betacellulin) is present in the medium at a concentration of 10 ng/ml-50 ng/ml, 10 ng/ml-40 ng/ml, 10 ng/ml-30 ng/ml, 10 ng/ml-20 ng/ml, 20 ng/ml-50 ng/ml, 20 ng/ml-40 ng/ml, 20 ng/ml-30 ng/ml, 30 ng/ml-50 ng/ml, 30 ng/ml-40 ng/ml, or 40 ng/ml-50 ng/ml. In some embodiments, an epidermal growth factor (e.g., betacellulin) is present in the medium at a concentration of 10 ng/ml-30 ng/ml (e.g., 10 ng/ml, 20 ng/ml, 20 ng/ml). In some embodiments, an epidermal growth factor (e.g., betacellulin) is present in the medium at a concentration of 20 ng/ml.

In some embodiments, a notch signaling pathway inhibitor (e.g., γ-secretase inhibitor such as XXI) is present in the medium at a concentration of 0.1 µM-10 µM. In some embodiments, a notch signaling pathway inhibitor (e.g., γ-secretase inhibitor such as XXI) is present in the medium at a concentration of 0.1 µM-10 µM, 0.1 µM-9 µM, 0.1 µM-8 µM, 0.1 µM-7 µM, 0.1 µM-6 µM, 0.1 µM-5 µM, 0.1 µM-4 µM, 0.1 µM-3 µM, 0.1 µM-2 µM, 0.1 µM-1 µM, 0.1 µM-0.5 µM, 0.5 µM-10 µM, 0.5 µM-9 µM, 0.5 µM-8 µM, 0.5 µM-7 µM, 0.5 µM-6 µM, 0.5 µM-5 µM, 0.5 µM-4 µM, 0.5 µM-3 µM, 0.5 µM-2 µM, 0.5 µM-1 µM, 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a notch signaling pathway inhibitor (e.g., γ-secretase inhibitor such as XXI) is present in the medium at a concentration of 0.5 µM-5 µM (e.g., 0.5 µM, 1 µM, 1.5 µM, 2 µM, 2.5 µM, 3 µM, 3.5 µM, 4 µM, 4.5 µM, or 5 µM). In some embodiments, a notch signaling pathway inhibitor (e.g., γ-secretase inhibitor such as XXI) is present in the medium at a concentration of 2 µM.

In some embodiments, a TGFβ-R1 kinase inhibitor (e.g., ALK5i) is present in the medium at a concentration of 1 µM-50 µM. In some embodiments, a TGFβ-R1 kinase inhibitor (e.g., ALK5i) is present in the medium at a concentration of 1 µM-50 µM, 1 µM-40 µM, 1 µM-30 µM, 1 µM-20 µM, 1 µM-10 µM, 10 µM-50 µM, 10 µM-40 µM, 10 µM-30 µM, 10 µM-20 µM, 20 µM-50 µM, 20 µM-40 µM, 20 µM-30 µM, 30 µM-50 µM, 30 µM-40 µM, or 40 µM-50 µM. In some embodiments, a TGFβ-R1 kinase inhibitor (e.g., ALK5i) is present in the medium at a concentration of 5 µM-20 µM (e.g., 5 µM, 10 µM, 15 µM, or 20 µM). In some embodiments, a TGFβ-R1 kinase inhibitor (e.g., ALK5i) is present in the medium at a concentration of 10 µM.

In some embodiments, a thyroid hormone (e.g., GC-1) is present in the medium at a concentration of 0.1 µM-10 µM. In some embodiments, a thyroid hormone (e.g., GC-1) is present in the medium at a concentration of 0.1 µM-10 µM, 0.1 µM-9 µM, 0.1 µM-8 µM, 0.1 µM-7 µM, 0.1 µM-6 µM, 0.1 µM-5 µM, 0.1 µM-4 µM, 0.1 µM-3 µM, 0.1 µM-2 µM, 0.1 µM-1 µM, 0.1 µM-0.5 µM, 0.5 µM-10 µM, 0.5 µM-9 µM, 0.5 µM-8 µM, 0.5 µM-7 µM, 0.5 µM-6 µM, 0.5 µM-5 µM, 0.5 µM-4 µM, 0.5 µM-3 µM, 0.5 µM-2 µM, 0.5 µM-1 µM, 1 µM-10 µM, 1 µM-9 µM, 1 µM-8 µM, 1 µM-7 µM, 1 µM-6 µM, 1 µM-5 µM, 1 µM-4 µM, 1 µM-3 µM, 1 µM-2 µM, 2 µM-10 µM, 2 µM-9 µM, 2 µM-8 µM, 2 µM-7 µM, 2 µM-6 µM, 2 µM-5 µM, 2 µM-4 µM, 2 µM-3 µM, 3 µM-10 µM, 3 µM-9 µM, 3 µM-8 µM, 3 µM-7 µM, 3 µM-6 µM, 3 µM-5 µM, 3 µM-4 µM, 4 µM-10 µM, 4 µM-9 µM, 4 µM-8 µM, 4 µM-7 µM, 4 µM-6 µM, 4 µM-5 µM, 5 µM-10 µM, 5 µM-9 µM, 5 µM-8 µM, 5 µM-7 µM, 5 µM-6 µM, 6 µM-10 µM, 6 µM-9 µM, 6 µM-8 µM, 6 µM-7 µM, 7 µM-10 µM, 7 µM-9 µM, 7 µM-8 µM, 8 µM-10 µM, 8 µM-9 µM, or 9 µM-10 µM. In some embodiments, a thyroid hormone (e.g., GC-1) is present in the medium at a concentration of 0.5 µM-5 µM (e.g., 0.5 µM, 1 µM, 1.5 µM, 2 µM, 2.5 µM, 3 µM, 3.5 µM, 4 µM, 4.5 µM, or 5 µM). In some embodiments, a thyroid hormone (e.g., GC-1) is present in the medium at a concentration of 1 µM.

In some embodiments, a bone morphogenetic (BMP) signaling pathway inhibitor (e.g., LDN-193189) is present in the medium at a concentration of 0.05 µM-0.5 µM. In some embodiments, a bone morphogenetic (BMP) signaling pathway inhibitor (e.g., LDN-193189) is present in the medium at a concentration of 0.05 µM-0.5 µM, 0.1 µM-0.5 µM, 0.15 µM-0.5 µM, 0.2 µM-0.5 µM, 0.25 µM-0.5 µM, 0.3 µM-0.5 µM, 0.35 µM-0.5 µM, 0.4 µM-0.5 µM, 0.45 µM-0.5 µM, 0.05 µM-0.4 µM, 0.1 µM-0.4 µM, 0.15 µM-0.4 µM, 0.2 µM-0.4 µM, 0.25 µM-0.4 µM, 0.3 µM-0.4 µM, 0.35 µM-0.4 µM, 0.05 µM-0.3 µM, 0.1 µM-0.3 µM, 0.15 µM-0.3 µM, 0.2 µM-0.3 µM, 0.25 µM-0.3 µM, 0.05 µM-0.2 µM, 0.1 µM-0.2 µM, 0.15 µM-0.2 µM, or 0.05 µM-0.1 µM. In some embodiments, a bone morphogenetic (BMP) signaling pathway inhibitor (e.g., LDN-193189) is present in the medium at a concentration of 0.05 µM-0.2 µM (e.g., 0.05 µM, 0.1 µM, 0.15 µM, or 0.2 µM). In some embodiments, a bone morphogenetic (BMP) signaling pathway inhibitor (e.g., LDN-193189) is present in the medium at a concentration of 0.1 µM.

In some embodiments, a Rho-associated, coiled-coil containing protein kinase (ROCK) inhibitor (e.g., thiazovivin) is present in the medium at a concentration of 1 µM-10 µM. In some embodiments, a Rho-associated, coiled-coil containing protein kinase (ROCK) inhibitor (e.g., thiazovivin) is present in the medium at a concentration of 1 µM-10 µM, 1

μM-9 μM, 1 μM-8 μM, 1 μM-7 μM, 1 μM-6 μM, 1 μM-5 μM, 1 μM-4 μM, 1 μM-3 μM, 1 μM-2 μM, 2 μM-10 μM, 2 μM-9 μM, 2 μM-8 μM, 2 μM-7 μM, 2 μM-6 μM, 2 μM-5 μM, 2 μM-4 μM, 2 μM-3 μM, 3 μM-10 μM, 3 μM-9 μM, 3 μM-8 μM, 3 μM-7 μM, 3 μM-6 μM, 3 μM-5 μM, 3 μM-4 μM, 4 μM-10 μM, 4 μM-9 μM, 4 μM-8 μM, 4 μM-7 μM, 4 μM-6 μM, 4 μM-5 μM, 5 μM-10 μM, 5 μM-9 μM, 5 μM-8 μM, 5 μM-7 μM, 5 μM-6 μM, 6 μM-10 μM, 6 μM-9 μM, 6 μM-8 μM, 6 μM-7 μM, 7 μM-10 μM, 7 μM-9 μM, 7 μM-8 μM, 8 μM-10 μM, 8 μM-9 μM, or 9 μM-10 μM. In some embodiments, a Rho-associated, coiled-coil containing protein kinase (ROCK) inhibitor (e.g., thiazovivin) is present in the medium at a concentration of 1 μM-5 μM (e.g., 1 μM, 1.5 μM, 2 μM, 2.5 μM, 3 μM, 3.5 μM, 4 μM, 4.5 μM, or 5 μM). In some embodiments, a Rho-associated, coiled-coil containing protein kinase (ROCK) inhibitor (e.g., thiazovivin) is present in the medium at a concentration of 2.5 μM.

In some embodiments, a protein kinase inhibitor (e.g., staurosporine) is present in the medium at a concentration of 0.5 nM-10 nM. In some embodiments, a protein kinase inhibitor (e.g., staurosporine) is present in the medium at a concentration of 0.5 nM-10 nM, 0.5 nM-9 nM, 0.5 nM-8 nM, 0.5 nM-7 nM, 0.5 nM-6 nM, 0.5 nM-5 nM, 0.5 nM-4 nM, 0.5 nM-3 nM, 0.5 nM-2 nM, 0.5 nM-1 nM, 1 nM-10 nM, 1 nM-9 nM, 1 nM-8 nM, 1 nM-7 nM, 1 nM-6 nM, 1 nM-5 nM, 1 nM-4 nM, 1 nM-3 nM, 1 nM-2 nM, 2 nM-10 nM, 2 nM-9 nM, 2 nM-8 nM, 2 nM-7 nM, 2 nM-6 nM, 2 nM-5 nM, 2 nM-4 nM, 2 nM-3 nM, 3 nM-10 nM, 3 nM-9 nM, 3 nM-8 nM, 3 nM-7 nM, 3 nM-6 nM, 3 nM-5 nM, 3 nM-4 nM, 4 nM-10 nM, 4 nM-9 nM, 4 nM-8 nM, 4 nM-7 nM, 4 nM-6 nM, 4 nM-5 nM, 5 nM-10 nM, 5 nM-9 nM, 5 nM-8 nM, 5 nM-7 nM, 5 nM-6 nM, 6 nM-10 nM, 6 nM-9 nM, 6 nM-8 nM, 6 nM-7 nM, 7 nM-10 nM, 7 nM-9 nM, 7 nM-8 nM, 8 nM-10 nM, 8 nM-9 nM, or 9 nM-10 nM. In some embodiments, a protein kinase inhibitor (e.g., staurosporine) is present in the medium at a concentration of 1 nM-5 nM (e.g., 1 nM, 2 nM, 3 nM, 4 nM, or 5 nM). In some embodiments, a protein kinase inhibitor (e.g., staurosporine) is present in the medium at a concentration of 3 nM.

In some embodiments, a histone methyltransferase EZH2 inhibitor (e.g., DZNEP) is present in the medium at a concentration of 0.05 μM-0.5 μM. In some embodiments, a histone methyltransferase EZH2 inhibitor (e.g., DZNEP) is present in the medium at a concentration of 0.05 μM-0.5 μM, 0.1 μM-0.5 μM, 0.15 μM-0.5 μM, 0.2 μM-0.5 μM, 0.25 μM-0.5 μM, 0.3 μM-0.5 μM, 0.35 μM-0.5 μM, 0.4 μM-0.5 μM, 0.45 μM-0.5 μM, 0.05 μM-0.4 μM, 0.1 μM-0.4 μM, 0.15 μM-0.4 μM, 0.2 μM-0.4 μM, 0.25 μM-0.4 μM, 0.3 μM-0.4 μM, 0.35 μM-0.4 μM, 0.05 μM-0.3 μM, 0.1 μM-0.3 μM, 0.15 μM-0.3 μM, 0.2 μM-0.3 μM, 0.25 μM-0.3 μM, 0.05 μM-0.2 μM, 0.1 μM-0.2 μM, 0.15 μM-0.2 μM, or 0.05 μM-0.1 μM. In some embodiments, a histone methyltransferase EZH2 inhibitor (e.g., DZNEP) is present in the medium at a concentration of 0.05 μM-0.2 μM (e.g., 0.05 μM, 0.1 μM, 0.15 μM, or 0.2 μM). In some embodiments, a histone methyltransferase EZH2 inhibitor (e.g., DZNEP) is present in the medium at a concentration of 0.1 μM.

In some embodiments, retinoic acid is present in the medium at a concentration of 0.02 μM-0.5 μM. In some embodiments, retinoic acid is present in the medium at a concentration of 0.02 μM-0.5 μM, 0.05 μM-0.5 μM, 0.1 μM-0.5 μM, 0.15 μM-0.5 μM, 0.2 μM-0.5 μM, 0.25 μM-0.5 μM, 0.3 μM-0.5 μM, 0.35 μM-0.5 μM, 0.4 μM-0.5 μM, 0.45 μM-0.5 μM, 0.02 μM-0.4 μM, 0.05 μM-0.4 μM, 0.1 μM-0.4 μM, 0.15 μM-0.4 μM, 0.2 μM-0.4 μM, 0.25 μM-0.4 μM, 0.3 μM-0.4 μM, 0.35 μM-0.4 μM, 0.02 μM-0.3 μM, 0.05 μM-0.3 μM, 0.1 μM-0.3 μM, 0.15 μM-0.3 μM, 0.2 μM-0.3 μM, 0.25 μM-0.3 μM, 0.02 μM-0.2 μM, 0.05 μM-0.2 μM, 0.1 μM-0.2 μM, 0.15 μM-0.2 μM, 0.02 μM-0.1 μM, 0.05 μM-0.1 μM, or 0.02 μM-0.05 μM. In some embodiments, retinoic acid is present in the medium at a concentration of 0.02 μM-0.2 μM (e.g., 0.02 μM, 0.05 μM, 0.1 μM, 0.15 μM, or 0.2 μM). In some embodiments, retinoic acid is present in the medium at a concentration of 0.05 μM.

In some embodiments, an acetyl CoA related metabolite (e.g., acetate) is present in the medium at a concentration of 0.1 mM-10 mM. In some embodiments, an acetyl CoA related metabolite (e.g., acetate) is present in the medium at a concentration of 0.1 mM-10 mM, 0.1 mM-9 mM, 0.1 mM-8 mM, 0.1 mM-7 mM, 0.1 mM-6 mM, 0.1 mM-5 mM, 0.1 mM-4 mM, 0.1 mM-3 mM, 0.1 mM-2 mM, 0.1 mM-1 mM, 0.1 mM-0.5 mM, 0.5 mM-10 mM, 0.5 mM-9 mM, 0.5 mM-8 mM, 0.5 mM-7 mM, 0.5 mM-6 mM, 0.5 mM-5 mM, 0.5 mM-4 mM, 0.5 mM-3 mM, 0.5 mM-2 mM, 0.5 mM-1 mM, 1 mM-10 mM, 1 mM-9 mM, 1 mM-8 mM, 1 mM-7 mM, 1 mM-6 mM, 1 mM-5 mM, 1 mM-4 mM, 1 mM-3 mM, 1 mM-2 mM, 2 mM-10 mM, 2 mM-9 mM, 2 mM-8 mM, 2 mM-7 mM, 2 mM-6 mM, 2 mM-5 mM, 2 mM-4 mM, 2 mM-3 mM, 3 mM-10 mM, 3 mM-9 mM, 3 mM-8 mM, 3 mM-7 mM, 3 mM-6 mM, 3 mM-5 mM, 3 mM-4 mM, 4 mM-10 mM, 4 mM-9 mM, 4 mM-8 mM, 4 mM-7 mM, 4 mM-6 mM, 4 mM-5 mM, 5 mM-10 mM, 5 mM-9 mM, 5 mM-8 mM, 5 mM-7 mM, 5 mM-6 mM, 6 mM-10 mM, 6 mM-9 mM, 6 mM-8 mM, 6 mM-7 mM, 7 mM-10 mM, 7 mM-9 mM, 7 mM-8 mM, 8 mM-10 mM, 8 mM-9 mM, or 9 mM-10 mM. In some embodiments, an acetyl CoA related metabolite (e.g., acetate) is present in the medium at a concentration of 0.5 mM-5 mM (e.g., 0.5 mM, 1 mM, 1.5 mM, 2 mM, 2.5 mM, 3 mM, 3.5 mM, 4 mM, 4.5 mM, or 5 mM). In some embodiments, an acetyl CoA related metabolite (e.g., acetate) is present in the medium at a concentration of 1 mM.

In some embodiments, an HDAC inhibitor (e.g., β-hydroxybutyrate) is present in the medium at a concentration of 0.05 μM-0.5 μM. In some embodiments, an HDAC inhibitor (e.g., β-hydroxybutyrate) is present in the medium at a concentration of 0.05 μM-0.5 μM, 0.1 μM-0.5 μM, 0.15 μM-0.5 μM, 0.2 μM-0.5 μM, 0.25 μM-0.5 μM, 0.3 μM-0.5 μM, 0.35 μM-0.5 μM, 0.4 μM-0.5 μM, 0.45 μM-0.5 μM, 0.05 μM-0.4 μM, 0.1 μM-0.4 μM, 0.15 μM-0.4 μM, 0.2 μM-0.4 μM, 0.25 μM-0.4 μM, 0.3 μM-0.4 μM, 0.35 μM-0.4 μM, 0.05 μM-0.3 μM, 0.1 μM-0.3 μM, 0.15 μM-0.3 μM, 0.2 μM-0.3 μM, 0.25 μM-0.3 μM, 0.05 μM-0.2 μM, 0.1 μM-0.2 μM, 0.15 μM-0.2 μM, or 0.05 μM-0.1 μM. In some embodiments, an HDAC inhibitor (e.g., β-hydroxybutyrate) is present in the medium at a concentration of 0.1 μM-0.5 μM (e.g., 0.1 μM, 0.2 μM, 0.3 μM, 0.4 μM, 0.5 μM). In some embodiments, an HDAC inhibitor is present in the medium at a concentration of 0.2 μM.

In some embodiments, a redox homeostasis regulator (e.g., taurine) is present in the medium at a concentration of 20 μM-100 μM. In some embodiments, a redox homeostasis regulator (e.g., taurine) is present in the medium at a concentration of 20 μM-100 μM, 20 μM-90 μM, 20 μM-80 μM, 20 μM-70 μM, 20 μM-60 μM, 20 μM-50 μM, 20 μM-40 μM, 20 μM-30 μM, 30 μM-100 μM, 30 μM-90 μM, 30 μM-80 μM, 30 μM-70 μM, 30 μM-60 μM, 30 μM-50 μM, 30 μM-40 μM, 40 μM-100 μM, 40 μM-90 μM, 40 μM-80 μM, 40 μM-70 μM, 40 μM-60 μM, 40 μM-50 μM, 50 μM-100 μM, 50 μM-90 μM, 50 μM-80 μM, 50 μM-70 μM, 50 μM-60 μM, 60 μM-100 μM, 60 μM-90 μM, 60 μM-80 μM, 60 μM-70 μM, 70 μM-100 μM, 70 μM-90 μM, 70 μM-80 μM, 80 μM-100 μM, 80 μM-90 μM, or 90 μM-100 μM. In some embodiments, a redox homeostasis regulator (e.g., taurine)

is present in the medium at a concentration of 50 µM-100 µM (e.g., 50 µM, 60 µM, 70 µM, 80 µM, 90 µM, or 100 µM). In some embodiments, a redox homeostasis regulator (e.g., taurine) is present in the medium at a concentration of 90 µM.

In some embodiments, a one carbon metabolism pathway intermediate (e.g., formate) is present in the medium at a concentration of 20 µM-100 µM. In some embodiments, a one carbon metabolism pathway intermediate (e.g., formate) is present in the medium at a concentration of 20 µM-100 µM, 20 µM-90 µM, 20 µM-80 µM, 20 µM-70 µM, 20 µM-60 µM, 20 µM-50 µM, 20 µM-40 µM, 20 µM-30 µM, 30 µM-100 µM, 30 µM-90 µM, 30 µM-80 µM, 30 µM-70 µM, 30 µM-60 µM, 30 µM-50 µM, 30 µM-40 µM, 40 µM-100 µM, 40 µM-90 µM, 40 µM-80 µM, 40 µM-70 µM, 40 µM-60 µM, 40 µM-50 µM, 50 µM-100 µM, 50 µM-90 µM, 50 µM-80 µM, 50 µM-70 µM, 50 µM-60 µM, 60 µM-100 µM, 60 µM-90 µM, 60 µM-80 µM, 60 µM-70 µM, 70 µM-100 µM, 70 µM-90 µM, 70 µM-80 µM, 80 µM-100 µM, 80 µM-90 µM, or 90 µM-100 µM. In some embodiments, a one carbon metabolism pathway intermediate (e.g., formate) is present in the medium at a concentration of 20 µM-80 µM (e.g., 20 µM, 30 µM, 40 µM, 50 µM, 60 µM, 70 µM, or 80 µM). In some embodiments, a one carbon metabolism pathway intermediate (e.g., formate) is present in the medium at a concentration of 50 µM.

In some embodiments, a vitamin (e.g., biotin) is present in the medium at a concentration of 0.1 µM-5 µM. In some embodiments, a vitamin (e.g., biotin) is present in the medium at a concentration of 0.1 µM-5 µM, 0.1 µM-4 µM, 0.1 µM-3 µM, 0.1 µM-2 µM, 0.1 µM-1 µM, 0.1 µM-0.5 µM, 0.5 µM-5 µM, 0.5 µM-4 µM, 0.5 µM-3 µM, 0.5 µM-2 µM, 0.5 µM-1 µM, 1 µM-5 µM, 1 µM-4 µM, 1 µM-3 µM, 1 µM-2 µM, 2 µM-5 µM, 2 µM-4 µM, 2 µM-3 µM, 3 µM-5 µM, 3 µM-4 µM, or 4 µM-5 µM. In some embodiments, a vitamin (e.g., biotin) is present in the medium at a concentration of 0.5 µM-2 µM (e.g., 0.5 µM, 0.8 µM, 1 µM, 1.5 µM, 2 µM). In some embodiments, a vitamin (e.g., biotin) is present in the medium at a concentration of 0.8 µM.

In some embodiments, glutamine (e.g., L-glutamine) is present in the medium at a concentration of 1 mM-10 mM. In some embodiments, glutamine (e.g., L-glutamine) is present in the medium at a concentration of 1 mM-10 mM, 1 mM-9 mM, 1 mM-8 mM, 1 mM-7 mM, 1 mM-6 mM, 1 mM-5 mM, 1 mM-4 mM, 1 mM-3 mM, 1 mM-2 mM, 2 mM-10 mM, 2 mM-9 mM, 2 mM-8 mM, 2 mM-7 mM, 2 mM-6 mM, 2 mM-5 mM, 2 mM-4 mM, 2 mM-3 mM, 3 mM-10 mM, 3 mM-9 mM, 3 mM-8 mM, 3 mM-7 mM, 3 mM-6 mM, 3 mM-5 mM, 3 mM-4 mM, 4 mM-10 mM, 4 mM-9 mM, 4 mM-8 mM, 4 mM-7 mM, 4 mM-6 mM, 4 mM-5 mM, 5 mM-10 mM, 5 mM-9 mM, 5 mM-8 mM, 5 mM-7 mM, 5 mM-6 mM, 6 mM-10 mM, 6 mM-9 mM, 6 mM-8 mM, 6 mM-7 mM, 7 mM-10 mM, 7 mM-9 mM, 7 mM-8 mM, 8 mM-10 mM, 8 mM-9 mM, or 9 mM-10 mM. In some embodiments, glutamine (e.g., L-glutamine) is present in the medium at a concentration of 2 mM-6 mM (e.g., 2 mM, 3 mM, 4 mM, 5 mM, or 6 mM). In some embodiments, glutamine (e.g., L-glutamine) is present in the medium at a concentration of 4 mM.

In some embodiments, the medium comprises a PKC activator (e.g., PdBu) at a concentration of 0.2 µM-1 µM, a Wnt signaling pathway inhibitor (e.g., a tankyrase inhibitor such as NVP-TNKS656) at a concentration of 0.5 µM-5 µM, a sonic hedgehog (SHH) signaling pathway inhibitor (e.g., SANT-1) at a concentration of 0.1 µM-0.5 µM, an epidermal growth factor (e.g., betacellulin) at a concentration of 10 ng/ml-30 ng/ml, a notch signaling pathway inhibitor (e.g., γ-secretase inhibitor such as XXI) at a concentration of 0.5 µM-5 µM, a TGFβ-R1 kinase inhibitor (e.g., ALK5i) at a concentration of 5 µM-20 µM, a thyroid hormone (e.g., GC-1) at a concentration of 0.5 µM-5 µM, a bone morphogenetic (BMP) signaling pathway inhibitor (e.g., LDN-193189) at a concentration of 0.05 µM-0.2 µM, a Rho-associated, coiled-coil containing protein kinase (ROCK) inhibitor (e.g., thiazovivin) at a concentration of 1 µM-5 µM, a protein kinase inhibitor (e.g., staurosporine) at a concentration of 1 nM-5 nM, a histone methyltransferase EZH2 inhibitor (e.g., DZNEP) at a concentration of 0.05 µM-0.2 µM, retinoic acid at a concentration of 0.02 µM-0.2 µM, an acetyl CoA related metabolite (e.g., acetate) at a concentration of 0.5 mM-5 mM, an HDAC inhibitor (e.g., β-hydroxybutyrate) at a concentration of 0.1 µM-0.5 µM, a redox homeostasis regulator (e.g., taurine) at a concentration of 50 µM-100 µM, an one carbon metabolism pathway intermediate (e.g., formate) at a concentration of 20 µM-80 µM, a vitamin (e.g., biotin) at a concentration of 0.5 µM-2 µM, glutamine (e.g., L-glutamine) at a concentration of 2 mM-6 mM.

In some embodiments, the medium comprises a PKC activator (e.g., PdBu) at a concentration of 0.5 µM, a Wnt signaling pathway inhibitor (e.g., a tankyrase inhibitor such as NVP-TNKS656) at a concentration of 2 µM, a sonic hedgehog (SHH) signaling pathway inhibitor (e.g., SANT-1) at a concentration of 0.25 µM, an epidermal growth factor (e.g., betacellulin) at a concentration of 20 ng/ml, a notch signaling pathway inhibitor (e.g., γ-secretase inhibitor such as XXI) at a concentration of 2 µM, a TGFβ-R1 kinase inhibitor (e.g., ALK5i) at a concentration of 10 µM, a thyroid hormone (e.g., GC-1) at a concentration of 1 µM, a bone morphogenetic (BMP) signaling pathway inhibitor (e.g., LDN-193189) at a concentration of 0.1 µM, a Rho-associated, coiled-coil containing protein kinase (ROCK) inhibitor (e.g., thiazovivin) at a concentration of 2.5 µM, a protein kinase inhibitor (e.g., staurosporine) at a concentration of 3 nM, a histone methyltransferase EZH2 inhibitor (e.g., DZNEP) at a concentration of 0.1 µM, retinoic acid at a concentration of 0.05 µM, an acetyl CoA related metabolite (e.g., acetate) at a concentration of 4 mM, an HDAC inhibitor (e.g., (3-hydroxybutyrate) at a concentration of 50 µM, a redox homeostasis regulator (e.g., taurine) at a concentration of 90 µM, an one carbon metabolism pathway intermediate (e.g., formate) at a concentration of 50 µM, a vitamin (e.g., biotin) at a concentration of 0.8 µM, glutamine (e.g., L-glutamine) at a concentration of 4 mM.

In some embodiments, an in vitro composition described herein further comprises a water-soluble synthetic polymer. In some embodiments, the water-soluble synthetic polymer is polyvinyl alcohol (PVA), poloxamer, polyvinylpyrrolidone, polyethylene glycol (PEG), PEG copolymers, poly(N-isopropylacrylamide), or polyacrylamide, optionally wherein the water-soluble synthetic polymer is polyvinyl alcohol. In some embodiments, the water-soluble synthetic polymer is polyvinyl alcohol (PVA). In some embodiments, the water-soluble synthetic polymer has a concentration of 0.005% to 0.5% (w/v), 0.01% to 0.2% (w/v), 0.02% to 0.1% (w/v), or 0.03% to 0.08% (w/v) of the culture medium. In some embodiments, the water-soluble synthetic polymer has a concentration of 0.005% (w/v), 0.01% (w/v), 0.05% (w/v), 0.1% (w/v), 0.15% (w/v), 0.2% (w/v), 0.25% (w/v), 0.3% (w/v), 0.35% (w/v), to 0.4% (w/v), 0.45% (w/v), or 0.5% (w/v) of the medium. Polyvinyl alcohol described herein can refer to a water-soluble synthetic polymer that has an idealized formula [CH$_2$CH(OH)]n, which can be either partially or completed hydrolyzed. In some cases, the polyvinyl alcohol is manufactured by either partial or complete hydrolysis of polyvinyl acetate to remove acetate groups. In some cases, the polyvinyl alcohol is at most 85% hydrolyzed, e.g., 80% hydrolyzed. The percentage of hydrolyzation measures the approximate percentage (e.g., average percentage) of acetate residue that is hydrolyzed in the polyvinyl acetate precursor polymer. In some cases, the polyvinyl alcohol is at least 85% hydrolyzed, e.g., 87-89% hydrolyzed, 87-90% hydrolyzed, or 99% hydrolyzed. In some embodiments, the polyvinyl alcohol is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the water-soluble synthetic polymer is polyvinyl alcohol (PVA), and the PVA is at most 90% (e.g., 87%-89%) hydrolyzed. In some embodiments, the PVA is 80% hydrolyzed (e.g., in stages 1-4). In some embodiments, the PVA is 89% hydrolyzed (e.g., in stage 5).

In some embodiments, an in vitro composition described herein comprises a population of pancreatic progenitor cells comprising cells that are PDX1-positive and NKX6.1-positive, and insulin-negative. In some embodiments, an in vitro composition comprising described herein comprises a population of pancreatic progenitor cells comprising cells that are PDX1-positive and NKX6.1-positive, and insulin-positive. In some embodiments, an in vitro composition comprising described herein comprises a population of pancreatic progenitor cells comprising cells that are PDX1-positive and NKX6.1-positive, and insulin-negative and cells that are PDX1-positive and NKX6.1-positive, and insulin-positive.

In some embodiments, the population of pancreatic progenitor cells comprises more cells that are PDX1-positive, NKX6.1-positive, and insulin-negative than cells that are PDX1-positive, NKX6.1-positive and insulin-positive. In some embodiments, at least 50% (e.g., at least 50%, at least 60%, at least 70%, at least 80%, or at least 90%) of the population of pancreatic progenitor cells are PDX1-positive, NKX6.1-positive, and insulin-negative. In some embodiments, no more than 50% (e.g., no more than 50%, no more than 40%, no more than 30%, no more than 20%, or no more than 10%) of the population of pancreatic progenitor cells are pancreatic progenitor cells that are PDX1-positive, NKX6.1-positive, and insulin-positive. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive, NKX6.1-positive, and insulin-negative. In some embodiments, 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive, NKX6.1-positive, and insulin-positive. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive, NKX6.1-positive, and insulin-negative and 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive, NKX6.1-positive, and insulin-positive. In some embodiments, at least 50% of the population of pancreatic progenitor cells are PDX1-positive, NKX6.1-positive, and insulin-negative, and no more than 50% of the population of pancreatic progenitor cells are pancreatic progenitor cells that are PDX1-positive, NKX6.1-positive, and insulin-positive.

In some embodiments, the population of pancreatic progenitor cells comprises more cells that are PDX1-positive, NKX6.1-positive, and insulin-positive than cells that are PDX1-positive, NKX6.1-positive, and insulin-negative. In some embodiments, at least 50% (e.g., at least 50%, at least 60%, at least 70%, at least 80%, or at least 90%) of the population of pancreatic progenitor cells are PDX1-positive, NKX6.1-positive, and insulin-positive. In some embodiments, no more than 50% (e.g., no more than 50%, no more than 40%, no more than 30%, no more than 20%, or no more than 10%) of the population of pancreatic progenitor cells are pancreatic progenitor cells that are PDX1-positive, NKX6.1-positive, and insulin-negative. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive, NKX6.1-positive, and insulin-positive. In some embodiments, 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive, NKX6.1-positive, and insulin-negative. In some embodiments, 50%-90% (e.g., 50%-90%, 50%-80%, 50%-70%, 50%-60%, 60%-90%, 60%-80%, 60%-70%, 30%-80%, 70%-90%, 70%-80%, or 80%-90%) of the population of pancreatic progenitor cells are PDX1-positive, NKX6.1-positive, and insulin-positive and 10%-50% (e.g., 10%-50%, 20%-50%, 30%-50%, 40%-50%, 10%-40%, 20%-40%, 30%-40%, 10%-30%, 20%-30%, or 10%-20%) of the population of pancreatic progenitor cells are pancreatic progenitor cells that are PDX1-positive, NKX6.1-positive, and insulin-negative. In some embodiments, at least 50% of the population of pancreatic progenitor cells are PDX1-positive, NKX6.1-positive, and insulin-positive, and no more than 50% of the population of pancreatic progenitor cells are pancreatic progenitor cells that are PDX1-positive, NKX6.1-positive, and insulin-negative.

Methods of Producing Pancreatic Islet Cells

In aspects, the present disclosure relates to compositions and methods of generating endocrine cells from pancreatic progenitor cells or precursors. Certain exemplary detailed protocols of generating endocrine cells to provide at least one SC-β cell are described in U.S. Patent Application Publication No. US20150240212, US20150218522, US 20200332262, US 20210198632, US 20220090020, US 2021-0238553, U.S. Pat. Nos. 10,030,229; 10,443,042; and published application WO2022147056, each of which is herein incorporated by reference in its entirety.

In some embodiments, a method of generating a population of endocrine cells leads to increased percentage of pancreatic α and/or δ cells and decreased percentage of pancreatic EC cells when generating pancreatic β cells. In some embodiments, a method described herein may be used to obtain an enriched population of α cells. In some embodiments, a method described herein may be used to obtain an enriched population of β cells. In some embodiments, a method described herein may be used to obtain an enriched population of α cells and β cells. In some embodiments, a method described herein may be used to obtain an increased yield of pancreatic endocrine cells.

The differentiation of hPSC cells to hormone-expressing pancreatic endocrine cells may be conducted by transitioning hPSC cells through major stages of embryonic development; differentiation to mesendoderm and definitive endoderm, establishment of the primitive gut endoderm, patterning of the posterior foregut, and specification and maturation of pancreatic endoderm and endocrine precursors. Through these stages, hPSC cells can obtain pancreatic endocrine phenotype and ability of glucose responsive insulin secretion in vitro.

Generally, the at least one pancreatic SC-α, SC-β and/or SC-δ cell or precursor thereof, e.g., pancreatic progenitors produced according to the methods disclosed herein can comprise a mixture or combination of different cells, e.g., for example a mixture of cells such as a PDX1-positive pancreatic progenitors, pancreatic progenitors co-expressing PDX1 and NKX6-1, a Ngn3-positive endocrine progenitor cell, an insulin-positive endocrine cell (e.g., NKX6.1-positive, ISL1-positive cells, or β-like cells), and/or other pluripotent or stem cells.

The at least one pancreatic α, β and/or δ cell or precursor thereof can be produced according to any suitable culturing protocol to differentiate a stem cell or pluripotent cell to a desired stage of differentiation. In some embodiments, the at least one pancreatic α, β and/or δ cell or the precursor thereof are produced by culturing at least one pluripotent cell for a period of time and under conditions suitable for the at least one pluripotent cell to differentiate into the at least one pancreatic α, β and/or δ cell or the precursor thereof.

In some embodiments, the at least one pancreatic α, β and/or δ cell or precursor thereof is a substantially pure population of pancreatic α, β and/or δ cells or precursors thereof. In some embodiments, a population of pancreatic α, β and/or δ cells or precursors thereof comprises a mixture of pluripotent cells or differentiated cells. In some embodiments, a population pancreatic α, β and/or δ cells or precursors thereof are substantially free or devoid of embryonic stem cells or pluripotent cells or iPS cells. In some embodiments, a method described herein produces a population of cells comprising pancreatic α, β and/or δ cells at a ratio that resembles that of a natural pancreatic islet.

In some embodiments, a method described herein comprises (i) culturing a first population of cells comprising pancreatic progenitor cells (e.g., cells that are PDX1-positive, NKX6.1-negative; or a mixture of cells that are PDX1-positive, NKX6.1-negative and cells that are PDX1-positive, NKX6.1-positive) in a first medium comprising a Forkhead Box O1 (FoxO1) inhibitor and a notch signaling pathway inhibitor for a period of time to obtain a second population of cells (e.g., a population of cells that comprises more PDX1-positive, NKX6.1-positive cells than the first population); and (ii) culturing the second population of cells in a second medium comprising a PKC activator and a Wnt signaling pathway inhibitor. In some embodiments, the method generates a population of cells comprising cells that are PDX1-positive, NKX6.1-positive, and insulin-positive.

In some embodiments, a method described herein comprises culturing a first population of cells in a first medium, wherein the first population of cells comprises pancreatic progenitor cells that are PDX1-positive and NKX6.1 negative, and pancreatic progenitor cells that are PDX1-positive and NKX6.1 positive; and the first medium comprises a Forkhead Box O1 (FoxO1) inhibitor (e.g., AS1842856 or a derivative thereof). In some embodiments, the first medium further comprises a notch signaling pathway inhibitor. In some embodiments, the notch signaling pathway inhibitor is a γ-secretase inhibitor (e.g., XXI, DAPT or derivatives thereof). In some embodiments, the γ-secretase inhibitor is XXI. In some embodiments, the first medium does not comprise a Wnt signaling pathway inhibitor.

In some embodiments, the first population of cells comprises pancreatic progenitor cells that are PDX1-positive and NKX6.1 positive. In some embodiments, the first population of cells comprises more pancreatic progenitor cells that are PDX1-positive and NKX6.1 negative than pancreatic progenitor cells that are PDX1-positive and NKX6.1 positive. In some embodiments, the first population of cells comprises more pancreatic progenitor cells that are PDX1-positive and NKX6.1 positive than pancreatic progenitor cells that are PDX1-positive and NKX6.1 negative.

In some embodiments, first medium further comprises a PKC activator (e.g., PdBU, TPB, phorbol 12-myristate 13-acetate, bryostatin 1, or derivatives thereof). In some embodiments, the PKC activator is PdBU. In some embodiments, the first medium further comprises one or more (e.g., 1, 2, 3, 4, 5) agents selected from a fibroblast growth factor (e.g., KGF), a sonic hedgehog (SHH) signaling pathway inhibitor (e.g., SANT-1), retinoic acid, a Rho-associated, coiled-coil containing protein kinase (ROCK) inhibitor (e.g., triazovivin), and a TGF-β ligand (e.g., activin A). In some embodiments, the first medium further comprises a water-soluble synthetic polymer (e.g., PVA such as PVA80%). In some embodiments, the first medium comprises a FoxO1 inhibitor (e.g., AS1842856 or a derivative thereof), a notch signaling pathway inhibitor (e.g., γ-secretase inhibitor such as XXI), a PKC activator (e.g., PdBU), a fibroblast growth factor (e.g., KGF), a sonic hedgehog (SHH) signaling pathway inhibitor (e.g., SANT-1), retinoic acid, a Rho-associated, coiled-coil containing protein kinase (ROCK) inhibitor (e.g., triazovivin), and a TGF-β ligand (e.g., activin A), and a water-soluble synthetic polymer (e.g., PVA such as PVA80%).

In some embodiments, the first population of cells are cultured in the first medium for a period of about 12-72 hours (e.g., about 12-72 hours, 12-66 hours, 12-60 hours, 12-54 hours, 12-48 hours, 12-42 hours, 12-36 hours, 12-30 hours, 12-24 hours, 12-18 hours, 18-72 hours, 18-66 hours, 18-60 hours, 18-54 hours, 18-48 hours, 18-42 hours, 18-36 hours, 18-30 hours, 18-24 hours, 24-72 hours, 24-66 hours, 24-60 hours, 24-54 hours, 24-48 hours, 24-42 hours, 24-36 hours, 24-30 hours, 30-72 hours, 30-66 hours, 30-60 hours, 30-54 hours, 30-48 hours, 30-42 hours, 30-36 hours, 36-72 hours, 36-66 hours, 36-60 hours, 36-54 hours, 36-48 hours, 36-42 hours, 42-72 hours, 42-66 hours, 42-60 hours, 42-54 hours, 42-48 hours, 48-72 hours, 48-66 hours, 48-60 hours, 48-54 hours, 54-72 hours, 54-66 hours, 54-60 hours, 60-72 hours, 60-66 hours, or 66-72 hours). In some embodiments, the first population of cells are cultured in the first medium for a period of about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In some embodiments, the first population of cells are cultured in the first medium for a period of about 24 hours. In some embodiments, the first population of cells are cultured in the first medium for a period of about 48 hours.

In some embodiments, culturing the first population of cells in the first media for a contacting period described herein (e.g., 24 or 48 hours) results in a second population of cells. In some embodiments, the second population of cells comprises pancreatic progenitor cells that are PDX1-positive and NKX6.1 positive and pancreatic progenitor cells that are PDX1-positive and NKX6.1 negative. In some embodiments, the second population of cells comprises more pancreatic progenitor cells that are PDX1-positive and NKX6.1-positive than the first population of cells. In some embodiments, the second population of cells comprises more pancreatic progenitor cells that are PDX1-positive and NKX6.1 positive than pancreatic progenitor cells that are PDX1-positive and NKX6.1 negative. In some embodiments, the second population of cells comprises trace amounts (e.g., less than 5%, less than 4%, less than 3%, less than 2%, less than 1% of the second population of cells) of pancreatic progenitor cells that are PDX1-positive and NKX6.1 negative.

In some embodiments, a method described herein further comprises culturing the second population of cells with a second medium comprising a Wnt signaling pathway inhibitor (e.g., a tankyrase inhibitor such as NVP-TNKS656). In some embodiments, the second medium comprises a PKC activator (e.g., PdBu). In some embodiments, the second medium further comprises one or more (e.g., 1, 2, 3, 4, 5, 6, 7, 8, 9, 10) agents selected from an epidermal growth factor (e.g., betacellulin), a thyroid hormone (e.g., GC-1), a TGFβ-R1 kinase inhibitor (e.g., ALK5i), a notch signaling pathway inhibitor (e.g., a γ-secretase inhibitor such as XXI), a sonic hedgehog (SHH) signaling pathway inhibitor (e.g., SANT-1), retinoic acid, a Rho-associated, coiled-coil containing protein kinase (ROCK) inhibitor (e.g., triazovivin), a protein kinase inhibitor (e.g., staurosporine), a bone morphogenetic (BMP) signaling pathway inhibitor (e.g., LDN193189), and a histone methyltransferase EZH2 inhibitor (e.g., DZNep). In some embodiments, the second medium further comprises one or more (e.g., 1, 2, 3, 4) agents selected from an acetyl CoA related metabolite (e.g., acetate), an HDAC inhibitor (e.g., β-hydroxybutyrate), a redox homeostasis regulator (e.g., taurine), and a one carbon metabolism pathway intermediate (e.g., formate). In some embodiments, the second medium further comprises a vitamin (e.g., biotin). In some embodiments, the second medium further comprises glutamine. In some embodiments, the second medium further comprises a water soluble synthetic polymer (e.g., PVA such as PVA 87-89%). In some embodiments, the second medium does not comprise a FOXO1 inhibitor. In some embodiments, the second medium comprises a Wnt signaling pathway inhibitor (e.g., a tankyrase inhibitor such as NVP-TNKS656), a PKC activator (e.g., PdBu), an epidermal growth factor (e.g., betacellulin), a thyroid hormone (e.g., GC-1), a TGFβ-R1 kinase inhibitor (e.g., ALK5i), a notch signaling pathway inhibitor (e.g., a γ-secretase inhibitor such as XXI), a sonic hedgehog (SHH) signaling pathway inhibitor (e.g., SANT-1), retinoic acid, a Rho-associated, coiled-coil containing protein kinase (ROCK) inhibitor (e.g., triazovivin), a protein kinase inhibitor (e.g., staurosporine), a bone morphogenetic (BMP) signaling pathway inhibitor (e.g., LDN193189), a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), a one carbon metabolism pathway intermediate (e.g., formate), a vitamin (e.g., biotin), glutamine and a water soluble synthetic polymer (e.g., PVA such as PVA 87-89%), and does not comprise a FOXO1 inhibitor.

In some embodiments, the second population of cells are cultured in the second medium for a period of about 12-72 hours (e.g., about 12-72 hours, 12-66 hours, 12-60 hours, 12-54 hours, 12-48 hours, 12-42 hours, 12-36 hours, 12-30 hours, 12-24 hours, 12-18 hours, 18-72 hours, 18-66 hours, 18-60 hours, 18-54 hours, 18-48 hours, 18-42 hours, 18-36 hours, 18-30 hours, 18-24 hours, 24-72 hours, 24-66 hours, 24-60 hours, 24-54 hours, 24-48 hours, 24-42 hours, 24-36 hours, 24-30 hours, 30-72 hours, 30-66 hours, 30-60 hours, 30-54 hours, 30-48 hours, 30-42 hours, 30-36 hours, 36-72 hours, 36-66 hours, 36-60 hours, 36-54 hours, 36-48 hours, 36-42 hours, 42-72 hours, 42-66 hours, 42-60 hours, 42-54 hours, 42-48 hours, 48-72 hours, 48-66 hours, 48-60 hours, 48-54 hours, 54-72 hours, 54-66 hours, 54-60 hours, 60-72 hours, 60-66 hours, or 66-72 hours). In some embodiments, the second population of cells are cultured in the second medium for a period of about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In some embodiments, the second population of cells are cultured in the second medium for a period of about 48 hours.

In some embodiments, culturing the second population of cells in the second media for a contacting period described herein (e.g., 48 hours) results in a third population of cells. In some embodiments, the third population of cells comprises pancreatic progenitor cells that are PDX1-positive and NKX6.1-positive. In some embodiments, the third population of cells comprises cells that are ISL1-positive. In some embodiments, the third population of cells comprises cells that are ISL1-negative. In some embodiments, the third population of cells comprises cells that are ISL1-positive. In some embodiments, the third population of cells comprises more cells that are ISL1-positive than the first and second population of cells. In some embodiments, the third population of cells comprises more cells that are ISL1-negative than cells that are ISL1-positive. In some embodiments, the third population of cells comprises cells that are insulin-negative. In some embodiments, the third population of cells comprises cells that are insulin-positive. In some embodiments, the third population of cells comprises more cells that are insulin-negative than cells that are insulin-positive. In some embodiments, the third population of cells comprises more cells that are insulin-positive than the first and second population of cells.

In some embodiments, the method further comprises culturing the third population of cells in a third medium comprising one or more agents selected from: a notch signaling pathway inhibitor (e.g., a γ-secretase inhibitor such as XXI), a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep). In some embodiments, the third medium further comprises one or more agents selected from an acetyl CoA related metabolite (e.g., acetate), an HDAC inhibitor (e.g., β-hydroxybutyrate), a redox homeostasis regulator (e.g., taurine), and an one carbon metabolism pathway intermediate (e.g., formate). In some embodiments, the third medium further comprises a vitamin (e.g., biotin). In some embodiments, the third medium further comprises glutamine. In some embodiments, the third medium further comprises a water soluble synthetic polymer (e.g., PVA such as PVA 87-89%).

In some embodiments, the third medium does not comprise a Wnt signaling pathway inhibitor or a PKC activator. In some embodiments, the third medium comprises a notch signaling pathway inhibitor (e.g., a γ-secretase inhibitor such as XXI), a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), a one carbon metabolism pathway intermediate (e.g., formate), a vitamin (e.g., biotin), glutamine and a water soluble synthetic polymer (e.g., PVA such as PVA 87-89%), and does not comprise a Wnt signaling pathway inhibitor and a PKC activator. In some embodiments, the third population of cells are cultured in the third medium (e.g., the third medium that does not comprise a Wnt signaling pathway inhibitor or a PKC activator) for a period of about 24-96 hours (e.g., about 24-96 hours, 24-84 hours, 24-72 hours, 24-60 hours, 24-48 hours, 24-36 hours, 36-96 hours, 36-84 hours, 36-72 hours, 36-60 hours, 36-48 hours, 48-96 hours, 48-84 hours, 48-72 hours, 48-60 hours, 60-96 hours, 60-84 hours, 60-72 hours, 72-96 hours, 72-84 hours, or 84-96 hours). In some embodiments, the third population of cells are cultured in the third medium for a period of about 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours. In some embodiments, the third population of cells are cultured in the third medium for a period of about 96 hours.

In some embodiments, the third medium further comprises a Wnt signaling pathway inhibitor but does not comprise a PKC activator. In some embodiments, the third medium comprises Wnt signaling pathway inhibitor (e.g., a tankyrase inhibitor such as NVP-TNKS656), a notch signaling pathway inhibitor (e.g., a γ-secretase inhibitor such as XXI), a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), a one carbon metabolism pathway intermediate (e.g., formate), a vitamin (e.g., biotin), glutamine and a water soluble synthetic polymer (e.g., PVA such as PVA 87-89%), and does not comprise a PKC activator. In some embodiments, the third population of cells are cultured in the third medium (e.g., the third medium that comprises a Wnt signaling pathway inhibitor but not a PKC activator) for a period of about 24-48 hours (e.g., about 24-48 hours, 24-36 hours, or 36-48 hours), after which the Wnt signaling pathway inhibitor is removed from the third medium and the cells are further cultured for about 24-48 hours ((e.g., about 24-48 hours, 24-36 hours, or 36-48 hours). In some embodiments, the third population of cells are cultured in the third medium (e.g., the third medium that comprises a Wnt signaling pathway inhibitor but not a PKC activator) for a period of about 48 hours, after which the Wnt signaling pathway inhibitor is removed from the third medium and the cells are further cultured for about 48 hours.

In some embodiments, culturing the third population of cells in the third media for a contacting period described herein (e.g., 96 hours) results in a fourth population of cells. In some embodiments, the fourth population of cells comprises cells that are PDX1-positive and NKX6.1 positive. In some embodiments, the fourth population of cells comprises cells that are insulin-positive. In some embodiments, the fourth population of cells comprises cells that are PDX1-positive, NKX6.1 positive, and insulin-positive. In some embodiments, the fourth population of cells comprise cells that are ISL1-positive. In some embodiments, the fourth population of cells comprises cells that are ISL-1 negative. In some embodiments, at least 30% (e.g., at least 30%, at least 40%, at least 50%, or at least 60%)) of the fourth population of cells are insulin-positive. In some embodiments, 30%-50%, 30%-40%, or 40%-50% of the fourth population of cells are insulin-positive.

In some embodiments, the method further comprises culturing the fourth population of cells in a fourth medium comprising one or more agents selected from: a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep). In some embodiments, the fourth medium further comprises one or more agents selected from an acetyl CoA related metabolite (e.g., acetate), an HDAC inhibitor (e.g., β-hydroxybutyrate), a redox homeostasis regulator (e.g., taurine), and an one carbon metabolism pathway intermediate (e.g., formate). In some embodiments, the fourth medium further comprises a vitamin (e.g., biotin). In some embodiments, the fourth medium further comprises one or more of glutamine (e.g., L-glutamine), glutamate (e.g., L-glutamate), and carnitine (e.g., L-carnitine). In some embodiments, the fourth medium further comprises albumin (e.g., human serum albumin or HSA). In some embodiments, the fourth medium further comprises $ZnSO_4$. In some embodiments, the fourth media does not comprise a Wnt signaling pathway inhibitor or a PKC activator. In some embodiments, the fourth medium comprises a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), a one carbon metabolism pathway intermediate (e.g., formate), a vitamin (e.g., biotin), glutamine, glutamate, carnitine, albumin (e.g., human serum albumin or HSA), and $ZnSO_4$, and does not comprise a Wnt signaling pathway inhibitor or a PKC activator.

In some embodiments, the fourth population of cells are cultured in the fourth medium for a period of about 24-96 hours (e.g., about 24-96 hours, 24-84 hours, 24-72 hours, 24-60 hours, 24-48 hours, 24-36 hours, 36-96 hours, 36-84 hours, 36-72 hours, 36-60 hours, 36-48 hours, 48-96 hours, 48-84 hours, 48-72 hours, 48-60 hours, 60-96 hours, 60-84 hours, 60-72 hours, 72-96 hours, 72-84 hours, or 84-96 hours). In some embodiments, the fourth population of cells are cultured in the fourth medium for a period of about 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours. In some embodiments, the fourth population of cells are cultured in the fourth medium for a period of about 72 hours.

In some embodiments, culturing the fourth population of cells in the fourth media for a contacting period described herein (e.g., 96 hours) results in a fifth population of cells. In some embodiments, a method described herein further comprises culturing the fifth population of cells in a fifth medium comprising glutamine, albumin (e.g., human serum albumin or HSA), and ZnSO₄. In some embodiments, the fifth medium comprises glutamine, albumin (e.g., human serum albumin or HSA) and ZnSO₄, and does not comprise any one of the agents selected from: a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), and a histone methyltransferase EZH2 inhibitor (e.g., DZNep). In some embodiments, the fifth media further comprises a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), a one carbon metabolism pathway intermediate (e.g., formate), a vitamin (e.g., biotin), glutamine, glutamate, and carnitine. In some embodiments, the fifth medium comprises a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), an one carbon metabolism pathway intermediate (e.g., formate), a vitamin (e.g., biotin), glutamate, glutamine, carnitine, albumin (e.g., human serum albumin or HSA), and ZnSO₄, and does not comprise any one of the agents selected from: a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., thiazovivin), a protein kinase inhibitor (e.g., staurosporine), and a histone methyltransferase EZH2 inhibitor (e.g., DZNep). In some embodiments, the fifth medium comprises albumin (e.g., human serum albumin or HSA), and ZnSO₄, and does not comprise any one of the agents selected from: a TGFβ-R1 kinase inhibitor (e.g., ALK5i), a thyroid hormone (e.g., GC-1), a bone morphogenetic (BMP) signaling pathway inhibitor (e.g., LDN193189), a Rho-associated, coiled-coil containing protein kinase (ROCK) inhibitor (e.g., triazovivin), a protein kinase inhibitor (e.g., staurosporine), a histone methyltransferase EZH2 inhibitor (e.g., DZNep), an acetyl CoA related metabolite (e.g., acetate), an HDAC inhibitor (e.g., β-hydroxybutyrate), a redox homeostasis regulator (e.g., taurine), an one carbon metabolism pathway intermediate (e.g., formate), a vitamin (e.g., biotin), carnitine, glutamate, and glutamine.

In some embodiments, the fifth population of cells are cultured in the fifth medium for a period of about 96-240 hours (e.g., about 96-240 hours, 96-216 hours, 96-192 hours, 96-168 hours, 96-144 hours, 96-120 hours; 120-240 hours, 120-216 hours, 120-192 hours, 120-168 hours, 120-144 hours, 144-240 hours, 144-216 hours, 144-192 hours, 144-168 hours, 168-240 hours, 168-216 hours, 168-192 hours, 192-240 hours, 192-216 hours, or 192-240 hours). In some embodiments, the fifth population of cells are cultured in the fifth medium for a period of about 24, 48, 72, 96, 120, 144, 168, 192, 216, or 240 hours. In some embodiments, the fifth population of cells are cultured in the fifth medium for a period of about 192 hours.

In some embodiments, culturing the fifth population of cells in the fifth media for a contacting period described herein (e.g., 192 hours) results in a sixth population of cells. In some embodiments, at least 15% (e.g., at least 15%, at least 20%, at least 25%, at least 30%, at least 35%, at least 40% or more) of the sixth population of cells are NKX6.1-negative, ISL-positive; and wherein less than 12% (e.g., less than 12%, less than 10%, less than 8%, less than 6%, less than 4%, less than 2% or less) of the sixth population of cells are NKX6.1-negative, ISL-negative.

In some embodiments, a method described herein comprises:
(i) culturing a first population of cells in a first medium to obtain a second population of cells, wherein the first population of cells comprises pancreatic progenitor cells that are PDX1-positive and NKX6.1 negative, and pancreatic progenitor cells that are PDX1-positive and NKX6.1 positive; and the first medium comprises: a FoxO1 inhibitor, a notch signaling pathway inhibitor, a PKC activator, a fibroblast growth factor, a sonic hedgehog (SHH) signaling pathway inhibitor, retinoic acid, a Rho-associated, coiled-coil containing protein kinase (ROCK) inhibitor, a TGF-β ligand, and a water-soluble synthetic polymer;
(ii) culturing the second population of cells obtained in (i) with a second medium to obtain a third population of cells, wherein the second medium comprises: a Wnt signaling pathway inhibitor, a PKC activator, an epidermal growth factor, a thyroid hormone, a TGFβ-R1 kinase inhibitor, a notch signaling pathway inhibitor, a sonic hedgehog (SHH) signaling pathway inhibitor, retinoic acid, a Rho-associated, coiled-coil containing protein kinase (ROCK) inhibitor, a protein kinase inhibitor, a bone morphogenetic (BMP) signaling pathway inhibitor, a histone methyltransferase EZH2 inhibitor, an acetyl CoA related metabolite, an HDAC inhibitor, a redox homeostasis regulator, a one carbon metabolism pathway intermediate, a vitamin, glutamine and a water soluble synthetic polymer (e.g., PVA), and wherein the second medium does not comprise a FOXO1 inhibitor;
(iii) culturing the third population of cells obtained in (ii) with a third medium to obtain a fourth population of cells, wherein the third medium comprises: a notch signaling pathway inhibitor, a TGFβ-R1 kinase inhibitor, a thyroid hormone, a bone morphogenetic (BMP) signaling pathway, a Rho-associated, coiled-coil containing protein kinase (ROCK) inhibitor, a protein kinase inhibitor, and a histone methyltransferase EZH2 inhibitor, an acetyl CoA related metabolite, an HDAC inhibitor, a redox homeostasis regulator, an one carbon metabolism pathway intermediate, a vitamin, glutamine and a water soluble synthetic polymer, and wherein the third medium does not comprise a Wnt signaling pathway inhibitor and a PKC activator;
(iv) culturing the fourth population of cells obtained in (iii) with a fourth medium to obtain a fifth population of cells, wherein the fourth medium comprises a notch signaling pathway inhibitor, a TGFβ-R1 kinase inhibitor, a thyroid hormone, a bone morphogenetic (BMP) signaling pathway inhibitor, a Rho-associated, coiled-coil containing protein kinase (ROCK) inhibitor, a protein kinase inhibitor, a histone methyltransferase EZH2 inhibitor, an acetyl CoA related metabolite, an HDAC inhibitor, a redox homeostasis regulator, a one carbon metabolism pathway intermediate, a vitamin, glutamine, glutamate, carnitine, albumin, and ZnSO4, and wherein the fourth medium does not comprise a Wnt signaling pathway inhibitor and a PKC activator; and
(v) culturing the fifth population of cells obtained in (iv) with a fifth medium to obtain a sixth population of cells, wherein the fifth medium comprises albumin (e.g., human serum albumin or HSA) and ZnSO4.

In some embodiments, a method described herein further comprises generating the first population of cells comprising pancreatic progenitor cells that are PDX1-positive and NKX6.1 negative and pancreatic progenitor cells that are PDX1-positive and NKX6.1 positive. In some embodiments, the first population of cells are differentiated from stem cells (e.g., embryonic stem cells or pluripotent stem cells). In some embodiments, the stem cells (e.g., embryotic stem cells) are generated from the inner cell mass of blastocyst-stage embryos represent. Stem cells can be maintained in culture, renew for themselves, proliferate unlimitedly as undifferentiated ES cells, and are capable of differentiating into all cell types of the body as the ectoderm, mesoderm, and endoderm lineage cells or tissues.

Cell Types During Pancreatic Differentiation

Aspects of the present disclosure provide cell types of the pancreatic lineage obtained during differentiation of stem cells to generate pancreatic islet cells. Such cells include any cell that is capable of differentiating into a pancreatic islet cell, including for example, a pluripotent stem cell, a definitive endoderm cell, a primitive gut tube cell, a pancreatic progenitor cell, or endocrine progenitor cell, when cultured under conditions suitable for differentiating the precursor cell into the pancreatic islet cell.

Stem Cells

"Stem cell" refers to a cell (e.g., plant stem cell, vertebrate stem cell) that has the ability both to self-renew and to generate a differentiated cell type (Morrison et al. (1997) Cell 88:287-298). In the context of cell ontogeny, the adjective "differentiated," or "differentiating" is a relative term. A "differentiated cell" is a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391): 1145-7) whereas induced pluripotent stem cells (iPSCs) are derived from somatic cells (Takahashi et. al, Cell. 2007 Nov. 30; 13 l(5):861-72; Takahashi et. al, Nat Protoc. 2007; 2(l2):3081-9; Yu et. al, Science. 2007 Dec. 21; 318(5858): 1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

By "embryonic stem cell" (ESC) is meant a PSC that is isolated from an embryo, typically from the inner cell mass of the blastocyst. ESC lines are listed in the NIH Human Embryonic Stem Cell Registry, e.g. hESBGN-O1, hESBGN-02, hESBGN-03, hESBGN-04 (BresaGen, Inc); HES-1, HES-2, HES-3, HES-4, HES-5, HES-6 (ES Cell International); Miz-hESI (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g., human, equine, bovine, porcine, canine, feline, rodent, e.g. mice, rats, hamster, primate, etc. (Thomson et al. (1998) Science 282: 1145; Thomson et al. (1995) Proc. Natl. Acad. Sci USA 92:7844; Thomson et al. (1996) Biol. Reprod. 55:254;

Shamblott et al., Proc. Natl. Acad. Sci. USA 95: 13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell," it is meant a PSC that is derived from germ cells and/or germ cell progenitors, e.g., primordial germ cells, i.e. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95: 13726; and Koshimizu, U., et al. (1996) Development, 122: 1235, each of which are incorporated herein by its entirety. By "induced pluripotent stem cell" or "iPSC," it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26al, TERT, and zfp42. Examples of methods of generating and characterizing iPSCs can be found in, for example, Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g., Oct4, SOX2, KLF4, MYC, Nanog, Lin28, etc.) known in the art to reprogram the somatic cells to become pluripotent stem cells.

By "somatic cell," it is meant any cell in an organism that, in the absence of experimental manipulation, does not ordinarily give rise to all types of cells in an organism. In other words, somatic cells are cells that have differentiated sufficiently that they do not naturally generate cells of all three germ layers of the body, i.e., ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages.

In certain examples, the stem cells can be undifferentiated (e.g., a cell not committed to a specific lineage) prior to exposure to at least one cell maturation factor according to the methods as disclosed herein, whereas in other examples it may be desirable to differentiate the stem cells to one or more intermediate cell types prior to exposure of the at least one cell maturation factor (s) described herein. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of suitable nutrients and optionally other cells such that the stem cells can grow and optionally differentiate. For example, embryonic fibroblasts or fibroblast-like cells may be present in the culture to assist in the growth of the stem cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells have the characteristic of being capable under appropriate conditions of producing progeny of different cell types, e.g., derivatives of all of at least one of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-O1, hES-BGN-02, hESBGN-03, hESBGN-04 (BresaGen, Inc.); HES-1, HES-2, HES-3, HES-4, HES-5, HES-6 (ES Cell International); Miz-hESI (MizMedi Hospital-Seoul National University); HSF-1, FISF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo.

In another embodiment, the stem cells can be isolated from tissue including solid tissue. In some embodiments, the tissue is skin, fat tissue (e.g., adipose tissue), muscle tissue, heart or cardiac tissue. In other embodiments, the tissue is for example but not limited to, umbilical cord blood, placenta, bone marrow, or chondral.

Stem cells of interest also include embryonic cells of various types, exemplified by human embryonic stem (hES) cells, described by Thomson et al, (1998) Science 282: 1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95: 13726, 1998). Also of interest are lineage committed stem cells, such as mesodermal stem cells and other early cardiogenic cells (see Reyes et al, (2001) Blood 98:2615-2625; Eisenberg & Bader (1996) Circ Res. 78(2):205-16; etc.) The stem cells may be obtained from any mammalian species, e.g., human, equine, bovine, porcine, canine, feline, rodent, e.g., mice, rats, hamster, primate, etc. In some embodiments, a human embryo was not destroyed for the source of pluripotent cell used on the methods and compositions as disclosed herein.

A mixture of cells from a suitable source of endothelial, muscle, and/or neural stem cells can be harvested from a mammalian donor by methods known in the art. A suitable source is the hematopoietic microenvironment. For example, circulating peripheral blood, preferably mobilized (i.e., recruited), may be removed from a subject. In an embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

Definitive Endoderm Cells

The definitive endoderm can be generated in vivo from the inner cell mass by the process of gastrulation of embryogenesis, in which epiblast cells are instructed to form the three germ layers. Definitive endoderm can give rise to diverse cells and tissues that contribute to vital organs as the pancreatic β cells, liver hepatocytes, lung alveolar cells, thyroid, thymus, and the epithelial lining of the alimentary and respiratory tract. It is different from the primitive endoderm of extraembryonic tissues, which can give rise to the visceral and parietal endoderm. The definitive endoderm derived from ES cells is theoretically capable of becoming any endoderm derivatives.

Precise patterning of anterior-posterior axis of the definitive endoderm can eventually form the primitive gut tube. The definitive endoderm-derived primitive gut tube induces the pharynx, esophagus, stomach, duodenum, small and large intestine along the anterior-posterior axis as well as associated organs, including pancreas, lung, thyroid, thymus, parathyroid, and liver. The anterior portion of the foregut of the primitive gut tube becomes lung, thyroid, esophagus, and stomach. The pancreas, liver, and duodenum originate from the posterior portion of the foregut. The midgut and hindgut of primitive gut tube gives rise to the small and large intestine. The anterior foregut expresses developmental markers, NK2 homeobox 1 (NKX2-1) and SRY (sex determining region Y)-box 2 (SOX2); the posterior foregut expresses hematopoietically expressed homeobox (HHEX), pancreatic and duodenal homeobox 1 (PDX1), one cut homeobox 1 (ONECUTI, known as HNF6), and hepatocyte nuclear factor 4 alpha (HNF4A); and the midgut/hindgut expresses caudal type homeobox 1 (CDX1), caudal type homeobox 2 (CDX2), and motor neuron and pancreas homeobox 1 (MNX1) (3, 19, 20).

As described herein definitive endoderm cells of use herein can be derived from any source or generated in accordance with any suitable protocol. In some aspects, pluripotent stem cells, e.g., iPSCs or hESCs, are differentiated to endoderm cells. In some aspects, the endoderm cells (stage 1) are further differentiated, e.g., to primitive gut tube cells (stage 2), PDX1-positive pancreatic progenitor cells (stage 3), NKX6.1-positive pancreatic progenitor cells (stage 4), or Ngn3-positive endocrine progenitor cells or insulin-positive endocrine cells (stage 5), followed by induction or maturation to SC-β cells (stage 6).

In some embodiments, definitive endoderm cells can be obtained by differentiating at least some pluripotent cells in a population into definitive endoderm cells, e.g., by contacting a population of pluripotent cells with i) at least one growth factor from the TGF-β superfamily, and ii) a WNT signaling pathway activator, to induce the differentiation of at least some of the pluripotent cells into definitive endoderm cells, wherein the definitive endoderm cells express at least one marker characteristic of definitive endoderm.

Any growth factor from the TGF-β superfamily capable of inducing the pluripotent stem cells to differentiate into definitive endoderm cells (e.g., alone, or in combination with a WNT signaling pathway activator) can be used in the method provided herein. In some embodiments, the growth factor from the TGF-β superfamily comprises Activin A. In some embodiments, the growth factor from the TGF-β superfamily comprises growth differentiating factor 8 (GDF8). Any WNT signaling pathway activator capable of inducing the pluripotent stem cells to differentiate into definitive endoderm cells (e.g., alone, or in combination with a growth factor from the TGF-β superfamily) can be used in the method provided herein. In some embodiments, the WNT signaling pathway activator comprises CHIR99021. In some embodiments, the WNT signaling pathway activator comprises Wnt3a recombinant protein.

In some embodiments, differentiating at least some pluripotent cells in a population into definitive endoderm cells is achieved by a process of contacting a population of pluripotent cells with i) Activin A, and ii) CHIR99021 for a suitable period of time, e.g., about 2 days, about 3 days, about 4 days, or about 5 days to induce the differentiation of at least some of the pluripotent cells in the population into definitive endoderm cells, wherein the definitive endoderm cells express at least one marker characteristic of definitive endoderm. In some embodiments, the process comprises contacting a population of pluripotent cells with activin A and CHIR99021 for 1 day, and then with activin A (in the absence of CHIR99021) for a further 1 or 2 days.

In some examples, the method comprises differentiating pluripotent cells into definitive endoderm cells by contacting a population of pluripotent cells with a suitable concentration of the growth factor from the TGF-β superfamily (e.g., Activin A), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some embodiments, the method comprises use of about 70-130 ng·ml, 80-120 ng/ml, or 90-110 ng/ml Activin A for differentiation of pluripotent cells into definitive endoderm cells. In some embodiments, the method comprises use of about 100 ng/mL Activin A for differentiation of pluripotent cells into definitive endoderm cells. In some embodiments, the method comprises use of about 200 ng/mL Activin A for differentiation of pluripotent cells into definitive endoderm cells.

In some examples, the method comprises differentiating pluripotent cells into definitive endoderm cells by contacting a population of pluripotent cells with a suitable concentration of the WNT signaling pathway activator (e.g., CHIR99021), such as, about 0.01 μM, about 0.05 μM, about 0.1 μM, about 0.2 μM, about 0.5 μM, about 0.8 μM, about 1 μM, about 1.5 μM, about 2 μM, about 2.5 μM, about 3 μM, about 3.5 μM, about 4 μM, about 5 μM, about 8 μM, about 10 μM, about 12 μM, about 15 μM, about 20 μM, about 30 μM, about 50 μM, about 100 μM, or about 200 μM. In some embodiments, the method comprises use of about 1-5 μM or 2-4 μM CHIR99021 for differentiation of pluripotent cells into definitive endoderm cells. In some embodiments, the method comprises use of about 2 μM CHIR99021 for differentiation of pluripotent cells into definitive endoderm cells. In some embodiments, the method comprises use of about 3 μM CHIR99021 for differentiation of pluripotent cells into definitive endoderm cells. In some embodiments, the method comprises use of about 5 μM CHIR99021 for differentiation of pluripotent cells into definitive endoderm cells.

In some embodiments, the cells are further contacted with a water-soluble synthetic polymer. In some embodiments, the water-soluble synthetic polymer is polyvinyl alcohol. In some cases, the polyvinyl alcohol is at least 78% hydrolyzed, e.g., 79-81% hydrolyzed, 87-89% hydrolyzed, 87-90% hydrolyzed, or 99% hydrolyzed. In some embodiments, the polyvinyl alcohol is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the PVA is 80% hydrolyzed.

In some embodiments, a definitive endoderm cell produced by the methods as disclosed herein expresses at least one marker selected from the group consisting of: Nodal, Tmprss2, Tmem30b, St14, Spink3, Sh3gl2, Ripk4, Rab1S, Npnt, Clic6, Cldn5, Cacna1b, Bnip1, Anxa4, Emb, FoxA1, Sox17, and Rbm35a, wherein the expression of at least one marker is upregulated to by a statistically significant amount in the definitive endoderm cell relative to the pluripotent stem cell from which it was derived. In some embodiments, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some embodiments, a definitive endoderm cell produced by the methods as disclosed herein does not express by a statistically significant amount at least one marker selected the group consisting of: Zic1, Pax6, Flk1 and CD31 relative to the pluripotent stem cell from which it was derived. In some embodiments, a definitive endoderm cell produced by the methods as disclosed herein has a higher level of phosphorylation of Smad2 by a statistically significant amount relative to the pluripotent stem cell from which it was derived. In some embodiments, a definitive endoderm cell produced by the methods as disclosed herein has the capacity to form gut tube in vivo. In some embodiments, a definitive endoderm cell produced by the methods as disclosed herein can differentiate into a cell with morphology characteristic of a gut cell, and wherein a cell with morphology characteristic of a gut cell expresses FoxA2 and/or Claudin6. In some embodiments, a definitive endoderm cell produced by the methods as disclosed herein can be further differentiated into a cell of endoderm origin.

In some embodiments, a population of pluripotent stem cells are cultured in the presence of at least one β cell differentiation factor prior to any differentiation or during the first stage of differentiation. One can use any pluripotent stem cell, such as a human pluripotent stem cell, or a human iPS cell or any of pluripotent stem cell as discussed herein or other suitable pluripotent stem cells. In some embodiments, a β cell differentiation factor as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one β cell differentiation factor prior to any differentiation. In other examples, a population of pluripotent stem cells may be exposed to at least one β cell differentiation factor during the first stage of differentiation.

Primitive Gut Tube Cells

Aspects of the disclosure involve primitive gut tube cells. Primitive gut tube cells of use herein can be derived from any source or generated in accordance with any suitable protocol. In some aspects, definitive endoderm cells are differentiated to primitive gut tube cells. In some aspects, the primitive gut tube cells are further differentiated, e.g., to PDX1-positive pancreatic progenitor cells, NKX6.1-positive pancreatic progenitor cells, Ngn3-positive endocrine progenitor cells, insulin-positive endocrine cells, followed by induction or maturation to SC-β cells.

In some embodiments, primitive gut tube cells can be obtained by differentiating at least some definitive endoderm cells in a population into primitive gut tube cells, e.g., by contacting definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of primitive gut tube cells.

Any growth factor from the FGF family capable of inducing definitive endoderm cells to differentiate into primitive gut tube cells (e.g., alone, or in combination with other factors) can be used in the method provided herein. In some embodiments, the at least one growth factor from the FGF family comprises keratinocyte growth factor (KGF). In some embodiments, the at least one growth factor from the FGF family comprises FGF2. In some embodiments, the at least one growth factor from the FGF family comprises FGF8B. In some embodiments, the at least one growth factor from the FGF family comprises FGF10. In some embodiments, the at least one growth factor from the FGF family comprises FGF21.

In some embodiments, primitive gut tube cells can be obtained by differentiating at least some definitive endoderm cells in a population into primitive gut tube cells, e.g., by contacting definitive endoderm cells with KGF for a certain period of time, e.g., about 1 day, about 2 days, about 3 days, or about 4 days, to induce the differentiation of at least some of the definitive endoderm cells into primitive gut tube cells.

In some embodiments, the method comprises differentiating definitive endoderm cells into primitive gut tube cells by contacting definitive endoderm cells with a suitable concentration of the growth factor from the FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some embodiments, the method comprises use of about 20-80 ng/ml, 30-70 ng/ml, or 40-60 ng/mL KGF for differentiation of definitive endoderm cells into primitive gut tube cells. In some embodiments, the method comprises use of about 50 ng/mL KGF for differentiation of definitive endoderm cells into primitive gut tube cells. In some embodiments, the method comprises use of about 100 ng/mL KGF for differentiation of definitive endoderm cells into primitive gut tube cells.

In some embodiments, the cells are further contacted with a water-soluble synthetic polymer. In some embodiments, the water-soluble synthetic polymer is polyvinyl alcohol. In some cases, the polyvinyl alcohol is at least 78% hydrolyzed, e.g., 79-81% hydrolyzed, 87-89% hydrolyzed, 87-90% hydrolyzed, or 99% hydrolyzed. In some embodiments, the polyvinyl alcohol (PVA) is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the PVA is 80% hydrolyzed.

PDX1-Positive Pancreatic Progenitor Cells

Aspects of the disclosure involve PDX1-positive pancreatic progenitor cells. PDX1-positive pancreatic progenitor cells of use herein can be derived from any source or generated in accordance with any suitable protocol. In some aspects, primitive gut tube cells are differentiated to PDX1-positive pancreatic progenitor cells. In some aspects, the PDX1-positive pancreatic progenitor cells are NKX6.1 negative, and can be further differentiated to, e.g., NKX6.1-positive pancreatic progenitor cells, Ngn3-positive endocrine progenitor cells, insulin-positive endocrine cells, followed by induction or maturation to SC-β cells.

In some aspects, PDX1-positive pancreatic progenitor cells can be obtained by differentiating at least some primitive gut tube cells in a population into PDX1-positive pancreatic progenitor cells, e.g., by contacting primitive gut tube cells with one or more of i) at least one BMP signaling pathway inhibitor, ii) a growth factor from TGF-0 superfamily, iii) at least one growth factor from the FGF family, iv) at least one SHH pathway inhibitor, v) at least one retinoic acid (RA) signaling pathway activator; vi) at least one protein kinase C activator, and vii) a ROCK inhibitor to induce the differentiation of at least some of the primitive gut tube cells into PDX1-positive pancreatic progenitor cells, wherein the PDX1-positive pancreatic progenitor cells express PDX1.

In some aspects, PDX1-positive pancreatic progenitor cells can be obtained by differentiating at least some primitive gut tube cells in a population into PDX1-positive pancreatic progenitor cells, e.g., by contacting primitive gut tube cells with one or more of i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; and vi) at least one protein kinase C activator, to induce the differentiation of at least some of the primitive gut tube cells into PDX1-positive pancreatic progenitor cells, wherein the PDX1-positive pancreatic progenitor cells express PDX1.

In some embodiments, PDX1-positive pancreatic progenitor cells can be obtained by differentiating at least some primitive gut tube cells in a population into PDX1-positive pancreatic progenitor cells, e.g., by contacting primitive gut tube cells with one or more of i) at least one BMP signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into PDX1-positive pancreatic progenitor cells, wherein the PDX1-positive pancreatic progenitor cells express PDX1.

In some embodiments, PDX1-positive pancreatic progenitor cells can be obtained by differentiating at least some primitive gut tube cells in a population into PDX1-positive pancreatic progenitor cells, e.g., by contacting primitive gut tube cells with i) at least one SHH pathway inhibitor, ii) at least one retinoic acid (RA) signaling pathway activator; and iii) at least one protein kinase C activator, wherein the PDX1-positive pancreatic progenitor cells express PDX1.

In some embodiments, PDX1-positive pancreatic progenitor cells can be obtained by differentiating at least some primitive gut tube cells in a population into PDX1-positive pancreatic progenitor cells, e.g., by contacting primitive gut tube cells with i) at least one growth factor from the FGF family, and ii) at least one retinoic acid (RA) signaling pathway activator, to induce the differentiation of at least some of the primitive gut tube cells into PDX1-positive pancreatic progenitor cells, wherein the PDX1-positive pancreatic progenitor cells express PDX1.

Any BMP signaling pathway inhibitor capable of inducing primitive gut tube cells to differentiate into PDX1-positive pancreatic progenitor cells (e.g., alone, or with any combination of a growth factor from TGF-β superfamily, at least one growth factor from the FGF family, at least one SHH pathway inhibitor, at least one retinoic acid signaling pathway activator, at least one protein kinase C activator, and ROCK inhibitor) can be used in the method provided herein. In some embodiments, the BMP signaling pathway inhibitor comprises LDN193189 or DMH-1. In some examples, the method comprises contacting primitive gut tube cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM. In some examples, the method comprises contacting primitive gut tube cells with a concentration of BMP signaling pathway inhibitor (e.g., DMH-1), such as, about 0.01 µM, about 0.02 µM, about 0.05 µM, about 0.1 µM, about 0.2 µM, about 0.5 µM, about 0.8 µM, about 1 µM, about 1.2 µM, about 1.5 µM, about 1.75 µM, about 2 µM, about 2.2 µM, about 2.5 µM, about 2.75 µM, about 3 µM, about 3.25 µM, about 3.5 µM, about 3.75 µM, about 4 µM, about 4.5 µM, about 5 µM, about 8 µM, about 10 µM, about 15 µM, about 20 µM, about 30 µM, about 40 µM, about 50 µM, or about 100 µM. In some examples, the method comprises contacting primitive gut tube cells with a concentration of BMP signaling pathway inhibitor (e.g., DMH-1), such as, about 220-280 nM, about 230-270 nM, about 240-260 nM, or about 245-255 nM. In some examples, the method comprises contacting primitive gut tube cells with a concentration of BMP signaling pathway inhibitor (e.g., DMH-1) about 250 nM.

Any growth factor from the TGF-β superfamily capable of inducing primitive gut tube cells to differentiate into PDX1-positive pancreatic progenitor cells (e.g., alone, or with any combination of at least one BMP signaling pathway inhibitor, a growth factor from the FGF family, at least one SHH pathway inhibitor, at least one retinoic acid signaling pathway activator, at least one protein kinase C activator, and ROCK inhibitor) can be used. In some embodiments, the growth factor from TGF-β family comprises Activin A. In some embodiments, the growth factor from TGF-β family comprises GDF8. In some examples, the method comprises contacting primitive gut tube cells with a concentration of a growth factor from TGF-β superfamily (e.g., Activin A), such as, about 5 ng/mL, about 7.5 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 35 ng/mL, about 40 ng/mL, about 50 ng/mL, or about 100 ng/mL. In some examples, the method comprises contacting primitive gut tube cells with a concentration of a growth factor from TGF-β superfamily (e.g., Activin A), such as, about 17-23 ng/ml, about 18-22 ng/ml, or about 19-21 ng/ml. In some examples, the method comprises contacting primitive gut tube cells with a concentration of a growth factor from TGF-β superfamily (e.g., Activin A) of about 20 ng/ml.

Any growth factor from the FGF family capable of inducing primitive gut tube cells to differentiate into PDX1-positive pancreatic progenitor cells (e.g., alone, or with any combination of at least one BMP signaling pathway inhibitor, a growth factor from TGF-β superfamily, at least one SHH pathway inhibitor, at least one retinoic acid signaling pathway activator, at least one protein kinase C activator, and ROCK inhibitor) can be used. In some embodiments, the at least one growth factor from the FGF family comprises keratinocyte growth factor (KGF). In some embodiments, the at least one growth factor from the FGF family is selected from the group consisting of FGF2, FGF8B, FGF10, and FGF21. In some examples, the method comprises contacting primitive gut tube cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some examples, the method comprises contacting primitive gut tube cells with a concentration of a growth factor from FGF family (e.g., KGF), such as, about 20-80 ng/ml, about 30-70 ng/ml, about 40-60 ng/ml, or about 45-55 ng/ml. In some examples, the method comprises contacting primitive gut tube cells with a concentration of a growth factor from FGF family (e.g., KGF) of about 50 ng/ml.

Any SHH pathway inhibitor capable of inducing primitive gut tube cells to differentiate into PDX1-positive pancreatic progenitor cells (e.g., alone, or with any combination of at least one BMP signaling pathway inhibitor, at least one growth factor from the FGF family, a growth factor from TGF-β superfamily, at least one retinoic acid signaling pathway activator, at least one protein kinase C activator, and ROCK inhibitor) can be used. In some embodiments, the SHH pathway inhibitor comprises Sant1. In some examples, the method comprises contacting primitive gut tube cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting primitive gut tube cells with a concentration of a SHH pathway inhibitor (e.g., Sant1), such as, about 220-280 nM, about 230-270 nM, about 240-260 nM, or about 245-255 nM. In some examples, the method comprises contacting primitive gut tube cells with a concentration of a SHH pathway inhibitor (e.g., Sant1) of about 250 nM.

Any RA signaling pathway activator capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, at least one protein kinase C activator, and ROCK inhibitor) can be used. In some embodiments, the RA signaling pathway activator comprises retinoic acid. In some examples, the method comprises contacting primitive gut tube cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM. In some examples, the method comprises contacting primitive gut tube cells with a concentration of an RA signaling pathway activator (e.g., retinoic acid), such as, about 1.7-2.3 µM, about 1.8-2.2 µM, or about 1.9-2.1 µM. In some examples, the method comprises contacting primitive gut tube cells with a concentration of an RA signaling pathway activator (e.g., retinoic acid) of about 2 µM.

Any PKC activator capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, at least one RA signaling pathway activator, and ROCK inhibitor) can be used. In some embodiments, the PKC activator comprises PdBU. In some embodiments, the PKC activator comprises TPPB. In some examples, the method comprises contacting primitive gut tube cells with a concentration of a PKC activator (e.g., PdBU or TPPB), such as, about 10 nM, 50 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 10 µM, about 20 µM, about 50 µM, about 75 µM, about 80 µM, about 100 µM, about 120 µM, about 140 µM, about 150 µM, about 175 µM, about 180 µM, about 200 µM, about 210 µM, about 220 µM, about 240 µM, about 250 µM, about 260 µM, about 280 µM, about 300 µM, about 320 µM, about 340 µM, about 360 µM, about 380 µM, about 400 µM, about 420 µM, about 440 µM, about 460 µM, about 480 µM, about 500 µM, about 520 µM, about 540 µM, about 560 µM, about 580 µM, about 600 µM, about 620 µM, about 640 µM, about 660 µM, about 680 µM, about 700 µM, about 750 µM, about 800 µM, about 850 µM, about 900 µM, about 1 mM, about 2 mM, about 3 mM, about 4 mM, or about 5 mM. In some embodiments, the method comprises contacting primitive gut tube cells with a concentration of a PKC activator (e.g., PdBU or TPPB) of 10 nM-1 mM, 10 nM-500 µM, 10 nM-1 µM, 10-800 nM, 100-900 nM, 300-800 nM, 300-600 nM, 400-600 nM, 450-550 nM, or about 500 nM. In some examples, the method comprises contacting primitive gut tube cells with a concentration of a PKC activator (e.g., PdBU or TPPB), such as, about 450-550 mM, about 475-525 nM, about 490-510 nM, or about 495-505 nM. In some examples, the method comprises contacting primitive gut tube cells with a concentration of a PKC activator (e.g., PdBU or TPPB) of about 500 nM. In some embodiments, primitive gut tube cells are not treated with a PKC activator (e.g., PDBU).

Any ROCK inhibitor capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, PKC activator, and at least one RA signaling pathway activator) can be used. In some embodiments, the ROCK inhibitor comprises Thiazovivin, Y-27632, Fasudil/HA1077, or H-1152. In some embodiments, the ROCK inhibitor comprises Y-27632. In some embodiments, the ROCK inhibitor comprises Thiazovivin. In some examples, the method comprises contacting primitive gut tube cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM. In some examples, the method comprises contacting primitive gut tube cells with a concentration of a ROCK inhibitor (e.g., Y-27632 or Thiazovivin), such as, about 2.2-2.8 µM, about 2.3-2.7 µM, or about 2.4-2.6 µM. In some examples, the method comprises contacting primitive gut tube cells with a concentration of a ROCK inhibitor (e.g., Y-27632 or Thiazovivin) of about 2.5 µM.

In some embodiments, the cells are further contacted with a water-soluble synthetic polymer. In some embodiments, the water-soluble synthetic polymer is polyvinyl alcohol. In some cases, the polyvinyl alcohol is at least 78% hydrolyzed, e.g., 79-81% hydrolyzed, 87-89% hydrolyzed, 87-90% hydrolyzed, or 99% hydrolyzed. In some embodiments, the polyvinyl alcohol (PVA) is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the PVA is 80% hydrolyzed.

In some embodiments, PDX1-positive pancreatic progenitor cells can be obtained by differentiating at least some primitive gut tube cells in a population into PDX1-positive pancreatic progenitor cells, e.g., by contacting primitive gut tube cells with retinoic acid, KGF, Sant1, DMH-1, PdBU, thiazovivin, and Activin A, for a suitable period of time, e.g., about 1 day, about 2 days, about 3 days, or about 4 days. In some embodiments, PDX1-positive pancreatic progenitor cells can be obtained by differentiating at least some primitive gut tube cells in a population into PDX1-positive pancreatic progenitor cells, e.g., by contacting primitive gut tube cells with retinoic acid, KGF, Sant1, DMH-1, PdBU, thiazovivin, and Activin A, for about 2 days. In some embodiments, PDX1-positive pancreatic progenitor cells can be obtained by differentiating at least some primitive gut tube cells in a population into PDX1-positive pancreatic progenitor cells, e.g., by contacting primitive gut tube cells with retinoic acid, KGF, Sant1, DMH-1, PdBU, thiazovivin, and Activin A for 1 day, followed by contacting the cells with retinoic acid, KGF, Sant1, PdBU, thiazovivin, and Activin A for 1 day (in the absence of DMH-1).

NKX6.1-positive Pancreatic Progenitor Cells

Aspects of the disclosure involve NKX6.1-positive pancreatic progenitor cells. NKX6.1-positive pancreatic progenitor cells of use herein can be derived from any source or generated in accordance with any suitable protocol. In some aspects, PDX1-positive, NKX6.1-negative pancreatic progenitor cells are differentiated to PDX1-positive, NKX6.1-positive pancreatic progenitor cells. In some aspects, the NKX6.1-positive pancreatic progenitor cells are further differentiated, e.g., to Ngn3-positive endocrine progenitor cells, or insulin-positive endocrine cells, followed by induction or maturation to SC-β cells.

In some aspects, a method of producing a NKX6.1-positive pancreatic progenitor cell from a PDX1-positive pancreatic progenitor cell comprises contacting a population of cells (e.g., under conditions that promote cell clustering and/or promoting cell survival) comprising PDX1-positive pancreatic progenitor cells with at least two β cell-differentiation factors comprising a) at least one growth factor from the fibroblast growth factor (FGF) family, b) a sonic hedgehog pathway inhibitor, and optionally c) a low concentration of a retinoic acid (RA) signaling pathway activator, to induce the differentiation of at least one PDX1-positive pancreatic progenitor cell in the population into NKX6.1-positive pancreatic progenitor cells, wherein the NKX6.1-positive pancreatic progenitor cells expresses NKX6.1.

In some embodiments, the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a RA signaling pathway activator, to induce the differentiation of at least some of the PDX1-positive pancreatic progenitor cells into PDX1-positive, NKX6.1-positive pancreatic progenitor cells, wherein the PDX1-positive, NKX6.1-positive pancreatic progenitor cells express PDX1 and NKX6.1.

In some embodiments, the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a RA signaling pathway activator, iv) ROCK inhibitor, and v) at least one growth factor from the TGF-β superfamily, to induce the differentiation of at least some of the PDX1-positive pancreatic progenitor cells into PDX1-positive, NKX6.1-positive pancreatic progenitor cells. In some embodiments, following 3, 4, or 5 days of contacting the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a RA signaling pathway activator, iv) ROCK inhibitor, and v) at least one growth factor from the TGF-β superfamily; the cells are then contacted with i) at least one growth factor from the FGF family, ii) at least one SHH pathway inhibitor, and optionally iii) a RA signaling pathway activator, iv) ROCK inhibitor, and v) at least one growth factor from the TGF-β superfamily, and vi) a PKC activator and optionally vii) a gamma-secretase inhibitor. In some embodiments, the PDX1-positive, NKX6.1-positive pancreatic progenitor cells are obtained by contacting PDX1-positive pancreatic progenitor cells under conditions that promote cell clustering with at least one growth factor from the FGF family. In some embodiments, the growth factor from the FGF family is KGF.

In some embodiments, the disclosure provides for a method in which a first population of cells comprising PDX1-positive, NKX6.1-negative cells is cultured in a media comprising any one or combination of: i) at least one growth factor from the FGF family, ii) at least one SHH pathway inhibitor, iii) a RA signaling pathway activator, iv) a ROCK inhibitor, and v) a growth factor from the TGF-β superfamily for a period of about 1, 2, 3, 4 or 5 days (e.g., 2-4, 3-4, or 4-5 days); thereby generating a second population of cells. In some embodiments, the second population of cells is then incubated in a composition comprising any one or combination of: i) at least one growth factor from the FGF family, ii) at least one SHH pathway inhibitor, iii) a RA signaling pathway activator, iv) a ROCK inhibitor, v) a growth factor from the TGF-β superfamily, vi) a PKC activator, vii) a FoxO1 inhibitor, and optionally viii) a notch signaling inhibitor for about 1, 2, or 3 days (e.g., 1-2, 1-3, or 2-3 days).

In some embodiments, in the media for culturing the first population of cells, the growth factor from the FGF family is present at a concentration of about 45-55 ng/ml, about 46-54 ng/ml, about 47-53 ng/ml, about 48-52 ng/ml, or about 49-51 ng/ml, the SHH pathway inhibitor is present at a concentration of about 200-300 nM, about 220-280 nM, or about 240-260 nM, the RA signaling pathway activator is present at a concentration of about 1.7-2.3 µM, about 1.8-2.2 µM, or about 1.9-2.1 µM, the ROCK inhibitor is present at a concentration of about 2-3 µM, about 2.2-2.8 µM, or about 2.4-2.6 µM, and/or the growth factor from the TGF-β superfamily is present at a concentration of about 2-8 ng/ml, about 3-7 ng/ml or about 4-6 ng/ml.

In some embodiments, in the media for culturing the second population of cells, the growth factor from the FGF family is present at a concentration of about 45-55 ng/ml, about 46-54 ng/ml, about 47-53 ng/ml, about 48-52 ng/ml, or about 49-51 ng/ml, the SHH pathway inhibitor is present at a concentration of about 200-300 nM, about 220-280 nM, or about 240-260 nM, the RA signaling pathway activator is present at a concentration of about 1.7-2.3 µM, about 1.8-2.2 µM, or about 1.9-2.1 µM, the ROCK inhibitor is present at a concentration of about 2-3 µM, about 2.2-2.8 µM, or about 2.4-2.6 µM, the growth factor from the TGF-β superfamily is present at a concentration of 2 about −8 ng/ml, about 3-7 ng/ml or about 4-6 ng/ml, the PKC activator is present at a concentration of about 0.2-0.8 µM, about 0.3-0.7 µM, or about 0.4-0.6 µM, and the FoxO1 inhibitor is present at a concentration of about 0.7-1.3 µM, about 0.8-1.2 µM, or about 0.9-1.1 µM, and optionally the notch signaling inhibitor is present at a concentration of about 1.7-2.3 µM, about 1.8-2.2 µM, or about 1.9-2.1 µM.

In some embodiments, the PDX1-positive pancreatic progenitor cells are produced from a population of pluripotent cells. In some embodiments, the PDX1-positive pancreatic progenitor cells are produced from a population of iPS cells. In some embodiments, the PDX1-positive pancreatic progenitor cells are produced from a population of ESC cells. In some embodiments, the PDX1-positive pancreatic progenitor cells are produced from a population of definitive endoderm cells. In some embodiments, the PDX1-positive pancreatic progenitor cells are produced from a population of primitive gut tube cells.

Any growth factor from the FGF family capable of inducing PDX1-positive pancreatic progenitor cells to differentiate into NKX6.1-positive pancreatic progenitor cells (e.g., alone, or with any combination of at least one SHH pathway inhibitor, a ROCK inhibitor, a growth factor from the TGF-β superfamily, and at least one retinoic acid signaling pathway activator) can be used in the method provided herein. In some embodiments, the at least one growth factor from the FGF family comprises keratinocyte growth factor (KGF). In some embodiments, the at least one growth factor from the FGF family is selected from the group consisting of FGF8B, FGF 10, and FGF21. In some examples, the method comprises contacting PDX1-positive pancreatic progenitor cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some examples, the method comprises contacting PDX1-positive pancreatic progenitor cells with a concentration of a growth factor from FGF family (e.g., KGF), such as, about 20-80 ng/ml, about 30-70 ng/ml, about 40-60 ng/ml, or about 45-55 ng/ml. In some examples, the method comprises contacting PDX1-positive pancreatic progenitor cells with a concentration of a growth factor from FGF family (e.g., KGF) of about 50 ng/ml.

Any SHH pathway inhibitor capable of inducing PDX1-positive pancreatic progenitor cells to differentiate into NKX6.1-positive pancreatic progenitor cells (e.g., alone, or with any combination of at least one growth factor from the FGF family, a retinoic acid signaling pathway activator, ROCK inhibitor, and at least one growth factor from the TGF-β superfamily) can be used in the method provided herein. In some embodiments, the SHH pathway inhibitor comprises Sant1. In some examples, the method comprises contacting PDX1-positive pancreatic progenitor cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting PDX1-positive pancreatic progenitor cells with a concentration of a SHH pathway inhibitor (e.g., Sant1), such as, about 220-280 nM, about 230-270 nM, about 240-260 nM, or about 245-255 nM. In some examples, the method comprises contacting PDX1-positive pancreatic progenitor cells with a concentration of a SHH pathway inhibitor (e.g., Sant1) of about 250 nM.

Any RA signaling pathway activator capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, ROCK inhibitor, and at least one growth factor from the TGF-β superfamily) can be used. In some embodiments, the RA signaling pathway activator comprises retinoic acid. In some examples, the method comprises contacting PDX1-positive pancreatic progenitor cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM. In some examples, the method comprises contacting PDX1-positive pancreatic progenitor cells with a concentration of an RA signaling pathway activator (e.g., retinoic acid), such as, about 70-130 nM, about 80-120 nM, about 90-110 nM, or about 95-105 nM. In some examples, the method comprises contacting PDX1-positive pancreatic progenitor cells with a concentration of an RA signaling pathway activator (e.g., retinoic acid) of about 100 nM. Any ROCK inhibitor capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and at least one growth factor from the TGF-β superfamily) can be used. In some embodiments, the ROCK inhibitor comprises Thiazovivin, Y-27632, Fasudil/HA1077, or 14-1152. In some examples, the method comprises contacting PDX1-positive pancreatic progenitor cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM. In some examples, the method comprises contacting PDX1-positive pancreatic progenitor cells with a concentration of a ROCK inhibitor (e.g., Y-27632 or Thiazovivin), such as, about 2.2-2.8 µM, about 2.3-2.7 µM, or about 2.4-2.6 µM. In some examples, the method comprises contacting PDX1-positive pancreatic progenitor cells with a concentration of a ROCK inhibitor (e.g., Y-27632 or Thiazovivin) of about 2.5 µM.

Any activator from the TGF-β superfamily capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and ROCK inhibitor) can be used. In some embodiments, the activator from the TGF-β superfamily comprises Activin A or GDF8. In some examples, the method comprises contacting PDX1-positive pancreatic progenitor cells with a concentration of a growth factor from TGF-β superfamily (e.g., Activin A), such as, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 1 ng/mL, about 1.2 ng/mL, about 1.4 ng/mL, about 1.6 ng/mL, about 1.8 ng/mL, about 2 ng/mL, about 2.2 ng/mL, about 2.4 ng/mL, about 2.6 ng/mL, about 2.8 ng/mL, about 3 ng/mL, about 3.2 ng/mL, about 3.4 ng/mL, about 3.6 ng/mL, about 3.8 ng/mL, about 4 ng/mL, about 4.2 ng/mL, about 4.4 ng/mL, about 4.6 ng/mL, about 4.8 ng/mL, about 5 ng/mL, about 5.2 ng/mL, about 5.4 ng/mL, about 5.6 ng/mL, about 5.8 ng/mL, about 6 ng/mL, about 6.2 ng/mL, about 6.4 ng/mL, about 6.6 ng/mL, about 6.8 ng/mL, about 7 ng/mL, about 8 ng/mL, about 9 ng/mL, about 10 ng/mL, about 20 ng/mL, about 30 ng/mL, or about 50 ng/mL. In some examples, the method comprises contacting PDX1-positive pancreatic progenitor cells with a concentration of a growth factor from TGF-β superfamily (e.g., Activin A), such as, about 2-8 ng/ml, about 3-7 ng/ml, about 4-6 ng/ml, or about 4.5-5.5 ng/ml. In some examples, the method comprises contacting PDX1-positive pancreatic progenitor cells with a concentration of a growth factor from TGF-β superfamily (e.g., Activin A), such as, about 5 ng/mL.

Any FoxO1 inhibitor capable of inducing PDX1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, at least one growth factor from the TGF-β superfamily, PKC activator, and Notch signaling inhibitor) can be used in the method provided herein. In some embodiments, the FoxO1 inhibitor is AS1842856. In some examples, the method comprises contacting PDX1-positive pancreatic progenitor cells with a concentration of a FoxO1 inhibitor (e.g., AS1842856), such as, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting PDX1-positive pancreatic progenitor cells with a concentration of a FoxO1 inhibitor (e.g., AS1842856), such as, about 0.7-1.3 µM, about 0.8-1.2 µM, about or 0.9-1.1 µM. In some examples, the method comprises contacting PDX1-positive pancreatic progenitor cells with a concentration of a FoxO1 inhibitor (e.g., AS1842856), such as, about 1 µM.

Any PKC activator capable of inducing PDX1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, at least one growth factor from the TGF-β superfamily, FoxO1 inhibitor, and Notch signaling inhibitor) can be used in the method provided herein. In some embodiments, the PKC activator is PDBU. In some examples, the method comprises contacting PDX1-positive pancreatic progenitor cells with a concentration of a PKC activator (e.g., PDBU), such as, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting PDX1-positive pancreatic progenitor cells with a concentration of a PKC activator (e.g., PDBU), such as, about 0.2-0.8 µM, about 0.3-0.7 µM, about 0.4-0.6 µM. In some examples, the method comprises contacting PDX1-positive pancreatic progenitor cells with a concentration of a PKC activator (e.g., PDBU), such as, about 0.5 µM.

Any Notch signaling inhibitor capable of inducing PDX1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, at least one growth factor from the TGF-β superfamily, FoxO1 inhibitor, and PKC activator) can be used in the method provided herein. In some embodiments, the Notch signaling inhibitor is XXI. In some examples, the method comprises contacting PDX1-positive pancreatic progenitor cells with a concentration of a Notch signaling inhibitor (e.g., XXI), such as, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting PDX1-positive pancreatic progenitor cells with a concentration of a Notch signaling inhibitor (e.g., XXI), such as, about 1.7-2.3 µM, about 1.8-2.2 µM, or about 1.9-2.1 µM. In some examples, the method comprises contacting PDX1-positive pancreatic progenitor cells with a concentration of a Notch signaling inhibitor (e.g., XXI), such as, about 2 µM.

In some embodiments, the cells are further contacted with a water-soluble synthetic polymer. In some embodiments, the water-soluble synthetic polymer is polyvinyl alcohol. In some cases, the polyvinyl alcohol is at least 78% hydrolyzed, e.g., 79-81% hydrolyzed, 87-89% hydrolyzed, 87-90% hydrolyzed, or 99% hydrolyzed. In some embodiments, the polyvinyl alcohol (PVA) is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the PVA is 80% hydrolyzed.

In some embodiments, the PDX1-positive, NKX6.1-positive pancreatic progenitor cells are obtained by contacting PDX1-positive pancreatic progenitor cells under conditions that promote cell clustering with KGF, Sant1, and RA, for a period of 5 days or 6 days. In some embodiments, the PDX1-positive, NKX6.1-positive pancreatic progenitor cells are obtained by contacting PDX1-positive pancreatic progenitor cells under conditions that promote cell clustering with KGF, Sant1, RA, thiazovivin, and Activin A, for a period of 5 or 6 days. In some embodiments, the PDX1-positive, NKX6.1-positive pancreatic progenitor cells are obtained by contacting PDX1-positive pancreatic progenitor cells under conditions that promote cell clustering with KGF for a period of 5 days. In some embodiments, the PDX1- positive, NKX6.1-positive pancreatic progenitor cells are obtained by contacting PDX1-positive pancreatic progenitor cells under conditions that promote cell clustering with KGF for a period of 6 days. In some embodiments, the PDX1-positive, NKX6.1-positive pancreatic progenitor cells are obtained by: a) contacting PDX1-positive pancreatic progenitor cells with KGF, Sant1, RA, thiazovivin, and Activin A, for a period of 3, 4 or 5 days (e.g., 4 days), followed by; b) contacting the cells of a) with PDBU, XXI, KGF, Sant1, RA, thiazovivin, and Activin A and optionally AS1842856 for a period of 1, 2 or 3 days (e.g., 2 days).

Insulin-Positive Endocrine Cells

Aspects of the disclosure involve insulin-positive endocrine cells (e.g., NKX6.1-positive, ISL1-positive cells, or β-like cells) and additional methods of generating insulin-positive endocrine cells. Insulin-positive endocrine cells of use herein can be derived from any source or generated in accordance with any suitable protocol. In some aspects, NKX6.1-positive pancreatic progenitor cells are differentiated to insulin-positive endocrine cells (e.g., NKX6.1-positive, ISL1-positive cells, or β-like cells), In some aspects, the insulin-positive endocrine cells are further differentiated, e.g., by induction or maturation to SC-β cells.

In some aspects, a method of producing an insulin-positive endocrine cell from an NKX6.1-positive pancreatic progenitor cell comprises contacting a population of cells (e.g., under conditions that promote cell clustering) comprising NKX6-1-positive pancreatic progenitor cells with a) a TGF-β signaling pathway inhibitor, b) a thyroid hormone signaling pathway activator, c) a BMP pathway inhibitor, and/or d) a protein kinase inhibitor to induce the differentiation of at least one NKX6.1-positive pancreatic progenitor cell in the population into an insulin-positive endocrine cell, wherein the insulin-positive endocrine ceil expresses insulin. In some embodiments, insulin-positive endocrine cells express PDX1, NKX6.1, ISL1, NKX2.2, Mafb, glis3, Sur1, Kir6.2, Znt8, SLC2A1, SLC2A3 and/or insulin.

Any TGF-β signaling pathway inhibitor capable of inducing the differentiation of NKX6.1-positive pancreatic progenitor cells to differentiate into insulin-positive endocrine cells (e.g., alone, or in combination with other β cell-differentiation factors, e.g., a thyroid hormone signaling pathway activator) can be used. In some embodiments, the TGF-β signaling pathway comprises TGF-β receptor type I kinase signaling. In some embodiments, the TGF-β signaling pathway inhibitor comprises Alk5 inhibitor II. In some examples, the method comprises contacting NKX6.1-positive pancreatic progenitor cells with a concentration of a TGF-β signaling pathway inhibitor (e.g., Alk5 inhibitor such as Alk5 inhibitor II), such as, about 0.1 μM, about 0.5 μM, about 1 μM, about 1.5 μM, about 2 μM, about 2.5 μM, about 3 μM, about 3.5 μM, about 4 μM, about 4.5 μM, about 5 μM, about 5.5 μM, about 6 μM, about 6.5 μM, about 7 μM, about 7.5 μM, about 8 μM, about 8.5 μM, about 9 μM, about 9.5 μM, about 10 μM, about 10.5 μM, about 11 μM, about 11.5 μM, about 12 μM, about 12.5 μM, about 13 μM, about 13.5 μM, about 14 μM, about 14.5 μM, about 15 μM, about 15.5 μM, about 16 μM, about 16.5 μM, about 17 μM, about 17.5 μM, about 18 μM, about 18.5 μM, about 19 μM, about 19.5 μM, about 20 μM, about 25 μM, about 30 μM, about 35 μM, about 40 μM, about 45 μM, or about 50 μM. In some examples, the method comprises contacting NKX6.1-positive pancreatic progenitor cells with a concentration of a TGF-β signaling pathway inhibitor (e.g., Alk5 inhibitor such as Alk5 inhibitor II), such as, about 7-13 μM, about 8-12 μM, about 9-11 μM. In some examples, the method comprises contacting NKX6.1-positive pancreatic progenitor cells with a concentration of a TGF-β signaling pathway inhibitor (e.g., Alk5 inhibitor such as Alk5 inhibitor II), such as, about 10 μM.

Any thyroid hormone signaling pathway activator capable of inducing the differentiation of NKX6.1-positive pancreatic progenitor cells to differentiate into insulin-positive endocrine cells (e.g., alone, or in combination with other β cell-differentiation factors, e.g., a TGF-β signaling pathway inhibitor) can be used. In some embodiments, the thyroid hormone signaling pathway activator comprises triiodothyronine (T3). In some embodiments, the thyroid hormone signaling pathway activator comprises GC-1. In some examples, the method comprises contacting NKX6.1-positive pancreatic progenitor cells with a concentration of thyroid hormone signaling pathway activator (e.g., GC-1), such as, about 0.1 μM, about 0.12 μM, about 0.13 μM, about 0.14 μM, about 0.15 μM, about 0.16 μM, about 0.17 μM, about 0.18 μM, about 0.19 μM, about 0.2 μM, about 0.21 μM, about 0.22 μM, about 0.23 μM, about 0.24 μM, about 0.25 μM, about 0.26 μM, about 0.27 μM, about 0.28 μM, about 0.29 μM, about 0.3 μM, about 0.31 μM, about 0.32 μM, about 0.33 μM, about 0.34 μM, about 0.35 μM, about 0.4 μM, about 0.45 μM, about 0.5 μM, about 0.6 μM, about 0.8 μM, about 1 μM, about 2 μM, or about 5 μM. In some examples, the method comprises contacting NKX6.1-positive pancreatic progenitor cells with a concentration of thyroid hormone signaling pathway activator (e.g., GC-1), such as, about 0.7-1.3 μM, about 0.8-1.2 μM, or about 0.9-1.1 μM. In some examples, the method comprises contacting NKX6.1-positive pancreatic progenitor cells with a concentration of thyroid hormone signaling pathway activator (e.g., GC-1), such as, about 1 μM.

In some embodiments, the method comprises contacting the population of cells (e.g., NKX6.1-positive pancreatic progenitor cells) with at least one additional factor. In some embodiments, the method comprises contacting the PDX1-positive NKX6.1-positive pancreatic progenitor cells with at least one of i) a SHH pathway inhibitor, ii) a γ-secretase inhibitor, iii) at least one growth factor from the epidermal growth factor (EGF) family, iv) a TGF-β signaling pathway inhibitor, or vii) a thyroid hormone signaling pathway activator. In some embodiments, the method comprises contacting the population of cells (e.g., NKX6.1-positive pancreatic progenitor cells) with at least one additional factor. In some embodiments, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a TGF-β signaling pathway inhibitor, vii) a thyroid hormone signaling pathway activator, viii) a wnt signaling pathway inhibitor, or ix) a PKC activator.

In some embodiments, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) a protein kinase inhibitor, or ix) a ROCK inhibitor.

In some embodiments, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, or x) a ROCK inhibitor. In some embodiments, the method comprises contacting the PDX1-positive, NKX6.1-positive pancreatic progenitor cells in a culture with a i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, x) a ROCK inhibitor, xi) a PKC activator and xii) a Wnt signaling pathway inhibitor for 1, 2, or 3 days (e.g., 1-2, 1-3, or 2-3 days), and then contacting the cells in the culture with i) a γ-secretase inhibitor, ii) at least one growth factor from the epidermal growth factor (EGF) family, iii) at least one bone morphogenetic protein (BMP) signaling pathway inhibitor, iv) a TGF-β signaling pathway inhibitor, v) a thyroid hormone signaling pathway activator, vi) an epigenetic modifying compound, vii) a protein kinase inhibitor, and viii) a ROCK inhibitor for a period of 1, 2, 3, 4, 5, 6, or 7 days (e.g., 1-7, 1-5, 1-3, 3-7, 3-5, 5-7, or 4-6 days) in the absence of a SHH pathway inhibitor, a RA signaling pathway activator, a Wnt signaling pathway inhibitor, PKC activator, and/or growth factor from the epidermal growth factor (EGF) family.

In some embodiments, in the method of generating the insulin-positive endocrine cells from the PDX1-positive NKX6.1-positive pancreatic progenitor cells, some of the differentiation factors are present only for the first 1, 2, 3, 4, or 5 days during the differentiation step. In some embodiments, some of the differentiation factors, such as the SHH pathway inhibitor, the RA signaling pathway activator, the PKC activator, and the at least one growth factor from the EGF family are removed from the culture medium after the first 1, 2, or 3 days of incubation.

Any γ-secretase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the γ-secretase inhibitor comprises XXI. In some embodiments, the γ-secretase inhibitor comprises DAPT. In some examples, the method comprises contacting NKX6.1-positive pancreatic progenitor cells with a concentration of a γ-secretase inhibitor (e.g., XXI), such as, about 0.01 µM, about 0.02 µM, about 0.05 µM, about 0.075 µM, about 0.1 µM, about 0.2 µM, about 0.3 µM, about 0.4 µM, about 0.5 µM, about 0.6 µM, about 0.7 µM, about 0.8 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 2.9 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.2 µM, about 5.4 µM, about 5.6 µM, about 5.8 µM, about 6 µM, about 6.2 µM, about 6.4 µM, about 6.6 µM, about 6.8 µM, about 7 µM, about 8 µM, about 9 µM, about 10 µM, about 20 µM, about 30 µM, or about 50 µM. In some examples, the method comprises contacting NKX6.1-positive pancreatic progenitor cells with a concentration of a γ-secretase inhibitor (e.g., XXI), such as, about 1.7-2.3 µM, about 1.8-2.2 µM, or about 1.9-2.1 µM. In some examples, the method comprises contacting NKX6.1-positive pancreatic progenitor cells with a concentration of a γ-secretase inhibitor (e.g., XXI), such as about 2 µM.

Any growth factor from the EGF family capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the at least one growth factor from the EGF family comprises betacellulin. In some embodiments, at least one growth factor from the EGF family comprises EGF. In some examples, the method comprises contacting NKX6.1-positive pancreatic progenitor cells with a concentration of a growth factor from EGF family (e.g., betacellulin), such as, about 1 ng/mL, about 2 ng/mL, about 4 ng/mL, about 6 ng/mL, about 8 ng/mL, about 10 ng/mL, about 12 ng/mL, about 14 ng/mL, about 16 ng/mL, about 18 ng/mL, about 20 ng/mL, about 22 ng/mL, about 24 ng/mL, about 26 ng/mL, about 28 ng/mL, about 30 ng/mL, about 40 ng/mL, about 50 ng/mL, about 75 ng/mL, about 80 ng/mL, about 90 ng/mL, about 95 ng/mL, about 100 ng/mL, about 150 ng/mL, about 200 ng/mL, about 250 ng/mL, or about 300 ng/mL. In some examples, the method comprises contacting NKX6.1-positive pancreatic progenitor cells with a concentration of a growth factor from EGF family (e.g., betacellulin), such as, about 17-23 ng/ml, about 18-22 ng/ml, or about 19-21 ng/ml. In some examples, the method comprises contacting NKX6.1-positive pancreatic progenitor cells with a concentration of a growth factor from EGF family (e.g., betacellulin), such as, about 20 ng/ml.

Any RA signaling pathway activator capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some embodiments, the RA signaling pathway activator comprises RA. In some examples, the method comprises contacting NKX6.1-positive pancreatic progenitor cells with a concentration of an RA signaling pathway activator (e.g., retinoic acid), such as, about 0.02 µM, about 0.05 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM. In some examples, the method comprises contacting NKX6.1-positive pancreatic progenitor cells with a concentration of an RA signaling pathway activator (e.g., retinoic acid), such as, about 20-80 nM, about 30-70 nM, or about 40-60 nM. In some examples, the method comprises contacting NKX6.1-positive pancreatic progenitor cells with a concentration of an RA signaling pathway activator (e.g., retinoic acid), such as, about 50 nM.

Any SHH pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used in the method provided herein. In some embodiments, the SHH pathway inhibitor comprises Sant1. In some examples, the method comprises contacting NKX6.1-positive pancreatic progenitor cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting NKX6.1-positive pancreatic progenitor cells with a concentration of a SHH pathway inhibitor (e.g., Sant1), such as, about 220-280 nM, about 230-270 nM, about 240-260 nM, or about 245-255 nM. In some examples, the method comprises contacting NKX6.1-positive pancreatic progenitor cells with a concentration of a SHH pathway inhibitor (e.g., Sant1), such as, about 250 nM.

Any BMP signaling pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some embodiments, the BMP signaling pathway inhibitor comprises LDN193189 or DMH-1. In some examples, the method comprises contacting NKX6.1-positive pancreatic progenitor cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM. In some examples, the method comprises contacting NKX6.1-positive pancreatic progenitor cells with a concentration of BMP signaling pathway inhibitor (e.g., LDN1931189), such as, about 70-130 nM, about 80-120 nM, about 90-110 nM. In some examples, the method comprises contacting NKX6.1-positive pancreatic progenitor cells with a concentration of BMP signaling pathway inhibitor (e.g., LDN1931189), such as, about 100 nM.

Any ROCK inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the ROCK inhibitor comprises Thiazovivin, Y-27632, Fasudil/HA1077, or H-1152. In some embodiments, the ROCK inhibitor comprises Y-27632. In some embodiments, the ROCK inhibitor comprises Thiazovivin. In some examples, the method comprises contacting PDX1-positive, NKX6.1-positive pancreatic progenitor cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM. In some embodiments, the ROCK inhibitor comprises Thiazovivin. In some examples, the method comprises contacting PDX1-positive, NKX6.1-positive pancreatic progenitor cells with a concentration of a ROCK inhibitor (e.g., Y-27632 or Thiazovivin), such as, about 2.2-2.8 µM, about 2.3-2.7 µM, or about 2.4-2.6 µM. In some embodiments, the ROCK inhibitor comprises Thiazovivin. In some examples, the method comprises contacting PDX1-positive, NKX6.1-positive pancreatic progenitor cells with a concentration of a ROCK inhibitor (e.g., Y-27632 or Thiazovivin), such as, about 2.5 µM.

Any epigenetic modifying compound that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the epigenetic modifying compound comprises a histone methyltransferase inhibitor or a HDAC inhibitor. In some embodiments, the epigenetic modifying compound comprises a histone methyltransferase inhibitor, e.g., DZNep. In some embodiments, the epigenetic modifying compound comprises a HDAC inhibitor, e.g., KD5170. In some examples, the method comprises contacting PDX1-positive, NKX6.1-positive pancreatic progenitor cells with a concentration of an epigenetic modifying compound (e.g., DZNep or KD5170), such as, about 0.01 µM, about 0.025 µM, about 0.05 µM, about 0.075 µM, about 0.1 µM, about 0.15 µM, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 15 µM, about 20 µM, about 25 µM, about 30 µM, about 35 µM, about 40 µM, about 50 µM, or about 100 µM. In some examples, the method comprises contacting PDX1-positive, NKX6.1-positive pancreatic progenitor cells with a concentration of an epigenetic modifying compound (e.g., DZNep or KD5170), such as, about 70-130 nM, about 80-120 nM, or about 90-110 nM. In some examples, the method comprises contacting PDX1-positive, NKX6.1-positive pancreatic progenitor cells with a concentration of an epigenetic modifying compound (e.g., DZNep or KD5170), such as, about 100 nM.

Any Wnt signaling pathway inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the Wnt signaling pathway inhibitor comprises a tankyrase inhibitor. In some embodiments, the tankyrase inhibitor is NVP-TNKS656. In some examples, the method comprises contacting PDX1-positive, NKX6.1-positive pancreatic progenitor cells with a concentration of a Wnt signaling pathway inhibitor (e.g., a tankyrase inhibitor such as NVP-TNKS656), such as, about 0.1 µM, about 0.15

µM, about 0.2 µM, about 0.25 µM, about 0.3 µM, about 0.35 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 0.95 µM, about 1 µM, about 1.5 µM, about 2 µM, about 2.5 µM, about 3 µM, about 3.5 µM, about 4 µM, about 4.5 µM, or about 5 µM. In some examples, the method comprises contacting PDX1-positive, NKX6.1-positive pancreatic progenitor cells with a concentration of a Wnt signaling pathway inhibitor (e.g., a tankyrase inhibitor such as NVP-TNKS656), such as, about 1.7-2.3 µM, about 1.8-2.2 µM, or about 1.9-2.1 µM. In some examples, the method comprises contacting PDX1-positive, NKX6.1-positive pancreatic progenitor cells with a concentration of a Wnt signaling pathway inhibitor (e.g., a tankyrase inhibitor such as NVP-TNKS656), such as, about 2 µM.

Any PKC activator that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some embodiments, the PKC activator is TPB or PDBU. In some examples, the method comprises contacting PDX1-positive, NKX6.1-positive pancreatic progenitor cells with a concentration of a PKC activator (TPB or PDBU), such as, about 0.01 µM, about 0.025 µM, about 0.05 µM, about 0.075 µM, about 0.1 µM, about 0.15 µM, about 0.2 µM, about 0.25 µM, about 0.3 µM, about 0.35 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 0.95 µM, about 1 µM, about 2 µM, about 3 µM, about 4 µM, about 5 µM, about 6 µM, about 7 µM, about 7.5 µM, about 8 µM, about 9 µM, about 10 µM, about 15 µM, or about 20 µM. In some examples, the method comprises contacting PDX1-positive, NKX6.1-positive pancreatic progenitor cells with a concentration of a PKC activator (TPB or PDBU), such as, about 450-550 mM, about 475-525 nM, about 490-510 nM, or about 495-505 nM. In some examples, the method comprises contacting PDX1-positive, NKX6.1-positive pancreatic progenitor cells with a concentration of a PKC activator (TPB or PDBU), such as, about 500 nM.

In some embodiments, the population of cells is optionally contacted with a protein kinase inhibitor. In some embodiments, the population of cells is not contacted with the protein kinase inhibitor. In some embodiments, the population of cells is contacted with the protein kinase inhibitor. Any protein kinase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some embodiments, the protein kinase inhibitor comprises staurosporine. In some examples, the method comprises contacting NKX6.1-positive pancreatic progenitor cells with a concentration of a protein kinase inhibitor (e.g., staurosporine), such as, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, about 2.0 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 µM, about 4.9 nM, or about 5 nM. In some examples, the method comprises contacting NKX6.1-positive pancreatic progenitor cells with a concentration of a protein kinase inhibitor (e.g., staurosporine), such as, about 1-5 nM, about 2-4 nM, or about 2.5-3.5 nM. In some examples, the method comprises contacting NKX6.1-positive pancreatic progenitor cells with a concentration of a protein kinase inhibitor (e.g., staurosporine), such as, about 3 nM.

In some embodiments, the cells are further contacted with a water-soluble synthetic polymer. In some embodiments, the water-soluble synthetic polymer is polyvinyl alcohol. In some cases, the polyvinyl alcohol is at least 78% hydrolyzed, e.g., 79-81% hydrolyzed, 87-89% hydrolyzed, 87-90% hydrolyzed, or 99% hydrolyzed. In some embodiments, the polyvinyl alcohol (PVA) is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. In some embodiments, the PVA is 89% hydrolyzed.

In some embodiments, the method comprises contacting the population of cells (e.g., NKX6.1-positive pancreatic progenitor cells) with XXI, Alk5i, T3 or GC-1, RA, Sant1, and betacellulin, PDBU, and NVP-TNKS656 for a period of 7 days, to induce the differentiation of at least one NKX6.1-positive pancreatic progenitor cell in the population into an insulin-positive endocrine cell, wherein the insulin-positive endocrine cell expresses insulin. In some embodiments, the method comprises contacting the population of cells (e.g., NKX6.1-positive pancreatic progenitor cells) with XXI, Alk5i, T3 or GC-1, RA, Sant1, betacellulin, and LDN193189 for a period of 7 days, to induce the differentiation of at least one NKX6.1-positive pancreatic progenitor cell in the population into an insulin-positive endocrine cell, wherein the insulin-positive endocrine cell expresses insulin. In some embodiments, one or more differentiation factors are added in a portion of the Stage 5, for instance, only the first 1, 2, 3, 4, 5, or 6 days of the period of time for Stage 5, or the last 1, 2, 3, 4, 5, or 6 days of the period of time for Stage 5. In one example, the cells are contacted with SHH signaling pathway inhibitor the PKC activator, the retinoic acid, and/or the wnt signaling pathway inhibitor for only the first 2, 3, 4, or 5 days during Stage 5, after which the SHH signaling pathway inhibitor, the PKC activator, the retinoic acid, and/or the wnt signaling pathway inhibitor are not included in or removed from the culture medium. In another example, the cells are contacted with BMP signaling pathway inhibitor for only the first 1, 2, or 3 days during Stage 5, after which the BMP signaling pathway inhibitor is removed from the culture medium.

In some embodiments, the method comprises contacting the population of cells (e.g., NKX6.1-positive pancreatic progenitor cells) with one or more metabolites. In some embodiments, the method comprises contacting the population of cells (e.g., NKX6.1-positive pancreatic progenitor cells) with one or more of an acetyl CoA-related metabolite, a vitamin, histone deacetylase inhibitor (HDACi), a redox homeostasis regulator, a one carbon metabolism pathway intermediate, and/or glutamine. Examples of metabolites include glutamine, taurine, acetate, beta-hydroxybutyrate, biotin, and formate.

In some embodiments, a composition (e.g., medium) of the disclosure comprises an acetyl CoA-related metabolite. Exemplary acetyl CoA-related metabolites include, but are not limited to acetate, pyruvate, ketogenic amino acids, valine, leucine, isoleucine, phenylalanine, tyrosine, lysine, tryptophan, fatty acids, CoA, Isovaleryl-CoA, and β-hydroxybutyrate. In some embodiments, the acetyl CoA-related metabolite is acetate. In some embodiments, the acetyl CoA-related metabolite is present in or is added to a composition of the disclosure at a concentration of about 10 nM, about 50 nM, about 80 nM, about 100 nM, about 120 nM, about 140 nM, about 150 nM, about 200 nM, about 300 nM, about 500 nM, about 800 nM, about 1 µM, about 10 µM, about 100 µM, about 500 µM, about 800 µM, about 900 µM, about 1 mM, about 2 mM, about 3 mM, about 5 mM, or about 10 mM. In some embodiments, the acetyl CoA-related metabolite is present in or is added to a composition of the disclosure at a concentration of about 0.01-50 mM, 0.1-50 mM, 0.5-50 mM, 0.01-20 mM, 0.1-20 mM, 0.5-20 mM, 0.01-10 mM, 0.1-10 mM, 0.5-10 mM, 0.8-25 mM, 0.8-10 mM, 0.8-5 mM, 0.8-2 mM, 0.8-1.5 mM, 0.8-1.2 mM, 0.9-1.1 mM, or 0.95-1.05 mM. In some embodiments, the acetyl CoA-related metabolite is acetate present at a concentration of about 1 mM. In some embodiments, the acetyl CoA-related metabolite is acetate present at a concentration of about 50-1000 nM, 50-800 nM, 50-500 nM, 50-300 nM, 50-250 nM, 100-200 nM, or 125-175 nM. In some embodiments, the acetyl CoA-related metabolite is acetate present at a concentration of about 160 nM.

In some embodiments, a composition (e.g., medium) of the disclosure comprises one or
more vitamins. Exemplary vitamins include, but are not limited to biotin, vitamin B1 (thiamine), vitamin B2 (riboflavin), vitamin B3 (niacin), vitamin B6 (pyridoxine) and vitamin B12
(cyanocobalamin). In some embodiments the vitamin modulates fatty acid synthesis. In some embodiments the vitamin modulates branched-chain amino acid metabolism. In some embodiments the vitamin modulates or participates as a co-factor in the TCA cycle, e.g., as a cofactor for pyruvate carboxylase. In some embodiments, the vitamin is biotin. In some embodiments, the vitamin is present in or is added to a composition of the disclosure at a concentration of about 100 nM, about 300 nM, about 500 nM, about 600 nM, about 700 nM, about 800 nM, about 900 nM, about 1 µM, about 1.5 µM, about 3 µM, about 5 µM, about 10 µM, or about 100 µM. In some embodiments, the vitamin is biotin present at a concentration of about 800 nM. In some embodiments, the vitamin is present in or is added to a composition of the disclosure at a concentration of about 1 nM to 500 µM, 1 nM to 100 µM, 1 nM to 10 µM, 1 nM to 1 µM, 1 nM to 800 nM, 1 nM to 600 nM, 1 nM to 400 nM, 1 nM to 300 nM, 1 nM to 200 nM,
25 nM to 500 µM, 25 nM to 100 µM, 25 nM to 10 µM, 25 nM to 1 µM, 25 nM to 800 nM, 25 nM to 600 nM, 25 nM to 400 nM, 25 nM to 300 nM, 25 nM to 200 nM, 50 nM to 500 µM, 50 nM to 100 µM, 50 nM to 10 µM, 50 nM to 1 µM, 50 nM to 800 nM, 50 nM to 600 nM, 50 nM to 400 nM, 50 nM to 300 nM, 50 nM to 200 nM, 100 nM to 500 µM, 100 nM to 100 µM, 100 nM to 10 µM, 100 nM to 1 µM, 100 nM to 800 nM, 100 nM to 600 nM, 100 nM to 400 nM, 100 nM to 300 nM, or 100 nM to 200 nM.

In some embodiments, a composition (e.g., medium) of the disclosure comprises a histone deacetylase inhibitor (HDACi). Exemplary histone deacetylase inhibitors (HDACi) include, but are not limited to β-Hydroxybutyrate, butyric acid, class I HDACi, class IIA HDACi, class IIB HDACi, class III HDACi, class IV HDACi, HDAC-1, HDAC-2, HDAC-3, HDAC-4, HDAC-5, HDAC-6, HDAC-7, HDAC-8, HDAC-9, HDAC-10, HDAC-11, sirtuins, SIRT1, SIRT2, SIRT3, SIRT4, SIRT5, SIRT6, SIRT7, Vorinostat (suberoylanilide hydroxamic acid, SAHA, MK0683), Entinostat (MS-275, SNDX-275), Panobinostat (LBH589, NVP-LBH589), Trichostatin A (TSA), Mocetinostat (MGCD0103, MG0103), GSK3117391 (GSK3117391A, HDAC-IN-3), BRD3308, BRD3308, Tubastatin A TFA (Tubastatin A trifluoroacetate salt), Tubastatin A, SIS17, NKL 22, BML-210 (CAY10433), TC-H 106, SR-4370, Belinostat (PXD101, NSC726630, PX-105684), Romidepsin (FK228, Depsipeptide, FR 901228, NSC 630176), MC1568, Givinostat (ITF2357), Dacinostat (LAQ824, NVP-LAQ824), CUDC-101, Quisinostat (JNJ-26481585), Pracinostat (SB939), PCI-34051, Droxinostat (NS 41080), Abexinostat (PCI-24781), Abexinostat (PCI-24781, CRA-024781), RGFP966, AR-42 (HDAC-42), Ricolinostat (ACY-1215, Rocilinostat), Valproic acid sodium salt (Sodium valproate), Tacedinaline (CI994, PD-123654, GOE-5549, Acetyldinaline), Fimepinostat (CUDC-907), Sodium butyrate (NaB), Curcumin, Diferuloylmethane, M344, Tubacin, RG2833 (RGFP109), RG2833 (RGFP109), Resminostat (RAS2410), Divalproex Sodium, Scriptaid (GCK 1026), Sodium Phenylbutyrate, Sinapinic acid (Sinapic acid), TMP269, Santacruzamate A (CAY10683), TMP195 (TFMO 2), Valproic acid (VPA), UF010, Tasquinimod (ABR-215050), SKLB-23bb, Isoguanosine, Sulforaphane, BRD73954, Citarinostat (ACY-241, HDAC-IN-2), Suberohydroxamic acid, Splitomicin, HPOB, LMK-235, Biphenyl-4-sulfonyl chloride (p-Phenylbenzenesulfonyl, 4-Phenylbenzenesulfonyl, p-Biphenylsulfonyl), Nexturastat A, TH34, Tucidinostat (Chidamide, HBI-8000, CS-055), (−)-Parthenolide, WT161, CAY10603, CAY10603, ACY-738, Raddeanin A, Tinostamustine (EDO-S101), Domatinostat (4SC-202), and BG45. In some embodiments, the HDACi is β-Hydroxybutyrate. In some embodiments, the HDACi is present in or is added to a composition of the disclosure at a concentration of about 100 nM, about 300 nM, about 500 nM, about 600 nM, about 700 nM, about 800 nM, about 900 nM, about 1 µM, about 1.5 µM, about 3 µM, about 5 µM, about 10 µM, or about 100 µM. In some embodiments, the HDACi is β-Hydroxybutyrate present at a concentration of about 200 nM. In some embodiments, the HDACi is present in or is added to a composition of the
disclosure at a concentration of about 1 nM to 500 µM, 1 nM to 100 µM, 1 nM to 10 µM, 1 nM to 1 µM, 1 nM to 800 nM, 1 nM to 600 nM, 1 nM to 400 nM, 1 nM to 300 nM, 1 nM to 200 nM,
25 nM to 500 µM, 25 nM to 100 µM, 25 nM to 10 µM, 25 nM to 1 µM, 25 nM to 800 nM, 25 nM to 600 nM, 25 nM to 400 nM, 25 nM to 300 nM, 25 nM to 200 nM, 50 nM to 500 µM, 50 nM to 100 µM, 50 nM to 10 µM, 50 nM to 1 µM, 50 nM to 800 nM, 50 nM to 600 nM, 50 nM to 400 nM, 50 nM to 300 nM, 50 nM to 200 nM, 100 nM to 500 µM, 100 nM to 100 µM, 100 nM to 10 µM, 100 nM to 1 µM, 100 nM to 800 nM, 100 nM to 600 nM, 100 nM to 400 nM, 100 nM to 300 nM, or 100 nM to 200 nM.

In some embodiments, a composition (e.g., medium) of the disclosure comprises a redox homeostasis regulator. Exemplary redox homeostasis regulators include, but are not limited to taurine, respiratory chain regulators, free radical scavengers, regulators of mitochondrial protein synthesis, allium sulphur compounds, anthocyanins, beta-carotene, catechins, copper, cryptoxanthins, flavonoids, indoles, isoflavonoids, lignans, lutein, lycopene, alpha lipoic acid, ellagic acid, manganese, polyphenols, selenium, glutathione, vitamin A, vitamin C, vitamin E, zinc, superoxide disutases, GSHPx, Prx-I, catalase, and co-enzyme Q10. In some embodiments, the redox homeostasis regulator is taurine. In some embodiments, the redox homeostasis regulator is present in or is added to a composition of the disclosure at a concentration of about 100 nM, about 500 nM, 1 µM, about 10 µM, about 20 µM, about 30 µM, about 40 µM, about 50 µM, about 60 µM, about 70 µM, about 80 µM, about 90 µM, about 100 µM, about 110 µM, about 110 µM, about 150 µM, or about 200 µM. In some embodiments, the redox homeostasis regulator is taurine. In some embodiments, the redox homeostasis regulator is taurine present at a concentration of about 90 µM. In some embodiments, the redox homeostasis regulator intermediate is present or is added at a concentration of about 100 nM to 1 mM, 500 nM to 1 mM, 1 µM to 1 mM, 10 µM to 1 mM, 20 µM to 1 mM, 30 µM to 1 mM, 30 µM to 1 mM, 40 µM to 1 mM, 50 µM to 1 mM, 60 µM to 1 mM, 70 µM to 1 mM, 80 µM to 1 mM, 100 nM to 250 µM, 500 nM to 250 µM, 1 µM to 250 µM, 10 µM to 250 µM, 20 µM to 250 µM, 30 µM to 250 µM, 30 µM to 250 µM, 40 µM to 250 µM, 50 µM to 250 µM, 60 µM to 250 µM, 70 µM to 250 µM, 100 nM to 100 µM, 500 nM to 100 µM, 1 µM to 100 µM, 10 µM to 100 µM, 20 µM to 100 µM, 30 µM to 100 µM, 40 µM to 100 µM, 50 µM to 100 µM, 60 µM to 100 µM, 70 µM to 100 µM, or 80 µM to 100 µM.

In some embodiments, a composition (e.g., medium) of the disclosure comprises a one carbon metabolism pathway intermediate. Exemplary one carbon metabolism pathway intermediates include, but are not limited to formate, tetrahydrofolate (THF), 10-formylTHF; 5,10-meTHF; 5,10-meTHF; and 10-formylTHF. In some embodiments, the one carbon metabolism pathway intermediate is formate present at a concentration of about 50 µM. In some embodiments, the one carbon metabolism pathway intermediate is present or is added at a concentration of about 100 nM to 1 mM, 500 nM to 1 mM, 1 µM to 1 mM, 10 µM to 1 mM, M to 1 mM, 30 µM to 1 mM, 100 nM to 250 µM, 500 nM to 250 µM, 1 µM to 250 µM, 10 µM to 250 µM, 20 µM to 250 µM, 30 µM to 250 µM, 100 nM to 100 µM, 500 nM to 100 µM, 1 µM to 100 µM, 10 µM to 100 µM, 20 µM to 100 µM, 30 µM to 100 µM, 100 nM to 60 µM, 500 nM to 60 µM, 1 µM to 60 µM, 10 µM to 60 µM, 20 µM to 60 µM, 30 µM to 60 µM, 40 µM to 60 µM, or 45 µM to 55 µM.

In some embodiments, a composition (e.g., medium) of the disclosure comprises glutamine. Thus in some embodiments, compositions and methods of the disclosure utilize glutamine in a form with increased bioavailability, such as a free glutamine form, such as a non-dipeptide form, a non-alanine-glutamine dipeptide form (e.g., a non-alanyl-1-glutamine form), a non-glycine-glutamine dipeptide form (e.g., a non-glycyl-1-glutamine form), a form that in which glutamine is not conjugated to another amino acid or stabilizing moiety, a monomeric form, a free form, or a combination thereof. In some embodiments, glutamine is provided as a protein hydrolysate. In some embodiments, glutamine is present or is added to a composition of the disclosure at a concentration of from 0.5-20 mM, 0.5-10 mM, 0.5-5 mM, 1-5 mM, 2-5 mM, or 1 mM to 10 mM. In some embodiments, glutamine is present or is added to a composition of the disclosure at a concentration of 3.8-4.2 mM. In some embodiments, glutamine is present or is added to a composition of the disclosure at a concentration of 1-10, 1-7, 1-8, 1-6, 1-5, 1-4, 2-10, 2-7, 2-8, 2-6, 2-5, 2-4, 3-10, 3-7, 3-8, 3-6, 3-5, 3-4, 3.5-4.5, 3.8-4.2, or 3.9-4.1 mM. In some embodiments, glutamine is present or is added to a composition of the disclosure at a concentration of about 4 mM. In some embodiments, at least 0.5 mM, 0.6 mM, 0.7 mM, 0.8 mM, 0.9 mM, 1 mM, 1.5 mM, 2 mM, 2.5 mM, 3 mM, 3.5 mM, 4 mM, 4.5 mM, or 5 mM of the glutamine is not in a dipeptide form. In some embodiments, at least 500 µM, at least 750 µM, at least 1 mM, at least 1.5 mM, at least 2 mM, at least 2.5 mM, at least 2.6 mM, at least 2.7 mM, at least 2.8 mM, at least 2.9 mM, at least 3 mM, at least 3.1 mM, at least 3.2 mM, at least 3.3 mM, at least 3.4 mM, at least 3.5 mM, at least 3.6 mM, at least 3.7 mM, at least 3.8 mM, at least 3.9 mM, at least 4 mM, at least 5 mM, at least 5.5 mM, at least 6 mM, at least 6.5 mM, at least 7 mM, at least 7.5 mM, at least 8 mM, at least 8.5 mM, at least 9 mM, at least 9.5 mM, or at least 10 mM of the glutamine is in a free form.

In some embodiments, the method comprises culturing the population of cells (e.g., NKX6.1-positive pancreatic progenitor cells) in a medium, to induce the differentiation of at least one NKX6.1-positive pancreatic progenitor cell in the population into an insulin-positive endocrine cell, wherein the insulin-positive endocrine cell expresses insulin.

Aspects of the disclosure involve treatment of cell population comprising PDX1-positive, NKX6.1-positive pancreatic progenitor cells with PKC activator and/or wnt signaling pathway inhibitor, which can lead to increase in percentage of pancreatic α cells, increase in percentage of pancreatic δ cells, increase in percentage of pancreatic β cells, reduction in percentage of EC cells, or any combination thereof, in the cell population of pancreatic endocrine cells generated according to the method disclosed herein.

In some embodiments, the method comprises contacting a population of cells comprising PDX1-positive, NKX6.1-positive pancreatic progenitor cells with a first composition comprising a FOXO1 inhibitor, notch signaling inhibitor, a PKC activator, a ROCK inhibitor, a growth factor from TGFβ superfamily, a growth factor from FGF family, a RA signaling pathway activator, and a SHH pathway inhibitor, for one to two days, thereby obtaining a first transformation cell population comprising PDX1-positive, NKX6.1-positive pancreatic progenitor cells; and contacting the first transformation cell population comprising PDX1-positive, NKX6.1-positive pancreatic progenitor cells with a second composition comprising the PKC activator, notch signaling inhibitor, a TGF-0 signaling pathway inhibitor, a TH signaling pathway activator, BMP pathway inhibitor, ROCK inhibitor, retinoic acid, and EGF-family growth factor, wnt signaling pathway inhibitor, and/or an epigenetic modifying compound, for one to two days, thereby obtaining a second transformation cell population comprising NKX6.1-positive, ISL1-positive endocrine cells.

Pancreatic β Cells

Aspects of the disclosure involve generating pancreatic β cells (e.g., non-native pancreatic β cells/SC-β cells) and additional methods of generating them. Non-native pancreatic β cells, In some embodiments, resemble endogenous mature β cells in form and function, but nevertheless are distinct from native β cells.

In some embodiments, the insulin-positive pancreatic endocrine cells generated using the method provided herein can form a cell cluster, alone or together with other types of cells, e.g., precursors thereof, e.g., stem cell, definitive endoderm cells, primitive gut tube cell, PDX1-positive pancreatic progenitor cells, or NKX6.1-positive pancreatic progenitor cells.

In some embodiments, any of the cells or populations of cells disclosed herein are in a cell cluster. In some embodiments, the disclosure provides for a composition comprising one or more cell clusters. In some embodiments, the composition comprises 500-20000, 500-15000, 500-10000, 500-5000, 500-2000, 500-1000, 1000-20000, 1000-15000, 1000-10000, 1000-5000, 1000-2000, 2000-20000, 2000-15000, 2000-10000, 2000-5000, 5000-20000, 5000-15000, 5000-10000, 10000-20000, 10000-15000, 15000-20000, or 3000-9000 cell clusters. In some aspects, provided herein are cell clusters that resemble the functions and characteristics of endogenous pancreatic islets. Such cell clusters can mimic the function of endogenous pancreatic islets in regulating metabolism, e.g., glucose metabolism in a subject.

In some embodiments, a composition or cell population of the present disclosure comprises NKX6.1-positive, ISL-positive cells that express lower levels of MAFA than NKX6.1-positive, ISL-positive cells from the pancreas of a healthy control adult subject. In some embodiments, the composition or cell population comprises NKX6.1-positive, ISL-positive cells that express higher levels of MAFB than NKX6.1-positive, ISL-positive cells from the pancreas of a healthy control adult subject. In some embodiments, the composition or cell population comprises NKX6.1-positive, ISL-positive cells that express higher levels of SIX2, HOPX, IAPP and/or UCN3 than NKX6.1-positive, ISL-positive cells from the pancreas of a healthy control adult subject.

In some embodiments, a composition or cell population of the present disclosure comprises NKX6.1-positive, ISL-positive cells that do not express MAFA. In some embodiments, the composition or cell population comprises NKX6.1-positive, ISL-positive cells that express MAFB.

In some embodiments, the cell population comprising the insulin-positive endocrine cells can be directly induced to mature into SC-β cells without addition of any exogenous differentiation factors (such as inhibitor of TGF-β signaling pathway, thyroid hormone signaling pathway activator, PKC activator, growth factors from TGF-β superfamily, FGF family, or EGF family, SHH signaling pathway inhibitor, γ-secretase inhibitor, ROCK inhibitor, or BMP signaling pathway inhibitor). In some embodiments, the method provided herein comprises contacting a cell population comprising NKX6.1-positive, ISL1-positive endocrine cells with a serum albumin protein, a TGF-β signaling pathway inhibitor, a SHH pathway inhibitor, a TH signaling pathway activator, a protein kinase inhibitor, a ROCK inhibitor, a BMP signaling pathway inhibitor, and/or an epigenetic modifying compound. In some embodiments, the method provided herein comprises contacting a cell population comprising NKX6.1-positive, ISL1-positive endocrine cells with human serum albumin protein. In some embodiments, the method provided herein comprises contacting a cell population comprising NKX6.1-positive, ISL1-positive endocrine cells with a PKC activator.

In some embodiments, the cell population comprising the insulin-positive endocrine cells can be induced to mature into SC-β cells by contacting the insulin-positive endocrine cells with differentiation factors. The differentiation factors can comprise at least one inhibitor of TGF-β signaling pathway and thyroid hormone signaling pathway activator as described herein. In some embodiments, SC-β cells can be obtained by contacting a population of cells comprising insulin-positive endocrine cells with Alk5i and T3 or GC-1.

In some embodiments, the method provided herein comprises contacting a cell population comprising NKX6.1-positive, ISL1-positive endocrine cells with (i) a TGF-β signaling pathway inhibitor, (ii) a thyroid hormone signaling pathway activator, (iii) an epigenetic modifying compound, (iv) a BMP signaling pathway inhibitor, (v) a ROCK inhibitor, and/or (vi) a protein kinase inhibitor (e.g., staurosporine).

In some embodiments, the method provided herein comprises contacting a cell population comprising NKX6.1-positive, ISL1-positive endocrine cells with (i) a growth factor from the FGF family, (ii) a TGF-β signaling pathway inhibitor, (iii) a thyroid hormone signaling pathway activator, (iv) an epigenetic modifying compound, (v) a protein kinase inhibitor, (vi) a ROCK inhibitor, (vii) a BMP signaling pathway inhibitor, and (viii) a lipase inhibitor for about one two five days. In some embodiments, the contacting is for about three days.

Any TGF-β signaling pathway inhibitor capable of inducing the differentiation of insulin-positive endocrine cells to mature into SC-β cells (e.g., alone, or in combination with other β cell-differentiation factors, e.g., a thyroid hormone signaling pathway activator) can be used. In some embodiments, the TGF-β signaling pathway comprises TGF-β receptor type I kinase signaling. In some embodiments, the TGF-β signaling pathway inhibitor comprises Alk5 inhibitor II. In some examples, the method comprises contacting insulin-positive endocrine cells with a concentration of a TGF-β signaling pathway inhibitor (e.g., Alk5 inhibitor such as Alk5 inhibitor II), such as, about 0.1 µM, about 0.5 µM, about 1 µM, about 1.5 µM, about 2 µM, about 2.5 µM, about 3 µM, about 3.5 µM, about 4 µM, about 4.5 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 10.5 µM, about 11 µM, about 11.5 µM, about 12 µM, about 12.5 µM, about 13 µM, about 13.5 µM, about 14 µM, about 14.5 µM, about 15 µM, about 15.5 µM, about 16 µM, about 16.5 µM, about 17 µM, about 17.5 µM, about 18 µM, about 18.5 µM, about 19 µM, about 19.5 µM, about 20 µM, about 25 µM, about 30 µM, about 35 µM, about 40 µM, about 45 µM, or about 50 µM. In some examples, the method comprises contacting insulin-positive endocrine cells with a concentration of a TGF-β signaling pathway inhibitor (e.g., Alk5 inhibitor such as Alk5 inhibitor II), such as, about 7-13 µM, about 8-12 µM, or about 9-11 µM. In some examples, the method comprises contacting insulin-positive endocrine cells with a concentration of a TGF-β signaling pathway inhibitor (e.g., Alk5 inhibitor such as Alk5 inhibitor II), such as, about 10 µM.

Any thyroid hormone signaling pathway activator capable of inducing the differentiation of insulin-positive endocrine cells to mature into SC-β cells (e.g., alone, or in combination with other β cell-differentiation factors, e.g., a TGF-β signaling pathway inhibitor) can be used. In some embodiments, the thyroid hormone signaling pathway activator comprises triiodothyronine (T3). In some embodiments, the thyroid hormone signaling pathway activator comprises GC-1. In some examples, the method comprises contacting insulin-positive endocrine cells with a concentration of thyroid hormone signaling pathway activator (e.g., GC-1), such as, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM. In some examples, the method comprises contacting insulin-positive endocrine cells with a concentration of thyroid hormone signaling pathway activator (e.g., GC-1), such as, about 0.7-1.3 µM, about 0.8-1.2 µM, or about 0.9-1.1 µM. In some examples, the method comprises contacting insulin-positive endocrine cells with a concentration of thyroid hormone signaling pathway activator (e.g., GC-1), such as, about 1 µM.

Any BMP signaling pathway inhibitor capable of inducing the differentiation of insulin-positive endocrine cells to mature into SC-β cells (e.g., alone, or in combination with any of a TGF-β signaling pathway inhibitor and/or a thyroid hormone signaling pathway activator) can be used. In some embodiments, the BMP signaling pathway inhibitor comprises LDN193189 or DMH-1. In some examples, the method comprises contacting insulin-positive endocrine cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM. In some examples, the method comprises contacting insulin-positive endocrine cells with a concentration of BMP signaling pathway inhibitor (e.g., LDN1931189), such as, about 70-130 nM, about 80-120 nM, about 90-110 nM. In some examples, the method comprises contacting NKX6.1-positive pancreatic progenitor cells with a concentration of BMP signaling pathway inhibitor (e.g., LDN1931189), such as, about 100 nM.

Any ROCK inhibitor that is capable of inducing the differentiation of insulin-positive endocrine cells to mature into SC-β cells (e.g., alone, or in combination with any of a TGF-β signaling pathway inhibitor and/or a thyroid hormone signaling pathway activator) can be used. In some embodiments, the ROCK inhibitor comprises Thiazovivin, Y-27632, Fasudil/HA1077, or H-1152. In some embodiments, the ROCK inhibitor comprises Y-27632.

In some embodiments, the ROCK inhibitor comprises Thiazovivin. In some examples, the method comprises contacting insulin-positive endocrine cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM. In some embodiments, the ROCK inhibitor comprises Thiazovivin. In some examples, the method comprises contacting insulin-positive endocrine cells with a concentration of a ROCK inhibitor (e.g., Y-27632 or Thiazovivin), such as, about 2.2-2.8 µM, about 2.3-2.7 µM, or about 2.4-2.6 µM. In some embodiments, the ROCK inhibitor comprises Thiazovivin. In some examples, the method comprises contacting insulin-positive endocrine cells with a concentration of a ROCK inhibitor (e.g., Y-27632 or Thiazovivin), such as, about 2.5 µM.

Any epigenetic modifying compound that is capable of inducing the differentiation of insulin-positive endocrine cells to mature into SC-β cells (e.g., alone, or in combination with any of a TGF-β signaling pathway inhibitor and/or a thyroid hormone signaling pathway activator) can be used. In some embodiments, the epigenetic modifying compound comprises a histone methyltransferase inhibitor or a HDAC inhibitor. In some embodiments, the epigenetic modifying compound comprises a histone methyltransferase inhibitor, e.g., DZNep. In some embodiments, the epigenetic modifying compound comprises a HDAC inhibitor, e.g., KD5170. In some examples, the method comprises contacting insulin-positive endocrine cells to mature into SC-β cells with a concentration of an epigenetic modifying compound (e.g., DZNep or KD5170), such as, about 0.01 µM, about 0.025 µM, about 0.05 µM, about 0.075 µM, about 0.1 µM, about 0.15 µM, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 15 µM, about 20 µM, about 25 µM, about 30 µM, about 35 µM, about 40 µM, about 50 µM, or about 100 µM. In some examples, the method comprises contacting insulin-positive endocrine cells to mature into SC-β cells with a concentration of an epigenetic modifying compound (e.g., DZNep or KD5170), such as, about 70-130 nM, about 80-120 nM, or about 90-110 nM. In some examples, the method comprises contacting insulin-positive endocrine cells to mature into SC-β cells with a concentration of an epigenetic modifying compound (e.g., DZNep or KD5170), such as, about 100 nM.

Any protein kinase inhibitor that is capable of inducing the differentiation insulin-positive endocrine cells to mature into SC-β cells (e.g., alone, or in combination with any of a TGF-β signaling pathway inhibitor and/or a thyroid hormone signaling pathway activator). In some embodiments, the protein kinase inhibitor comprises staurosporine. In some examples, the method comprises contacting insulin-positive endocrine cells with a concentration of a protein kinase inhibitor (e.g., staurosporine), such as, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, about 2.0 nM, about 2.1 nM, about 2.2 nM, about 2.3 nM, about 2.4 nM, about 2.5 nM, about 2.6 nM, about 2.7 nM, about 2.8 µM, about 2.9 nM, about 3 nM, about 3.1 nM, about 3.2 nM, about 3.3 nM, about 3.4 nM, about 3.5 nM, about 3.6 nM, about 3.7 nM, about 3.8 nM, about 3.9 nM, about 4.0 nM, about 4.1 nM, about 4.2 nM, about 4.3 nM, about 4.4 nM, about 4.5 nM, about 4.6 nM, about 4.7 nM, about 4.8 µM, about 4.9 nM, or about 5 nM. In some examples, the method comprises contacting insulin-positive endocrine cells with a concentration of a protein kinase inhibitor (e.g., staurosporine), such as, about 1-5 nM, about 2-4 nM, or about 2.5-3.5 nM. In some examples, the method comprises contacting insulin-positive endocrine cells with a concentration of a protein kinase inhibitor (e.g., staurosporine), such as, about 3 nM.

In some embodiments, the method comprises contacting the population of cells (e.g., NKX6.1-positive, ISL1-positive, insulin-positive cells) with one or more metabolites. In some embodiments, the method comprises contacting the population of cells (e.g., NKX6.1-positive, ISL1-positive, insulin-positive cells) with one or more of an acetyl CoA-related metabolite, a vitamin, histone deacetylase inhibitor (HDACi), a redox homeostasis regulator, a one carbon metabolism pathway intermediate, glutamate, and/or carnitine. Examples of metabolites include taurine, acetate, beta-hydroxybutyrate, biotin, carnitine, glutamate, and formate.

In some embodiments, a composition (e.g., medium) of the disclosure comprises an acetyl CoA-related metabolite. Exemplary acetyl CoA-related metabolites include, but are not limited to acetate, pyruvate, ketogenic amino acids, valine, leucine, isoleucine, phenylalanine, tyrosine, lysine, tryptophan, fatty acids, CoA, Isovaleryl-CoA, and β-hydroxybutyrate. In some embodiments, the acetyl CoA-related metabolite is acetate. In some embodiments, the acetyl CoA-related metabolite is present in or is added to a composition of the disclosure at a concentration of about 10 nM, about 50 nM, about 80 nM, about 100 nM, about 120 nM, about 140 nM, about 150 nM, about 200 nM, about 300 nM, about 500 nM, about 800 nM, about 1 µM, about 10 µM, about 100 µM, about 500 µM, about 800 µM, about 900 µM, about 1 mM, about 2 mM, about 3 mM, about 5 mM, or about 10 mM. In some embodiments, the acetyl CoA-related metabolite is present in or is added to a composition of the disclosure at a concentration of about 0.01-50 mM, 0.1-50 mM, 0.5-50 mM, 0.01-20 mM, 0.1-20 mM, 0.5-20 mM, 0.01-10 mM, 0.1-10 mM, 0.5-10 mM, 0.8-25 mM, 0.8-10 mM, 0.8-5 mM, 0.8-2 mM, 0.8-1.5 mM, 0.8-1.2 mM, 0.9-1.1 mM, or 0.95-1.05 mM. In some embodiments, the acetyl CoA-related metabolite is acetate present at a concentration of about 1 mM. In some embodiments, the acetyl CoA-related metabolite is acetate present at a concentration of about 50-1000 nM, 50-800 nM, 50-500 nM, 50-300 nM, 50-250 nM, 100-200 nM, or 125-175 nM. In some embodiments, the acetyl CoA-related metabolite is acetate present at a concentration of about 160 nM.

In some embodiments, a composition (e.g., medium) of the disclosure comprises one or more vitamins. Exemplary vitamins include, but are not limited to biotin, vitamin B1 (thiamine), vitamin B2 (riboflavin), vitamin B3 (niacin), vitamin B6 (pyridoxine) and vitamin B12 (cyanocobalamin). In some embodiments the vitamin modulates fatty acid synthesis. In some embodiments the vitamin modulates branched-chain amino acid metabolism. In some embodiments the vitamin modulates or participates as a co-factor in the TCA cycle, e.g., as a cofactor for pyruvate carboxylase. In some embodiments, the vitamin is biotin. In some embodiments, the vitamin is present in or is added to a composition of the disclosure at a concentration of about 100 nM, about 300 nM, about 500 nM, about 600 nM, about 700 nM, about 800 nM, about 900 nM, about 1 µM, about 1.5 µM, about 3 µM, about 5 µM, about 10 µM, or about 100 µM. In some embodiments, the vitamin is biotin present at a concentration of about 800 nM. In some embodiments, the vitamin is present in or is added to a composition of the disclosure at a concentration of about 1 nM to 500 µM, 1 nM to 100 µM, 1 nM to 10 µM, 1 nM to 1 µM, 1 nM to 800 nM, 1 nM to 600 nM, 1 nM to 400 nM, 1 nM to 300 nM, 1 nM to 200 nM, 25 nM to 500 µM, 25 nM to 100 µM, 25 nM to 10 µM, 25 nM to 1 µM, 25 nM to 800 nM, 25 nM to 600 nM, 25 nM to 400 nM, 25 nM to 300 nM, 25 nM to 200 nM, 50 nM to 500 µM, 50 nM to 100 µM, 50 nM to 10 µM, 50 nM to 1 µM, 50 nM to 800 nM, 50 nM to 600 nM, 50 nM to 400 nM, 50 nM to 300 nM, 50 nM to 200 nM, 100 nM to 500 µM, 100 nM to 100 µM, 100 nM to 10 µM, 100 nM to 1 µM, 100 nM to 800 nM, 100 nM to 600 nM, 100 nM to 400 nM, 100 nM to 300 nM, or 100 nM to 200 nM.

In some embodiments, a composition (e.g., medium) of the disclosure comprises a histone deacetylase inhibitor (HDACi). Exemplary histone deacetylase inhibitors (HDACi) include, but are not limited to β-Hydroxybutyrate, butyric acid, class I HDACi, class IIA HDACi, class IIB HDACi, class III HDACi, class IV HDACi, HDAC-1, HDAC-2, HDAC-3, HDAC-4, HDAC-5, HDAC-6, HDAC-7, HDAC-8, HDAC-9, HDAC-10, HDAC-11, sirtuins, SIRT1, SIRT2, SIRT3, SIRT4, SIRT5, SIRT6, SIRT7, Vorinostat (suberoylanilide hydroxamic acid, SAHA, MK0683), Entinostat (MS-275, SNDX-275), Panobinostat (LBH589, NVP-LBH589), Trichostatin A (TSA), Mocetinostat (MGCD0103, MG0103), GSK3117391 (GSK3117391A, HDAC-IN-3), BRD3308, BRD3308, Tubastatin A TFA (Tubastatin A trifluoroacetate salt), Tubastatin A, SIS17, NKL 22, BML-210 (CAY10433), TC-H 106, SR-4370, Belinostat (PXD101, NSC726630, PX-105684), Romidepsin (FK228, Depsipeptide, FR 901228, NSC 630176), MC1568, Givinostat (ITF2357), Dacinostat (LAQ824, NVP-LAQ824), CUDC-101, Quisinostat (JNJ-26481585), Pracinostat (SB939), PCI-34051, Droxinostat (NS 41080), Abexinostat (PCI-24781), Abexinostat (PCI-24781, CRA-024781), RGFP966, AR-42 (HDAC-42), Ricolinostat (ACY-1215, Rocilinostat), Valproic acid sodium salt (Sodium valproate), Tacedinaline (CI994, PD-123654, GOE-5549, Acetyldinaline), Fimepinostat (CUDC-907), Sodium butyrate (NaB), Curcumin, Diferuloylmethane, M344, Tubacin, RG2833 (RGFP109), RG2833 (RGFP109), Resminostat (RAS2410), Divalproex Sodium, Scriptaid (GCK 1026), Sodium Phenylbutyrate, Sinapinic acid (Sinapic acid), TMP269, Santacruzamate A (CAY10683), TMP195 (TFMO 2), Valproic acid (VPA), UF010, Tasquinimod (ABR-215050), SKLB-23bb, Isoguanosine, Sulforaphane, BRD73954, Citarinostat (ACY-241, HDAC-IN-2), Suberohydroxamic acid, Splitomicin, HPOB, LMK-235, Biphenyl-4-sulfonyl chloride (p-Phenylbenzenesulfonyl, 4-Phenylbenzenesulfonyl, p-Biphenylsulfonyl), Nexturastat A, TH34, Tucidinostat (Chidamide, HBI-8000, CS-055), (−)-Parthenolide, WT161, CAY10603, CAY10603, ACY-738, Raddeanin A, Tinostamustine (EDO-S101), Domatinostat (4SC-202), and BG45. In some embodiments, the HDACi is β-Hydroxybutyrate. In some embodiments, the HDACi is present in or is added to a composition of the disclosure at a concentration of about 100 nM, about 300 nM, about 500 nM, about 600 nM, about 700 nM, about 800 nM, about 900 nM, about 1 µM, about 1.5 µM, about 3 µM, about 5 µM, about 10 µM, or about 100 µM. In some embodiments, the HDACi is β-Hydroxybutyrate present at a concentration of about 200 nM. In some embodiments, the HDACi is present in or is added to a composition of the disclosure at a concentration of about 1 nM to 500 µM, 1 nM to 100 µM, 1 nM to 10 µM, 1 nM to 1 µM, 1 nM to 800 nM, 1 nM to 600 nM, 1 nM to 400 nM, 1 nM to 300 nM, 1 nM to 200 nM, 25 nM to 500 µM, 25 nM to 100 µM, 25 nM to 10 µM, 25 nM to 1 µM, 25 nM to 800 nM, 25 nM to 600 nM, 25 nM to 400 nM, 25 nM to 300 nM, 25 nM to 200 nM, 50 nM to 500 µM, 50 nM to 100 µM, 50 nM to 10 µM, 50 nM to 1 µM, 50 nM to 800 nM, 50 nM to 600 nM, 50 nM to 400 nM, 50 nM to 300 nM, 50 nM to 200 nM, 100 nM to 500 µM, 100 nM to 100 µM, 100 nM to 10 µM, 100 nM to 1 µM, 100 nM to 800 nM, 100 nM to 600 nM, 100 nM to 400 nM, 100 nM to 300 nM, or 100 nM to 200 nM.

In some embodiments, a composition (e.g., medium) of the disclosure comprises a redox homeostasis regulator. Exemplary redox homeostasis regulators include, but are not limited to taurine, respiratory chain regulators, free radical scavengers, regulators of mitochondrial protein synthesis, allium sulphur compounds, anthocyanins, beta-carotene, catechins, copper, cryptoxanthins, flavonoids, indoles, isoflavonoids, lignans, lutein, lycopene, alpha lipoic acid, ellagic acid, manganese, polyphenols, selenium, glutathione, vitamin A, vitamin C, vitamin E, zinc, superoxide disutases, GSHPx, Prx-I, catalase, and co-enzyme Q10. In some embodiments, the redox homeostasis regulator is taurine. In some embodiments, the redox homeostasis regulator is present in or is added to a composition of the disclosure at a concentration of about 100 nM, about 500 nM, 1 µM, about 10 µM, about 20 µM, about 30 µM, about 40 µM, about 50 µM, about 60 µM, about 70 µM, about 80 µM, about 90 µM, about 100 µM, about 110 µM, about 110 µM, about 150 µM, or about 200 µM. In some embodiments, the redox homeostasis regulator is taurine. In some embodiments, the redox homeostasis regulator is taurine present at a concentration of about 90 µM. In some embodiments, the redox homeostasis regulator intermediate is present or is added at a concentration of about 100 nM to 1 mM, 500 nM to 1 mM, 1 µM to 1 mM, 10 µM to 1 mM, 20 µM to 1 mM, 30 µM to 1 mM, 30 µM to 1 mM, 40 µM to 1 mM, 50 µM to 1 mM, 60 µM to 1 mM, 70 µM to 1 mM, 80 µM to 1 mM, 100 nM to 250 µM, 500 nM to 250 µM, 1 µM to 250 µM, 10 µM to 250 µM, 20 µM to 250 µM, 30 µM to 250 µM, 30 µM to 250 µM, 40 µM to 250 µM, 50 µM to 250 µM, 60 µM to 250 µM, 70 µM to 250 µM, 100 nM to 100 µM, 500 nM to 100 µM, 1 µM to 100 µM, 10 µM to 100 µM, 20 µM to 100 µM, 30 µM to 100 µM, 40 µM to 100 µM, 50 µM to 100 µM, 60 µM to 100 µM, 70 µM to 100 µM, or 80 µM to 100 µM.

In some embodiments, a composition (e.g., medium) of the disclosure comprises a one carbon metabolism pathway intermediate. Exemplary one carbon metabolism pathway intermediates include, but are not limited to formate, tetrahydrofolate (THF), 10-formylTHF; 5,10-meTHF; 5,10-meTHF; and 10-formylTHF. In some embodiments, the one carbon metabolism pathway intermediate is formate present at a concentration of about 50 µM. In some embodiments, the one carbon metabolism pathway intermediate is present or is added at a concentration of about 100 nM to 1 mM, 500 nM to 1 mM, 1 µM to 1 mM, 10 µM to 1 mM, M to 1 mM, 30 µM to 1 mM, 100 nM to 250 µM, 500 nM to 250 µM, 1 µM to 250 µM, 10 µM to 250 µM, 20 µM to 250 µM, 30 µM to 250 µM, 100 nM to 100 µM, 500 nM to 100 µM, 1 µM to 100 µM, 10 µM to 100 µM, 20 µM to 100 µM, 30 µM to 100 µM, 100 nM to 60 µM, 500 nM to 60 µM, 1 µM to 60 µM, 10 µM to 60 µM, 20 µM to 60 µM, 30 µM to 60 µM, 40 µM to 60 µM, or 45 µM to 55 µM.

In some embodiments, a composition (e.g., medium) of the disclosure comprises glutamate (e.g., L-glutamate). In some embodiments, glutamate can be present in a composition of the disclosure at a concentration of about 100 µM, about 200 µM, about 300 µM, about 400 µM, about 450 µM, about 500 µM, about 550 µM, about 600 µM, about 700 µM, about 800 µM, about 900 µM, about 1 mM, about 1.5 mM, about 2 mM, about 2.5 mM, about 3 mM, about 4 mM, or about 5 mM. In some embodiments, glutamate is present or is added to a composition of the disclosure at a concentration of about 500 µM. In some embodiments, glutamate is present or is added to a composition of the disclosure at a concentration of from about 100 µM to 5 mM, 200 µM to 5 mM, 300 µM to 5 mM, 400 µM to 5 mM, 100 µM to 3 mM, 200 µM to 3 mM, 300 µM to 3 mM, 400 µM to 3 mM, 100 µM to 2 mM, 200 µM to 2 mM, 300 µM to 2 mM, 400 µM to 2 mM, 100 µM to 1 mM, 200 µM to 1 mM, 300 µM to 1 mM, 400 µM to 1 mM, 100 µM to 700 µM, 200 µM to 700 µM, 300 µM to 700 µM, 400 µM to 700 µM, 100 µM to 600 µM, 200 µM to 600 µM, 300 µM to 600 µM, or 400 µM to 600 µM.

In some embodiments, a composition (e.g., medium) of the disclosure comprises carnitine. In some embodiments, carnitine is present in or is added to a composition of the disclosure at a concentration of about 100 nM, about 500 nM, about 1 µM, about 10 µM, about M, about 20 µM, about 25 µM, about 30 µM, about 35 µM, about 40 µM, about 45 µM, about 50 µM, about 55 µM, about 60 µM, about 75 µM, or about 100 µM. In some embodiments, carnitine is present or is added at a concentration of about 40 µM. In some embodiments, carnitine is present in or is added to a composition of the disclosure at a concentration of about 100 nM to 1 mM, 500 nM to 1 mM, 1 µM to 1 mM, 10 µM to 1 mM, 20 µM to 1 mM, 30 µM to 1 mM, 100 nM to 250 µM, 500 nM to 250 µM, 1 µM to 250 µM, 10 µM to 250 µM, 20 µM to 250 µM, 30 µM to 250 µM, 100 nM to 100 µM, 500 nM to 100 µM, 1 µM to 100 µM, 10 µM to 100 µM, 20 µM to 100 µM, 30 µM to 100 µM, 100 nM to 60 µM, 500 nM to 60 µM, 1 µM to 60 µM, 10 µM to 60 µM, 20 µM to 60 µM, 30 µM to 60 µM, 35 µM to 60 µM, or 30 µM to 50 µM.

In some embodiments, the method comprises contacting the population of cells (e.g., NKX6.1-positive, ISL1-positive, insulin-positive cells) with a serum albumin protein (e.g., HSA). In some embodiments, the serum albumin is present at a concentration of 0.01-2% HSA. In some embodiments, the serum albumin is present at a concentration of 0.03-0.1%, 0.03-0.07%, or 0.04-0.05%. In some embodiments, the serum albumin is present at a concentration of 0.05%. In some embodiments, the serum albumin is present at a concentration of 0.7-1.3%, 0.8-1.2%, 0.9-1.1% or at 1%. In some embodiments, the serum albumin is present at a concentration of 1%.

In some embodiments, the method comprises contacting the population of cells (e.g., NKX6.1-positive, ISL1-positive, insulin-positive cells) with $ZnSO_4$. In some embodiments, the method comprises contacting the cells with 1-100 µM, 1-50 µM, 1-20 µM, 1-12 µM, 5-15 µM, 8-12 µM or 9-11 µM of $ZnSO_4$. In some embodiments, the method comprises contacting the cells with about 10 µM of $ZnSO_4$.

In some embodiments, the method comprises contacting the population of cells (e.g., NKX6.1-positive, ISL1-positive, insulin-positive cells) with one or more of an a serum albumin protein, a TGF-β signaling pathway inhibitor, a TH signaling pathway activator, a protein kinase inhibitor, a ROCK inhibitor, a BMP signaling pathway inhibitor, an epigenetic modifying compound, acetyl CoA-related metabolite, a vitamin, histone deacetylase inhibitor (HDACi), a redox homeostasis regulator, a one carbon metabolism pathway intermediate, glutamate, and/or carnitine for a first period of 1, 2, 3, 4, 5, 6, or 7 days (e.g., 4 days). In some embodiments, the method further comprises contacting the population of cells following the first period with one or more of a serum albumin protein, an acetyl CoA-related metabolite, a vitamin, histone deacetylase inhibitor (HDACi), a redox homeostasis regulator, a one carbon metabolism pathway intermediate, glutamate, and/or carnitine for a second period of 1, 2, 3, 4, 5, 6, or 7 days (e.g., 3 days) or more in the absence of a TGF-β signaling pathway inhibitor, a TH signaling pathway activator, a protein kinase inhibitor, a ROCK inhibitor, a BMP signaling pathway inhibitor, and/or an epigenetic modifying compound. In some embodiments, the cells are contacted with a higher concentration of the serum albumin in the second period as compared to the first period. In some embodiments, the compositions further comprise $ZnSO_4$. In some embodiments, the method further comprises contacting the population of cells following the first period with human serum albumin, but in the absence of a TGF-β signaling pathway inhibitor, a TH signaling pathway activator, a protein kinase inhibitor, a ROCK inhibitor, a BMP signaling pathway inhibitor, an epigenetic modifying compound, an acetyl CoA-related metabolite, a vitamin, histone deacetylase inhibitor (HDACi), a redox homeostasis regulator, a one carbon metabolism pathway intermediate, glutamate, and/or carnitine.

In some embodiments, the method comprises contacting the population of cells (e.g., NKX6.1-positive, ISL1-positive, insulin-positive cells) with one or more of HSA, Alk5 inhibitor II, GC-1, staurosporine, thiazovivin, LDN193189, DZNEP, taurine, acetate, beta-hydroxybutyrate, biotin, carnitine, glutamate, and formate for a first period of 1, 2, 3, 4, 5, 6, or 7 days (e.g., 4 days). In some embodiments, the method further comprises contacting the population of cells following the first period with one or more of HSA, taurine, acetate, beta-hydroxybutyrate, biotin, carnitine, glutamate, and formate for a second period of 1, 2, 3, 4, 5, 6, or 7 days (e.g., 3 days) or more in the absence of an Alk5 inhibitor II, GC-1, staurosporine, thiazovivin, LDN193189, DZNEP. In some embodiments, the compositions further comprise $ZnSO_4$. In some embodiments, the cells are contacted with a higher concentration of the HSA (e.g., about 1.0%) in the second period as compared to the first period (e.g., about 0.05%).

In some examples, insulin-positive endocrine cells can be matured in a NS-GFs medium, MCDB131 medium, DMEM medium, or CMRL medium. In some embodiments, the insulin-positive endocrine cells can be matured in a CMRL medium supplemented with 10% FBS. In some embodiments, the insulin-positive endocrine cells can be matured in a DMEM/F12 medium supplemented with 1% HSA. In other cases, SC-β cells can be obtained by culturing the population of cells containing the insulin-positive endocrine cells in a MCDB131 medium that can be supplemented by 2% BSA. In some embodiments, the MCDB131 medium with 2% BSA for maturation of insulin-positive endocrine cells into SC-β cells can be comprise no small molecule factors as described herein. In some case, the MCDB131 medium with 2% BSA for maturation of insulin-positive endocrine cells into SC-β cells can comprise no serum (e.g., no FBS). In other cases, SC-β cells can be obtained by culturing the population of cells containing the insulin-positive endocrine cells in a MCDB131 medium that can be supplemented by 0.05% HSA and vitamin C. In some embodiments, SC-β cells can be obtained by culturing the population of cells containing the insulin-positive endocrine cells in a MCDB131 medium that can be supplemented by 0.05% HSA, ITS-X, vitamin C, and glutamine (Gln, e.g., 4 mM). In some embodiments, the type of culture medium may be changed during S6. For instance, the S6 cells are cultured in a MCDB131 medium that can be supplemented by 0.05% HSA and vitamin C for the first two to four days, and then followed by a DMEM/F12 medium supplemented with 1% HSA. In some embodiments, additional factors are introduced into the culture medium. For instance, S6 cells can be cultured in a MCDB131 medium that can be supplemented by 0.05% HSA, ITS-X, vitamin C, and glutamine (Gln, e.g., 4 mM) throughout the 10-12 days, during which $ZnSO_4$ is introduced from day 4 of S6.

In some embodiments, the medium used to culture the cells as described herein can be xeno-free. A xeno-free medium for culturing cells and/or cell clusters of originated from an animal can have no product from other animals. In some embodiments, a xeno-free medium for culturing human cells and/or cell clusters can have no products from any non-human animals. For example, a xeno-free medium for culturing human cells and/or cell clusters can comprise human platelet lysate (PLT) instead of fetal bovine serum (FBS). For example, a medium can comprise from about 1% to about 20%, from about 5% to about 15%, from about 8% to about 12%, from about 9 to about 11% serum. In some embodiments, medium can comprise about 10% of serum. In some embodiments, the medium can be free of small molecules and/or FBS. For example, a medium can comprise MCDB131 basal medium supplemented with 2% BSA. In some embodiments, the medium is serum-free. In some examples, a medium can comprise no exogenous small molecules or signaling pathway agonists or antagonists, such as, growth factor from fibroblast growth factor family (FGF, such as FGF2, FGF8B, FGF 10, or FGF21), Sonic Hedgehog Antagonist (such as Sant1, Sant2, Sant4, Sant4, Cur61414, forskolin, tomatidine, AY9944, triparanol, cyclopamine, or derivatives thereof), Retinoic Acid Signaling agonist (e.g., retinoic acid, CD1530, AM580, TTHPB, CD437, Ch55, BMS961, AC261066, AC55649, AM80, BMS753, tazarotene, adapalene, or CD2314), inhibitor of Rho-associated, coiled-coil containing protein kinase (ROCK) (e.g., Thiazovivin, Y-27632, Fasudil/HA1077, or 14-1152), activator of protein kinase C (PKC) (e.g., phorbol 12,13-dibutyrate (PDBU), TPB, phorbol 12-myristate 13-acetate, bryostatin 1, or derivatives thereof), antagonist of TGF R super family (e.g., Alk5 inhibitor II (CAS 446859-33-2), A83-01, SB431542, D4476, GW788388, LY364947, LY580276, SB505124, GW6604, SB-525334, SD-208, SB-505124, or derivatives thereof), inhibitor of Bone Morphogenetic Protein (BMP) type 1 receptor (e.g., LDN193189 or derivatives thereof), thyroid hormone signaling pathway activator (e.g., T3, GC-1 or derivatives thereof), gamma-secretase inhibitor (e.g., XXI, DAPT, or derivatives thereof), activator of TGF-β signaling pathway (e.g., WNT3a or Activin A) growth factor from epidermal growth factor (EGF) family (e.g., betacellulin or EGF), broad kinase (e.g., staurosporine or derivatives thereof), non-essential amino acids, vitamins or antioxidants (e.g., cyclopamine, vitamin D, vitamin C, vitamin A, or derivatives thereof), or other additions like N-acetyl cysteine, zinc sulfate, or heparin. In some embodiments, the reaggregation medium can comprise no exogenous extracellular matrix molecule. In some embodiments, the reaggregation medium does not comprise Matrigel™. In some embodiments, the reaggregation medium does not comprise other extracellular matrix molecules or materials, such as, collagen, gelatin, poly-L-lysine, poly-D-lysine, vitronectin, laminin, fibronectin, PLO laminin, fibrin, thrombin, and RetroNectin and mixtures thereof, for example, or lysed cell membrane preparations.

A person of ordinary skill in the art will appreciate that the concentration of serum albumin supplemented into the medium may vary. For example, a medium (e.g., MCDB131) can comprise about 0.01%, 0.05%, 0.1%, 1%, about 2%, about 3%, about 4%, about 5%, about 10%, or about 15% BSA. In other cases, a medium can comprise about 0.01%, 0.05%, 0.1%, 1%, about 2%, about 3%, about 4%, about 5%, about 10%, or about 15% HSA. The medium used (e.g., MCDB131 medium) can contain components not found in traditional basal media, such as trace elements, putrescine, adenine, thymidine, and higher levels of some amino acids and vitamins. These additions can allow the medium to be supplemented with very low levels of serum or defined components. The medium can be free of proteins and/or growth factors, and may be supplemented with EGF, hydrocortisone, and/or glutamine. The medium can comprise one or more extracellular matrix molecules (e.g., extracellular proteins). Non-limiting exemplary extracellular matrix molecules used in the medium can include collagen, placental matrix, fibronectin, laminin, merosin, tenascin, heparin, heparin sulfate, chondroitin sulfate, dermatan sulfate, aggrecan, biglycan, thrombospondin, vitronectin, and decorin. In some embodiments, the medium comprises laminin, such as LN-332. In some embodiments, the medium comprises heparin.

The medium can be changed periodically in the culture, e.g., to provide optimal environment for the cells in the medium. When culturing the cells dissociated from the first cell cluster for re-aggregation, the medium can be changed at least or about every 4 hours, 12 hours, 24 hours, 48 hours, 3 days or 4 days. For example, the medium can be changed about every 48 hours.

In some embodiments, cells can be cultured under dynamic conditions (e.g., under conditions in which the cells are subject to constant movement or stirring while in the suspension culture). For dynamic culturing of cells, the cells can be cultured in a container (e.g., an non-adhesive container such as a spinner flask (e.g., of 200 ml to 3000 ml, for example 250 ml; of 100 ml; or in 125 ml Erlenmeyer), which can be connected to a control unit and thus present a controlled culturing system. Alternatively, the cells can be cultured in a bioreactor. In some embodiments, cells can be cultured under non-dynamic conditions (e.g., a static culture) while preserving their proliferative capacity. For non-dynamic culturing of cells, the cells can be cultured in an adherent culture vessel. An adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations.

Medium in a dynamic cell culture vessel (e.g., a spinner flask or bioreactor) can be stirred (e.g., by a stirrer). The spinning speed can correlate with the size of the re-aggregated second cell cluster. The spinning speed can be controlled so that the size of the second cell cluster can be similar to an endogenous pancreatic islet. In some embodiments, the spinning speed is controlled so that the size of the second cell cluster can be from about 75 μm to about 250 μm. The spinning speed of a dynamic cell culture vessel (e.g., a spinner flask or bioreactor) can be about 20 rounds per minute (rpm) to about 100 rpm, e.g., from about 30 rpm to about 90 rpm, from about 40 rpm to about 60 rpm, from about 45 rpm to about 50 rpm. In some embodiments, the spinning speed can be about 50 rpm.

Stage 6 cells as provided herein may or may not be subject to the dissociation and reaggregation process as described herein. In some embodiments, the cell cluster comprising the insulin-positive endocrine cells can be reaggregated. The reaggregation of the cell cluster can enrich the insulin-positive endocrine cells. In some embodiments, the insulin-positive endocrine cells in the cell cluster can be further matured into pancreatic β cells. For example, after reaggregation, the second cell cluster can exhibit in vitro GSIS, resembling native pancreatic islet. For example, after reaggregation, the second cell cluster can comprise non-native pancreatic β cell that exhibits in vitro GSIS. In some embodiments, the reaggregation process can be performed according to the disclosure of PCT application PCT/US2018/043179, which is incorporated herein by reference in its entirety.

Stage 6 cells obtained according to methods provided herein can have high recovery yield after cryopreservation and reaggregation procedures. In some embodiments, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without such treatment. In some embodiments, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without treatment of a BMP signaling pathway inhibitor (e.g., DMH-1 or LDN) and a growth factor from TGF-β superfamily (e.g., Activin A) at stage 3. In some embodiments, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a recovery yield after cryopreservation post stage 5 that is at least about 35%, 37.5%, 40%, 42.5%, 45%, 47.5%, 48%, 49%, or 50%. The recovery yield can be calculated as a percentage of cells that survive and form reaggregated cell clusters after cryopreservation, thawing and recovery, and reaggregation procedures, as compared to the cells before the cryopreservation.

In some embodiments, the present disclosure relates to cryopreservation of the non-native pancreatic β cells or precursors thereof obtained using the methods provided herein. In particular embodiments, the cells are cryopreserved following stage 5 and before stage 6. In some embodiments, the cell population comprising non-native pancreatic β cells can be stored via cryopreservation. For instances, the cell population comprising non-native β cells, e.g., Stage 6 cells are thawed. In some embodiments, the cells can be dissociated into cell suspension, e.g., single cell suspension, and the cell suspension can be cryopreserved, e.g., frozen in a cryopreservation solution. The dissociation of the cells can be conducted by any of the technique provided herein, for example, by enzymatic treatment. The cells can be frozen at a temperature of at highest −20° C., at highest −30° C., at highest −40° C., at highest −50° C., at highest −60° C., at highest −70° C., at highest −80° C., at highest −90° C., at highest −100° C., at highest −110° C., at highest −120° C., at highest −130° C., at highest −140° C., at highest −150° C., at highest −160° C., at highest −170° C., at highest −180° C., at highest −190° C., or at highest −200° C. In some embodiments, the cells are frozen at a temperature of about −80° C. In some embodiments, the cells are frozen at a temperature of about −195° C. Any cooling methods can be used for providing the low temperature needed for cryopreservation, such as, but not limited to, electric freezer, solid carbon dioxide, and liquid nitrogen. In some embodiments, any cryopreservation solution available to one skilled in the art can be used for incubating the cells for storage at low temperature, including both custom made and commercial solutions. For example, a solution containing a cryoprotectant can be used. The cryoprotectant can be an agent that is configured to protect the cell from freezing damage. For instance, a cryoprotectant can be a substance that can lower the glass transition temperature of the cryopreservation solution. Exemplary cryoprotectants that can be used include DMSO (dimethyl sulfoxide), glycols (e.g., ethylene glycol, propylene glycol and glycerol), dextran (e.g., dextran-40), and trehalose. Additional agents can be added in to the cryopreservation solution for other effects. In some embodiments, commercially available cryopreservation solutions can be used in the method provided herein, for instance, FrostaLife™, pZerve™, Prime-XV®, Gibco Synth-a-Freeze Cryopreservation Medium, STEM-CELL-BANKER®, CryoStor® Freezing Media, HypoThermosol® FRS Preservation Media, and CryoDefend® Stem Cells Media.

During the differentiation process, the cells can be subject to irradiation treatment as provided herein. In some embodiments, the cell population at Stage 6, e.g., the cell population or cell cluster that has cells being differentiated from insulin-positive endocrine cells into pancreatic β cells, is irradiated for a period of time. In some embodiments, the cell population at Stage 6 after reaggregation following the recovery from cryopreservation is irradiated for a period of time. In some embodiments, the cryopreserved cells (e.g., the cells that are cryopreserved at the end of Stage 5) are irradiated for a certain period of time prior to thawing and recovery for subsequent differentiation process.

In some embodiments, the stage 6 cells comprise NKX6.1-positive, insulin-positive cells. In some embodiments, the stage 6 cells comprise NKX6.1-positive, insulin-negative cells. In some embodiments, the stage 6 cells comprise C-peptide positive cells. In some embodiments, Stage 6 cells or cells that have characteristics of stage 6 cells are incubated in NS-GFs medium, MCDB131 medium, DMEM medium, or CMRL medium. In some embodiments, the stage 6 cells or cells that have characteristics of stage 6 cells are contacted with any one or more of a vitamin or anti-oxidant (e.g., vitamin C), an albumin protein (e.g., a human serum albumin protein), a TGF-beta pathway inhibitor (e.g., an ALK5 inhibitor II), a bone morphogenic protein (BMP) type 1 receptor inhibitor (e.g., LDN193189), a Rho-associated coiled-coil containing protein kinase (ROCK) inhibitor (e.g., thiazovivin), a histone methyltransferase inhibitor (e.g., DZNEP), and a protein kinase inhibitor (e.g., staurosporine). See, e.g., WO2020264072. In some embodiments, the stage 6 cells are contacted with a PKC activator (see, e.g., WO2019217487, which is incorporated by reference herein in its entirety).

Differentiation Factors

Aspects of the disclosure relate to contacting progenitor cells (e.g., stem cells, e.g., iPS cells, definitive endoderm cells, primitive gut tube cells, PDX1-positive pancreatic progenitor cells, NKX6.1-positive pancreatic progenitor cells, insulin-positive endocrine cells) with β cell differentiation factors, for example, to induce the maturation of the insulin-positive endocrine cells or differentiation of other progenitor cells into SC-β cells (e.g., mature pancreatic β cells). In some embodiments, the differentiation factor can induce the differentiation of pluripotent cells (e.g., iPSCs or hESCs) into definitive endoderm cells, e.g., in accordance with a method described herein. In some embodiments, the differentiation factor can induce the differentiation of definitive endoderm cells into primitive gut tube cells, e.g., in accordance with a method described herein. In some embodiments, the differentiation factor(s) can induce the differentiation of primitive gut tube cells into PDX1-positive pancreatic progenitor cells, e.g., in accordance with a method described herein. In some embodiments, the differentiation factor(s) can induce the differentiation of PDX1-positive pancreatic progenitor cells into NKX6-1-positive pancreatic progenitor cells, e.g., in accordance with a method described herein. In some embodiments, the differentiation factor(s) can induce the differentiation of NKX6-1-positive pancreatic progenitor cells into insulin-positive endocrine cells, e.g., in accordance with a method described herein. In some embodiments, the differentiation factor(s) can induce the maturation of insulin-positive endocrine cells into pancreatic islet cells, e.g., in accordance with a method described herein.

At least one differentiation factor described herein can be used alone, or in combination with other differentiation actors, to generate pancreatic islet cells (e.g., SC-beta cells) according to the methods as disclosed herein. In some embodiments, at least two, at least three, at least four, at least five, at least six, at least seven, at least eight, at least nine, or at least ten differentiation factors described herein are used in the methods of generating pancreatic islet cells.

In some embodiments, a composition described herein does not comprise one or more of the differentiation factors provided herein.

Forkhead Box O1 (FoxO1) Inhibitor

Aspects of the disclosure relate to the use of Forkhead Box O1 (FoxO1) inhibitors as differentiation factors. In some embodiments, the FoxO1 inhibitor used in the compositions and methods described herein is a compound of Formula (I):

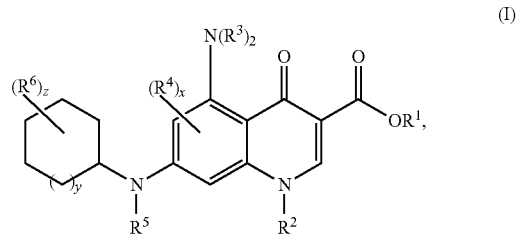

or a pharmaceutically acceptable salt, solvate, hydrate, polymorph, co-crystal, tautomer, stereoisomer, isotopically labeled derivative, prodrug, composition, or mixture thereof, wherein:

$R^1$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^2$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^3$ is independently optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^3$ are taken together with their intervening atoms to form a substituted or unsubstituted heterocyclic or substituted or unsubstituted heteroaryl ring;

each instance of $R^4$ is independently halogen, optionally substituted acyl, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, $-OR^{c1}$, $-NO_2$, $-N(R^{c2})_2$, $-SR^{c1}$, $-CN$, or $-SCN$;

R⁵ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R⁶ is independently halogen, optionally substituted acyl, optionally substituted alkyl, optionally substituted heteroalkyl, optionally substituted alkenyl, optionally substituted alkynyl, optionally substituted carbocyclyl, optionally substituted heterocyclyl, optionally substituted aryl, optionally substituted heteroaryl, —OR$^{c1}$, —NO₂, —N(R$^{c2}$), —SR$^{c1}$, —CN, or —SCN;

wherein R$^{c1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

wherein each instance of R$^{c2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of R² are taken together with their intervening atoms to form a substituted or unsubstituted heterocyclic or substituted or unsubstituted heteroaryl ring;

x is 0, 1, or 2;
y is 0 or 1; and
z is 0, 1, 2, 3, 4, 5, 6, 7, 8, 9, or 10, as valency permits.

In some embodiments, the compound is of Formula (I-A):

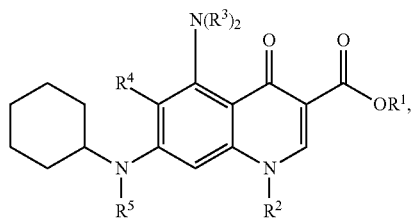

(I-A)

or a pharmaceutically acceptable salt, solvate, hydrate, polymorph, co-crystal, tautomer, stereoisomer, isotopically labeled derivative, prodrug, composition, or mixture thereof, wherein:

R¹ is hydrogen, optionally substituted alkyl, optionally substituted alkenyl, or optionally substituted alkynyl;

R² is hydrogen, optionally substituted alkyl, optionally substituted alkenyl, or optionally substituted alkynyl;

each instance of R³ is independently hydrogen, optionally substituted alkyl, optionally substituted alkenyl, or optionally substituted alkynyl;

R⁴ is halogen, optionally substituted acyl, optionally substituted alkyl, optionally substituted heteroalkyl, optionally substituted alkenyl; and R⁵ is hydrogen, optionally substituted alkyl, optionally substituted alkenyl, or optionally substituted alkynyl.

In some embodiments, R¹ is hydrogen. In some embodiments, R² is optionally substituted alkyl. In some embodiments, R² is ethyl. In some embodiments, at least one instance of R³ is hydrogen. In some embodiments, both instances of R³ are hydrogen. In some embodiments, at least one instance of R⁴ is halogen. In some embodiments, at least one instance of R⁴ is fluorine. In some embodiments, x is 1. In some embodiments, R⁵ is hydrogen. In some embodiments, y is 1. In some embodiments, z is 0.

In some embodiments, the compound is of formula:

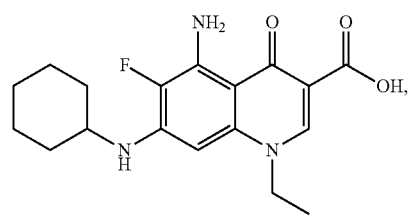

(AS1842856)

or a pharmaceutically acceptable salt, solvate, hydrate, polymorph, co-crystal, tautomer, stereoisomer, isotopically labeled derivative, prodrug, composition, or mixture thereof.

In some embodiments, the compound is AS1842856.

In some embodiments, a medium described herein does not comprise a FoxO1 inhibitor.

Transforming Growth Factor-β (TGF-β) Superfamily

Aspects of the disclosure relate to the use of growth factors from the transforming growth factor-β (TGF-β) superfamily as differentiation factors. The "TGF-β superfamily" means proteins having structural and functional characteristics of known TGFβ family members. The TGFβ family of proteins can include the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins can be based on specific binding to certain receptors on various cell types. Members of this family can share regions of sequence identity, particularly at the C-terminus, that correlate to their function. The TGFβ family can include more than one hundred distinct proteins, all sharing at least one region of amino acid sequence identity. Members of the family that can be used in the method disclosed herein can include, but are not limited to, the following proteins, as identified by their GenBank accession numbers: P07995, P18331, P08476, Q04998, P03970, P43032, P55102, P27092, P42917, P09529, P27093, P04088, Q04999, P17491, P55104, Q9WUK5, P55103, O88959, O08717, P58166, O61643, P35621, P09534, P48970, Q9NR23, P25703, P30884, P12643, P49001, P21274, O46564, O19006, P22004, P20722, Q04906, Q07104, P30886, P18075, P23359, P22003, P34821, P49003, Q90751, P21275, Q06826, P30885, P34820, Q29607, P12644, Q90752, O46576, P27539, P48969, Q26974, P07713, P91706, P91699, P27091, O42222, Q24735, P20863, O18828, P55106, Q9PTQ2, 014793, O08689, O42221, O18830, O18831, O18836, O35312, O42220, P43026, P43027, P43029, O95390, Q9R229, O93449, Q9Z1W4, Q9BDW8, P43028, Q7Z4P5, P50414, P17246, P54831, P04202, P01137, P09533, P18341, 019011, Q9Z1Y6, P07200, Q9Z217, O95393, P55105, P30371, Q9MZE2, Q07258, Q96S42, P97737, AAA97415.1, NP-776788.1, NP-058824.1, EAL24001.1, 1 S4Y, NP-001009856.1, NP-1-032406.1, NP-999193.1, XP-519063.1, AAG17260.1, CAA40806.1, NP-1-001009458.1, AAQ55808.1, AAK40341.1, AAP33019.1, AAK21265.1, AAC59738.1, CA146003.1, B40905, AAQ55811.1, AAK40342.1, XP-540364.1, P55102, AAQ55810.1, NP-990727.1, CAA51163.1, AAD50448.1, JC4862, PN0504, BAB17600.1, AAH56742.1, BAB17596.1, CAG06183.1, CAG05339.1, BAB17601.1, CAB43091.1, A36192, AAA49162.1, AAT42200.1, NP-789822.1, AAA59451.1, AAA59169.1, XP-541000.1, NP-990537.1, NP-1-002184.1, AAC14187.1, AAP83319.1, AAA59170.1, BAB16973.1, AAM66766.1, WFPGBB, 1201278C, AAH30029.1, CAA49326.1, XP-344131.1, AA-148845.1, XP-1-148966.3, 148235, B41398, AAH77857.1, AAB26863.1, 1706327A, BAA83804.1, NP-571143.1, CAG00858.1, BAB17599.1, BAB17602.1, AAB61468.1, PN0505, PN0506, CAB43092.1, BAB17598.1, BAA22570.1, BAB16972.1, BAC81672.1, BAA12694.1, BAA08494.1, B36192, C36192, BAB16971.1, NP-034695.1, AAA49160.1, CAA62347.1, AAA49161.1, AAD30132.1, CAA58290.1, NP-005529.1, XP-522443.1, AAM27448.1, XP-538247.1, AAD30133.1, AAC36741.1, AAH10404.1, NP-032408.1, AAN03682.1, XP-509161.1, AAC32311.1, NP-651942.2, AAL51005.1, AAC39083.1, AAH85547.1, NP-571023.1, CAF94113.1, EAL29247.1, AAW30007.1, AAH90232.1, A29619, NP-001007905.1, AAH73508.1, AADO2201.1, NP-999793.1, NP-990542.1, AAF19841.1, AAC97488.1, AAC60038.1, NP 989197.1, NP-571434.1, EAL41229.1, AAT07302.1, CA119472.1, NP-031582.1, AAA40548.1, XP-535880.1, NP-1-037239.1, AAT72007.1, XP-418956.1, CAA41634.1, BAC30864.1, CAA38850.1, CAB81657.2, CAA45018.1, CAA45019.1, BAC28247.1, NP-031581.1, NP-990479.1, NP-999820.1, AAB27335.1, S45355, CAB82007.1, XP-534351.1, NP-058874.1, NP-031579.1, 1REW, AAB96785.1, AAB46367.1, CAA05033.1, BAA89012.1, IES7, AAP20870.1, BAC24087.1, AAG09784.1, BAC06352.1, AAQ89234.1, AAM27000.1, AAH30959.1, CAGO1491.1, NP-571435.1, 1REU, AAC60286.1, BAA24406.1, A36193, AAH55959.1, AAH54647.1, AAH90689.1, CAG09422.1, BAD16743.1, NP-032134.1, XP-532179.1, AAB24876.1, AAH57702.1, AAA82616.1, CAA40222.1, CAB90273.2, XP-342592.1, XP-534896.1, XP-534462.1, 1LXI, XP-417496.1, AAF34179.1, AAL73188.1, CAF96266.1, AAB34226.1, AAB33846.1, AAT12415.1, AA033819.1, AAT72008.1, AAD38402.1, BAB68396.1, CAA45021.1, AAB27337.1, AAP69917.1, AAT12416.1, NP-571396.1, CAA53513.1, AA033820.1, AAA48568.1, BAC02605.1, BAC02604.1, BAC02603.1, BAC02602.1, BAC02601.1, BAC02599.1, BAC02598.1, BAC02597.1, BAC02595.1, BAC02593.1, BAC02592.1, BAC02590.1, AAD28039.1, AAP74560.1, AAB94786.1, NP-001483.2, XP-528195.1, NP-571417.1, NP-001001557.1, AAH43222.1, AAM33143.1, CAG10381.1, BAA31132.1, EAL39680.1, EAA12482.2, P34820, AAP88972.1, AAP74559.1, CA116418.1, AAD30538.1, XP-345502.1, NP-1-038554.1, CAG04089.1, CAD60936.2, NP-031584.1, B55452, AAC60285.1, BAA06410.1, AAH52846.1, NP-031580.1, NP-1-036959.1, CAA45836.1, CAA45020.1, Q29607, AAB27336.1, XP-547817.1, AAT12414.1, AAM54049.1, AAH78901.1, AA025745.1, NP-570912.1, XP-392194.1, AAD20829.1, AAC97113.1, AAC61694.1, AAH60340.1, AAR97906.1, BAA32227.1, BAB68395.1, BAC02895.1, AAWS 1451.1, AAF82188.1, XP-544189.1, NP-990568.1, BAC80211.1, AAW82620.1, AAF99597.1, NP-571062.1, CAC44179.1, AAB97467.1, AAT99303.1, AAD28038.1, AAH52168.1, NP-001004122.1, CAA72733.1, NP-032133.2, XP-394252.1, XP-224733.2, JH0801, AAP97721.1, NP-989669.1, S43296, P43029, A55452, AAH32495.1, XP-542974.1, NP-032135.1, AAK30842.1, AAK27794.1, BAC30847.1, EAA12064.2, AAP97720.1, XP-525704.1, AAT07301.1, BAD07014.1, CAF94356.1, AAR27581.1, AAG13400.1, AAC60127.1, CAF92055.1, XP-540103.1, AA020895.1, CAF97447.1, AAS01764.1, BAD08319.1, CAA10268.1, NP-998140.1, AAR03824.1, AAS48405.1, AAS48403.1, AAK53545.1, AAK84666.1, XP-395420.1, AAK56941.1, AAC47555.1, AAR88255.1, EAL33036.1, AAW47740.1, AAW29442.1, NP-722813.1, AARO8901.1, AAO 15420.2, CAC59700.1, AAL26886.1, AAK71708.1, AAK71707.1, CAC51427.2, AAK67984.1, AAK67983.1, AAK28706.1, P07713, P91706, P91699, CAG02450.1, AAC47552.1, NP-005802.1, XP-343149.1, AW34055.1, XP-538221.1, AAR27580.1, XP-125935.3, AAF21633.1, AAF21630.1, AAD05267.1, Q9Z1 W4, NP-1-031585.2, NP-571094.1, CAD43439.1, CAF99217.1, CAB63584.1, NP-722840.1, CAE46407.1, XP-1-417667.1, BAC53989.1, BAB19659.1, AAM46922.1, AAA81169.1, AAK28707.1, AAL05943.1, AAB17573.1, CAH25443.1, CAG10269.1, BAD16731.1, EAA00276.2, AAT07320.1, AAT07300.1, AAN15037.1, CAH25442.1, AAK08152.2, 2009388A, AAR12161.1, CAGO1961.1, CAB63656.1, CAD67714.1, CAF94162.1, NP-477340.1, EAL24792.1, NP-1-001009428.1, AAB86686.1, AAT40572.1, AAT40571.1, AAT40569.1, NP-033886.1, AAB49985.1, AAG39266.1, Q26974, AAC77461.1, AAC47262.1, BAC05509.1, NP-055297.1, XP-546146.1, XP-525772.1, NP-060525.2, AAH33585.1, AAH69080.1, CAG12751.1, AAH74757.2, NP-034964.1, NP-038639.1, 042221, AAF02773.1, NP-062024.1, AAR18244.1, AAR14343.1, XP-228285.2, AAT40573.1, AAT94456.1, AAL35278.1, AAL35277.1, AAL17640.1, AAC08035.1, AAB86692.1, CAB40844.1, BAC38637.1, BAB16046.1, AAN63522.1, NP-571041.1, AAB04986.2, AAC26791.1, AAB95254.1, BAA11835.1, AAR18246.1, XP-538528.1, BAA31853.1, AAK18000.1, XP-1-420540.1, AAL35276.1, AAQ98602.1, CAE71944.1, AAW50585.1, AAV63982.1, AAW29941.1, AAN87890.1, AAT40568.1, CAD57730.1, AAB81508.1, AAS00534.1, AAC59736.1, BAB79498.1, AAA97392.1, AAP85526.1, NP-999600.2, NP-878293.1, BAC82629.1, CAC60268.1, CAG04919.1, AAN10123.1, CAA07707.1 AAK20912.1, AAR88254.1, CAC34629.1, AAL35275.1, AAD46997.1, AAN03842.1, NP-571951.2, CAC50881.1, AAL99367.1, AAL49502.1, AAB71839.1, AAB65415.1, NP-624359.1, NP-990153.1, AAF78069.1, AAK49790.1, NP-919367.2, NP-001192.1, XP-544948.1, AAQ18013.1, AAV38739.1, NP-851298.1, CAA67685.1, AAT67171.1, AAT37502.1, AAD27804.1, AAN76665.1, BAC11909.1, XP-1-421648.1, CAB63704.1, NP-037306.1, A55706, AAF02780.1, CAG09623.1, NP-067589.1, NP-035707.1, AAV30547.1, AAP49817.1, BAC77407.1, AAL87199.1, CAG07172.1, B36193, CAA33024.1, NP-1-001009400.1, AAP36538.1, XP-512687.1, XP-510080.1, AAH05513.1, 1KTZ, AAH14690.1, AAA31526.1.

The growth factor from the TGF-β superfamily in the methods and compositions provided herein can be naturally obtained or recombinant. In some embodiments, the growth factor from the TGF-β superfamily comprises Activin A. The term "Activin A" can include fragments and derivatives of Activin A. The sequence of an exemplary Activin A is provided as SEQ ID NO: 1. Other non-limiting examples of Activin A are provided in SEQ ID NO: 3-16, and non-limiting examples of nucleic acids encoding Activin A are provided in SEQ ID NO: 2, SEQ ID NO: 17, and SEQ ID NO: 18. In some embodiments, the growth factor from the TGF-β superfamily comprises a polypeptide comprising an amino acid sequence that is at least 30%, at least 40%, at least 50%, at least 60%, at least 70%, at least 75%, at least 80%, at least 85%, at least 90%, at least 95%, at least 98% or at least 99% identical to the amino acid sequence of any one of SEQ ID NOs: 1 and 3-16, or functional fragments thereof. In some embodiments, the growth factor from the TGF-β superfamily comprises a polypeptide comprising the amino acid any one of SEQ ID NOs: 1 and 3-16.

*Homo sapiens* Inhibin beta A subunit (Activin A)
amino acid sequence:
SEQ ID NO: 1

GLECDGKVNICCKKQFFVSFKDIGWNDWIIAPSGYHANYCEGECPSHIAGTSGSSLSFHSTVIN

HYRMRGHSPFANLKSCCVPTKLRPMSMLYYDDGQNIIKKDIQNMIVEECGCS

*Homo sapiens* Inhibin beta A chain (Activin A)
nucleic acid sequence:
SEQ ID NO: 2

GGCTTGGAGTGTGATGGCAAGGTCAACATCTGCTGTAAGAAACAGTTCTTTGTCAGTTTCAAGG

ACATCGGCTGGAATGACTGGATCATTGCTCCCTCTGGCTATCATGCCAACTACTGCGAGGGTGA

GTGCCCGAGCCATATAGCAGGCACGTCCGGGTCCTCACTGTCCTTCCACTCAACAGTCATCAAC

CACTACCGCATGCGGGGCCATAGCCCCTTTGCCAACCTCAAATCGTGCTGTGTGCCCACCAAGC

TGAGACCCATGTCCATGTTGTACTATGATGATGGTCAAAACATCATCAAAAAGGACATTCAGAA

CATGATCGTGGAGGAGTGTGGGTGCTCATAG

*Homo sapiens* Erythroid differentiation protein (EDF)
ovarian amino acid sequence:
SEQ ID NO: 3

MPLLWLRGFLLASCWIIVRSSPTPGSEGHSAAPDCPSCALAALPKDVPNSQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEVWLFLKVPKANRTRTKVTIRLFQQQKHPQGSLDTGEEA

EEVGLKGERSELLLSEKVVDARKSTWHVFPVSSSIQRLLDQGKSSLDVRIACEQCQESGASLVL

LGKKKKKEEEGEGKKKGGGEGGAGADEEKEQSHRPFLMLQARQSEDHPHRRRRRGLECDGKVNI

CCKKQFFVSFKDIGWNDWIIAPSGYHANYCEGECPSHIAGTSGSSLSFHSTVINHYRMRGHSPF

ANLKSCCVPTKLRPMSMLYYDDGQNIIKKDIQNMIVEECGCS

*Homo sapiens* Inhibin B subunit amino acid sequence:
SEQ ID NO: 4

ARQSEDHPHRRRRRGLECDGKVNICCKKQFFVSFKDIGWNDWIIAPSGYHANYCEGECPSHIAG

TSGSSLSFHSTVINHYRMRGHSPFANLKSCCVPTKLRPMSMLYYDDGQNIIKKDIQNMIVEECG

CS

*Homo sapiens* Inhibin B subunit in testis *Homo sapiens*
amino acid sequence:
SEQ ID NO: 5

GLECDGKVNICCKKQFFVSFKDIGWNDWIIAPSGYHANYCEGECPSHIAGTSGSSLSFHSTVIN

HYACGHSPFANLKSCCVPTKLRPMSMLYYDDGQNIIKKDIQNMIVEECGCS

*Homo sapiens* Inhibin B subunit erythroid
differentiation protein (EDF), amino acid
sequence:
SEQ ID NO: 6

MPLLWLRGFLLASCWIIVRSSPTPGSEGHSAAPDCPSCALAALPKDVPNSQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEVWLFLKVPKANRTRTKVTIRLFQQQKHPQGSLDTGEEA

EEVGLKGERSELLLSEKVVDARKSTWHVFPVSSSIQRLLDQGKSSLDVRIACEQCQESGASLVL

LGKKKKKEEEGEGKKKGGGEGGAGADEEKEQSHRPFLMLQARQSEDHPHRRRRRGLECDGKVNI

CCKKQFFVSFKDIGWNDWIIAPSGYHANYCEGECPSHIAGTSGSSLSFHSTVINHYRMRGHSPF

ANLKSCCVPTKLRPMSMLYYDDGQNIIKKDIQNMIVEECGCS

*Mus musculus* (Mouse) Inhibin beta A chain (Activin
beta-A chain) amino acid sequence:
SEQ ID NO: 7

MPLLWLRGFLLASCWIIVRSSPTPGSEGHSAPDCPSCALATLPKDGPNSQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEVWLFLKVPKANRTRTKVTIRLFQQQKHPQGSLDTGDEA

```
EEMGLKGERSELLLSEKVVDARKSTWHIFPVSSSIQRLLDQGKSSLDVRIACEQCQESGASLVL

LGKKKKKEVDGDGKKKDGSDGGLEEEKEQSHRPFLMLQARQSEDHPHRRRRRGLECDGKVNICC

KKQFFVSFKDIGWNDWIIAPSGYHANYCEGECPSHIAGTSGSSLSFHSTVINHYRMRGHSPFAN

LKSCCVPTKLRPMSMLYYDDGQNIIKKDIQNMIVEECGCS

Rattus norvegicus (Rat) Inhibin beta A chain
(Activin beta-A chain) amino acid sequence:
                                          SEQ ID NO: 8
MPLLWLRGFLLASCWIIVRSSPTPGSEGHGAAPDCPSCALATLPKDGPNSQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEVWLFLKVPKANRTRTKVTIRLFQQQKHPQGSLDMGDEA

EEMGLKGERSELLLSEKVVDARKSTWHIFPVSSSIQRLLDQGKSSLDVRIACEQCQESGASLVL

LGKKKKKEVDGDGKKKDGSDGGLEEEKEQSHRPFLMLQARQSEDHPHRRRRRGLECDGKVNICC

KKQFFVSFKDIGWNDWIIAPSGYHANYCEGECPSHIAGTSGSSLSFHSTVINHYRMRGHSPFAN

LKSCCVPTKLRPMSMLYYDDGQNIIKKDIQNMIVEECGCS

Gallus (Chicken) Inhibin beta A chain (Activin
beta-A chain) amino acid sequence:
                                          SEQ ID NO: 9
MPLLWKRGFLLVICWIIVRSSPTPGSEGHSSVADCPSCALTTLSKDVPSSQPEMVEAVKKHILN

MLHLRDRPNITQPVPKAALLNATKKLHVGKVGDDGYVEIEDDVGRRAEMNEVVEQTSEIITFAE

SGTPKKTLHFEISKEGSELSVVEHAEVWLFLKVSKANRSRTKVTIRLFQQQRQPKGNSEAAEDM

EDMGLKGERSETLISEKAVDARKSTWHIFPISSSVQRLLDQGQSSLDVRIACDLCQETGASLVL

LGKKKKKEDDGEGKEKDGGELTGEEEKEQSHRPFLMMLARHSEDRQHRRRERGLECDGKVNICC

KKQFFVSFKDIGWSDWIIAPTGYHANYCEEECPSHIAGTSGSSLSFHSTVINHYRMRGHSPFAN

LKSCCVPTKLRPMSMLYYDDGQNIIKKDIQNMIVEECGCS

Bos taurus (Bovine) Inhibin beta A chain (Activin
beta-A chain) amino acid sequence:
                                          SEQ ID NO: 10
MPLLWLRGFLLASCWIIVRSSPTPGSEGHSAAPDCPSCALATLPKDVPNSQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEIWLFLKVPKANRTRSKVTIRLFQQQKHLQGSLDAGEEA

EEVGLKGEKSEMLISEKVVDARKSTWHIFPVSSCIQRLLDQGKSSLDIRIACEQCQETGASLVL

LGKKKKKEEEGEGKKRDGEGGAGGDEEKEQSHRPFLMLQARQSEDHPHRRRRRGLECDGKVNIC

CKKQFFVSFKDIGWNDWIIAPSGYHANYCEGECPSHIAGTSGSSLSFHSTVINHYRMRGHSPFA

NLKSCCVPTKLRPMSMLYYDDGQNIIKKDIQNMIVEECGCS

Equus caballus (Horse) Inhibin beta A chain
(Activin beta-A chain) amino acid sequence:
                                          SEQ ID NO: 11
MPLLWLRGFLLASCWIIVKSSPTPGSEGHSAAPNCPSCALATLPKDVPNAQPEMVEAVKKHILN

MLHLKKRPDVTQPVPKAALLNAIRKLHVGKVGENGYVEIEDDIGRRAEMNELMEQTSEIITFAE

SGTARKTLHFEISKEGSDLSVVERAEVWLFLKVPKANRTRSKVTIRLLQQQKHPQGSSDTREEA

EEADLMEERSEQLISEKVVDARKSTWHIFPVSSSIQRLLDQGKSSLDIRIACDQCHETGASLVL

LGKKKKKEEEGEGKKKDGGEAGAGVDEEKEQSHRPFLMLQARQSEDHPHRRRRRGLECDGKVNI

CCKKQFFVSFKDIGWNDWIIAPSGYHANYCEGECPSHIAGTSGSSLSFHSTVINQYRLRGHNPF

ANLKSCCVPTKLRPMSMLYYDDGQNIIKKDIQNMIVEECGCS
```

-continued

Sus scrofa (Pig) Inhibin beta A chain (Activin
beta-A chain) amino acid sequence:
SEQ ID NO: 12
MPLLWLRGFLLASCWIIVRSSPTPGSGGHSAAPDCPSCALATLPKDVPNSQPEMVEAVKKHILN

MLHLKKRPDVTQPVPKAALLNAIRKLHVGKVGENGYVELEDDIGRRAEMNELMEQTSEIITFAE

AGTARKTLRFEISKEGSDLSVVERAEIWLFLKVPKANRTRTKVSIRLFQQQRRPQGSADAGEEA

EDVGFPEEKSEVLISEKVVDARKSTWHIFPVSSSIQRLLDQGKSALDIRTACEQCHETGASLVL

LGKKKKKEEEAEGRKRDGEGAGVDEEKEQSHRPFLMLQARQSEEHPHRRRRRGLECDGKVNICC

KKQFFVSFKDIGWNDWIIAPSGYHANYCEGECPSHIAGTSGSSLSFHSTVINHYRMRGHSPFAN

LKSCCVPTKLRPMSMLYYDDGQNIIKKDIQNMIVEECGCS

Ovis aries (Sheep) Inhibin beta A chain (Activin
beta-A chain) amino acid sequence:
SEQ ID NO: 13
MPLLWLRGFLLASCWIIVRSSPTPGSEGHSAAPDCPSCALATLPKDVPNSQPEMVEAVKKHILN

MLHLKKRPDVTQPVPKAALLNAIRKLHVGKVGENGYVEIEDDIGRRAEMNELMEQTSEIITFAE

SGTARKTLHFEISQEGSDLSVVERAEIWLFLKVPKANRTRSKVTIRLFQQQKHLQGSLDAGEEA

EEVGLKGEKSEMLISEKVVDARKSTWHIFPVSSCIQRLLDQGKSSLDIRIACEQCQETGASLVL

LGKKKKRKEEEGEGKKRDGEGGAGGDEEKEQSHRPFLMLQARQSEDHPHRRRRRGLECDGKVNIC

CKKQFYVSFKDIGWNDWIIAPSGYHANYCEGECPSHIAGTSGSSLSFHSTVINHYRMRGHSPFA

NLKSCCVPTKLRPMSMLYYDDGQNIIKKDIQNMIVEECGCS

Felis catus (cat) Inhibin beta A chain (Activin
beta-A chain) amino acid sequence:
SEQ ID NO: 14
MPLLWLRGFLLASCWIIVRSSPTPGSEGPGAAPDCPSCALATLPKDVPNSQPEMVEAVKKHILN

MLHLKKRPEVTQPVPKAALLNAIRKLHVGKVGENGYVEIEDDIGRRAEMNELMEQTSEIITFAE

SGTARKTLHFEISKEGSDLSVVERAEVWLFLKVPKANRTRTKVTIQLLQKQPQGGVDAGEEAEE

MGLMEERNEVLISEKVVDARKSTWHIFPVSSSIQRLLDQGKSSLDVRIACEQCHETGASLVLLG

KKKKKEEEGEGKKKDGGDGAGADEDKEQSHRPFLMLQARQSEDHPHRRRRRGLECDGKVNICC

KKQFFVSFKDIGWNDWIIAPSGYHANYCEGECPSHIAGTSGSSLSFHSTVINHYRMRGHSPFAN

LKSCCVPTKLRPMSMLYYDDGQNIIKKDIQNMIVEECGCS

Danio rerio (zebrafish) Inhibin beta A chain
(Activin beta-A chain) amino acid sequence:
SEQ ID NO: 15
MSPLPLLSGILLLLIRSCSLSAMVTKGSLPMSEQQAGATVCPSCALARFRKGVSESEDEGAQQD

VVEAVKRHILNMLHLQERPNITHPVPRAALLNAIRKVHVGRVAKDGSVLIEDEASNRAETEQAE

QTEIITFAETGEAPGIVNFLISKEGGEMSVVDQANVWIFLRLPKGNRTRANVNIRLLLQQGAGE

KILAEKSVDTRRSGWHTFPASESVQSLLQRGGSTLSLRVSCPLCADARATPVLVSPGGSEREQS

HRPFLMAVVRQMDELSLRRRRKRGLECDGKARVCCKRQFYVNFKDIGWNDWIIAPSGYHANYCE

GDCASNVASITGNSLSFHSTVISHYRIRGYSPFTNIKSCCVPTRLRAMSMLYYNEEQKIVKKDI

QNMIVEECGCS

Carassius auratus (goldfish) Inhibin beta A chain
(Activin beta-A chain) amino acid sequence:
SEQ ID NO: 16
MSSLTLVNRGTAALRLFVRGLLTHSSREWLSGDGEPDDPVTPCPSCALAQRQKDSEEQTDMVEA

VKRHILNMLHLNTRPNVTHPVPRAALLNAIRRLHVGRVGEDGTVEMEEDGGGLGEHREQSEEQP

FEIITFAEPGDAPDIMKFDISMEGNTLSVVEQANVWLLLKVAKGSRGKGKVSVQLLQHGKADPG

SADGPQEAVVSEKTVDTRRSGWHTLPVSRTVQTLLDGDSSMLSLRVSCPMCAEAGAVPILVPTE

SNKGKEREQSHRPFLMVVLKPAEEHPHRRSKRGLECDGKIRVCCKRQFYVNFKDIGWSDWIIAP

```
SGYHANYCEGDCPSHVASITGSALSFHSTVINHYRMRGYSPFNNIKSCCVPTRLRAMSMLYYNE

EQKIIKKDIQNMIVEECGCS

Recombinant Inhibin B subunit nucleic acid sequence
                                                         SEQ ID NO: 17
GCCCGGCAGTCTGAAGACCACCCTCATCGCCGGCGTCGGCGGGGCTTGGAGTGTGATGGCAAGG

TCAACATCTGCTGTAAGAAACAGTTCTTTGTCAGTTTCAAGGACATCGGCTGGAATGACTGGAT

CATTGCTCCCTCTGGCTATCATGCCAACTACTGCGAGGGTGAGTGCCCGAGCCATATAGCAGGC

ACGTCCGGGTCCTCACTGTCCTTCCACTCAACAGTCATCAACCACTACCGCATGCGGGCCATA

GCCCCTTTGCCAACCTCAAATCGTGCTGTGTGCCCACCAAGCTGAGACCCATGTCCATGTTGTA

CTATGATGATGGTCAAAACATCATCAAAAAGGACATTCAGAACATGATCGTGGAGGAGTGTGGG

TGCTCATAGAGTTGCCCAGCCCAGGGGGAAAGGGAGCAAGA

Homo sapiens mature subunit beta(A) inhibin in
testis nucleic acid sequence
                                                         SEQ ID NO: 18
GGCCTGGAGTGCGACGGCAAGGTCAACATCTGCTGTAAGAAACAGTTCTTTGTCAGTTTCAAGG

ACATCGGCTGGAATGACTGGATCATTGCTCCCTCTGGCTATCATGCCAACTACTGCGAGGGTGA

GTGCCCGAGCCATATAGCAGGCACGTCCGGGTCCTCACTGTCCTTCCACTCAACAGTCATCAAC

CACTACGCATGCGGCCATAGCCCCTTTGCCAACCTCAAATCGTGCTGTGTGCCCACCAAGCTGA

GACCCATGTCCATGTTGTACTATGATGATGGTCAAAACATCATCAAAAAGGACATTCAGAACAT

GATCGTGGAGGAGTGCGGGTGCTCCTAA
```

In some embodiments, the growth factor from the TGF-β superfamily comprises growth differentiation factor 8 (GDF8). The term "GDF8" can include fragments and derivatives of GDF8. The sequences of GDF8 polypeptides are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF8 polypeptide sequence (GenBank Accession EAX10880).

In some embodiments, the growth factor from the TGF-β superfamily comprises a growth factor that is closely related to GDF8, e.g., growth differentiation factor 11 (GDF11). In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF11 polypeptide sequence (GenBank Accession AAF21630).

In some embodiments, the growth factor from the TGF-β superfamily can be replaced with an agent mimics the at least one growth factor from the TGF-β superfamily. Exemplary agents that mimic the at least one growth factor from the TGF-β superfamily, include, without limitation, IDE1 and IDE2.

In some embodiments, a medium described herein does not comprise a TGF-β superfamily protein.

Bone Morphogenetic Protein (BMP) Signaling Pathway Inhibitors

Aspects of the disclosure relate to the use of BMP signaling pathway inhibitors (which also may be referred to as "BMP inhibitors" herein) as cell differentiation factors. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

In some embodiments, the BMP signaling pathway inhibitor in the methods and composition provided herein comprises DMH-1, or a derivative, analogue, or variant thereof. In some embodiments, the BMP signaling pathway inhibitor in the methods and composition provided herein comprises the following compound or a derivative, analogue, or variant of the following compound:

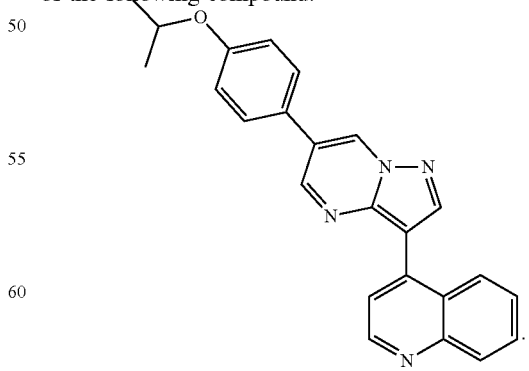

In some embodiments, the BMP signaling pathway inhibitor in the methods and composition provided herein comprises LDN193189 (also known as LDN193189, 1062368-

24-4, LDN-193189, DM 3189, DM-3189, IUPAC Name: 4-[6-(4-piperazin-1-ylphenyl)pyrazolo[1,5-a]pyrimidin-3-yl]quinolone). In some embodiments, the BMP signaling pathway inhibitor in the methods and composition provided herein comprises the following compound or a derivative, analogue, or variant of the following compound:

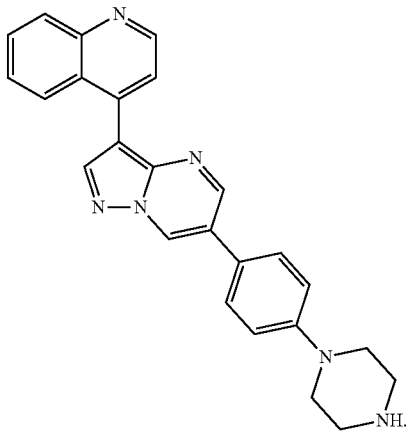 [SMILES: c1ccc2c(-c3cnn4cc(-c5ccc(N6CCNCC6)cc5)cnc34)ccnc2c1]

In some embodiments, DMH-1 can be more selective as compared to LDN193189. In some embodiments of the present disclosure, DMH-1 can be particularly useful for the methods provided herein. In some embodiments, the methods and compositions provided herein, or specific stages of the methods disclosed herein (e.g., stage 3), exclude use of LDN193189. In some embodiments, the methods and compositions provided herein exclude use of LDN193189, or a derivative, analogue, or variant thereof for generating PDX1-positive pancreatic progenitor cells from primitive gut tube cells. In some embodiments, the methods and compositions provided herein relate to use of DMH-1, or a derivative, analogue, or variant thereof for generating PDX1-positive pancreatic progenitor cells from primitive gut tube cells.

In some embodiments, the BMP signaling pathway inhibitor in the methods and composition provided herein comprise an analog or derivative of LDN193189, e.g., a salt, hydrate, solvent, ester, or prodrug of LDN193189. In some embodiments, a derivative (e.g., salt) of LDN193189 comprises LDN193189 hydrochloride.

In some embodiments, the BMP signaling pathway inhibitor in the methods and composition provided herein comprises a compound of Formula I from U.S. Patent Publication No. 2011/0053930.

In some embodiments, a medium described herein does not comprise a BMP signaling pathway inhibitor.

TGF-β Signaling Pathway Inhibitors

Aspects of the disclosure relate to the use of TGF-β signaling pathway inhibitors as cell differentiation factors.

In some embodiments, the TGF-β signaling pathway comprises TGF-β receptor type I kinase (TGF-0 RI) signaling. In some embodiments, the TGF-β signaling pathway inhibitor comprises ALK5 inhibitor II (CAS 446859-33-2, an ATP-competitive inhibitor of TGF-β RI kinase, also known as RepSox, IUPAC Name: 2-[5-(6-methylpyridin-2-yl)-1H-pyrazol-4-yl]-1,5-naphthyridine. In some embodiments, the TGF-β signaling pathway inhibitor is an analog or derivative of ALK5 inhibitor II.

In some embodiments, the analog or derivative of ALK5 inhibitor II (also named "ALK5i") is a compound of Formula I as described in U.S. Patent Publication No. 2012/0021519, incorporated by reference herein in its entirety.

In some embodiments, the TGF-β signaling pathway inhibitor in the methods and compositions provided herein is a TGF-β receptor inhibitor described in U.S. Patent Publication No. 2010/0267731. In some embodiments, the TGF-β signaling pathway inhibitor in the methods and compositions provided herein comprises an ALK5 inhibitor described in U.S. Patent Publication Nos. 2009/0186076 and 2007/0142376. In some embodiments, the TGF-β signaling pathway inhibitor in the methods and compositions provided herein is A 83-01. In some embodiments, the TGF-β signaling pathway inhibitor in the methods and compositions provided herein is not A 83-01. In some embodiments, the compositions and methods described herein exclude A 83-01. In some embodiments, the TGF-β signaling pathway inhibitor in the methods and compositions provided herein is SB 431542. In some embodiments, the TGF-β signaling pathway inhibitor is not SB 431542. In some embodiments, the compositions and methods described herein exclude SB 431542. In some embodiments, the TGF-β signaling pathway inhibitor in the methods and compositions provided herein is D 4476. In some embodiments, the TGF-β signaling pathway inhibitor is not D 4476. In some embodiments, the compositions and methods described herein exclude D 4476. In some embodiments, the TGF-β signaling pathway inhibitor in the methods and compositions provided herein is GW 788388. In some embodiments, the TGF-β signaling pathway inhibitor is not GW 788388. In some embodiments, the compositions and methods described herein exclude GW 788388. In some embodiments, the TGF-β signaling pathway inhibitor in the methods and compositions provided herein is LY 364947. In some embodiments, the TGF-β signaling pathway inhibitor is not LY 364947. In some embodiments, the compositions and methods described herein exclude LY 364947. In some embodiments, the TGF-β signaling pathway inhibitor in the methods and compositions provided herein is LY 580276. In some embodiments, the TGF-β signaling pathway inhibitor is not LY 580276. In some embodiments, the compositions and methods described herein exclude LY 580276. In some embodiments, the TGF-β signaling pathway inhibitor in the methods and compositions provided herein is SB 525334. In some embodiments, the TGF-β signaling pathway inhibitor is not SB 525334. In some embodiments, the compositions and methods described herein exclude SB 525334. In some embodiments, the TGF-β signaling pathway inhibitor in the methods and compositions provided herein is SB 505124. In some embodiments, the TGF-β signaling pathway inhibitor is not SB 505124. In some embodiments, the compositions and methods described herein exclude SB 505124. In some embodiments, the TGF-β signaling pathway inhibitor in the methods and compositions provided herein is SD 208. In some embodiments, the TGF-β signaling pathway inhibitor is not SD 208. In some embodiments, the compositions and methods described herein exclude SD 208. In some embodiments, the TGF-β signaling pathway inhibitor in the methods and compositions provided herein is GW 6604. In some embodiments, the TGF-β signaling pathway inhibitor is not GW 6604. In some embodiments, the compositions and methods described herein exclude GW 6604. In some embodiments, the TGF-β signaling pathway inhibitor in the methods and compositions provided herein is GW 788388. In some embodiments, the TGF-β signaling pathway inhibitor in the methods and compositions provided herein is not GW 788388. In some embodiments, the compositions and methods described herein exclude GW 788388.

From the collection of compounds described above, the following can be obtained from various sources: LY-364947, SB-525334, SD-208, and SB-505124 available from Sigma, P.O. Box 14508, St. Louis, Mo., 63178-9916; 616452 and 616453 available from Calbiochem (EMD Chemicals, Inc.), 480 S. Democrat Road, Gibbstown, N.J., 08027; GW788388 and GW6604 available from GlaxoSmithKline, 980 Great West Road, Brentford, Middlesex, TW8 9GS, United Kingdom; LY580276 available from Lilly Research, Indianapolis, Ind. 46285; and SM16 available from Biogen Idec, P.O. Box 14627, 5000 Davis Drive, Research Triangle Park, N.C., 27709-4627.

In some embodiments, a medium described herein does not comprise a TGF-β signaling pathway inhibitor.

WNT Signaling Pathway

Aspects of the disclosure relate to the use of activators of the WNT signaling pathway as cell differentiation factors.

In some embodiments, the WNT signaling pathway activator in the methods and compositions provided herein comprises CHIR99021. In some embodiments, the WNT signaling pathway activator in the methods and compositions provided herein comprises a derivative of CHIR99021, e.g., a salt of CHIR99021, e.g., trihydrochloride, a hydrochloride salt of CHIR99021. In some embodiments, the WNT signaling pathway activator in the methods and compositions provided herein comprises Wnt3a recombinant protein. In some embodiments, the WNT signaling pathway activator in the methods and compositions provided herein comprises a glycogen synthase kinase 3 (GSK3) inhibitor. Exemplary GSK3 inhibitors include, without limitation, 3F8, A 1070722, AR-A 014418, BIO, BIO-acetoxime, FRATide, 10Z-Hymenialdisine, Indirubin-3'oxime, kenpaullone, L803, L803-mts, lithium carbonate, NSC 693868, SB 216763, SB 415286, TC-G 24, TCS 2002, TCS 21311, TWS 119, and analogs or derivatives of any of these. In certain embodiments, the methods, compositions, and kits disclosed herein exclude a WNT signaling pathway activator.

In some embodiments, a medium described herein does not comprise a Wnt signaling pathway activator.

Aspects of the disclosure relate to the use of inhibitors of the WNT signaling pathway as β cell differentiation factors.

In some embodiments, the WNT signaling inhibitor is a tankyrase inhibitor that inhibits expression or activity of at least one tankyrase (TNKS) protein. In some embodiments, the at least one tankyrase protein is tankyrase 1 or tankyrase 2. In some embodiments, the WNT signaling inhibitor inhibits binding of a substrate to a nicotinamide subsite or an adenosine subsite, or both, of a tankyrase protein. In some embodiments, the tankyrase inhibitor is AZ 6102, JW55, MN64, IWR-1-endo, TC-E5001, WIKI4, TNKS 22, TNKS 49, 2X-121 (E7449), XAV-939 (XAV), G007-LK, NVP-TNKS656, decernotinib, (VX-509), vismodegib (GDC-0449), IM-12, GSK429286A, INO-1001, Ofloxacin, TG101209, FG-4592, 1-BET-762, LY2157299, MK-0752, Wnt-C59 (C59), MC1568, Pacritinib (SB 1518), SB415286, Drocinostat, IWR-1-endo, Norfloxacin, SH-4-54, Nexturastat A, SB216763, UNCO 79, dephnetin, GF109203X, RepSox, Sotrastaurin, SB431542, tofacitinib (CP-690550, Tasocitinib), AG-14361, CI994 (tacedinaline), Ro 31-8220 mesylate, resveratrol, NVP-TNKS656, or YO-01027. In some embodiments, said tankyrase inhibitor is AZ 6102, NVP-TNKS656, or IWR-1-endo. In some embodiments, the tankyrase inhibitor is NVP-TNKS656 (NVP). In some embodiments, the tankyrase inhibitor selectively inhibits tankyrase 1 over tankyrase 2. In some embodiments, the tankyrase inhibitor selectively inhibits tankyrase 2 over tankyrase 1.

In some embodiments, a medium described herein does not comprise a Wnt signaling pathway inhibitor.

Fibroblast Growth Factor (FGF) Family

Aspects of the disclosure relate to the use of growth factors from the FGF family as cell differentiation factors.

In some embodiments, the growth factor from the FGF family in the methods and compositions provided herein comprises keratinocyte growth factor (KGF). The polypeptide sequences of KGF are available to the skilled artisan. An example of human KGF amino acid sequence is provided in GenBank Accession No. AAB21431, provided as SEQ ID NO: 19). In some embodiments, the growth factor from the FGF family comprises a polypeptide comprises an amino acid sequence that is at least 30%, at least 40%, at least 50%, at least 60%, at least 70%, at least 75%, at least 80%, at least 85%, at least 90%, at least 95%, at least 98% or at least 99% identical to the amino acid sequence of SEQ ID NO: 19, or a functional fragment thereof. In some embodiments, the growth factor from the FGF family comprises a polypeptide comprising the amino acid sequence of SEQ ID NO: 19.

```
Human KGF amino acid sequence
(GenBank Accession AAB21431; SEQ ID NO: 19)
MHKWILTWILPTLLYRSCFHIICLVGTISLACNDMTPEQMATNVNCSSPE

RHTRSYDYMEGGDIRVRRLFCRTQWYLRIDKRGKVKGTQEMKNNYNIMEI

RTVAVGIVAIKGVESEFYLAMNKEGKLYAKKECNEDCNFKELILENHYNT

YASAKWTHNGGEMFVALNQKGIPVRGKKTKKEQKTAHFLPMAIT
```

In some embodiments, the growth factor from the FGF family in the methods and composition provided herein comprises FGF2. The polypeptide sequences of FGF2 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF2 polypeptide sequence (GenBank Accession NP-001997).

In some embodiments, the at least one growth factor from the FGF family in the methods and composition provided herein comprises FGF8B. The polypeptide sequences of FGF8B are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF8B polypeptide sequence (GenBank Accession AAB40954).

In some embodiments, the at least one growth factor from the FGF family in the methods and composition provided herein comprises FGF10. The polypeptide sequences of FGF10 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF10 polypeptide sequence (GenBank Accession CAG46489).

In some embodiments, the at least one growth factor from the FGF family in the methods and composition provided herein comprises FGF21. The polypeptide sequences of FGF21 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF21 polypeptide sequence (GenBank Accession AAQ89444.1).

In some embodiments, a medium described herein does not comprise a FGF family protein.

Sonic Hedgehog (SHH) Signaling Pathway

Aspects of the disclosure relate to the use of SHH signaling pathway inhibitors as cell differentiation factors.

In some embodiments, the SHH signaling pathway inhibitor in the methods and composition provided herein comprises Sant1. In some embodiments, the SHH signaling pathway inhibitor in the methods and composition provided herein comprises SANT2. In some embodiments, the SHH signaling pathway inhibitor in the methods and composition provided herein comprises SANT3. In some embodiments, the SHH signaling pathway inhibitor in the methods and composition provided herein comprises SANT4. In some embodiments, the SHH signaling pathway inhibitor comprises Cur61414. In some embodiments, the SHH signaling pathway inhibitor in the methods and composition provided herein comprises forskolin. In some embodiments, the SHH signaling pathway inhibitor in the methods and composition provided herein comprises tomatidine. In some embodiments, the SHH signaling pathway inhibitor in the methods and composition provided herein comprises AY9944. In some embodiments, the SHH signaling pathway inhibitor in the methods and composition provided herein comprises triparanol. In some embodiments, the SHH signaling pathway inhibitor in the methods and composition provided herein comprises compound A or compound B (as disclosed in U.S. Pub. No. 2004/0060568). In some embodiments, the SHH signaling pathway inhibitor in the methods and composition provided herein comprises a steroidal alkaloid that antagonizes hedgehog signaling (e.g., cyclopamine or a derivative thereof) as disclosed in U.S. Pub. No. 2006/0276391. In certain embodiments, the methods, compositions, and kits disclosed herein exclude a SHH signaling pathway inhibitor.

Rho Kinase (ROCK) Signaling Pathway

Aspects of the disclosure relate to the use of ROCK signaling pathway inhibitors (ROCK inhibitors) as cell differentiation factors.

In some embodiments, the ROCK inhibitor in the methods and composition provided herein comprises Y-27632 or Thiazovivin. In some embodiments, the ROCK inhibitor in the methods and composition provided herein comprises Thiazovivin. In some embodiments, the ROCK inhibitor in the methods and composition provided herein comprises Y-27632. In some embodiments, the ROCK inhibitor in the methods and composition provided herein comprises the following compound or a derivative thereof:

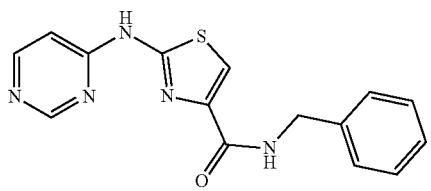 [SMILES: O=C(NCc1ccccc1)c1csc(Nc2ccncn2)n1]

In some embodiments, the ROCK inhibitor in the methods and composition provided herein comprises the following compound or a derivative thereof:

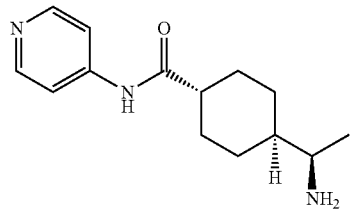 [SMILES: C[C@@H](N)[C@H]1CC[C@H](C(=O)Nc2ccncc2)CC1]

Non-limiting examples of ROCK inhibitor that can be used in the methods and compositions provided herein include Thiazovivin, Y-27632, Fasudil/HA1077, H-1152, Ripasudil, Y39983, Wf-536, SLx-2119, Azabenzimidazole-aminofurazans, DE-104, Olefins, Isoquinolines, Indazoles, and pyridinealkene derivatives, ROKα inhibitor, XD-4000, HMN-1152, 4-(1-aminoalkyl)-N-(4-pyridyl)cyclohexane-carboxamides, Rhostatin, BA-210, BA-207, BA-215, BA-285, BA-1037, Ki-23095, VAS-012, and quinazoline.

In some embodiments, a medium described herein does not comprise a ROCK pathway inhibitor.

Retinoic Acid Signaling Pathway

Aspects of the disclosure relate to the use of modulators of retinoic acid signaling as cell differentiation factors.

In some embodiments, the modulator of retinoic acid signaling in the methods and composition provided herein comprises an activator of retinoic acid signaling. In some embodiments, the RA signaling pathway activator in the methods and composition provided herein comprises retinoic acid. In some embodiments, the RA signaling pathway activator in the methods and composition provided herein comprises a retinoic acid receptor agonist. Exemplary retinoic acid receptor agonists in the methods and composition provided herein include, without limitation, CD 1530, AM 580, TTNPB, CD 437, Ch 55, BMS 961, AC 261066, AC 55649, AM 80, BMS 753, tazarotene, adapalene, and CD 2314.

In some embodiments, the modulator of retinoic acid signaling in the methods and composition provided herein comprises an inhibitor of retinoic acid signaling. In some embodiments, the retinoic acid signaling pathway inhibitor comprises DEAB (IUPAC Name: 2-[2-(diethylamino)ethoxy]-3-prop-2-enylbenzaldehyde). In some embodiments, the retinoic acid signaling pathway inhibitor comprises an analog or derivative of DEAB.

In some embodiments, the retinoic acid signaling pathway inhibitor in the methods and composition provided herein comprises a retinoic acid receptor antagonist. In some embodiments, the retinoic acid receptor antagonist in the methods and composition provided herein comprises (E)-4-[2-(5,6-dihydro-5,5-dimethyl-8-phenyl-2-naphthalenyl)ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid. In some embodiments, the retinoic acid receptor antagonist comprises BMS 195614 (CAS #253310-42-8), ER 50891 (CAS #187400-85-7), BMS 493 (CAS #170355-78-9), CD 2665 (CAS #170355-78-9), LE 135 (CAS #155877-83-1), BMS 453 (CAS #166977-43-1), or MM 11253 (CAS #345952-44-5).

In certain embodiments, the methods, compositions, and kits disclosed herein exclude a modulator of retinoic acid signaling. In certain embodiments, the methods, compositions, and kits disclosed herein exclude a retinoic acid signaling pathway activator. In certain embodiments, the methods, compositions, and kits disclosed herein exclude a retinoic acid signaling pathway inhibitor.

In some embodiments, a medium described herein does not comprise retinoic acid.

Protein Kinase C Activator Aspects of the disclosure relate to the use of protein kinase C activators as cell differentiation factors. Protein kinase C is one of the largest families of protein kinase enzymes and is composed of a variety of isoforms. Conventional isoforms include a, βI, βII, γ; novel isoforms include δ, ε, η, Θ; and atypical isoforms include ξ, and ι/λ.. PKC enzymes are primarily cytosolic but translocate to the membrane when activated. In the cytoplasm, PKC is phosphorylated by other kinases or autophosphorylated. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell differentiation factors, of inducing the differentiation of at least one insulin-producing, endocrine cell or precursor thereof into a SC-β cell can be used in the methods, compositions, and kits described herein.

In some embodiments, any of the PKC activators disclosed herein is a PKC activator capable of binding to a DAG binding site on a PKC. In some embodiments, the PKC activator is capable of binding to a C1 domain of a PKC. In some embodiments, the PKC activator is a benzolactam-derivative. In some embodiments, the benzolactam-derivative is ((2S,5S)-(E,E)-8-(5-(4-(Trifluoromethyl)phenyl)-2,4-pentadienoylamino)benzolactam), which may be referred to herein as TPPB or TPB. In some embodiments, contacting a population of cells with a benzolactam-derivative PKC activator (e.g., TPPB) increases cell yield as compared to a population of cells not treated with the benzolactam-derivative PKC activator. In some embodiments, the PKC activator is a phorbol ester. In some embodiments, the phorbol ester is Phorbol 12,13-dibutyrate, which may be referred to herein as PDBU or PdbU. In some embodiments, contacting a population of cells with a benzolactam-derivative PKC activator (e.g., TPPB) increases cell yield as compared to a population of cells treated with a phorbol ester PKC activator (e.g., PdbU). In some embodiments, the PKC activator in the methods and composition provided herein comprises PdbU. In some embodiments, the PKC activator in the methods and composition provided herein comprises TPB. In some embodiments, the PKC activator in the methods and composition provided herein comprises cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some embodiments, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In certain embodiments, the methods, compositions, and kits disclosed herein exclude a protein kinase C activator.

In some embodiments, a medium described herein does not comprise a protein kinase C activator.

γ-Secretase Inhibitors

Aspects of the disclosure relate to the use of γ-secretase inhibitors as cell differentiation factors.

In some embodiments, the γ-secretase inhibitor in the methods and composition provided herein comprises XXI. In some embodiments, the γ-secretase inhibitor in the methods and composition provided herein comprises DAPT. Additional exemplary γ-secretase inhibitors in the methods and composition provided herein include, without limitation, the γ-secretase inhibitors described in U.S. Pat. Nos. 7,049,296, 8,481,499, 8,501,813, and WIPO Pub. No. WO/2013/052700. In certain embodiments, the methods, compositions, and kits disclosed herein exclude a γ-secretase inhibitor.

In some embodiments, a medium described herein does not comprise a γ-secretase inhibitor.

Thyroid Hormone Signaling Pathway Activators

Aspects of the disclosure relate to the use of thyroid hormone signaling pathway activators as cell differentiation factors.

In some embodiments, the thyroid hormone signaling pathway activator in the methods and composition provided herein comprises triiodothyronine (T3). In some embodiments, the thyroid hormone signaling pathway activator in the methods and composition provided herein comprises GC-1. In some embodiments, the thyroid hormone signaling pathway activator in the methods and composition provided herein comprises an analog or derivative of T3 or GC-1. Exemplary analogs of T3 in the methods and composition provided herein include, but are not limited to, selective and non-selective thyromimetics, TRO selective agonist-GC-1, GC-24,4-Hydroxy-PCB 106, MB07811, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (TOAM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), and 3,5-diiodothyropropionic acid (DITPA).

In some embodiments, the thyroid hormone signaling pathway activator in the methods and composition provided herein comprises a prodrug or prohormone of T3, such as T4 thyroid hormone (e.g., thyroxine or L-3,5,3',5'-tetraiodothyronine).

In some embodiments, the thyroid hormone signaling pathway activator in the methods and composition provided herein is an iodothyronine composition described in U.S. Pat. No. 7,163,918.

In some embodiments, a medium described herein does not comprise a thyroid hormone.

Epidermal Growth Factor (EGF) Family

Aspects of the disclosure relate to the use of growth factors from the EGF family as cell differentiation factors.

In some embodiments, the at least one growth factor from the EGF family in the methods and composition provided herein comprises betacellulin. An example of human betacellulin amino acid sequence is provided in GenBank Accession No.: AAB25452.1 (SEQ ID NO: 20). In some embodiments, the growth factor from the EGF family used in the compositions and methods described herein comprises an amino acid sequence that is at least 30%, at least 40%, at least 50%, at least 60%, at least 70%, at least 75%, at least 80%, at least 85%, at least 90%, at least 95%, at least 98% or at least 99% identical to the amino acid sequence of SEQ ID NO: 20, or a functional fragment thereof. In some embodiments, the growth factor from the EGF family used in the compositions and methods described herein comprises the amino acid sequence of SEQ ID NO: 20.

```
Human betacellulin amino acid sequence
(GenBank: AAB25452.1; SEQ ID NO: 20)
MDRAARCSGASSLPLLLALALGLVILHCVVADGNSTRSPETNGLLCGDPE

ENCAATTTQSKRKGHFSRCPKQYKHYCIKGRCRFVVAEQTPSCVCDEGYI

GARCERVDLFYLRGDRGQILVICLIAVMVVFIILVIGVCTCCHPLRKRRK

RKKKEEEMETLGKDITPINEDIEETN
```

In some embodiments, at least one growth factor from the EGF family in the methods and composition provided herein comprises EGF. Epidermal growth factor (EGF) is a 53 amino acid cytokine which is proteolytically cleaved from a large integral membrane protein precursor. In some embodiments, the growth factor from the EGF family in the methods and composition provided herein comprises a variant EGF polypeptide, for example an isolated epidermal growth factor polypeptide having at least 90% amino acid identity to the human wild-type EGF polypeptide sequence, as disclosed in U.S. Pat. No. 7,084,246. In some embodiments, the growth factor from the EGF family in the methods and composition provided herein comprises an engineered EGF mutant that binds to and agonizes the EGF receptor, as is disclosed in U.S. Pat. No. 8,247,531. Non-limiting examples of amino acid sequences of growth factors from the EGF family that may be used in the compositions and methods described are provided below. In some embodiments, the growth factor from the EGF family used in the compositions and methods described herein comprises an amino acid sequence that is at least 30%, at least 40%, at least 50%, at least 60%, at least 70%, at least 75%, at least 80%, at least 85%, at least 90%, at least 95%, at least 98% or at least 99% identical to the amino acid sequence of any one of SEQ ID NOs: 21-32, or a functional fragment thereof.

In some embodiments, the growth factor from the EGF family used in the compositions and methods described herein comprises the amino acid sequence of any one of SEQ ID NO: 21-32.

```
Homo sapiens epidermal growth factor (WT)
(Genbank: AAS83395.1; SEQ ID NO: 21)
NSDSECPLSHDGYCLHDGVCMYIEALDKYACNCVVGYIGERCQYRDLKWW

ELR

Homo sapiens epidermal growth factor (mutant)
                                  (SEQ ID NO: 22)
NSDSECPLSHDGYCLHGGVCMYIKAVDRYACNCVVGYIGERCQYRDLTWW

GPR

Homo sapiens epidermal growth factor (mutant)
                                  (SEQ ID NO: 23)
NSDSECPLSHDGYCLHDGVCMYIKALDKYACNCVVGYTGERCQYRDLRWW

GRR

Homo sapiens epidermal growth factor (mutant)
                                  (SEQ ID NO: 24)
NSNSECPLSHDGYCLHDGVCRYIEALDRYACNCVVGYIGERCQYGDLRWW

GRR

Homo sapiens epidermal growth factor (mutant)
                                  (SEQ ID NO: 25)
NSDSGCPLSHSGYCLHDGVCMYIKALDRYACNCVVGYAGERCQYRDLRWW

ARR

Homo sapiens epidermal growth factor (mutant)
                                  (SEQ ID NO: 26)
TRGSECPLSHDGYCLHDGVCMYIGALDRYACNCVVGYTGERCQYRDLRWW

ARR

Homo sapiens epidermal growth factor (mutant)
                                  (SEQ ID NO: 27)
NSDFGCPLSYDGYCLHDGVCMYIKALDKYACNCVVGYAGERCQYRDLRWW

GRR

Homo sapiens epidermal growth factor (mutant)
                                  (SEQ ID NO: 28)
SRGSKCPPSHDGYCLHDGVCMYIEALDRYACNCVVGYAGERCQYRDLRWW

ARR

Homo sapiens epidermal growth factor (mutant)
                                  (SEQ ID NO: 29)
SSGSECPSSHDGYCLHDACMYIEALDRYACNCAVGYAGERCQYRDLRWW

GRR

Homo sapiens epidermal growth factor (mutant)
                                  (SEQ ID NO: 30)
SSNSECPPSHDGYCLHDGVCMYIEALDRYACNCVVGYAGERCQYRDLRWW

ARR

Homo sapiens epidermal growth factor (mutant)
                                  (SEQ ID NO: 31)
NSYSECPPSYDGYCLHDGVCRYIEALDSYACNCVVGYAGERCQYRDLRWW

GRR

Homo sapiens epidermal growth factor (mutant)
                                  (SEQ ID NO: 32)
SSGSECPLSHDGYCLNDGVCMYIEALDKYACNCVVGYVGERCOYRDLRWW

ARR
```

In some embodiments, the at least one growth factor from the EGF family in the methods and composition provided herein is replaced with an agent that activates a signaling pathway in the EGF family. In some embodiments, the growth factor from the EGF family in the methods and composition provided herein comprises a compound that mimics EGF. In certain embodiments, the methods, compositions, and kits disclosed herein exclude a growth factor from the EGF family.

In some embodiments, a medium described herein does not comprise a EGF family growth factor.

Epigenetic Modifying Compounds

Aspects of the disclosure relate to the use of epigenetic modifying compound as cell differentiation factors.

The term "epigenetic modifying compound" can refer to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, can alter DNA accessibility and chromatin structure, thereby regulating patterns of gene expression. These processes can be crucial to normal development and differentiation of distinct cell lineages in the adult organism. They can be modified by exogenous influences, and, as such, can contribute to or be the result of environmental alterations of phenotype or pathophenotype. Importantly, epigenetic modification can have a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

In an embodiment, the histone methyltransferase inhibitor is an inhibitor of enhancer of zeste homolog 2 (EZH2). EZH2 is a histone-lysine N-methyltransferase enzyme. Non-limiting examples of an EZH2 inhibitor that can be used in the methods provided herein include 3-deazaneplanocin A (DZNep), EPZ6438, EPZ005687 (an S-adenosylmethionine (SAM) competitive inhibitor), Ell, GSK126, and UNC1999. DZNep can inhibit the hydrolysis of S-adenosyl-L-homocysteine (SAH), which is a product-based inhibitor of all protein methyltransferases, leading to increased cellular concentrations of SAH which in turn inhibits EZH2. DZNep may not be specific to EZH2 and can also inhibit other DNA methyltransferases. GSK126 is a SAM-competitive EZH2 inhibitor that has 150-fold selectivity over EZH1. UNC1999 is an analogue of GSK126, and it is less selective than its counterpart GSK126.

In an embodiment, the histone methyltransferase inhibitor is DZNep. In an embodiment, the HDAC inhibitor is a class I HDAC inhibitor, a class II HDAC inhibitor, or a combination thereof. In an embodiment, the HDAC inhibitor is KD5170 (mercaptoketone-based HDAC inhibitor), MC1568 (class IIa HDAC inhibitor), TMP195 (class IIa HDAC inhibitor), or any combination thereof. In some embodiments, HDAC inhibitor is vorinostat, romidepsin (Istodax), chidamide, panobinostat (farydak), belinostat (PXD101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, (a benzamide HDI), kevetrin, CUDC-101, AR-42, CHR-2845, CHR-3996, 4SC-202, CG200745, ACY-1215, ME-344, sulforaphane, or any variant thereof.

In some embodiments, a medium described herein does not comprise an epigenetic modifying compound.

Protein Kinase Inhibitors

Aspects of the disclosure relate to the use of protein kinase inhibitors as cell differentiation factors.

In some embodiments, the protein kinase inhibitor in the methods and composition provided herein comprises staurosporine. In some embodiments, the protein kinase inhibitor in the methods and composition provided herein comprises an analog of staurosporine. Exemplary analogs of staurosporine in the methods and composition provided herein include, without limitation, Ro-31-8220, a bisindolylmaleimide (Bis) compound, 10'-{5"-[(methoxycarbonyl)amino]-2"-methyl}-phenylaminocarbonylstaurosporine, a staralog (see, e.g., Lopez et al., "Staurosporine-derived inhibitors broaden the scope of analog-sensitive kinase technology", J. Am. Chem. Soc. 2013; 135(48):18153-18159), and, cgp41251.

In some embodiments, the protein kinase inhibitor in the methods and composition provided herein is an inhibitor of PKCβ. In some embodiments, the protein kinase inhibitor in the methods and composition provided herein is an inhibitor of PKCβ with the following structure or a derivative, analogue or variant of the compound as follows:

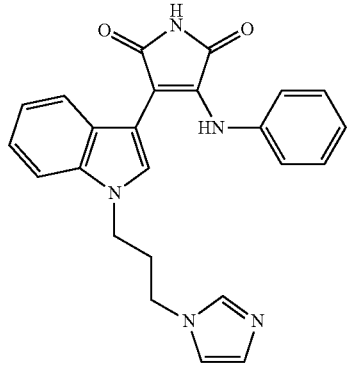 [SMILES: O=C1NC(=O)C(c2cn(CCCn3ccnc3)c3ccccc23)=C1Nc1ccccc1]

In some embodiments, the inhibitor of PKCβ is a GSK-2 compound with the following structure or a derivative, analogue or variant of the compound as follows:

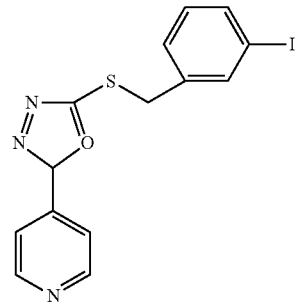

In some embodiments, the inhibitor of PKC in the methods and composition provided herein is a bisindolylmaleimide. Exemplary bisindolylmaleimides include, without limitation, bisindolylmaleimide I, bisindolylmaleimide II, bisindolylmaleimide III, hydrochloride, or a derivative, analogue or variant thereof.

In some embodiments, the PKC inhibitor in the methods and composition provided herein is a pseudohypericin, or a derivative, analogue, or variant thereof. In some embodiments, the PKC inhibitor in the methods and composition provided herein is indorublin-3-monoxime, 5-Iodo or a derivative, analogue or variant thereof. In certain embodiments, the methods, compositions, and kits disclosed herein exclude a protein kinase inhibitor.

In some embodiments, a medium described herein does not comprise a protein kinase inhibitor, or more specifically, does not comprise staurosporine.

Acetyl CoA-Related Metabolite

In some embodiments, a composition (e.g., medium) of the disclosure comprises an acetyl CoA-related metabolite. Metabolism of acetyl-coenzyme A (acetyl-CoA) can confer numerous metabolic functions, including energy production, lipid synthesis, and protein acetylation.

Exemplary acetyl CoA-related metabolites include, but are not limited to acetate, pyruvate, ketogenic amino acids, valine, leucine, isoleucine, phenylalanine, tyrosine, lysine, tryptophan, fatty acids, CoA, Isovaleryl-CoA, and β-hydroxybutyrate. In some embodiments, the acetyl CoA-related metabolite is acetate. In some embodiments, a composition of the disclosure contains two or more different acetyl CoA related metabolites, for example, 2, 3, 4, 5, 6, 7, 8, 9, 10, or more different acetyl CoA-related metabolites. In some embodiments, the acetyl CoA-related metabolite is acetate.

In some embodiments, a medium described herein does not include an acetyl CoA-related metabolite (e.g., does not include acetate).

Histone Deacetylase Inhibitor (HDACi)

In some embodiments, a composition (e.g., medium) of the disclosure comprises a histone deacetylase inhibitor (HDACi). Histone deacetylase inhibitors (HDACi) are a class of compounds that increase acetylation of lysine residues on histone proteins as well as other, nonhistone, proteins by inhibiting the activity of HDAC enzymes.

Exemplary histone deacetylase inhibitors (HDACi) include, but are not limited to (3-Hydroxybutyrate, butyric acid, class I HDACi, class IIA HDACi, class IIB HDACi, class III HDACi, class IV HDACi, HDAC-1, HDAC-2, HDAC-3, HDAC-4, HDAC-5, HDAC-6, HDAC-7, HDAC-8, HDAC-9, HDAC-10, HDAC-11, sirtuins, SIRT1, SIRT2, SIRT3, SIRT4, SIRT5, SIRT6, SIRT7, Vorinostat (suberoylanilide hydroxamic acid, SAHA, MK0683), Entinostat (MS-275, SNDX-275), Panobinostat (LBH589, NVP-LBH589), Trichostatin A (TSA), Mocetinostat (MGCD0103, MG0103), GSK3117391 (GSK3117391A, HDAC-IN-3), BRD3308, BRD3308, Tubastatin A TFA (Tubastatin A trifluoroacetate salt), Tubastatin A, SIS17, NKL 22, BML-210 (CAY10433), TC-H 106, SR-4370, Belinostat (PXD101, NSC726630, PX-105684), Romidepsin (FK228, Depsipeptide, FR 901228, NSC 630176), MC1568, Givinostat (ITF2357), Dacinostat (LAQ824, NVP-LAQ824), CUDC-101, Quisinostat (JNJ-26481585), Pracinostat (SB939), PCI-34051, Droxinostat (NS 41080), Abexinostat (PCI-24781), Abexinostat (PCI-24781, CRA-024781), RGFP966, AR-42 (HDAC-42), Ricolinostat (ACY-1215, Rocilinostat), Valproic acid sodium salt (Sodium valproate), Tacedinaline (CI994, PD-123654, GOE-5549, Acetyldinaline), Fimepinostat (CUDC-907), Sodium butyrate (NaB), Curcumin, Diferuloylmethane, M344, Tubacin, RG2833 (RGFP109), RG2833 (RGFP109), Resminostat (RAS2410), Divalproex Sodium, Scriptaid (GCK 1026), Sodium Phenylbutyrate, Sinapinic acid (Sinapic acid), TMP269, Santacruzamate A (CAY10683), TMP195 (TFMO 2), Valproic acid (VPA), UFO10, Tasquinimod (ABR-215050), SKLB-23bb, Isoguanosine, lforaphane, BRD73954, Citarinostat (ACY-241, HDAC-IN-2), Suberohydroxamic acid, plitomicin, HPOB, LMK-235, Biphenyl-4-sulfonyl chloride (p-Phenylbenzenesulfonyl, 4-henylbenzenesulfonyl, p-Biphenylsulfonyl), Nexturastat A, TH34, Tucidinostat (Chidamide, HBI-8000, CS-055), (–)-Parthenolide, WT161, CAY10603, CAY10603, ACY-738, RaddeaninA, Tinostamustine (EDO-S101), Domatinostat (4SC-202), and BG45.

In some embodiments, the HDACi is β-Hydroxybutyrate. β-Hydroxybutyric acid is a ketone body that, along with butyric acid, is an agonist of hydroxycarboxylic acid receptor 2 (HCA2), a Gi/o-coupled GPCR. In some embodiments, an HDACi inhibitor is an agonist of hydroxycarboxylic acid receptor 2.

In some embodiments, a medium described herein does not comprise an HDACi (e.g., does not include β-Hydroxybutyrate).

Redox Homeostasis Regulator

In some embodiments, a composition (e.g., medium) of the disclosure comprises a redoxhomeostasis regulator.

Exemplary redox homeostasis regulators include, but are not limited to taurine, respiratory chain regulators, free radical scavengers, regulators of mitochondrial protein synthesis, allium sulphur compounds, anthocyanins, beta-carotene, catechins, copper, cryptoxanthins, flavonoids, indoles, isoflavonoids, lignans, lutein, lycopene, alpha lipoic acid, ellagic acid, manganese, polyphenols, selenium, glutathione, vitamin A, vitamin C, vitamin E, zinc, superoxide disutases, GSHPx, Prx-I, catalase, and co-enzyme Q10.

In some embodiments, the redox homeostasis regulator is taurine.

In some embodiments, a medium described herein does not comprise a redox homeostasis regulator.

Taurine is a non-proteinogenic β-aminosulfonic acid that can be derived from methionine and cysteine metabolism. In some embodiments, taurine can inhibit ROS generation within the respiratory chain.

In some embodiments, a medium described herein does not comprise a redox homeostasis regulator (e.g., does not include taurine).

One Carbon Metabolism Pathway Intermediate

In some embodiments, a composition (e.g., medium) of the disclosure comprises a one carbon metabolism pathway intermediate. One-carbon metabolism mediated by folate cofactors, supports multiple physiological processes including amino acid homeostasis (methionine, glycine and serine), biosynthesis of nucleotides (purines, thymidine), epigenetic maintenance, and redox defense.

Exemplary one carbon metabolism pathway intermediates include, but are not limited to formate, tetrahydrofolate (THF), 10-formylTHF; 5,10-meTHF; 5,10-meTHF; and 10-formylTHF.

In some embodiments, a medium described herein does not comprise a one carbon metabolism pathway intermediate (e.g., does not include formate).

Glutamine

In some embodiments, a composition (e.g., medium) of the disclosure comprises glutamine. Glutamine (Gln or Q) is an alpha-amino acid. Glutamine can be an essential amino acid within in vitro cell cultures. Glutamine supports the growth of cells, including cells that have high energy demands and synthesize large amounts of proteins and nucleic acids. It is an alternative energy source for rapidly dividing cells and cells that use glucose inefficiently.

In some embodiments, compositions and methods of the disclosure utilize glutamine in a form with increased bioavailability. Because of its chemical instability and importance for cell growth and function, it is important that delivery of L-glutamine be tailored to each unique cell culture process. Glutamine (e.g., L-glutamine) in a free form can be unstable at physiological pH in liquid media, breaking down to ammonium and pyroglutamate at rates that make it a problem in many cell culture and biomanufacturing applications. Therefore, many cell culture media contain stabilized forms of glutamine, including dipeptide forms, such as alanyl-1-glutamine and glycyl-1-glutamine. However, these more stable forms of L-glutamine can also have limited bioavailability, for example, due to a requirement for processing by enzymes, such as cell surface peptidases. Thus in some embodiments, compositions and methods of the disclosure utilize glutamine in a form with increased bioavailability, such as a free glutamine form, such as a non-dipeptide form, a non-alanine-glutamine dipeptide form (e.g., a non-alanyl-1-glutamine form), a non-glycine-glutamine dipeptide form (e.g., a non-glycyl-1-glutamine form), a form that in which glutamine is not conjugated to another amino acid or stabilizing moiety, a monomeric form, a free form, or a combination thereof. In some embodiments, glutamine is provided as a protein hydrolysate.

In some embodiments, a basal media contains glutamine. In some embodiments, glutamine in a form as disclosed herein is added to a media that already contains glutamine. In some embodiments, glutamine in a form as disclosed herein is added to a basal media that contains no glutamine or only low levels of glutamine to increase the bioavailability of glutamine.

In some embodiments, a medium described herein does not comprise glutamine.

Glutamate

In some embodiments, a composition (e.g., medium) of the disclosure comprises glutamate (e.g., L-glutamate). Glutamate can be converted into, for example, g-amino butyric acid (GABA), ornithine, 2-oxoglutarate, glucose or glutathione. Glutamate and metabolites generated therefrom can contribute to, for example, redox homeostasis, cell signaling, nitrogen assimilation, amine catabolism, amino acid biosynthesis, nucleoside biosynthesis, and cofactor production.

In some embodiments, contacting cells with glutamate can improve production of SC-β cells in vitro, for example, providing higher cell yields and recoveries, increased numbers and relative percentages of SC-β cells, enhanced stability and shelf-life of SC-β cells, SC-islet clusters with advantageous characteristics such as reduced size and increased uniformity, improved function of the SC-β cells in vitro, improved cell viability, improved cell function, reduced immunogenicity after transplantation, or a combination thereof, e.g., relative to a composition that lacks glutamate, or contains a lower concentration of glutamate.

In some embodiments, a medium described herein does not comprise glutamate.

Vitamins

In some embodiments, a composition (e.g., medium) of the disclosure comprises one or more vitamins.

Exemplary vitamins include, but are not limited to biotin, vitamin B1 (thiamine), vitamin B2 (riboflavin), vitamin B3 (niacin), vitamin B6 (pyridoxine) and vitamin B12 (cyanocobalamin). In some embodiments the vitamin modulates fatty acid synthesis. In some embodiments the vitamin modulates branched-chain amino acid metabolism. In some embodiments the vitamin modulates or participates as a co-factor in the TCA cycle, e.g., as a cofactor for pyruvate carboxylase. In some embodiments, the vitamin is biotin. In some embodiments, a composition of the disclosure contains two or more different vitamins, for example, 2, 3, 4, 5, 6, 7, 8, 9, 10, or more different vitamins.

In some embodiments, a medium described herein does not comprise a vitamin.

Water-Soluble Synthetic Polymer

Water-soluble polymer described herein can refer to any polymer that has hydrophilic property and is soluble in aqueous solution at room temperature. The water-soluble polymer can be either naturally occurring or synthetic. In some embodiments, a water-soluble polymer is an albumin protein (e.g., human serum albumin or bovine serum albumin). In some embodiments, the water-soluble polymer is a water-soluble synthetic polymer. Water-soluble synthetic polymers described herein can refer to any synthetic polymer that has hydrophilic property and is soluble in aqueous solution at room temperature. Water-soluble synthetic polymers applicable in the subject methods and compositions include, but not limited to, poloxamer, polyvinyl alcohol, polyvinylpyrrolidone, polyethylene glycol (PEG), PEG copolymers, poly(Nisopropylacrylamide), and polyacrylamide. The water-soluble synthetic polymer can refer to a polymer compound or a mixture of polymer compounds that may have an idealized chemical formula but a variety of derivatives and/or precursors of the idealized formula, depending on the applicable manufacturing method. In some embodiments, the water-soluble synthetic polymer is used to replace at least partially serum or serum albumin, e.g., BSA or HSA, that is typically utilized in cell differentiation, e.g., differentiation of pancreatic β cells or precursor cells thereof. In some embodiments, the water-soluble synthetic polymer replaces 100% of serum albumin, e.g., BSA or HSA, that is typically utilized in cell differentiation, e.g., differentiation of pancreatic β cells or precursor cells thereof. In some embodiments, the water-soluble synthetic polymer reduces the amount of serum albumin, e.g., BSA or HSA, by at least 20%, 30%, 40%, 50%, 60%, 80%, 90%, 95%, or 99% of that is typically utilized in cell differentiation, e.g., differentiation of pancreatic β cells or precursor cells thereof. In some embodiments, the disclosure provides for a composition comprising a population of any of the cells disclosed herein (e.g., pluripotent stem cells; endoderm cells; primitive gut cells; PDX1-positive, NKX6.1-negative pancreatic progenitor cells; PDX1-positive, NKX6.1-positive pancreatic progenitor cells; insulin-positive cells; and/or pancreatic beta cells) and water soluble polymers, wherein at least 20%, 30%, 40%, 50%, 60%, 80%, 90%, 95%, or 99% of the water soluble polymers in the composition are water-soluble synthetic polymers (e.g., any of the PVA molecules disclosed herein) and wherein the remainder of the water soluble polymers are human serum albumin polypeptides. In some embodiments, the disclosure provides for a composition comprising a population of any of the cells disclosed herein (e.g., pluripotent stem cells; endoderm cells; primitive gut cells; PDX1-positive, NKX6.1-negative pancreatic progenitor cells; PDX1-positive, NKX6.1-positive pancreatic progenitor cells; insulin-positive cells; and/or pancreatic beta cells) and water soluble polymers, wherein no more than 1%, 2%, 3%, 4%, 5%, 6%, 7%, 8%, 9%, 10%, 15%, 20%, 30%, 40%, 50%, 60%, 80%, 90%, 95%, or 99% of the water soluble polymers are naturally occurring water-soluble polymers (e.g., HSA or BSA). In some embodiments, more than 90%, 95%, 99%, and up to 100% of the water soluble polymers in the composition are water-soluble synthetic polymers (e.g., PVA).

In some embodiments, the water-soluble synthetic polymer applicable to the subject compositions and methods includes polyvinyl alcohol (PVA). Polyvinyl alcohol described herein can refer to a water-soluble synthetic polymer that has an idealized formula [CH2CH(OH)]n, which can be either partially or completed hydrolyzed. In some embodiments, the polyvinyl alcohol is manufactured by either partial or complete hydrolysis of polyvinyl acetate to remove acetate groups. In some embodiments, the polyvinyl alcohol is at most 85% hydrolyzed, e.g., 80% hydrolyzed. The percentage of hydrolyzation measures the approximate percentage (e.g., average percentage) of acetate residue that is hydrolyzed in the polyvinyl acetate precursor polymer. In some embodiments, the polyvinyl alcohol is at least 85% hydrolyzed, e.g., 87-89% hydrolyzed, 87-90% hydrolyzed, or 99% hydrolyzed. In some embodiments, the polyvinyl alcohol is 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% hydrolyzed. Without wishing to be bound by a certain theory, the polyvinyl alcohol can assume a function of carrier-molecule in the culture medium, which is typically carried out by serum or serum albumin, e.g., HSA. The percentage of hydrolyzation of polyvinyl alcohol can be determined by the manufacturing method utilized to produce the polyvinyl alcohol, e.g., how polyvinyl acetate precursor polymer is converted into polyvinyl alcohol, e.g., conversion by base-catalyzed transesterification with ethanol. In some embodiments, the water-soluble synthetic polymer preparation, e.g., polyvinyl alcohol, that is used in the subject method or present in the subject composition has purity of at least 90%, such as at least 92%, at least 95%, at least 98%, at least 99%, at least 99.5%, at least 99.9%, or nearly 100%. Purity of polyvinyl alcohol measures the percentage of synthetic polymer that has the idealized formula [CH2CH(OH)]n in the preparation, which includes polyvinyl alcohol of any percentage of hydrolyzation. Impurity of polyvinyl alcohol preparation can include other polymer materials that do not have the idealized formula [CH2CH(OH)]n, or other organic inorganic materials.

In some embodiments, a medium described herein does not comprise a water-soluble synthetic polymer.

Stem Cell Derived Pancreatic Islet Cells, Compositions and Method of Use

In some aspects, a population of in vitro differentiated cells (e.g., stem cell-derived pancreatic islet cells) produced using the compositions and methods described herein are also provided. In some embodiments, the population of in vitro differentiated cells (e.g., stem cell-derived pancreatic islet cells) comprises NKX6.1-positive, ISL1-positive cells and NKX6.1-negative, ISL-positive cells. In some embodiments, the population comprises more NKX6.1-positive, ISL-positive cells than NKX6.1-negative, ISL-positive cells. In some embodiments, at least 15% of the cells in the population are NKX6.1-negative, ISL-positive cells; and wherein less than 12% of the cells in the population are NKX6.1-negative, ISL-negative cells. In some aspects, methods of using the population of in vitro differentiated cells (e.g., stem cell-derived pancreatic islet cells) described herein to treat diseases (e.g., diabetes) are provided. In some embodiments, the cells in any of the cell populations disclosed herein have not been previously subjected to a cell-sorting process (e.g., affinity binding purification or FACS).

In some embodiments, a population of in vitro differentiated cells described herein comprises NKX6.1-positive, ISL1-positive cells and NKX6.1-negative, ISL1-positive cells. In some embodiments, the population comprises more NKX6.1-positive, ISL1-positive cells than NKX6.1-negative, ISL1-positive cells.

In some embodiments, the disclosure provides for a composition comprising a plurality of cells (e.g., a composition comprising a cluster of cells or multiple clusters of cells); wherein at least 30% of the cells in the composition are NKX6.1-positive, ISL1-positive cells; wherein at least 25% of the cells in the composition are NKX6.1-negative, ISL1-positive cells; wherein there are more NKX6.1-positive, ISL1-positive cells than NKX6.1-negative, ISL1-positive cells in the composition; and wherein less than 12% of the cells in the composition are NKX6.1-negative, ISL1-negative cells. In some embodiments, the disclosure provides for a composition comprising a plurality of cells (e.g., a composition comprising a cluster of cells or multiple clusters of cells); wherein 30-60%, 30-55%, 30-50%, 30-45%, 30-40%, 30-35%, 35-60%, 35-55%, 35-50%, 35-45%, 35-40%, 40-60%, 40-55%, 40-50%, 40-45%, 45-60%, 45-55%, 45-50%, 50-60%, or 50-55% of the cells in the composition are NKX6.1-positive, ISL1-positive cells; wherein 20-50%, 20-45%, 20-40%, 20-35%, 20-30%, 20-25%, 25-50%, 25-45%, 25-40%, 25-35%, 25-30%, 30-50%, 30-45%, 30-40%, 30-35%, 35-50%, 35-35%, 35-40%, 40-50%, 40-45%, or 45-50% of the cells in the composition are NKX6.1-negative, ISL1-positive cells; wherein there are more NKX6.1-positive, ISL1-positive cells than NKX6.1-negative, ISL1-positive cells in the composition; and wherein 1-12%, 1-10%, 1-8%, 1-6%, 1-4%, 3-5%, 1-2%, 2-12%, 2-10%, 2-8%, 2-6%, 2-4%, 4-12%, 4-10%, 4-8%, 4-6%, 6-12%, 6-10%, 6-8%, 8-12%, 8-10%, or 10-12% of the cells in the composition are NKX6.1-negative, ISL1-negative cells. In some embodiments, the disclosure provides for a composition comprising a plurality of cells (e.g., a composition comprising a cluster of cells or multiple clusters of cells); wherein 35-50% of the cells in the composition are NKX6.1-positive, ISL1-positive cells; wherein 30-45% of the cells in the composition are NKX6.1-negative, ISL1-positive cells; wherein there are more NKX6.1-positive, ISL1-positive cells than NKX6.1-negative, ISL1-positive cells in the composition; and wherein 2-12% of the cells in the composition are NKX6.1-negative, ISL1-negative cells. In some embodiments, between 5-25%, 5-20%, 5-15%, 5-10%, 10-25%, 10-20%, 10-15%, 15-25%, 15-20% or 20-25% of the cells in the composition are NKX6.1-positive, ISL1-negative cells.

In some embodiments, the disclosure provides for a composition comprising a plurality of cells (e.g., a composition comprising a cluster of cells or multiple clusters of cells); wherein at least 30% of the cells in the composition are NKX6.1-positive, ISL1-positive cells; wherein at least 25% of the cells in the composition are NKX6.1-negative, ISL1-positive cells; wherein there are more NKX6.1-positive, ISL1-positive cells than NKX6.1-negative, ISL1-positive cells in the composition; and wherein between 9-25% of the cells in the composition are NKX6.1-positive, ISL1-negative cells. In some embodiments, the disclosure provides for a composition comprising a plurality of cells (e.g., a composition comprising a cluster of cells or multiple clusters of cells); wherein 30-60%, 30-55%, 30-50%, 30-45%, 30-40%, 30-35%, 35-60%, 35-55%, 35-50%, 35-45%, 35-40%, 40-60%, 40-55%, 40-50%, 40-45%, 45-60%, 45-55%, 45-50%, 50-60%, or 50-55% of the cells in the composition are NKX6.1-positive, ISL1-positive cells; wherein 20-50%, 20-45%, 20-40%, 20-35%, 20-30%, 20-25%, 25-50%, 25-45%, 25-40%, 25-35%, 25-30%, 30-50%, 30-45%, 30-40%, 30-35%, 35-50%, 35-35%, 35-40%, 40-50%, 40-45%, or 45-50% of the cells in the composition are NKX6.1-negative, ISL1-positive cells; wherein there are more NKX6.1-positive, ISL1-positive cells than NKX6.1-negative, ISL1-positive cells in the composition; and wherein 9-30%, 9-25%, 9-20%, 9-15%, 9-12%, 12-30%, 12-25%, 12-20%, 12-15%, 15-30%, 15-25%, 15-20%, 20-30%, 20-25% or 25-30% of the cells in the composition are NKX6.1-positive ISL-negative cells. In some embodiments, 1-12%, 1-10%, 1-8%, 1-6%, 1-4%, 3-5%, 1-2%, 2-12%, 2-10%, 2-8%, 2-6%, 2-4%, 4-12%, 4-10%, 4-8%, 4-6%, 6-12%, 6-10%, 6-8%, 8-12%, 8-10%, or 10-12% of the cells in the composition are NKX6.1-negative, ISL1-negative cells. In some embodiments, the disclosure provides for a composition comprising a plurality of cells (e.g., a composition comprising a cluster of cells or multiple clusters of cells); wherein 35-50% of the cells in the composition are NKX6.1-positive, ISL1-positive cells; wherein 30-45% of the cells in the composition are NKX6.1-negative, ISL1-positive cells; wherein there are more NKX6.1-positive, ISL1-positive cells than NKX6.1-negative, ISL1-positive cells in the composition; and wherein 9-25% of the cells in the composition are NKX6.1-positive, ISL1-negative cells.

In some embodiments, less than 12% of the cells (e.g., about 11%, about 10%, about 9%, about 8%, about 7%, about 6%, about 5%, about 4%, about 3%, about 2%, about 1%, or less) in the population are NKX6.1-negative, ISL1-negative cells. In some embodiments, less than 10%, less than 8%, less than 6%, less than 4%, 1%-11%, 2%-10%, 2%-12%, 4%-12%, 6%-12%, 8%-12%, 2%-8%, 4%-8%, 3%-6% or 3%-5% of the cells in the population are NKX6.1-negative, ISL1-negative cells. In some embodiments, 2%-12%, 4%-12%, 6%-12%, 8%-12%, 2%-8%, 4%-8%, 3%-6% or 3%-5% of the cells in the population are NKX6.1-negative, ISL1-negative cells.

In some embodiments, at least 15% of the cells (e.g., about 15%, about 20%, about 25%, about 30%, about 35%, about 40%, about 45%, about 50%, about 55%, about 60% or more) in the population are NKX6.1-negative, ISL1-positive cells. In some embodiments, at least 15%, at least 20%, at least 25%, at least 30%, at least 35%, at least 40%, at least 45%, at least 50%, at least 55%, at least 60%, 15%-60%, 15%-45%, 15%-30%, 30%-60%, 30%-45%, 45%-60% of the cells in the population are NKX6.1-negative, ISL1-positive cells. In some embodiments, 20%-60%, 20%-50%, 20%-40%, 20%-30%, 30%-60%, 30%-50%, 30%-40%, 40%-60%, 40%-50%, or 50%-60% of the cells in the population are NKX6.1-negative, ISL1-positive cells.

In some embodiments, at least 15% (e.g., 20%-60%, 20%-50%, 20%-40%, 20%-30%, 30%-60%, 30%-50%, 30%-40%, 40%-60%, 40%-50%, or 50%-60%) of the cells in the population are NKX6.1-negative, ISL1-positive cells and less than 12% (e.g., 2%-12%, 4%-12%, 6%-12%, 8%-12%, 2%-8%, 4%-8%, 3%-6% or 3%-5%) of the cells in the population are NKX6.1-negative, ISL1-negative cells.

In some embodiments, at least 60%, at least 65%, at least 70%, at least 73%, at least 74%, at least 75%, at least 80%, at least 85%, at least 90%, about 85-95%, or about 90-95% of the cells in the population are ISL1-positive cells. In some embodiments, 50-90%, 50-85%, 50-80%, 50-75%, 50-70%, 50-60%, 60-90%, 60-85%, 60-80%, 60-75%, 60-70%, 65-90%, 65-85%, 65-80%, 65-75%, 65-70%, 70-90%, 70-85%, 70-80%, 70-75%, 75-90%, 75-85%, 75-80%, 80-90%, 80-85%, or 85-90% of the cells in the population are ISL1-positive cells. In some embodiments, at least 74%, at least 75%, at least 80%, at least 85%, at least 90%, about 85-95%, or about 90-95% of the cells in the population are ISL1-positive cells. In some embodiments, about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99% of the cells in the population are ISL1-positive cells.

In some embodiments, a population of in vitro differentiated cells described herein comprises more NKX6.1-negative, ISL1-positive cells than NKX6.1-positive, ISL1-positive cells. In some embodiments, the population comprises more NKX6.1-positive, ISL1-positive cells that NKX6.1-negative, ISL1-positive cells. In some embodiments, at least 40% of the cells in the population are NKX6.1-negative, ISL1-positive cells. In some embodiments, at least 45%, at least 50%, about 40-50%, about 45-55%, or about 50-55% of the cells in the population are NKX6.1-negative, ISL1-positive cells. In some embodiments, about 40%, 41%, 42%, 43%, 44%, 45%, 46%, 47%, 48%, 49%, 50%, 51%, 52%, 53%, 54%, or about 55% of the cells in the population are NKX6.1-negative, ISL1-positive cells.

In some embodiments, at least 20% (e.g., at least 20%, at least 30%, at least 40%, at least 50%, at least 50%, at least 60% or more) of the ISL1-positive cells are NKX6.1-negative. In some embodiments, about 20%-60%, 20%-50%, 20%-40%, 20%-30%, 30%-60%, 30%-50%, 30%-40%, 40%-60%, 40%-50%, or 50%-60% of the ISL1-positive cells are NKX6.1-negative. In some embodiments, about 20%, 25%, 30%, 35%, 40%, 45%, 50%, 55%, 60% or more of the ISL1-positive cells are NKX6.1-negative.

In some embodiments, a population of in vitro differentiated cells described herein comprises at least 20% (e.g., at least 20%, 30%, 40%, 50% or 60%) of NXK6.1-positive, ISL1-positive cells. In some embodiments, a population of in vitro differentiated cells described herein comprises about 20%-50%, 20%-40%, 20%-30%, 30%-50%, 30%-40%, 40%-50%, 40%-60%, or 50-60% of NXK6.1-positive, ISL1-positive cells. In some embodiments, a population of in vitro differentiated cells described herein comprises about 20%-50%, 20%-40%, 20%-30%, 30%-50%, 30%-40%, or 40%-50% of NXK6.1-positive, ISL1-positive cells.

In some embodiments, a population of in vitro differentiated cells described herein comprises less than 25% (e.g., less than 25%, less than 20%, less than 15%, less than 10%, less than 5%, or less) of NKX6.1-positive, ISL1-negative cells. In some embodiments, a population of in vitro differentiated cells described herein comprises about 2%-25%, 2%-20%, 2%-15%, 2%-10%, 2%-5%, 5%-25%, 5%-20%, 5%-15%, 5%-10%, 10%-25%, 10%-20%, 10%-15%, 15%-25%, 15%-20%, or 20%-25% of NKX6.1-positive, ISL1-negative cells. In some embodiments, a population of in vitro differentiated cells described herein comprises about 2%-10%, 2%-8%, 2%-6%, 2%-4%, 4%-10%, 4%-8%, 4%-6%, 6%-10%, 6%-8%, or 8%-10% of NKX6.1-positive, ISL1-negative cells. In some embodiments, a population of in vitro differentiated cells described herein comprises about 2%, 4%, 6%, 8%, or 10% of NKX6.1-positive, ISL1-negative cells.

In some embodiments, a population of in vitro differentiated cells described herein comprises ghrelin-positive cells. In some embodiments, a population of in vitro differentiated cells described herein comprises less than 5% (e.g., less than 5%, less than 3%, less than 2%, less than 1% or less than 0.5%) ghrelin-positive cells. In some embodiments, a population of in vitro differentiated cells described herein comprises at least 0.05% (e.g., at least 0.05%, 0.1%, 0.2%, 0.3%, 0.4%, 0.5%, 0.6%, 0.8%, 1%, 1.2%, 1.5%, 1.8%, 2%, 3%, 4%, or 5%) ghrelin-positive cells. In some embodiments, a population of in vitro differentiated cells described herein comprises 1-5%, 2-5%, 3-5%, 0.1-5%, 0.1-3%, 0.1-2%, 0.1-1%, 0.5-5%, 0.5-3%, 0.5-2%, 0.5-1%, 0.5-0.8%, 0.05-1%, 0.05-0.7%, or 0.05-2% ghrelin-positive cells.

In some embodiments, a population of in vitro differentiated cells described herein comprises ARX-positive cells. In some embodiments, at least 4% (e.g., at least 4%, 5%, 6%, 7%, 8%, 9%, 10%, 11%, 12%, 14%, 16%, 18%, 20%, 22%, 24%, 26%, 28%, 30%, 35%, 40%, or 50%) of the cells in the population are ARX-positive cells. In some embodiments, less than 50% (e.g., less than 50%, 40%, 35%, 30%, 28%, 26%, 24%, 22%, 20%, 18%, 16%, 14%, 12%, 11%, 10%, 9%, 8%, 7%, 6%, 5%, or 4%) of the cells in the population are ARX-positive cells. In some embodiments, the population of cells comprises between 4-50%, 4-40%, 4-30%, 4-25%, 4-20%, 4-15%, 4-10%, 4-8%, 8-50%, 8-40%, 8-30%, 8-25%, 8-20%, 8-15%, 8-10%, 10-50%, 10-40%, 10-30%, 10-25%, 10-20%, or 10-15% ARX-positive cells.

In some embodiments, a population of in vitro differentiated cells described herein comprises cells that express insulin (e.g., cells that express insulin but not glucagon or somatostatin), cells that express glucagon (e.g., cells that express glucagon but not insulin or somatostatin), and cells that express somatostatin (e.g., cells that express somatostatin but not insulin or glucagon). In some embodiments, the expression of insulin in a cell of the compositions suggests that the cell is a SC-β cell. In some embodiments, the expression of glucagon and not expressing somatostatin in a cell of the composition suggests that the cell is a SC-α cell. In some embodiments, the expression of somatostatin and not expressing glucagon in a cell of the composition suggests that the cell is a SC-δ cell. In some embodiments, cells that express insulin are also glucose responsive insulin producing cells.

In some embodiments, cells that express insulin (i.e., SC-β cells) in a population of in vitro differentiated cells described herein exhibit glucose stimulated insulin secretion (GSIS). In some embodiments, cells that express insulin (i.e., SC-β cells) in a population of in vitro differentiated cells described herein further mature (e.g., further maturing in a subject after transplantation) into cells that exhibit glucose stimulated insulin secretion (GSIS).

In some embodiments, a population of in vitro differentiated cells described herein comprises at least 5% or at least 10% (e.g., at least 5%, at least 10%, at least 20%, at least 30%, at least 40%, at least 50%, or more) of stem cell-derived alpha cells. In some embodiments, a population of in vitro differentiated cells described herein comprises about 5%-50%, 10%-50%, 5%-25%, 5%-20%, 5%-15%, 10%-40%, 10%-30%, 10%-20%, 20%-50%, 20%-40%, 20%-30%, 30%-50%, 30%-40%, or 40%-50% of stem cell-derived alpha cells. In some embodiments, a population of in vitro differentiated cells described herein comprises about 5%, 10%, 15%, 20%, 25%, 30%, 35%, 40%, 45% or 50% of stem cell-derived alpha cells.

In some embodiments, a population of in vitro differentiated cells described herein comprises at least 30% (e.g., at least 30%, at least 35%, at least 40%, at least 45%, at least 50%, at least 55%, at least 60% or more) of stem cell-derived beta cells. In some embodiments, a population of in vitro differentiated cells described herein comprises about 30%-60%, 30%-50%, 30%-40%, 35%-60%, 35%-55%, 35%-50%, 35%-45%, 35%-40%, 40%-60%, 40%-55%, 40%-50%, 40%-45%, 45%-60%, 45%-55%, 45%-50%, 509%-60%, 50%-55%, or 55%-60% of stem cell-derived beta cells. In some embodiments, a population of in vitro differentiated cells described herein comprises about 35%, 40%, 45%, 50%, 55%, or 60% of stem cell-derived beta cells.

In some embodiments, a population of in vitro differentiated cells described herein comprises at least 4% (e.g., at least 4%, at least 5%, at least 10%, at least 15%, at least 20% or more) of stem cell-derived delta cells. In some embodiments, a population of in vitro differentiated cells described herein comprises about 5%-20%, 5%-15%, 5%-10%, 10%-20%, 10%-15%, or 15%-20% of stem cell-derived delta cells. In some embodiments, a population of in vitro differentiated cells described herein comprises about 4%, 5%, 10%, 15%, or 20% of stem cell-derived delta cells.

In some embodiments, a population of in vitro differentiated cells described herein comprises less than 5% (e.g., less than 5%, less than 3%, less than 2%, less than 1% or less than 0.5%) stem cell-derived epsilon cells. In some embodiments, a population of in vitro differentiated cells described herein comprises at least 0.05% (e.g., at least 0.05%, 0.1%, 0.2%, 0.3%, 0.4%, 0.5%, 0.6%, 0.8%, 1%, 1.2%, 1.5%, 1.8%, 2%, 3% 4%, or 5%) stem cell-derived epsilon cells. In some embodiments, a population of in vitro differentiated cells described herein comprises 1-5%, 2-5%, 3-5%, 0.1-5%, 0.1-3%, 0.1-2%, 0.1-1%, 0.5-5%, 0.5-3%, 0.5-2%, 0.5-1%, 0.5-0.8%, 0.05-1%, 0.05-0.7%, or 0.05-2% stem cell-derived epsilon cells.

In some embodiments, a population of in vitro differentiated cells described herein comprises at least 5% of (e.g., about 5%, 6%, 7%, 8%, 9%, or 10%) cells that are glucagon-positive and somatostatin-negative. In some embodiments, a population of in vitro differentiated cells described herein comprises at least 5% (e.g., about 5%, 6%, 7%, 8%, 9%, or 10%) of cells that are glucagon-negative and somatostatin-positive.

In some embodiments, a population of in vitro differentiated cells described herein comprises: (a) 30%-90%, 30%-80%, 30%-70%, 30%-60%, 30%-50%, 30%-40%, 40%-90%, 40%-80%, 40%-70%, 40%-60%, 40%-50%, 50%-90%, 50%-80%, 50%-70%, 50%-60%, 60%-90%, 60%-80%, 60%-70%, 70%-90%, 70%-80%, 70%-90%, 70%-80%, or 80%-90% of the cells in the population of cells express insulin; (b) 5%-40%, 5%-35%, 5%-30%, 5%-25%, 5%-20%, 5%-15%, 5%-10%, 10%-40%, 10%-35%, 10%-30%, 10%-25%, 10%-20%, 10%-15%, 15%-40%, 15%-35%, 15%-30%, 15%-25%, 15%-20%, 20%-40%, 20%-35%, 20%-30%, 20%-25%, 25%-40%, 25%-35%, 25%-30%, 30%-40%, 30%-35% or 35%-40% of the cells in the population of cells express glucagon but not somatostatin; and/or (c) 3%-20%, 3%-15%, 3%-12%, 3%-10%, 3%-8%, 3%-5%, 4%-20%, 4%-15%, 4%-12%, 4%-10%, 4%-8%, 4%-5%, 5%-20%, 5%-15%, 5%-12%, 5%-10%, 5%-8%, 7%-20%, 7%-15%, 7%-12%, 7%-10%, 9%-20%, 9%-15%, 9%-12%, 8%-10%, 8%-12%, 8%-15%, 8%-20%, 10%-20%, 10%-12%, 10%-15%, 12%-20%, 12%-15% or 15%-20% of the cells in the population of cells express somatostatin but not glucagon.

In some embodiments, a population of in vitro differentiated cells described herein comprises: (a) 30%-90%, 30%-80%, 30%-70%, 30%-60%, 30%-50%, 30%-40%, 40%-90%, 40%-80%, 40%-70%, 40%-60%, 40%-50%, 50%-90%, 50%-80%, 50%-70%, 50%-60%, 60%-90%, 60%-80%, 60%-70%, 70%-90%, 70%-80%, 70%-90%, 70%-80%, or 80%-90% of the cells in the population of cells express insulin; (b) 5%-40%, 5%-35%, 5%-30%, 5%-25%, 5%-20%, 5%-15%, 5%-10%, 10%-40%, 10%-35%, 10%-30%, 10%-25%, 10%-20%, 10%-15%, 15%-40%, 15%-35%, 15%-30%, 15%-25%, 15%-20%, 20%-40%, 20%-35%, 20%-30%, 20%-25%, 25%-40%, 25%-35%, 25%-30%, 30%-40%, 30%-35% or 35%-40% of the cells in the population of cells express glucagon but not somatostatin; and (c) 3%-20%, 3%-15%, 3%-12%, 3%-10%, 3%-8%, 3%-5%, 4%-20%, 4%-15%, 4%-12%, 4%-10%, 4%-8%, 4%-5%, 5%-20%, 5%-15%, 5%-12%, 5%-10%, 5%-8%, 7%-20%, 7%-15%, 7%-12%, 7%-10%, 9%-20%, 9%-15%, 9%-12%, 8%-10%, 8%-12%, 8%-15%, 8%-20%, 10%-20%, 10%-12%, 10%-15%, 12%-20%, 12%-15% or 15%-20% of the cells in the population of cells express somatostatin but not glucagon.

In some embodiments, a population of in vitro differentiated cells described herein comprises NKX6.1-positive, ISL1-positive cells that express lower levels of MAFA than NKX6.1-positive, ISL1-positive cells from the pancreas of a healthy control adult subject. In some embodiments, a population of in vitro differentiated cells described herein comprises NKX6.1-positive, ISL1-positive cells that express higher levels of MAFB than NKX6.1-positive, ISL1-positive cells from the pancreas of a healthy control adult subject. In some embodiments, a population of in vitro differentiated cells described herein comprises NKX6.1-positive, ISL1-positive cells that express higher levels of SIX2, HOPX, IAPP and/or UCN3 than NKX6.1-positive, ISL1-positive cells from the pancreas of a healthy control adult subject. In some embodiments, a population of in vitro differentiated cells described herein comprises NKX6.1-positive, ISL1-positive cells that do not express MAFA. In some embodiments, a population of in vitro differentiated cells described herein comprises NKX6.1-positive, ISL1-positive cells that express MAFB. As defined herein, the healthy control adult subject is a non-diabetic subject with a healthy functioning pancreas.

In some embodiments, the population comprises one or more NKX6.1-positive, ISL1-positive cells that express CHGA, MAFB, and/or ESRRG at a higher level (e.g., at least 10%, 30%, 50%, 70%, 100%, 125%, 150%, or 200% higher) than a NKX6.1-positive, ISL1-positive cell from the pancreas of a healthy control adult subject. In some embodiments, at least 30%, 40%, 50%, 60%, 70%, 80%, 90%, 95%, or 100% of the NKX6.1-positive, ISL1-positive cells in a population of cells express CHGA, MAFB, and/or ESRRG at a higher level than at least 30%, 40%, 50%, 60%, 70%, 80%, 90%, 95%, or 100% of the NKX6.1-positive, ISL1-positive cells from the pancreas of a healthy control adult subject. In some embodiments, the population comprises one or more NKX6.1-positive, ISL1-positive cells that express SIX3, MAFA, CHGB, RBP4 and/or FXYD2 at a lower level (e.g., at least 10%, 20%, 30%, 40%, 50%, 60%, 70%, 80%, 90% or 100% lower) than a NKX6.1-positive, ISL1-positive cell from the pancreas of a healthy control adult subject. In some embodiments, at least 30%, 40%, 50%, 60%, 70%, 80%, 90%, 95%, or 100% of the NKX6.1-positive, ISL1-positive cells in a population of cells express SIX3, MAFA, CHGB, RBP4 and/or FXYD2 at a lower level than at least 30%, 40%, 50%, 60%, 70%, 80%, 90%, 95%, or 100% of the NKX6.1-positive, ISL1-positive cells from the pancreas of a healthy control adult subject. In some embodiments, the population comprises NKX6.1-positive, ISL1-positive cells that express lower levels of MAFA than NKX6.1-positive, ISL1-positive cells from the pancreas of a healthy control adult subject. In some embodiments, the population comprises NKX6.1-positive, ISL1-positive cells that express lower levels of SIX3 than NKX6.1-positive, ISL1-positive cells from the pancreas of a healthy control adult subject. In some embodiments, the population comprises NKX6.1-positive, ISL1-positive cells that express lower levels of CHGB than NKX6.1-positive, ISL1-positive cells from the pancreas of a healthy control adult subject. In some embodiments, the population comprises NKX6.1-positive, ISL1-positive cells that express lower levels of RBP4 than NKX6.1-positive, ISL1-positive cells from the pancreas of a healthy control adult subject. In some embodiments, the population comprises NKX6.1-positive, ISL1-positive cells that express lower levels of FXYD2 than NKX6.1-positive, ISL1-positive cells from the pancreas of a healthy control adult subject.

In some embodiments, a population of in vitro differentiated cells described herein comprises a C-peptide content per 1,000 of the in vitro differentiated cells of at least 300 µM (e.g., at least 300 µM, at least 400 µm, at least 500 µm, 300 µm-500 µm, 300 µm-400 µm, or 400 µm-500 µm). In some embodiments, a population of in vitro differentiated cells described herein comprises a glucagon content per 1,000 of the in vitro differentiated cells of at least 100 µM (e.g., at least 100 µm, at least 200 µm, at least 300 µM, at least 400 µm, at least 500 µm, at least 600 µm, at least 700 µm, at least 800 µm, 100 µm-800 µm, 100 µm-700 µm, 100 µm-600 µm, 100 µm-500 µm, 100 µm-400 µm, 100 µm-300 µm, 100 µm-200 µm, 200 µm-800 µm, 200 µm-700 µm, 200 µm-600 µm, 200 µm-500 µm, 200 µm-400 µm, 200 µm-300 µm, 300 µm-800 µm, 300 µm-700 µm, 300 µm-600 µm, 300 µm-500 µm, 300 µm-400 µm, 400 µm-800 µm, 400 µm-700 µm, 400 µm-600 µm, 400 µm-500 µm, 500 µm-800 µm, 500 µm-700 µm, 500 µm-600 µm, 600 µm-800 µm, 600 µm-700 µm, or 700 µm-800 µm).

In some embodiments, the percentage of cells expressing a marker provided herein is measured by flow cytometry. The skilled worker is aware of representative methods for testing whether a cell or collection of cells is positive or negative for expression of a specific gene marker (e.g., NKX6.1, ISL1, INS, GCG, ARX, or ghrelin) by flow cytometry. In some embodiments, a cell is considered positive for expression of a particular gene (e.g., NKX6.1, ISL1, INS, GCG, ARX, or ghrelin) based on median fluorescence intensity (rMFI). As used herein, the term "rMFI" or relative median fluorescence intensity is the ratio between the fluorescence intensity measured by use of an antibody to a specific target (e.g., NKX6.1, ISL1, INS, GCG, ARX, or ghrelin) versus the intensity obtained from a control antibody (isotype control). In some embodiments, an anti-(human) NKX6.1, ISL1, INS, GCG, ARX or ghrelin antibody is used. Examples of suitable antibodies for use in flow cytometry are any of the antibodies disclosed in Table 8. An example of a suitable flow cytometer is the Accuri 6 flow cytometer. In some embodiments, the target-expressing cells (e.g., cells expressing NKX6.1 and/or ISL1), if tested, exhibit a target relative medium fluorescence intensity (rMFI) of at least 6, 6.5, 7, 8, 9 or 10 as measured by flow cytometry. In another embodiment, said rMFI is between 6.5 and 15, between 6.5 and 14, between 6.5 and 13, between 6.5 and 13, between 6.5 and 12, or between 6.5 and 10.

In some embodiments, the percentage of cells expressing a marker provided herein is measured by qRT-PCR. In some embodiments, the percentage of cells expressing a marker provided herein is measured by single cell RNA sequencing analysis. The skilled worker is aware of methods for testing whether a cell or collection of cells is positive for expression of a specific gene marker (e.g., NKX6.1, ISL1, INS, GCG, ARX, or ghrelin) by single cell RNA sequencing analysis.

In some embodiments, cells in a population of in vitro differentiated cells described herein form cell clusters. The terms "cluster" and "aggregate" can be used interchangeably, and refer to a group of cells that have close cell-to-cell contact, and in some embodiments, the cells in a cluster can be adhered to one another. A cell cluster comprises a plurality of cells. In some embodiments, a cell cluster comprises at least 10, at least 50, at least 200, at least 500, at least 750, at least 1000, at least 1500, at least 2000, at least 2500, at least 3000, at least 3500, at least 4000, at least 4500, at least 5000, at least 6000, at least 7000, at least 8000, at least 9000, at least 10,000, at least 20,000, at least 30,000, or at least 50,000 cells. In some embodiments, a cell cluster comprises between 10-10,000 cells, between 50-10,000, between 100-10,000, between 100-10,000, between 1,000-10,000, between 500 and 10,000, between 500 and 5,000, between 500 and 2,500, between 500 and 2,000, between 1,000 and 100,000, between 1,000 and 50,000, between 1,000 and 40,000, between 1,000 and 20,000, between 1,000 and 10,000, between 1,000 and 5,000 and between 1,000 and 3,000 cells. In some embodiments, a cell cluster comprises at least 500 cells. In some embodiments, a cell cluster comprises at least 1,000 cells. In some embodiments, a cell cluster comprises at least 2,000 cells. In some embodiments, a cell cluster comprises at least 5,000 cells. In some embodiments, a cell cluster comprises no more than 100,000, no more than 90,000, no more than 80,000, no more than 70,000, no more than 60,000, no more than 50,000, no more than 40,000, no more than 30,000, no more than 20,000, no more than 10,000, no more than 7,000, no more than 5,000, no more than 3,000, no more than 2,000 cells, or no more than 1,000 cells. In some embodiments, the cells in a cluster have not been previously subjected to a cell-sorting process (e.g., affinity binding purification or FACS). In some embodiments, a cell cluster comprises 300-1000, 300-900, 300-800, 300-700, 300-600, 300-500, 300-400, 400-1000, 400-900, 400-800, 400-700, 400-600, 400-500, 500-900, 500-800, 500-700, 500-600, 600-900, 600-800, 600-700, 700-900, 700-800, or 800-900 stem cell-derived beta cells. In some embodiments, a cell cluster comprises 300-1000, 300-900, 300-800, 300-700, 300-600, 300-500, 300-400, 400-1000, 400-900, 400-800, 400-700, 400-600, 400-500, 500-900, 500-800, 500-700, 500-600, 600-900, 600-800, 600-700, 700-900, 700-800, or 800-900 NKX6.1-positive, ISL1-positive cells.

A cell cluster can be in a size similar to an endogenous pancreatic islet. For example, a cell cluster can have a diameter similar to an endogenous pancreatic islet. A diameter of a cell cluster can refer to the largest linear distance between two points on the surface of the cell cluster. In some embodiments, the diameter of a cell cluster is at most 300 µm, 200 µm, 150 µm, 100 µm, 90 µm, 80 µm, 70 µm, 60 µm, 50 µm, or 40 µm. The diameter of a cell cluster can be from about 75 µm to about 250 µm. The diameter of a cell cluster can be at most 100 µm.

In some embodiments, a cell cluster is between about 80 and 270 microns in diameter. In some embodiments, a cell cluster is between about 100 and about 250 microns in diameter (e.g., about 125, about 140, about 150, about 160, about 170, about 180, about 190, about 200, about 200, about 210, about 215, about 220, or about 225, microns in diameter). For example, in some embodiments, the cell cluster is between about 125 and about 225, between about 130 and about 160, between about 170 and about 225, between about 140 and about 200, between about 140 and about 170, between about 160 and about 220, between about 170 and about 215, or between about 170 and about 200, microns in diameter.

In some embodiments, the disclosure provides for a composition comprising one or more cell clusters. In some embodiments, the composition comprises 500-20000, 500-15000, 500-10000, 500-5000, 500-2000, 500-1000, 1000-20000, 1000-15000, 1000-10000, 1000-5000, 1000-2000, 2000-20000, 2000-15000, 2000-10000, 2000-5000, 5000-20000, 5000-15000, 5000-10000, 10000-20000, 10000-15000, 15000-20000, or 3000-9000 cell clusters.

In some embodiments, any of the cells disclosed herein comprise a genomic disruption in at least one gene sequence, wherein said disruption reduces or eliminates expression of a protein encoded by said gene sequence. In some embodiments, said cells comprise a genomic disruption in at least one gene sequence, wherein said disruption reduces or eliminates expression of a protein encoded by said gene sequence. In some embodiments, said cells comprise a genomic disruption in at least one gene sequence, wherein said disruption reduces or eliminates expression of a protein encoded by said gene sequence. In some embodiments, any of the cells disclosed herein (e.g., any of the SC-derived beta cells or cells in any of the clusters disclosed herein) comprise a genomic disruption in at least one gene sequence, wherein said disruption reduces or eliminates expression of a protein encoded by said gene sequence. In some embodiments, said at least one gene sequence is the ABO sequence, such that the disruption results in the cell being blood type O. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said at least one gene sequence encodes CIITA. In some embodiments, the cells comprise a genomic disruption in the genes encoding HLA-A and HLA-B, but do not comprise a genomic disruption in the gene encoding HLA-C. In some embodiments, the cells comprise a genomic disruption in the gene encoding CXCL10. In some embodiments, the cells comprise a genomic disruption in the gene encoding renalase. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB). In some embodiments, the cells have reduced expression of one or more of beta-2 microglobulin, CIITA, HLA-A, HLA-B, HLA-C, HLA-DP, HLA-DQ, and HLADR, relative to stem cells that are not genetically modified. In some embodiments, the cells have increased expression of CD47, PDL1, HLA-G, CD46, CD55, CD59, CTLA, PDL2, HLA-C, HLA-E, HLA-G, C1-inhibitor, IL-35, DUX4, IDO1, IL10, CCL21, CCL22, CD16, CD52, H2-M3, CD200, FASLG, MFGE8, and/or SERPINB9 relative to cells that are not genetically modified. In particular embodiments, the pancreatic islet cells disclosed herein (e.g., the SC-beta cells) have increased expression of PDL1 as compared to endogenous pancreatic islet cells from a healthy control subject. In particular embodiments, the pancreatic islet cells disclosed herein (e.g., the SC-beta cells) have increased expression of CD47 as compared to endogenous pancreatic islet cells from a healthy control subject. In some embodiments, the genomic disruption is induced by use of a gene editing system, e.g., CRISPR Cas technology. In some embodiments, any of the isolated cells (e.g., a stem cell or a NKX6.1-positive, ISL1-positive cell) described herein comprises a disruption (e.g., deletion, insertion, translocation, inversion, or substitution of one or more nucleotides) in any one or more of the genes encoding: B2M, CIITA, CXCL10, renalase, HLA-A, HLA-B, HLA-C, RFX-ANK, NFY-A, NLRC5, RFX5, RFX-AP, HLA-G, HLA-E, NFY-B, PD-L1, NFY-C, IRF1, TAPI, GITR, 4-1BB, CD28, B7-1, CD47, B7-2, 0X40, CD27, HVEM, SLAM, CD226, ICOS, LAG3, TIGIT, TIM3, CD160, BTLA, CD244, LFA-1, ST2, HLA-F, CD30, B7-H3, VISTA, TLT, PD-L2, CD58, CD2, HELIOS, IDO1, TRAC, TRB, NFY-A, CCR5, F3, CD142, MICA, MICB, LRP1, HMGB1, ABO, RHD, FUT1, KDM5D, PDGFRa, OLIG2, and/or GFAP. In some embodiments, disruption of a gene results in an at least 10%, 20%, 30%, 40%, 50%, 60%, 70%, 80%, 90% or 100% decrease in expression of the gene as compared to the expression of the gene in the same type of cell without the disruption. In some embodiments, the gene is disrupted using CRISPR/Cas, piggybac transposon, TALEN, and/or zinc finger technology.

In some embodiments, a cell (e.g., an isolated stem cell or a NKX6.1-positive, ISL1-positive cell) described herein is negative for A antigen and negative for B antigen. In some embodiments, the cell described herein is negative for A antigen. In some embodiments, the cell described herein is negative for B antigen. In some embodiments, a cell (e.g., an isolated stem cell or a NKX6.1-positive, ISL1-positive cell) described herein is negative for Rh antigen. In some embodiments, a cell (e.g., an isolated stem cell or a NKX6.1-positive, ISL1-positive cell) described herein is negative for A antigen, negative for B antigen, and negative for Rh antigen. An "A antigen," as used herein, refers to a histo-blood group antigen produced by $3\alpha$-N-acetylgalactosaminyltransferase and expressed as a cell-surface antigen. A "B antigen," as used herein, refers to a histo-blood group antigen produced by $3\alpha$-galactosaminyltransferase and expressed as a cell-surface antigen. In some embodiments, the cell comprises a disruption in the ABO gene. In some embodiments, the cell comprises a disruption in the ABO gene such that the cell has reduced or absent levels of A and B antigens. In some embodiments, the cell comprises a disruption in the FUT1 gene. In some embodiments, the cell comprises a disruption in the FUT1 gene such that Galactoside 2-alpha-L-fucosyltransferase 1 expression is reduced or absent. An "Rh antigen," as used herein, refers to a highly immunogenic antigen encoded by two highly polymorphic genes, RHD and RHCE. Rh antigen proteins are transmembrane proteins. In some embodiments, the cell comprises a disruption in the RHAG gene. In some embodiments, the cell comprises a disruption in the RHAG gene such that the cell has reduced or absent levels of Rh-associated glycoprotein. In some embodiments, the cell has a reduced or eliminated Rh protein antigen expression selected from the group consisting of Rh C antigen, Rh E antigen, Kell K antigen (KEL), Duffy (FY) Fya antigen, Duffy Fy3 antigen, Kidd (JK) Jkb antigen, MNS antigen U, and MNS antigen S.

In some embodiments, any of the cells disclosed herein (e.g., any of the stem cells disclosed herein) comprises a "safety switch." In some embodiments, the safety switches are nucleic acid constructs encoding a switch protein that inducibly causes cell death or stops cell proliferation. In some embodiments, the safety switch is inserted at a defined, specific target locus (e.g., a safe harbor locus) in the genome of an engineered cell, usually at both alleles of the target locus. In some embodiments, the target locus is a safe harbor locus, such as ActB or CLYBL. In some embodiments, the target locus is a gene targeted for disruption (e.g., B2M or CIITA). In some embodiments, the switch protein is activated by contacting with an effective dose of a clinically acceptable orthologous small molecule. In some embodiments, when activated, the safety switch causes the cell to stop proliferation, in some embodiments by activating apoptosis of the cell. In some embodiments, the switch protein comprises herpes-simplex-thymidine-kinase. In some embodiments the switch protein comprises a human caspase protein, e.g. caspase 1, caspase 2, caspase 3, caspase 4, caspase 5, caspase 6, caspase 7, caspase 8, caspase 9, caspase 10, caspase 14, etc. In certain embodiments the protein is human caspase 9. In some embodiments, the caspase protein is fused to a sequence that provides for chemically induced dimerization (CID), in which dimerization occurs only in the presence of the orthologous activating agent. One or more CID domains may be fused to the caspase protein, e.g. two different CID domains may be fused to the caspase protein. In some embodiments the CID domain is a dimerization domain of FKBP or FRB (FKBP-rapamycin-binding) domain of mTOR, which are activated with rapamycin analogs. In some embodiments, the safety switch is any of the safety switches described in WO2021173449 and Jones et al., 2014, Frontiers in Pharmacology, 5(254):1-8, each of which is incorporated herein in its entirety.

In some embodiments, the population further comprises a medium. In some embodiments, the medium comprises a sugar. In some embodiments, the sugar is sucrose or glucose. In some embodiments, the medium comprises the sugar at a concentration of between about 0.05% and about 1.5%. In some embodiments, the medium is a CMRL medium; or wherein the medium is HypoThermosol® FRS Preservation Media.

Some aspects of the present disclosure provide compositions comprising population of in vitro differentiated cells described herein. In some embodiments, a composition comprising population of in vitro differentiated cells described herein are therapeutic compositions. The therapeutic compositions can further comprise a physiologically compatible solution including, for example, artificial cerebrospinal fluid or phosphate-buffered saline. The therapeutic composition can be used to treat, prevent, or stabilize a disease (e.g., diabetes).

In some embodiments, a therapeutic composition further comprises other active agents, such as anti-inflammatory agents, exogenous small molecule agonists, exogenous small molecule antagonists, anti-apoptotic agents, antioxidants, and/or growth factors known to a person having skill in the art.

In some embodiments, a therapeutic composition further comprises a pharmaceutically acceptable carrier (e.g. a medium or an excipient). The term pharmaceutically acceptable carrier (or medium), which may be used interchangeably with the term biologically compatible carrier or medium, can refer to reagents, cells, compounds, materials, compositions, and/or dosage forms that are not only compatible with the cells and other agents to be administered therapeutically, but also are suitable for use in contact with the tissues of human beings and animals without excessive toxicity, irritation, allergic response, or other complication. Suitable pharmaceutically acceptable carriers can include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical compositions comprising cellular components or products, but not live cells, can be formulated as liquids. Pharmaceutical compositions comprising living non-native pancreatic β cells can be formulated as liquids, semisolids (e.g., gels, gel capsules, or liposomes) or solids (e.g., matrices, scaffolds and the like).

In some embodiments, a therapeutic composition is formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

In some embodiments, a therapeutic composition is optionally manufactured in a conventional manner, such as, by way of example only, by means of conventional mixing, dissolving, granulating, dragee-making, levigating, emulsifying, encapsulating, entrapping or compression processes.

In some embodiments, a therapeutic composition comprises one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, a therapeutic composition further comprises one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, a therapeutic composition is suitable for administration by any administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes.

In some embodiments, a therapeutic composition is formulated for parenteral (e.g., intravenous, subcutaneous, intramuscular, intracerebral, intracerebroventricular, intra-articular, intraperitoneal, or intracranial) administration.

In some embodiments, a therapeutic composition further comprises one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, a therapeutic composition comprises a population of in vitro differentiated cells described herein in an amount that is effective to treat or prevent e.g., diabetes. In some embodiments, a therapeutic composition further comprises one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

In some embodiments, a therapeutic composition comprising cells, cell components or cell products may be delivered to the kidney of a patient in one or more of several methods of delivery known in the art. In some embodiments, the compositions are delivered to the kidney (e.g., on the renal capsule and/or underneath the renal capsule). In another embodiment, the compositions may be delivered to various locations within the kidney via periodic intraperitoneal or intrarenal injection. Alternatively, the compositions may be applied in other dosage forms known to those skilled in the art, such as pre-formed or in situ-formed gels or liposomes.

In some embodiments, therapeutic compositions comprising live cells in a semi-solid or solid carrier may be formulated for surgical implantation on or beneath the renal capsule. It should be appreciated that liquid compositions also may be administered by surgical procedures. In particular cases, semi-solid or solid pharmaceutical compositions may comprise semi-permeable gels, lattices, cellular scaffolds and the like, which may be non-biodegradable or biodegradable. For example, in certain cases, it may be desirable or appropriate to sequester the exogenous cells from their surroundings, yet enable the cells to secrete and deliver biological molecules (e.g., insulin) to surrounding cells or the blood stream. In these cases, cells may be formulated as autonomous implants comprising living cells by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression. Various encapsulation devices, degradable gels and networks can be used for the pharmaceutical compositions of the present disclosure. For example, degradable materials particularly suitable for sustained release formulations include biocompatible polymers, such as poly(lactic acid), poly (lactic-co-glycolic acid), methylcellulose, hyaluronic acid, collagen, and the like.

In some embodiments, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established. Examples of scaffold or matrix (sometimes referred to collectively as "framework") material that may be used in the present disclosure include nonwoven mats, porous foams, or self-assembling peptides. Nonwoven mats, for example, may be formed using fibers comprising a synthetic absorbable copolymer of glycolic and lactic acids (PGA/PLA), foams, and/or poly(epsilon-caprolactone)/poly(glycolic acid) (PCL/PGA) copolymer.

In some embodiments, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures. In many of the abovementioned cases, the framework may be molded into a useful shape. Furthermore, it will be appreciated that non-native pancreatic β cells may be cultured on pre-formed, non-degradable surgical or implantable devices.

In some embodiments, the matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some aspects, the present disclosure provided devices comprising a population of in vitro differentiated cells described herein. In some embodiments, the population of in vitro differentiated cells described herein form cell clusters. A device can be configured to house the cells described herein which, in particular embodiments, produce and release insulin when implanted into a subject. In some embodiment, a device can further comprise a semipermeable membrane. The semipermeable membrane can be configured to retain the cell cluster in the device and permit passage of insulin secreted by the cells. In some embodiments of the device, the cells can be encapsulated by the semipermeable membrane. The encapsulation can be performed by any technique available to one skilled in the art. The semipermeable membrane can also be made of any suitable material as one skilled in the art would appreciate and verify. For example, the semipermeable membrane can be made of polysaccharide or polycation. In some embodiments, the semipermeable membrane can be made of poly (lactide) (PLA), poly(glycolic acid) (PGA), poly(lactide-co-glycolide) (PLGA), and other polyhydroxyacids, poly (caprolactone), polycarbonates, polyamides, polyanhydrides, polyphosphazene, polyamino acids, poly-ortho esters, polyacetals, polycyanoacrylates, biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, or any combinations thereof. In some embodiments, the semipermeable membrane comprises alginate. In some embodiments, the cells are encapsulated in a microcapsule that comprises an alginate core surrounded by the semipermeable membrane. In some embodiments, the alginate core is modified, for example, to produce a scaffold comprising an alginate core having covalently conjugated oligopeptides with an RGD sequence (arginine, glycine, aspartic acid). In some embodiments, the alginate core is modified, for example, to produce a covalently reinforced microcapsule having a chemoenzymatically engineered alginate of enhanced stability. In some embodiments, the alginate core is modified, for example, to produce membrane-mimetic films assembled by in-situ polymerization of acrylate functionalized phospholipids. In some embodiments, microcapsules are composed of enzymatically modified alginates using epimerases. In some embodiments, microcapsules comprise covalent links between adjacent layers of the microcapsule membrane. In some embodiment, the microcapsule comprises a subsieve-size capsule comprising alginate coupled with phenol moieties. In some embodiments, the microcapsule comprises a scaffold comprising alginate-agarose. In some embodiments, the cells are modified with PEG before being encapsulated within alginate. In some embodiments, the cells are encapsulated in photoreactive liposomes and alginate. It should be appreciated that the alginate employed in the microcapsules can be replaced with other suitable biomaterials, including, without limitation, polyethylene glycol (PEG), chitosan, polyester hollow fibers, collagen, hyaluronic acid, dextran with ROD, BHD and polyethylene glycol-diacrylate (PEGDA), poly(MPC-co-n-butyl methacrylate-co-4-vinylphenyl boronic acid) (PMBV) and poly (vinyl alcohol) (PVA), agarose, agarose with gelatin, and multilayer cases of these. In some embodiments, the device provided herein comprise extracorporeal segment, e.g., part of the device can be outside a subject's body when the device is implanted in the subject. The extracorporeal segment can comprise any functional component of the device, with or without the cells or cell cluster provided herein.

Further provided herein are methods for treating or preventing a disease in a subject. A composition comprising a population of in vitro differentiated cells described herein can be administered into a subject to restore a degree of pancreatic function in the subject. In some embodiments, such composition is transplanted in a subject. The term "transplant" can refer to the placement of cells or cell clusters, any portion of the cells or cell clusters thereof, any compositions comprising cells, cell clusters or any portion thereof, into a subject, by a method or route which results in at least partial localization of the introduced cells or cell clusters at a desired site. In some embodiments, the desired site is the pancreas. In some embodiments, the desired site is a non-pancreatic location, such as in the liver or subcutaneously, for example, in a capsule (e.g., microcapsule) to maintain the implanted cells at the implant location and avoid migration. In some embodiments, the transplanted cells release insulin in an amount sufficient for a reduction of blood glucose levels in the subject.

In some embodiments, a composition comprising a population of in vitro differentiated cells described herein are housed in a device that is implanted in a subject. In some embodiments, a composition comprising a population of in vitro differentiated cells described herein are housed in a device suitable for implantation into a subject. In some embodiments, the device upon implantation in a subject releases insulin while retaining the cells in the device, and facilitates tissue vascularization in and around the device. Exemplary devices are described, for example in WO2018232180, WO2019068059, WO2019178134, WO2020/206150, and WO2020/206157, each of which is incorporated-by-reference in its entirety. In some embodiments, a subject is not administered an immune suppression agent during the implantation or vascularization of the device. In some embodiments, the device has a thickness of at least about 300 μm. In some embodiments, the device comprises a membrane comprising a plurality of nodes interconnected by a plurality of fibrils.

In some embodiments, the device comprises a first membrane having a first surface comprising a plurality of channels, and a plurality of second surfaces opposing the first surface; and a second membrane opposite and attached to the plurality of the second surfaces of the first membrane; wherein the first membrane and the second membrane form an enclosed compartment having a surface area to volume ratio of at least about 40 cm-1, and wherein the enclosed compartment provides a volume for housing a cell within the device.

In some embodiments, the enclosed compartment comprises a single continuous open chamber. In some embodiments, the volume is about 8 µL to about 1,000 µL. In some embodiments, the device has at least one of a length and a width of about 0.25 cm to about 3 cm. In some embodiments, the device has a thickness of at least about 300 µm.

In some embodiments, the plurality of channels is generally perpendicular with respect to the first membrane. In some embodiments, the plurality of channels is arranged in a rectilinear array. In some embodiments, the plurality of channels is arranged in a polar array. In some embodiments, the channel has an average diameter of about 400 µm to about 3,000 µm. In some embodiments, the diameter is measured at a narrowest point in the channel. In some embodiments, a center of each channel is separated from the center of another channel by a distance of about 75 µm to about 500 µm. In some embodiments, the channel has a height to diameter ratio of at least about 0.2. In some embodiments, the device has a number of channels per area along a transverse plane, and In some embodiments the number is greater than about 50/cm2.

In some embodiments, at least one of the first membrane and the second membrane comprise a plurality of nodes interconnected by a plurality of fibrils. In some embodiments, at least one of the first membrane and the second membrane comprise PVDF, PTFE, ePTFE, PCL, PE/PES, PP, PS, PMMA, PLGA, PLLA, or any combination thereof. In some embodiments, the device further comprises an opening through the first membrane and/or the second membrane within the channel. In some embodiments, the opening has a concentricity with respect to the channel of at most about 25% the diameter of the channel. In some embodiments is a frame configured to receive the device described herein. In some embodiments, the frame is configured to receive a plurality of cell housing devices. In some embodiments, the frame comprises a flexing mechanism configured to prevent buckling of the cell housing device.

In some embodiments, an implantable encapsulation device comprises an internal volume comprising, disposed therein, a population of in vitro differentiated cells or a composition comprising a population of in vitro differentiated cells described herein described herein. In some embodiments, the implantable encapsulation device comprises at least one membrane that at least partially defines the internal volume. In some embodiments, the at least one membrane includes a first membrane and a second membrane, wherein the first membrane and the second membrane are bonded together to form a seal extending at least partially around the internal volume disposed between the first membrane and the second membrane. In some embodiments, the at least one membrane comprises at least one selected from PVDF, PTFE, ePTFE, PCL, PE/PES, PP, PS, PMMA, PLGA, and PLLA. In some embodiments, the at least one membrane comprises ePTFE.

In some embodiments, a method described herein comprises transplanting a population of in vitro differentiated cells described herein to a subject using any means in the art. For example the methods can comprise transplanting the cell cluster via the intraperitoneal space, portal vein, renal subcapsule, renal capsule, omentum, subcutaneous space, or via pancreatic bed infusion. For example, transplanting can be subcapsular transplanting, intramuscular transplanting, or intraportal transplanting, e.g., intraportal infusion. Immunoprotective encapsulation can be implemented to provide immunoprotection to the cell clusters. In some embodiments, the methods of treatment provided herein can comprise administering one or more immune response modulators for modulating or reducing transplant rejection response or other immune response against the implant (e.g., the cells or the device). Examples of immune response modulator that can be used in the methods can include purine synthesis inhibitors like Azathioprine and Mycophenolic acid, pyrimidine synthesis inhibitors like Leflunomide and Teriflunomide, antifolate like Methotrexate, Tacrolimus, Ciclosporin, Pimecrolimus, Abetimus, Gusperimus, Lenalidomide, Pomalidomide, Thalidomide, PDE4 inhibitor, Apremilast, Anakinra, Sirolimus, Everolimus, Ridaforolimus, Temsirolimus, Umirolimus, Zotarolimus, Anti-thymocyte globulin antibodies, Anti-lymphocyte globulin antibodies, CTLA-4, fragment thereof, and fusion proteins thereof like Abatacept and Belatacept, TNF inhibitor like Etanercept and Pegsunercept, Aflibercept, Alefacept, Rilonacept, antibodies against complement component 5 like Eculizumab, anti-TNF antibodies like Adalimumab, Afelimomab, Certolizumab pegol, Golimumab, Infliximab, and Nerelimomab, antibodies against Interleukin 5 like Mepolizumab, anti-Ig E antibodies like Omalizumab, anti-Interferon antibodies like Faralimomab, anti-IL-6 antibodies like Elsilimomab, antibodies against IL-12 and IL-23 like Lebrikizumab and Ustekinumab, anti-IL-17A antibodies like Secukinumab, anti-CD3 antibodies like Muromonab-CD3, Otelixizumab, Teplizumab, and Visilizumab, anti-CD4 antibodies like Clenoliximab, Keliximab, and Zanolimumab, anti-CD11a antibodies like Efalizumab, anti-CD18 antibodies like Erlizumab, anti-CD20 antibodies like Obinutuzumab, Rituximab, Ocrelizumab and Pascolizumab, anti-CD23 antibodies like Gomiliximab and Lumiliximab, anti-CD40 antibodies like Teneliximab and Toralizumab, antibodies against CD62L/L-selectin like Aselizumab, anti-CD80 antibodies like Galiximab, anti-CD147/Basigin antibodies like Gavilimomab, anti-CD154 antibodies like Ruplizumab, anti-BLyS antibodies like Belimumab and Blisibimod, anti-CTLA-4 antibodies like Ipilimumab and Tremelimumab, anti-CAT antibodies like Bertilimumab, Lerdelimumab, and Metelimumab, anti-Integrin antibodies like Natalizumab, antibodies against Interleukin-6 receptor like Tocilizumab, anti-LFA-1 antibodies like Odulimomab, antibodies against IL-2 receptor/CD25 like Basiliximab, Daclizumab, and Inolimomab, antibodies against T-lymphocyte (Zolimomab aritox) like Atorolimumab, Cedelizumab, Fontolizumab, Maslimomab, Morolimumab, Pexelizumab, Reslizumab, Rovelizumab, Siplizumab, Talizumab, Telimomab aritox, Vapaliximab, and Vepalimomab.

As used herein, the term "treating" and "treatment" can refer to administering to a subject an effective amount of a composition (e.g., cell clusters or a portion thereof) so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (e.g., partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In preferred embodiments, the compositions are administered by intravenous infusion or injection.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, one or more symptoms of a disease or disorder are alleviated by at least 5%, at least 10%, at least 20%, at least 30%, at least 40%, or at least 50% in comparison to a non-treated subject.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In some embodiments, the reduction of blood glucose levels in the subject, as induced by the transplantation of the cell, or the composition or device provided herein, results in an amount of glucose which is lower than the diabetes threshold. In some embodiments, the subject is a mammalian subject. In some embodiments, the mammalian subject is human. In some embodiments, the amount of glucose is reduced to lower than the diabetes threshold in 1, 2, 3, 4, 5, 6, 7, 8, 9, or 10 days after the implanting.

A subject that can be treated by the methods herein can be a human or a non-human animal. In some embodiments, a subject can be a mammal. Examples of a subject include but are not limited to primates, e.g., a monkey, a chimpanzee, a bamboo, or a human. In some embodiments, a subject is a human. A subject can be non-primate animals, including, but not limited to, a dog, a cat, a horse, a cow, a pig, a sheep, a goat, a rabbit, and the like. In some embodiments, a subject receiving the treatment is a subject in need thereof, e.g., a human in need thereof.

The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

EXAMPLES

These examples are provided for illustrative purposes only and not to limit the scope of the claims provided herein.

Example 1. Safety and Efficacy of SC-Islet Cells in Diabetic Mice

The study described herein was designed to assess the pharmacological activity (efficacy or glycemic control), maturation (stabilization of human C-peptide levels over time), and function (glucose-stimulated human C-peptide secretion as measured during OGTT) of next generation stem cell (SC)-derived islets (SC-islets) compared to a matched and efficacious dose of control SC-islets when transplanted under the kidney capsule of diabetic NOD scid gamma (NSG) immunodeficient mice. Table 1 shows the study design of the present disclosure.

TABLE 1

Study Design

| Group # | Group ID | # of mice | Cell dose (×10$^6$)* | Implant site |
|---|---|---|---|---|
| 1 | Non-diabetic NSG control | 6 | N/A | N/A |
| 2 | Diabetic NSG control | 8 | N/A | N/A |
| 3 | Diabetic NSG + Protocol 1 (BR) | 12 | 4 | KC |
| 4 | Diabetic NSG + Protocol 1 (BR) | 12 | 8 | KC |
| 5 | Diabetic NSG + Protocol 2 (media modifications; SF to BR) | 11 | 4 | KC |

Abbreviations:
NSG = NOD scid gamma immunodeficient mouse;
BR = bioreactor;
SF = spinner flask;
KC = kidney capsule;
*= As measured by ViCell method, hemocytometer reading approximately 50%

Mice in groups 2-5 were administered streptozotocin (STZ) by intraperitoneal (i.p.) injection for five consecutive days at a dose of 45 mg/kg. STZ was prepared in 40 mM Sodium Citrate, pH 4.5. During STZ induction, blood glucose was measured on Days 1 and Day 5.

Body weight and health observations were monitored daily. Following STZ induction, blood glucose and body weight were measured for three consecutive days. Animals were considered diabetic if they exhibited two consecutive blood glucose readings about 250 mg/dL.

Figure 8A:
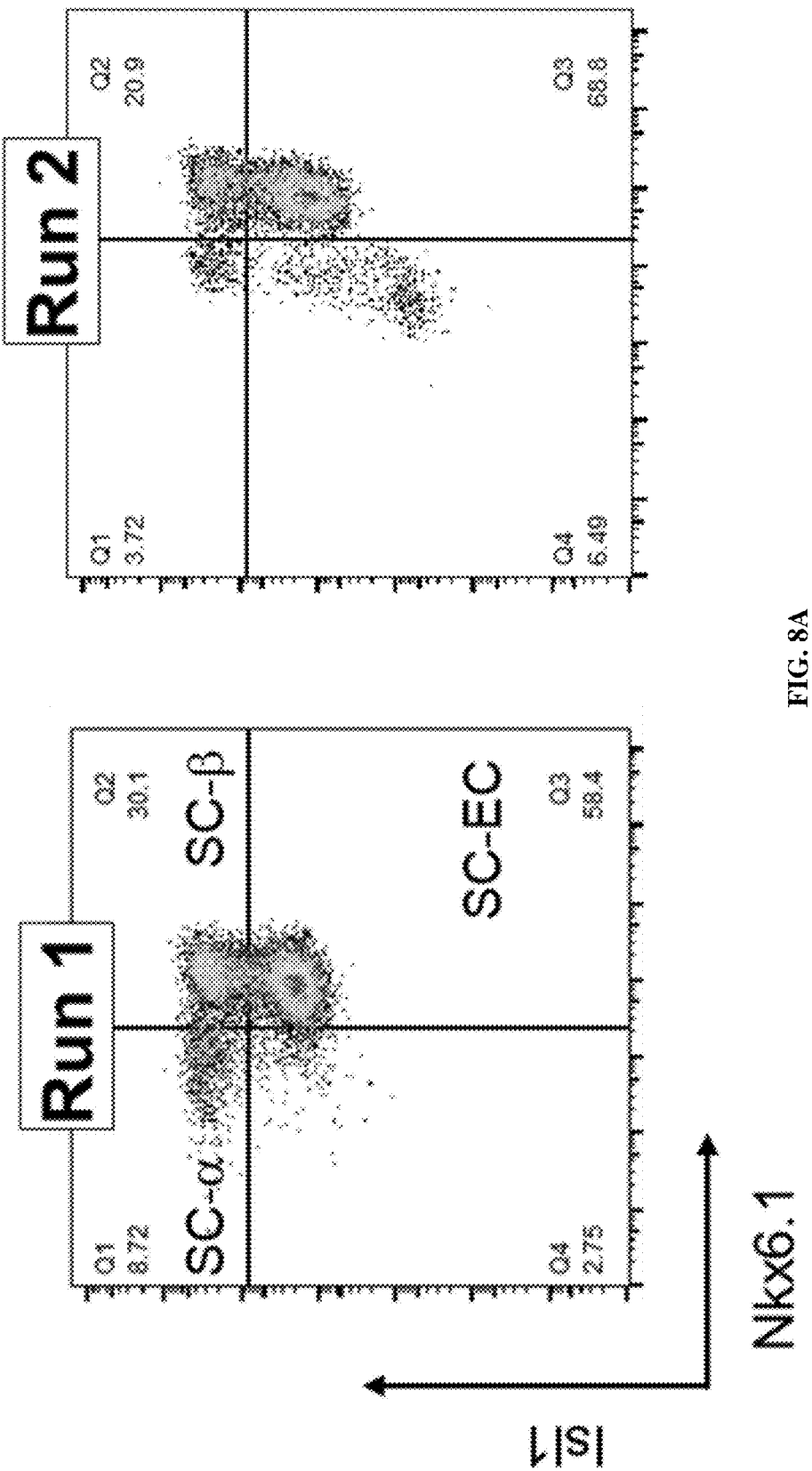
FIGS. 8A-8B are flow cytometry graphs showing the percentage of ISL1+ cells in S6 SC-islets. SC-islets differentiated using Protocol 2 (FIG. 8B) showed increased ISL1+ cells as compared with SC-islets differentiated using Protocol 1 (FIG. 8A).
Figure 8B:
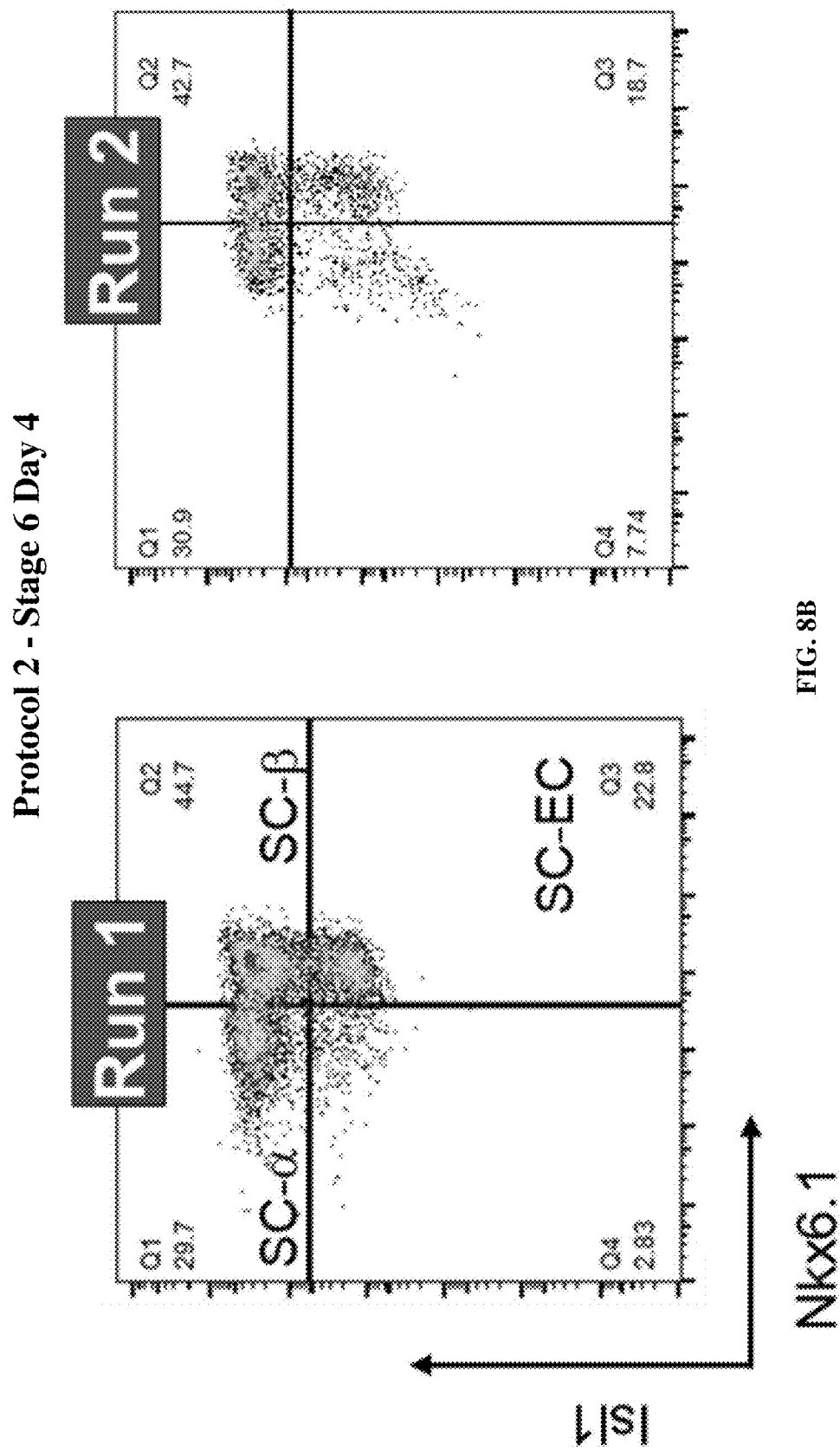

Mice in Groups 3-5 then underwent kidney subcapsular implantation surgery and were implanted with either SC-derived islet cells differentiated using the media described in Table 2 as Protocol 1 or SC-islet islets differentiated using the media described in Table 2 as Protocol 2. Compositions of cell populations obtained using differentiation Protocol 1 or Protocol 2 on S6D4, S6D6, and S6D7 are shown in Table 3. Differentiation using Protocol 2 enhanced the % of SC-0 Cells (about 50% increase) and SC-α Cells (about 3 fold increase), and reduced the % of SC-EC cells (about 50% decrease) in the composition. Additionally, differentiation using Protocol 2 also increased the percentage of SC-islet cells in the S6 islet cells up to about two fold (FIGS. 8A and 8B). SC-islet cells differentiated using media according to Protocol 2 also exhibit improved cell composition that is comparable to human pancreatic islets (Table 4).

TABLE 2

Differentiation Media (S1-S5)

| | Protocol 1 | Protocol 2 |
|---|---|---|
| S0D1-2 | bFGF (100 ng/ml) | bFGF (100 ng/ml) |
| S1D1 | Activin- A (100 ng/ml)<br>CHIR99021 (3 μM) | Activin- A (100 ng/ml)<br>CHIR99021 (3 μM)<br>PVA80 |
| S1D2-3 | Activin- A (100 ng/ml) | Activin- A (100 ng/ml)<br>PVA80 |
| S2D1-3 | KGF (50 ng/ml) | KGF (50 ng/ml)<br>PVA80 |
| S3D1 | KGF (50 ng/ml)<br>PDBU (500 nM)<br>Sant-1 (250 nM)<br>Retinoic Acid (2 μM)<br>Activin A (20 ng/ml)<br>Thiazovinin (2.5 μM)<br>DMH-1 (250 nM) | KGF (50 ng/ml)<br>PDBU (500 nM)<br>Sant-1 (250 nM)<br>Retinoic Acid (2 μM)<br>Activin A (20 ng/ml)<br>Thiazovinin (2.5 μM)<br>DMH-1 (250 nM)<br>PVA80 |
| S3D2 | KGF (50 ng/ml)<br>PDBU (500 nM)<br>Sant-1 (250 nM)<br>Retinoic Acid (2 μM)<br>Activin A (20 ng/ml)<br>Thiazovinin (2.5 μM) | KGF (50 ng/ml)<br>PDBU (500 nM)<br>Sant-1 (250 nM)<br>Retinoic Acid (2 μM)<br>Activin A (20 ng/ml)<br>Thiazovinin (2.5 μM)<br>PVA80 |
| S4D1-4 | KGF (50 ng/ml)<br>Sant-1 (250 nM)<br>Thiazovinin (2.5 μM)<br>Activin A (5 ng/ml)<br>Retinoic Acid (100 nM) | KGF (50 ng/ml)<br>Sant-1 (250 nM)<br>Thiazovinin (2.5 μM)<br>Activin A (5 ng/ml)<br>Retinoic Acid (100 nM)<br>PVA80 |
| S4D5-6 | KGF (50 ng/ml)<br>Sant-1 (250 nM)<br>Thiazovinin (2.5 μM)<br>Activin A (5 ng/ml)<br>Retinoic Acid (100 nM) | KGF (50 ng/ml)<br>Sant-1 (250 nM)<br>Thiazovinin (2.5 μM)<br>Activin A (5 ng/ml)<br>Retinoic Acid (100 nM)<br>PDBU (500 nM)<br>PVA80 |
| S5D1-3 | Sant-1 (250 nM)<br>Betacellulin (20 ng/ml)<br>XXI (2 μM)<br>Alk5i (10 μM)<br>GC-1 (1 μM)<br>LDN-193189 (100 nM)<br>Thiazovinin (2.5 μM)<br>Staurosporine (3 nM)<br>DZNEP (100 nM)<br>Retinoic Acid (50 nM) | Sant-1 (250 nM)<br>Betacellulin (20 ng/ml)<br>XXI (2 μM)<br>Alk5i (10 μM)<br>GC-1 (1 μM)<br>LDN-193189 (100 nM)<br>Thiazovinin (2.5 μM)<br>Staurosporine (3 nM)<br>DZNEP (100 nM)<br>Retinoic Acid (50 nM)<br>PDBU (500 nM)<br>L-glutamine (4 mM)<br>Formate (50 μM)<br>Taurine (90 μM)<br>Acetate (1 mM)<br>β-hydroxybutyrate (200 nM)<br>Biotin (800 nM)<br>PVA 87-89 |
| S5D4-7 | XXI (2 μM)<br>Alk5i (10 μM)<br>GC-1 (1 μM)<br>LDN-193189 (100 nM)<br>Thiazovinin (2.5 μM)<br>Staurosporine (3 nM)<br>DZNEP (100 nM) | XXI (2 μM)<br>Alk5i (10 μM)<br>GC-1 (1 μM)<br>LDN-193189 (100 nM)<br>Thiazovinin (2.5 μM)<br>Staurosporine (3 nM)<br>DZNEP (100 nM)<br>L-glutamine (4 mM)<br>Formate (50 μM)<br>Taurine (90 μM)<br>Acetate (1 mM)<br>β-hydroxybutyrate (200 nM)<br>Biotin (800 nM)<br>PVA 87-89 |

TABLE 3

Cell compositions in S6

| | Differentiation Protocol | S6D4 | S6D6 | S6D7 |
|---|---|---|---|---|
| SC-α Cell % (NKX6.1 − ISL1+) | Protocol 1 | 8.72 | 8.18 | 8.73 |
| | Protocol 2 | 29.7 | 27.2 | 25.6 |
| SC-β Cell % (NKX6.1 + ISL1+) | Protocol 1 | 30.1 | 29.4 | 31.7 |
| | Protocol 2 | 44.7 | 43.9 | 43.5 |
| SC-EC cell % (NKX6.1+ ISL1−) | Protocol 1 | 58.4 | 61.1 | 58.4 |
| | Protocol 2 | 22.8 | 26.1 | 27.9 |

TABLE 4

SC-Islet Composition

|  | Protocol 1 | Protocol 2 | Human Pancreatic Islets |
|---|---|---|---|
| α Cell % | 6% | 19% | 31% |
| β Cell % | 30% | 44% | 43% |
| δ Cell % | 3% | 8% | 9% |
| Other (exocrine, acinar) | 60% | 26% | 17% |

Following implantation, blood glucose and body weights of the mice were measured twice per week for the duration of the study. Blood glucose was measured using a commercially available glucometer and test strips. Non-fasted plasma samples were collected at baseline (Week-1; prior to implantation) and in weeks 4, 6, 8, and 12. Briefly, whole blood was collected by facial cheek vein using a 3-5 mm lancet into EDTA tubes and centrifuged for 3 min at 8000×g at 4° C. Plasma were collected and stored at −80° C. prior to being analyzed for human C-peptide and Rodent C-peptide content. Additionally, kidney grafts of mice in groups 3, 4, and 5 were harvested, incubated for 48 hours in 10% NBF at 4° C., and subjected to histological analysis to determine the contents of islet cells.

FIG. 1 shows the blood glucose readings of each group post-implantation. Non-diabetic controls maintained a euglycemic blood glucose level of 180 mg/dL while diabetic controls reached a blood glucose level of 600 mg/dL. Mice implanted with $4 \times 10^6$ SC-islet cells differentiated using Protocol 1 had a blood glucose level of 500 mg/dL at 84 days post-implantation, and mice implanted with $8 \times 10^6$ SC-islet cells differentiated using Protocol 1 had a blood glucose level of 250 mg/dL at 84 days post-implantation. In contrast, mice implanted with $4 \times 10^6$ SC-islet cells differentiated using Protocol 2 had a euglycemic blood glucose reading of 180 mg/dL 84 days post-implantation.

Figure 2A:
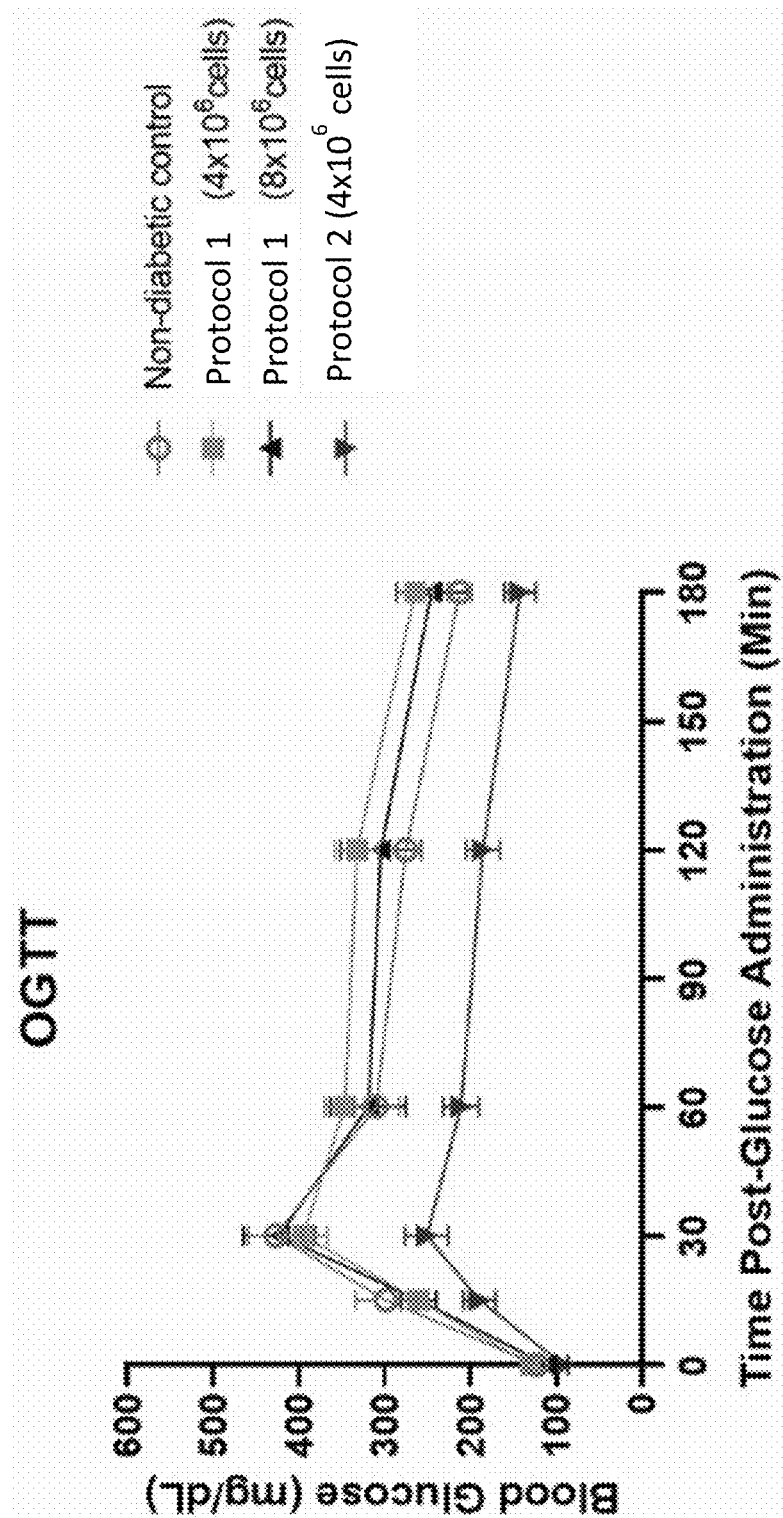
FIGS. 2A-2B are graphs showing oral glucose tolerance test (OGTT) results of mice transplanted with SC-islet cells differentiated using Protocol 1 or Protocol 2.
Figure 2B:
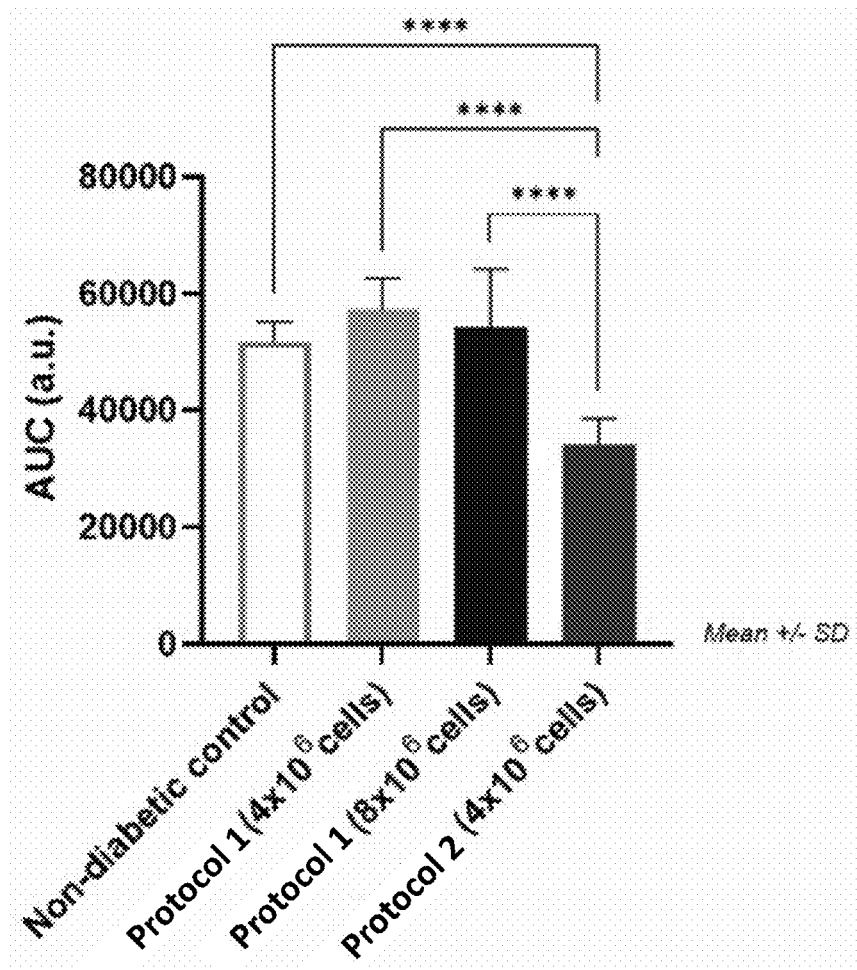

Mice were subsequently tested for glucose tolerance by oral glucose tolerance test (OGTT). Diabetic mice transplanted with SC-islet cells differentiated using Protocol 2 had significantly improved glucose tolerance as compared to non-diabetic control mice and mice transplanted with SC-islet cells differentiated using Protocol 1 (FIGS. 2A-2B).

Figure 3A:
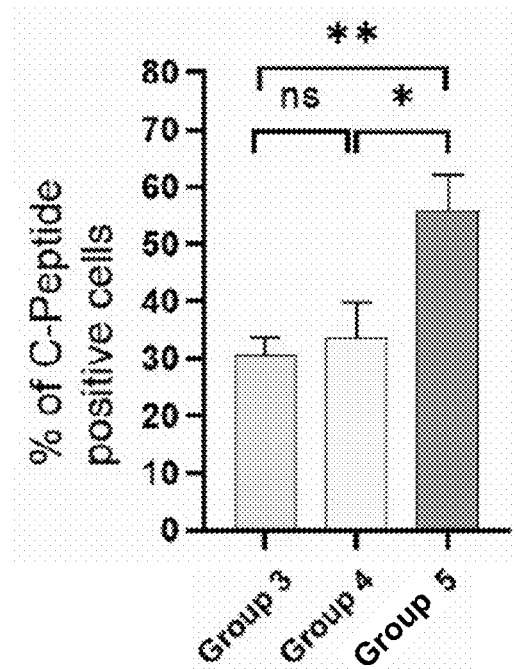
FIGS. 3A-3C are graphs showing the percentage of C-peptide positive cells (P cells), glucagon positive cells (α cells) and somatostatin positive cells (δ cells) in kidneys grafts of mice implanted with SC-islet cells differentiated using Protocol 1 (Group 3 and Group 4) or Protocol 2 (Group 5). Groups 3 and 5 were implanted with 4 million SC-islet cells, while Group 4 was implanted with 8 million SC-islet cells.
Figure 3B:
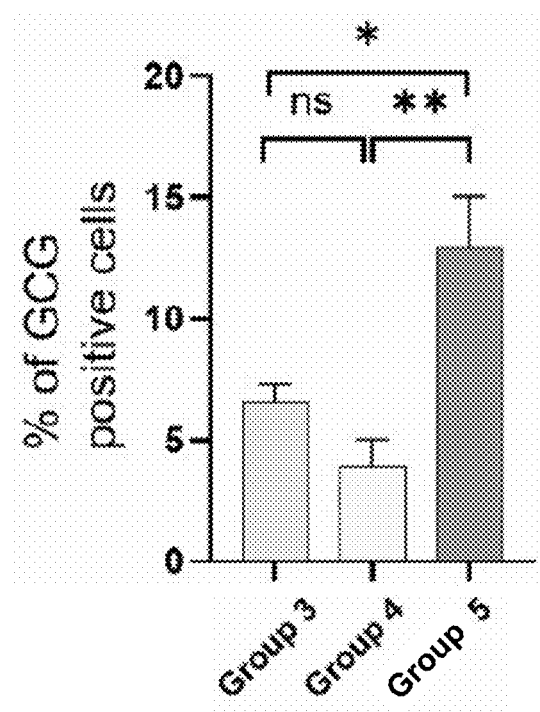
Figure 3C:
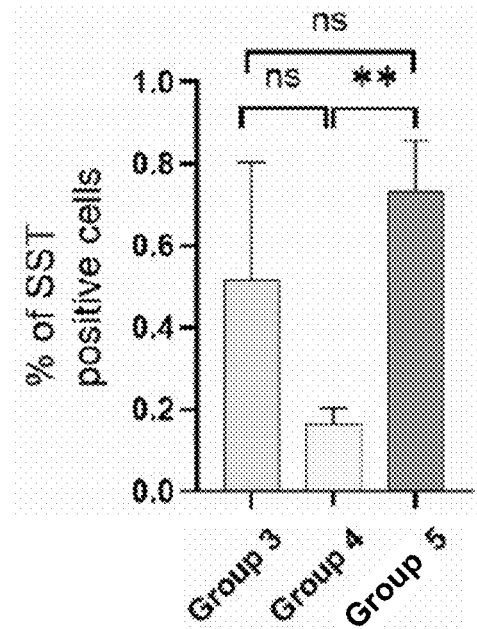
Figure 4A:
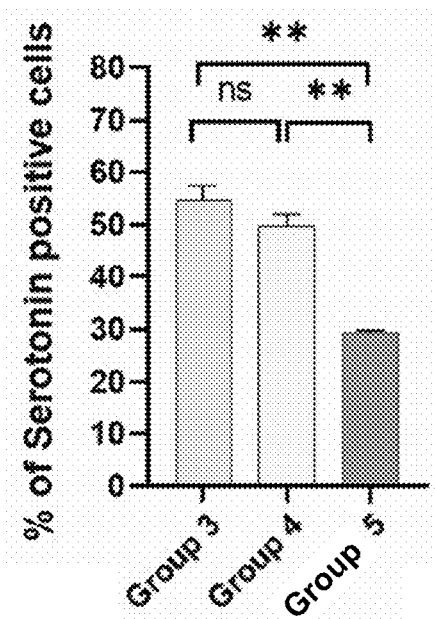
FIGS. 4A-4B are graphs showing the percentage of serotonin positive cells (FIG. 4A) and percentage of proliferating EC cells (FIG. 4B) in the kidney grafts of mice implanted with SC-islet cells differentiated using Protocol 1 (Group 3 and Group 4) or Protocol 2 (Group 5). Groups 3 and 5 were implanted with 4 million SC-islet cells, while Group 4 was implanted with 8 million SC-islet cells.
Figure 4B:
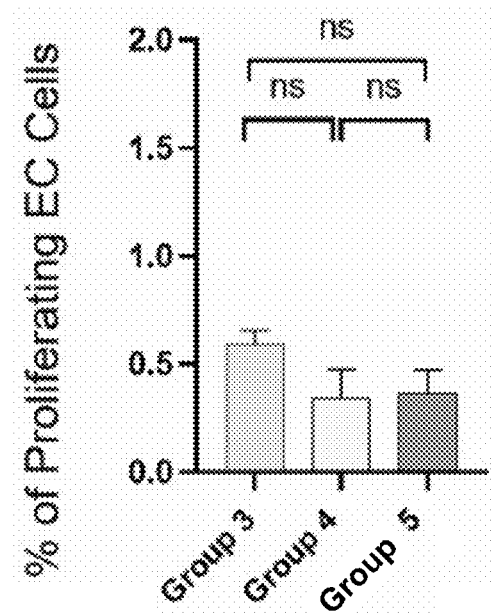
Figure 5:
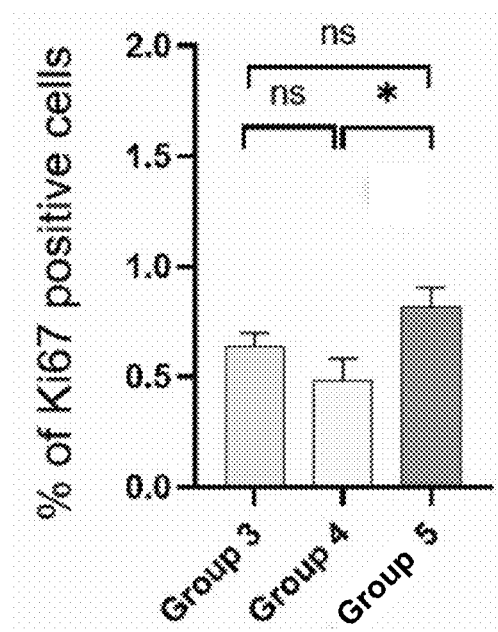
FIG. 5 is a graph showing the percentage of Ki67 positive cells in the kidney grafts of mice implanted with SC-islet cells differentiated using Protocol 1 (Group 3 and Group 4) or Protocol 2 (Group 5). Groups 3 and 5 were implanted with 4 million SC-islet cells, while Group 4 was implanted with 8 million SC-islet cells.
Figure 6A:
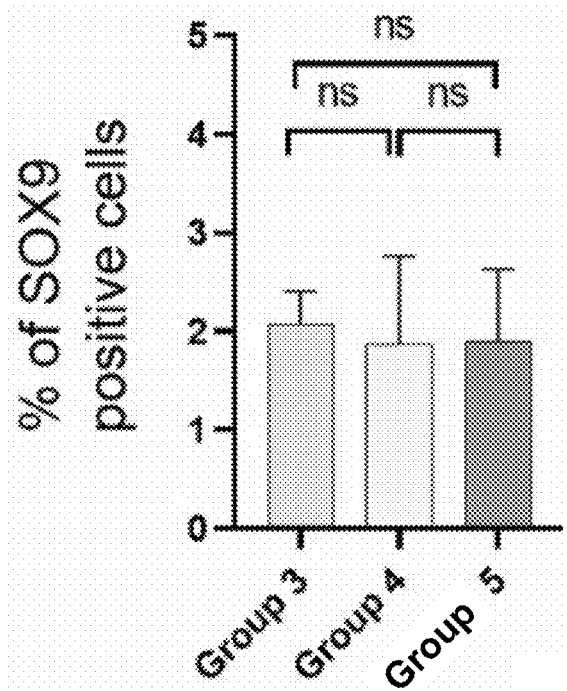
FIGS. 6A-6C are graphs showing the percentage of SOX9 positive cells (FIG. 6A), Ki67 positive cells (FIG. 6B), and SOX9 positive, Ki67 positive cells (FIG. 6C) in the kidney grafts of mice implanted with SC-islet cells differentiated using Protocol 1 (Group 3 and Group 4) or Protocol 2 (Group 5). Groups 3 and 5 were implanted with 4 million SC-islet cells, while Group 4 was implanted with 8 million SC-islet cells.
Figure 6B:
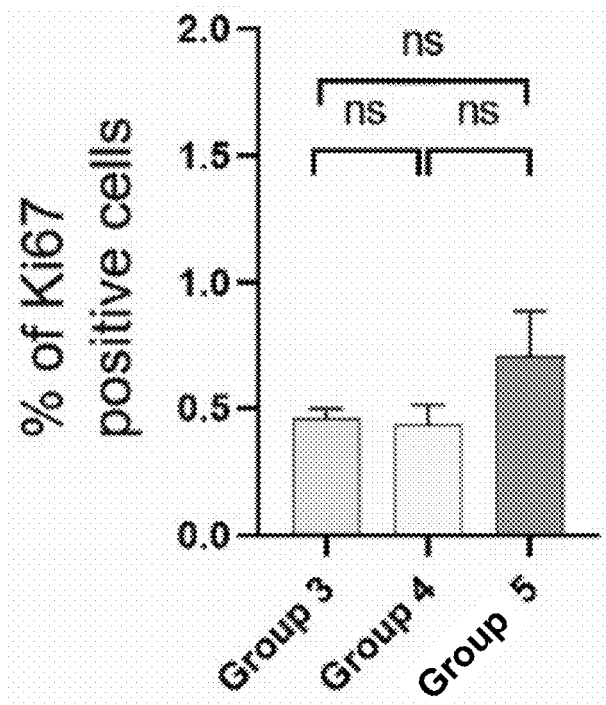
Figure 6C:
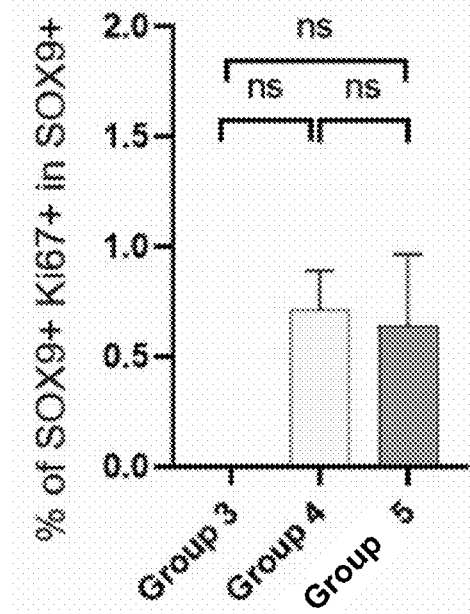
Figure 7:
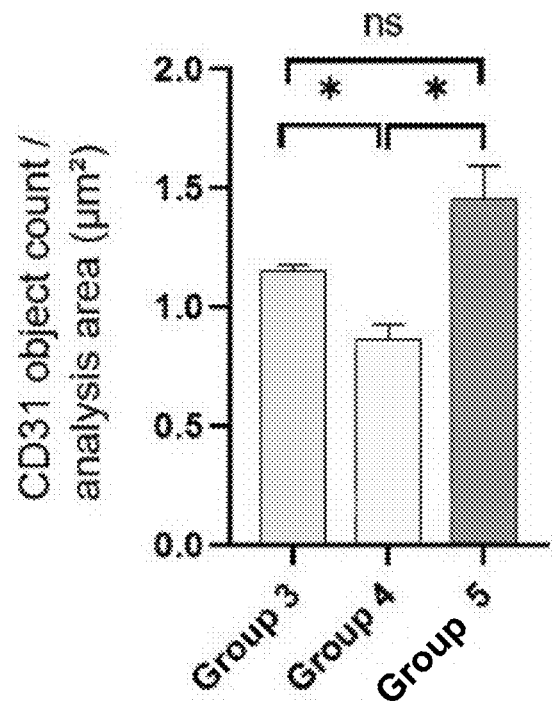
FIG. 7 is a graph showing the quantification of neovascularization in kidney grafts of mice implanted with SC-islet cells differentiated using Protocol 1 (Group 3 and Group 4) or Protocol 2 (Group 5). Neovascularization was indicated by CD31 expression level. Groups 3 and 5 were implanted with 4 million SC-islet cells, while Group 4 was implanted with 8 million SC-islet cells.

Mice kidney grafts were then analyzed for islet composition. Kidney grafts of diabetic mice transplanted with SC-islet cells differentiated using Protocol 2 (Groups 5) contained more cells positive for C-peptide (FIG. 3A), proglucagon gene (GCG) (FIG. 3B), and somatostatin (SST) (FIG. 3C), as compared to diabetic mice transplanted with SC-islet cells differentiated using Protocol 1 (Groups 3 and 4). Kidney grafts from diabetic mice transplanted with SC-islet cells differentiated using Protocol 2 (Groups 5) contained fewer cells positive for serotonin (FIG. 4A) and fewer proliferating enterochromaffin (EC) cells (FIG. 4B) as compared to diabetic mice transplanted with SC-islet cells differentiated using Protocol 1 (Groups 3 and 4). Diabetic mice transplanted with SC-islet cells differentiated using either Protocol 1 (Groups 3 and 4) or Protocol 2 (Groups 5) had comparable levels of proliferating EC cells (CDX2+/Ki67+) as control groups in the kidney grafts. Ki67+Single cell population was less than 1% in the kidney grafts of all transplanted mice (FIG. 5 and FIG. 6B). Expression of pancreatic ductal cells (SOX9+) was not different between groups (FIGS. 6A and 6C). Group 3 (Protocol 1) and Group 5 (Protocol 2) both had increased neo-vascularization in kidney grafts, as compared to Group 4 (Protocol 1) (FIG. 7).

Example 2. Effects of Differentiation Agents on Pancreatic Islet Cell Differentiation FoxO1 inhibitor (FoxOi), Wnt inhibitor (XAV), Notch inhibitor (XXI), and/or PKC activator (PDBU or TPB) were tested for their effects on pancreatic islet cell differentiation.

PDX1-positive, NKX-negative cells were administered KGF (50 ng/ml), Sant-1 (250 nM), thiazovivin (2.5 µM), activin A (5 ng/ml), and retinoic acid (100 nM) for a period of six days (S4D1-S4D6) in a media including polyvinyl alcohol-80 (PVA-80) to generate a second population of cells. On day S4D5, the cells may also have been administered an additional reagent or combination of reagents as outlined in Table 5. After the six days, the second population of cells was administered XXI (2 µM), Alk5i (10 µM), GC-1 (1 µM), LDN-193189 (100 nM), thiazovivin (2.5 µM), staurosporine (3 nM), DZNEP (100 nM), Sant-1 (250 nM), retinoic acid (50 nM), and betacellulin (20 ng/ml) for two days (S5D1-S5D2) in a media comprising PVA-89. On days S5D1 and S5D2, the cells may also have been administered an additional reagent or combination of reagents as outlined in Table 5. On days S5D3-S5D6, the cells were administered XXI (2 µM), Alk5i (10 µM), GC-1 (1 µM), LDN-193189 (100 nM), thiazovivin (2.5 µM), staurosporine (3 nM), and DZNEP (100 nM). Cells were collected for analysis on day S5D36.

TABLE 5

Differentiation agents and effects on beta cell percentage

Figure 9A:
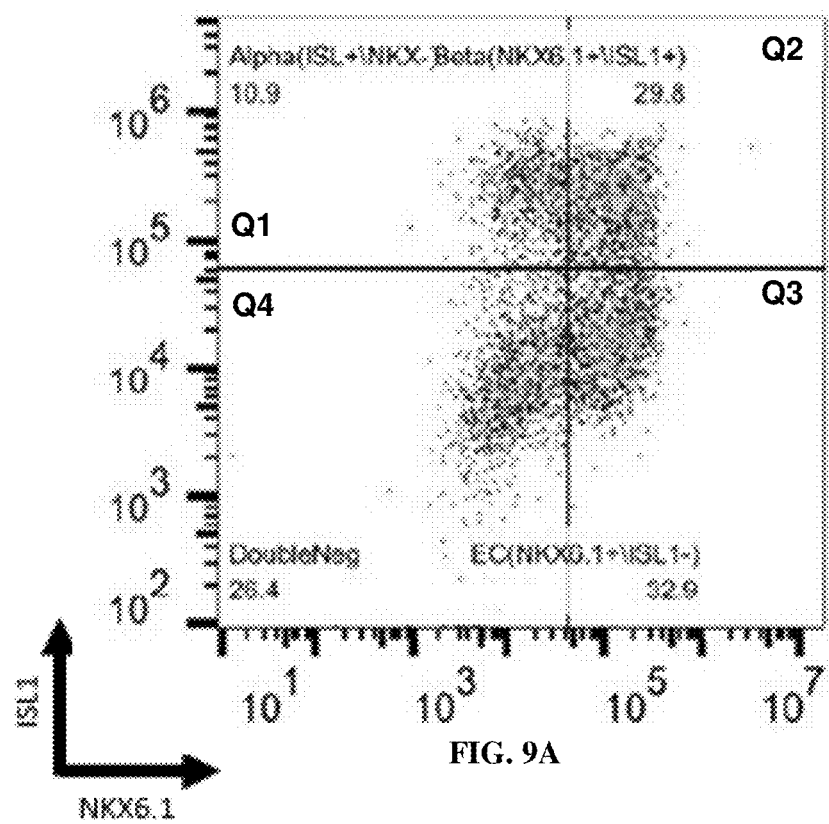
FIGS. 9A-9B are flow cytometry graphs showing ISL1/ NKX6.1 expression in pancreatic progenitor cells differentiated using Protocol 1 (FIG. 9A) or using Protocol 1 with the addition of a FoxO1 inhibitor on S4D5 (FIG. 9B).
Figure 9B:
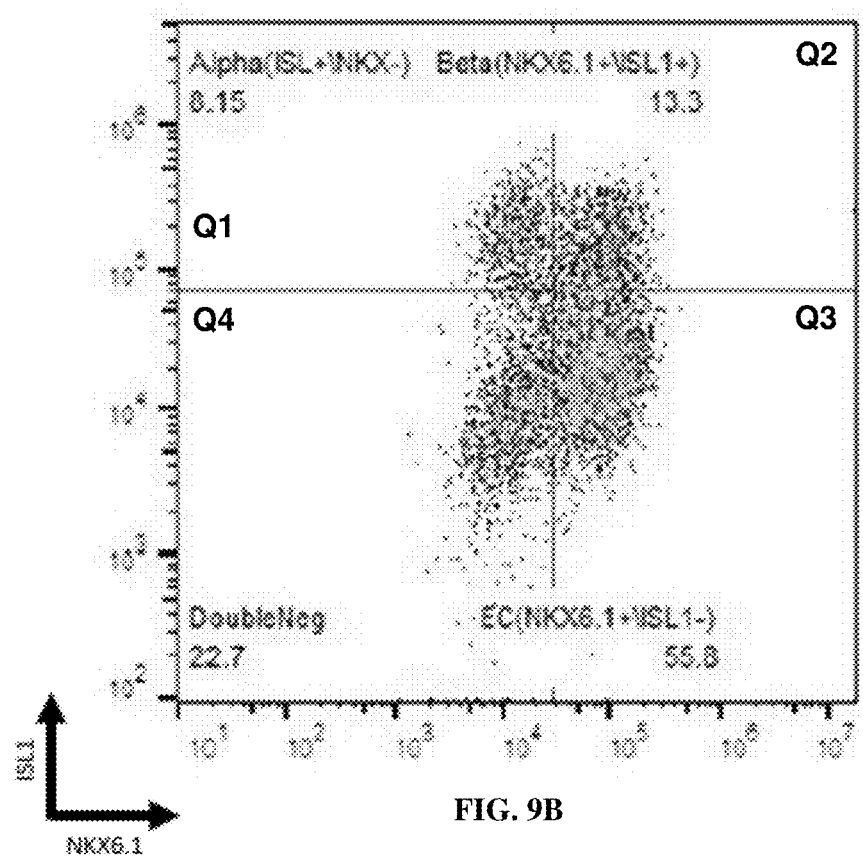
Figure 10A:
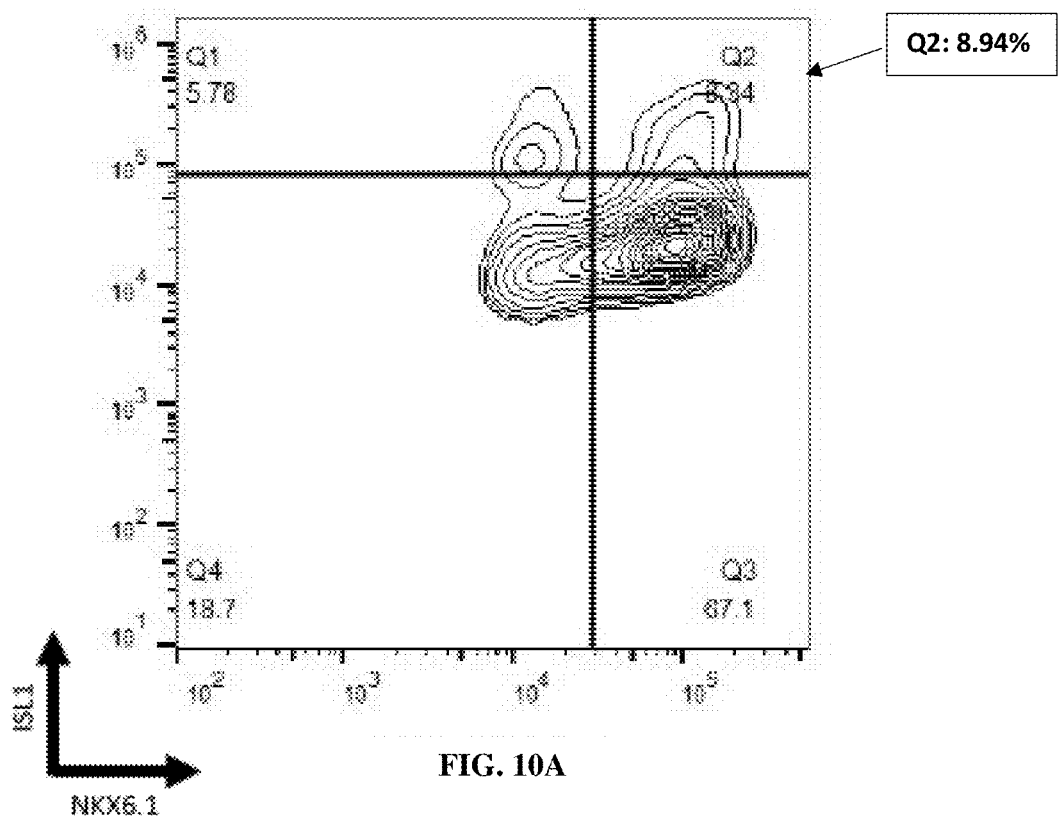
FIGS. 10A-10B are flow cytometry graphs showing ISL1/ Nkx6.1 expression in pancreatic progenitor cells progenitor differentiated using Protocol 1 (FIG. 10A) or using Protocol 1 with the addition of a Wnt inhibitor (XAV) on S5 Days 1-4 (FIG. 10B).
Figure 10B:
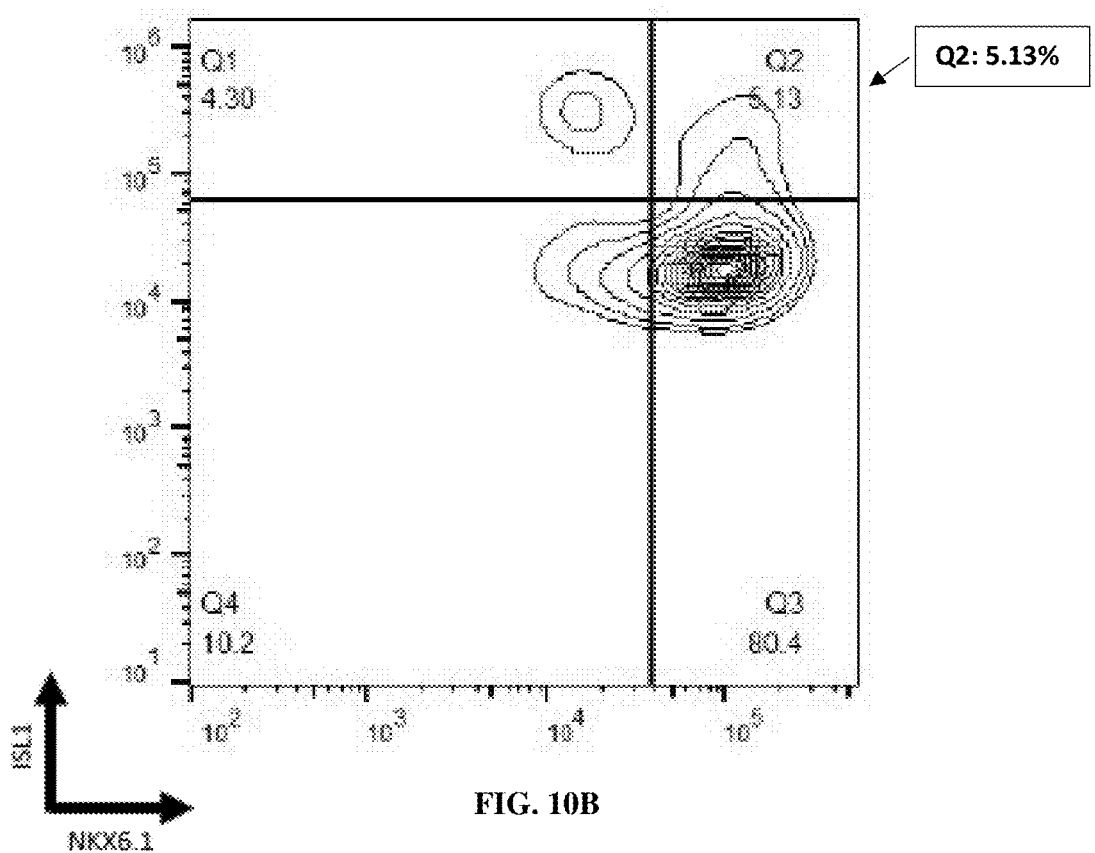
Figure 11A:
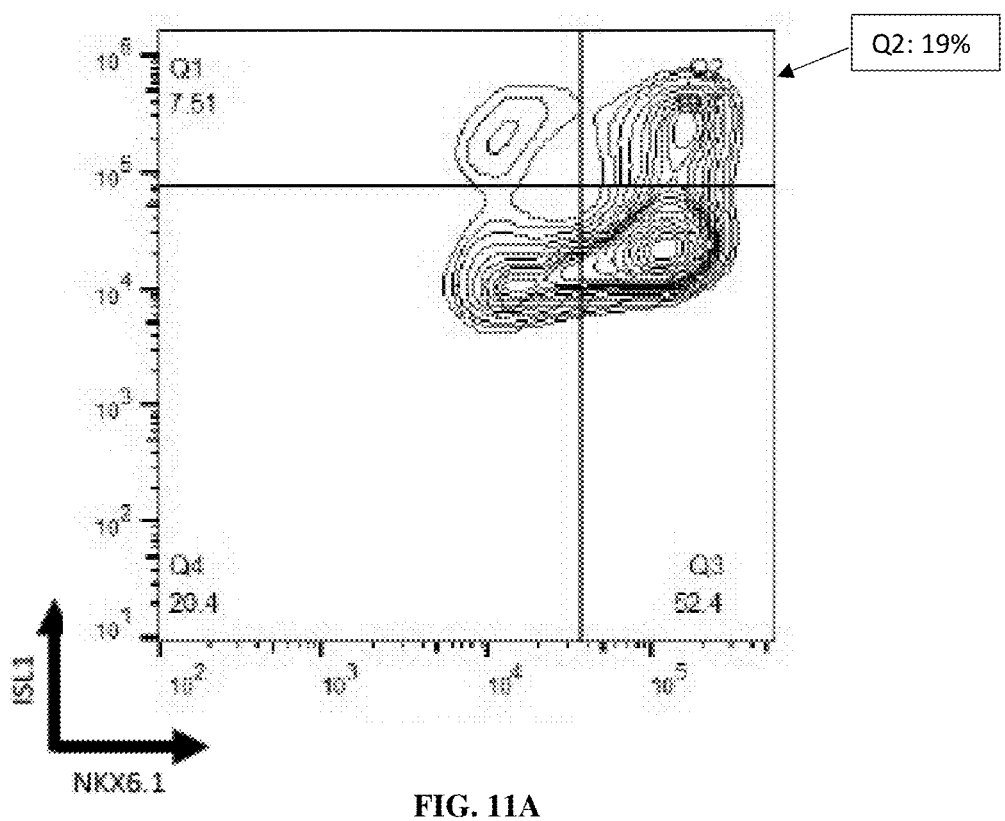
FIGS. 11A-11B are flow cytometry graphs showing ISL1/ NKX6.1 expression in pancreatic progenitor cells differentiated using Protocol 1 with the addition of a FoxO1 inhibitor on S4D5 (FIG. 11A) or with the addition of a FoxO1 inhibitor on S4D5 and a Wnt inhibitor (XAV) on S5 Days 1-4 (FIG. 11B).
Figure 11B:
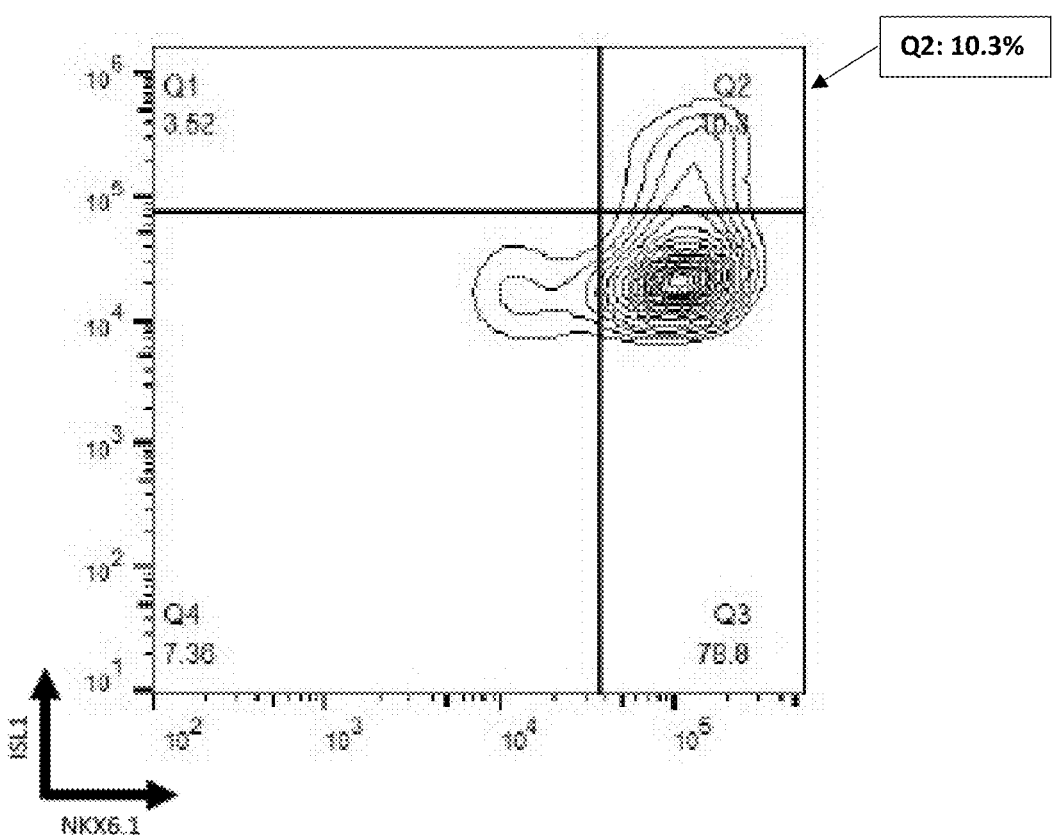
Figure 12A:
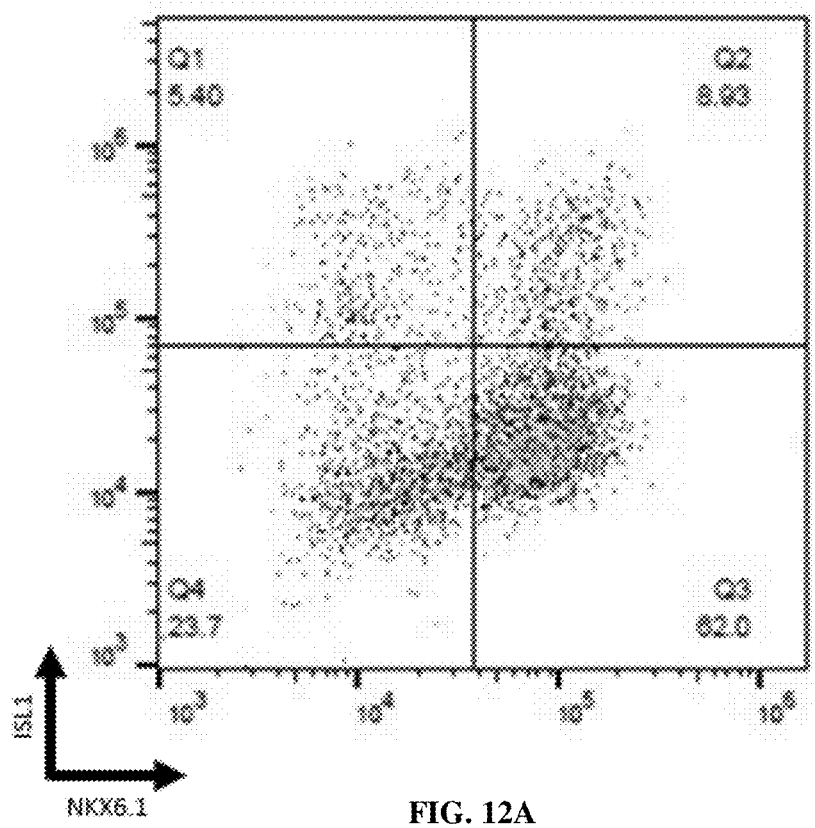
FIGS. 12A-12B are flow cytometry graphs showing ISL1/ NKX6.1 expression in pancreatic progenitor cells differentiated using Protocol 1 (FIG. 12A) or using Protocol 1 with the addition of a PKC activator (TPB) on S4D5 and S5 Days 1 and 2 (FIG. 12B).
Figure 12B:
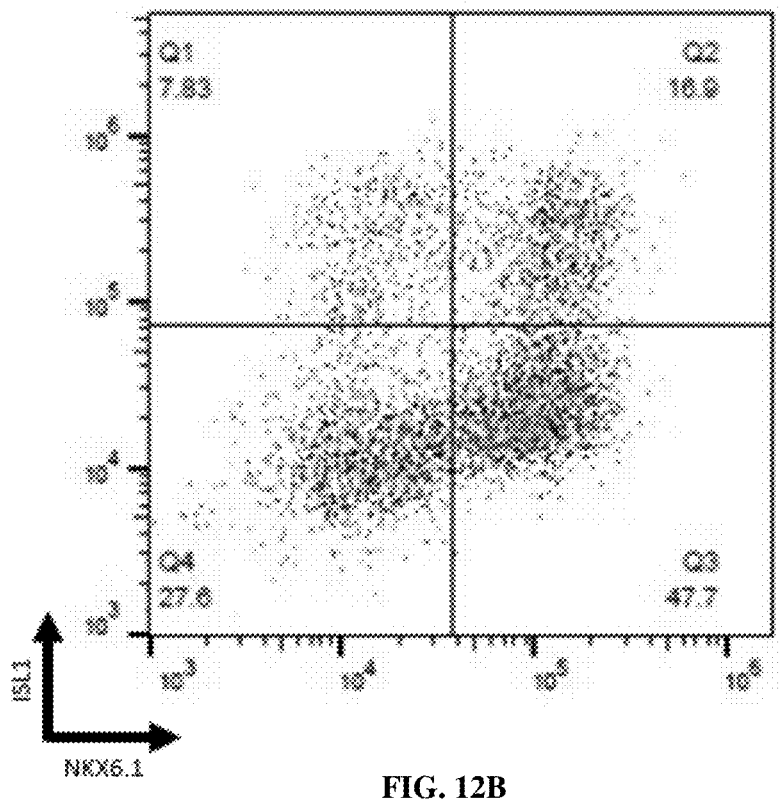
Figure 13A:
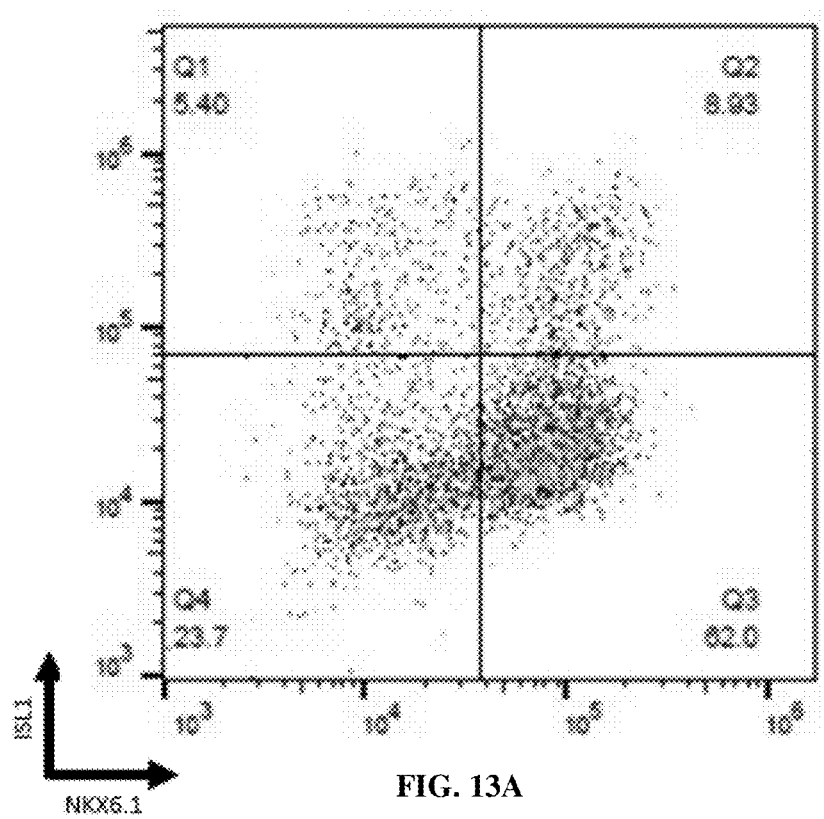
FIGS. 13A-13B are flow cytometry graphs showing ISL1/ NKX6.1 expression in pancreatic progenitor cells differentiated using Protocol 1 (FIG. 13A) or using Protocol 1 with the addition of a PKC activator (TPB) and a Notch inhibitor (XXI) on S4D5 followed by a PKC activator (TPB) alone on S5 Days 1-4 (FIG. 13B).
Figure 13B:
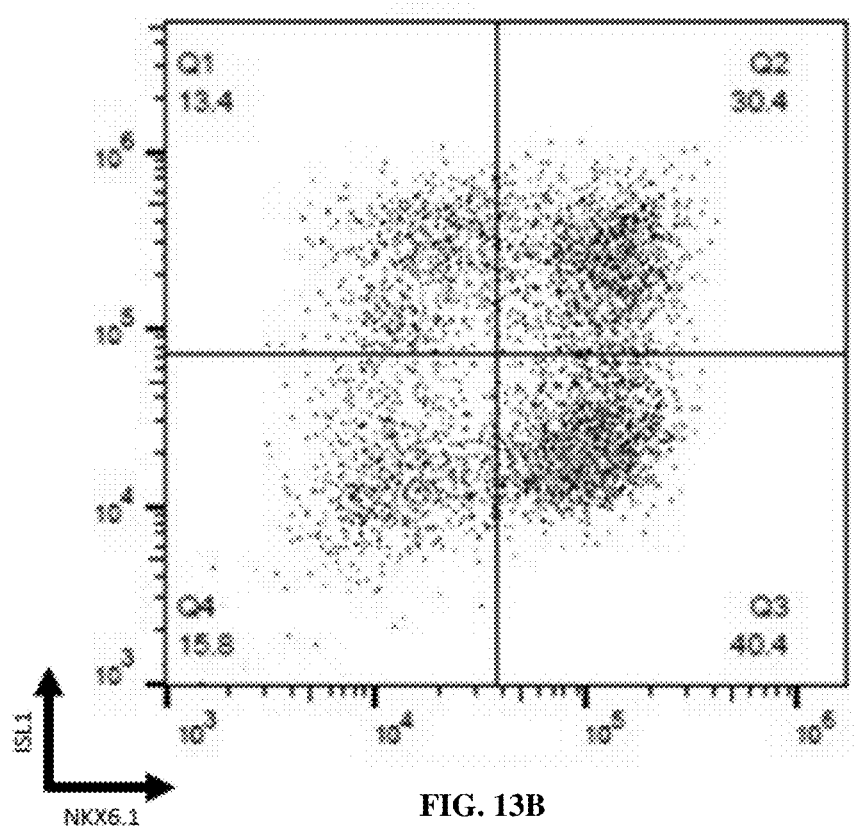
Figure 14A:
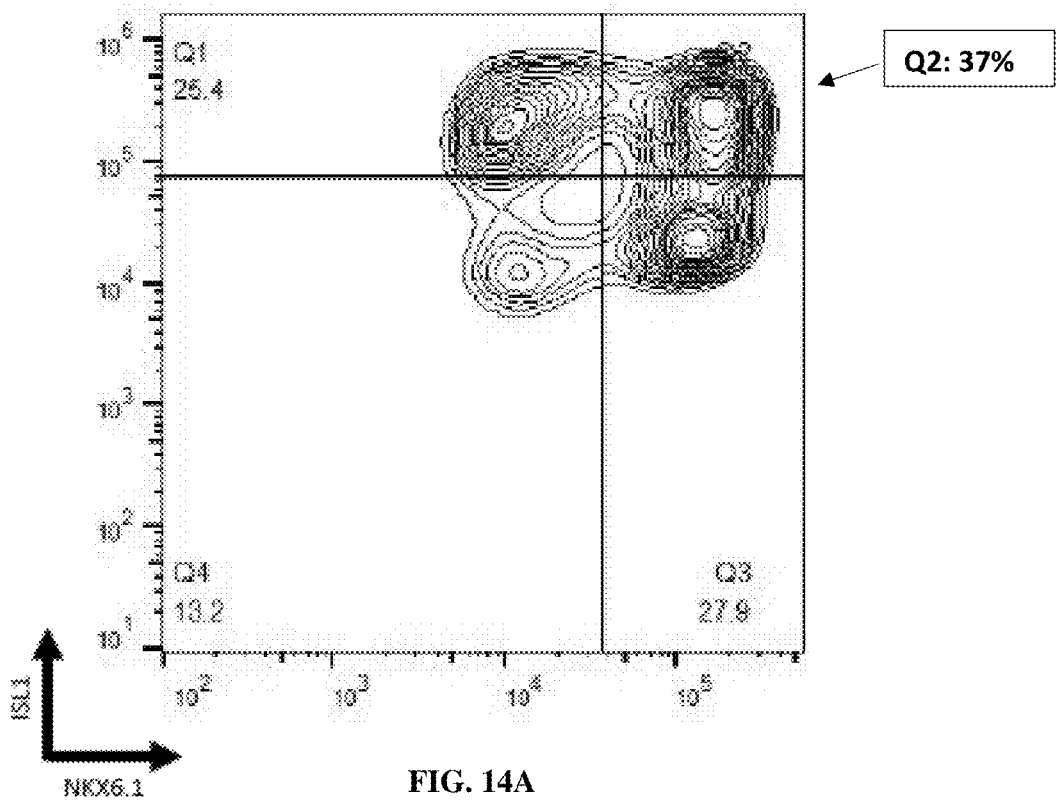
FIGS. 14A-14B are flow cytometry graphs showing ISL1/ NKX6.1 expression in pancreatic progenitor cells differentiated using Protocol 1 with the addition of a FoxO1 inhibitor, PKC activator (TPB), and a Notch inhibitor (XXI) on S4D5 (FIG. 14A) or with the addition of a FoxO1 inhibitor, PKC activator (TPB), and a Notch inhibitor (XXI) on S4D5 followed by a PKC activator (TPB) and a Wnt inhibitor (XAV) on S5 Days 1-4 (FIG. 14B).
Figure 14B:
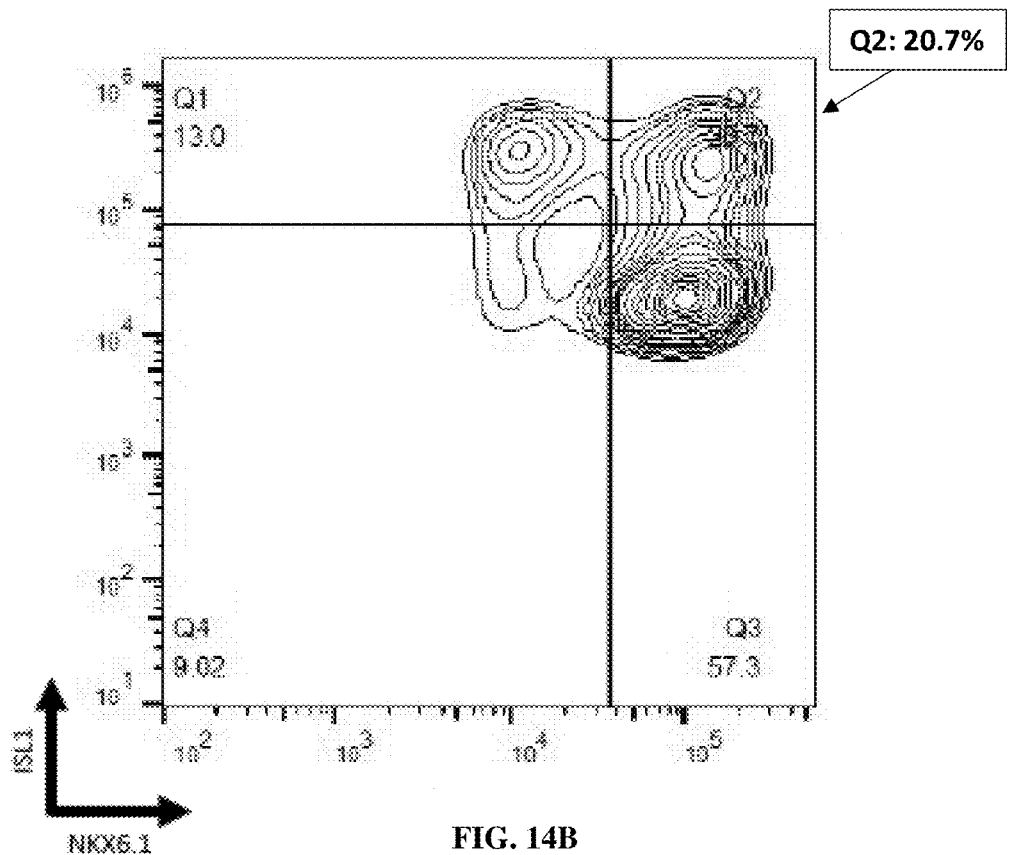
Figure 15A:
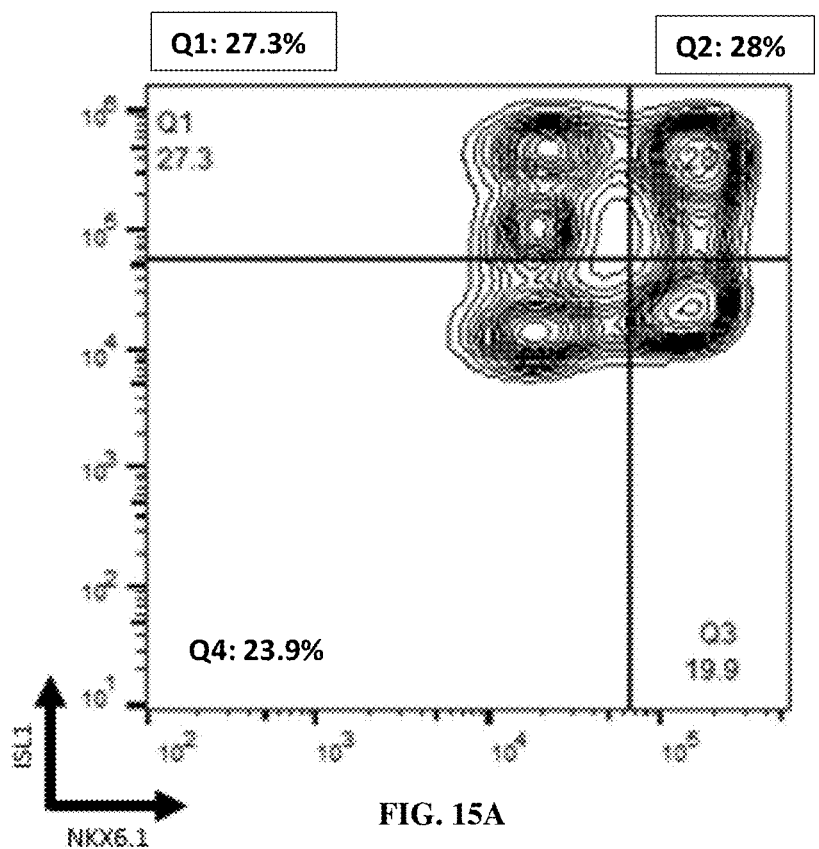
FIGS. 15A-15C are flow cytometry graphs showing ISL1/ NKX6.1 expression in pancreatic progenitor cells differentiated using Protocol 1 with the addition of a PKC activator (PDBU) on S4D5 (FIG. 15A), using Protocol 1 with the addition of a FoxO1 inhibitor, a PKC activator (PDBU) and a Notch inhibitor (XXI) on S4D5 (FIG. 15B), or using Protocol 1 with the addition of a FoxO1 inhibitor, a PKC activator (PDBU) and a Notch inhibitor (XXI) on S4D5 followed by a Wnt inhibitor (XAV) on S5 Days 1-4 (FIG. 15C).
Figure 15B:
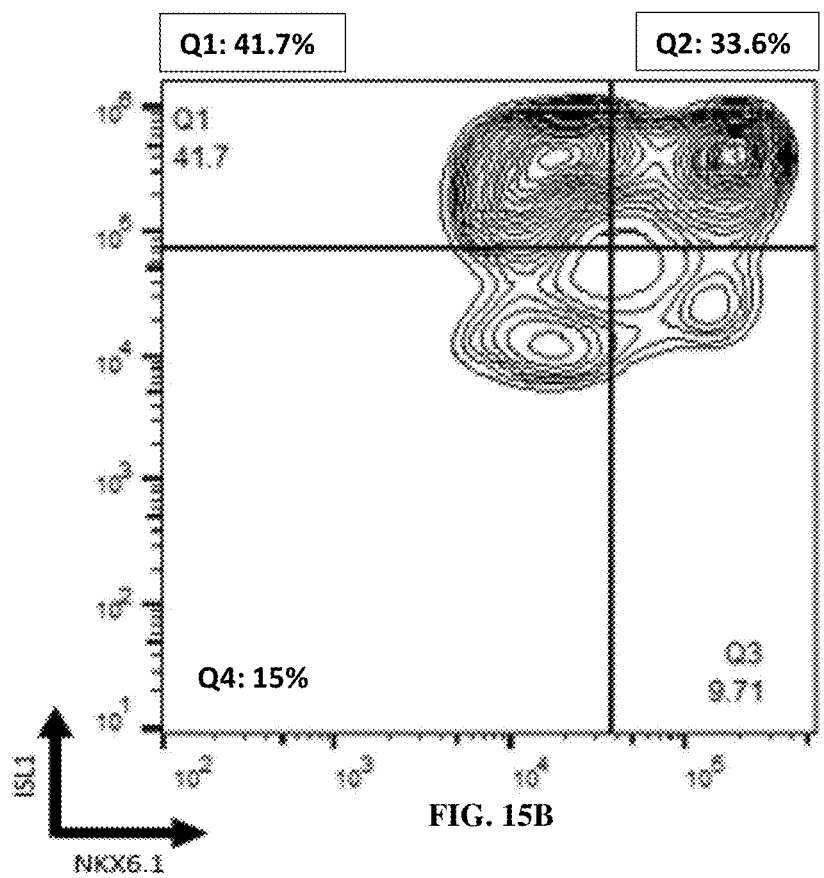
Figure 15C:
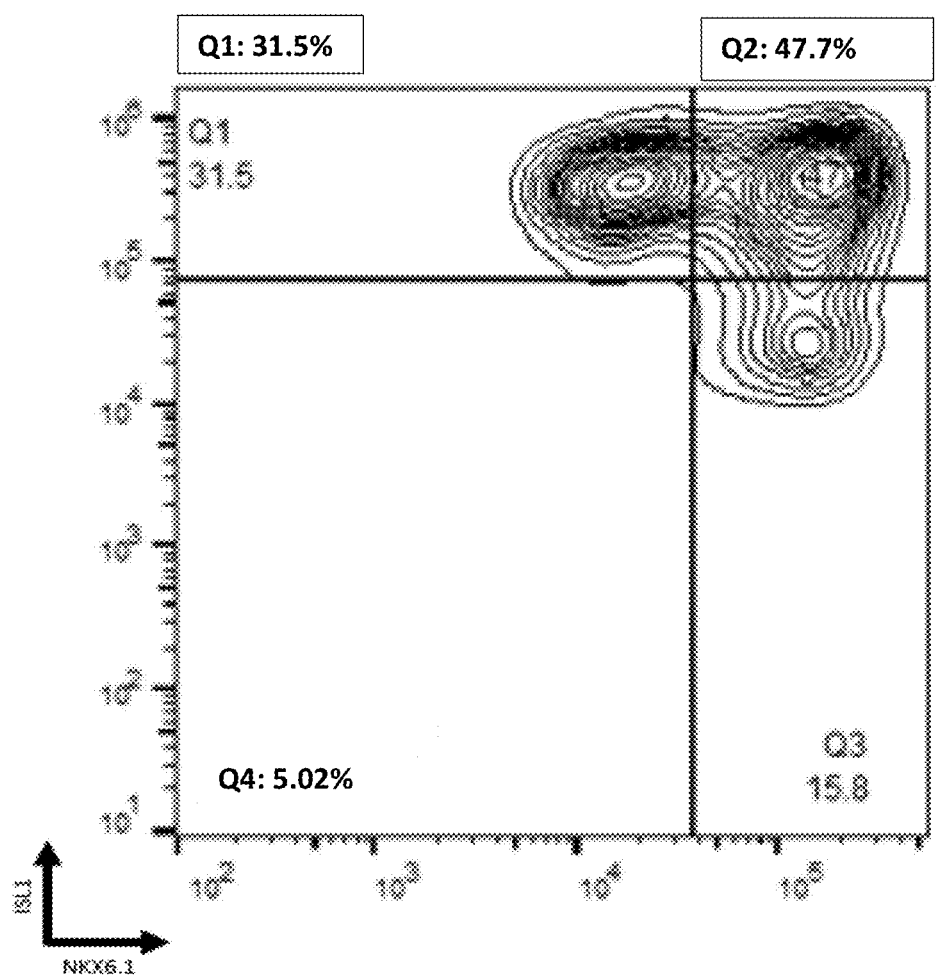
Figure 16B:
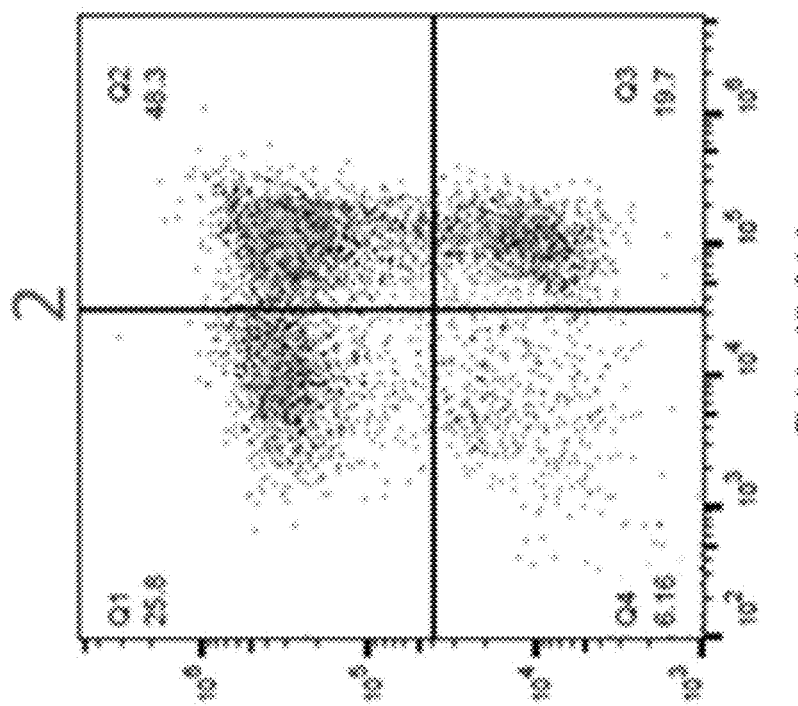
FIGS. 16A-16H are flow cytometry graphs showing ISL1/ NKX6.1 expression on S6D4 in SC-islet cells differentiated using the methods described in Table 6.
Figure 16A:
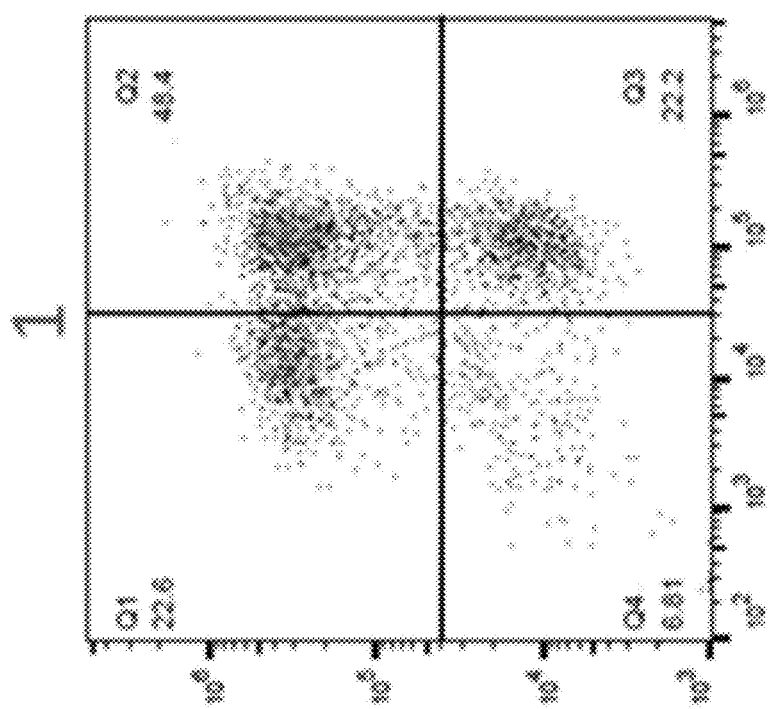
Figure 16D:
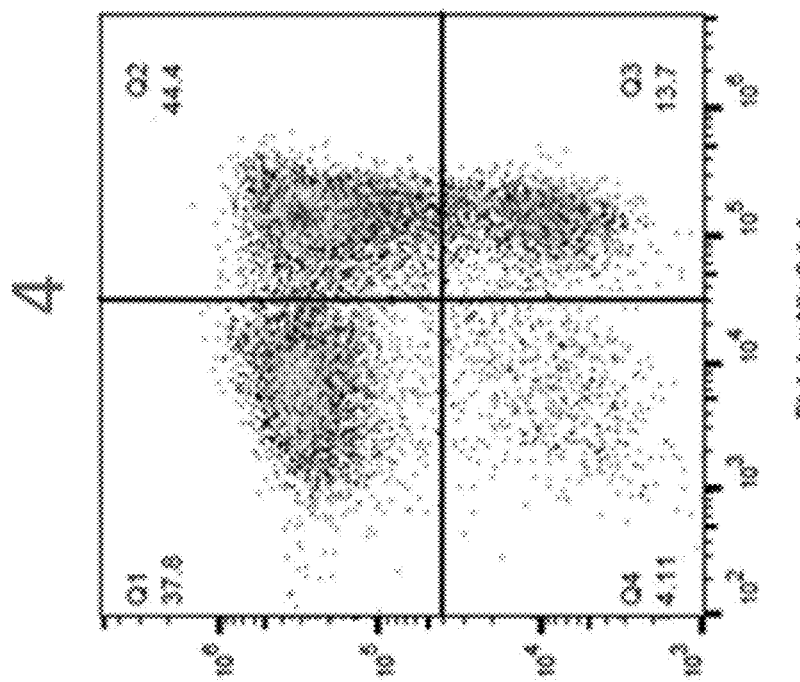
Figure 16C:
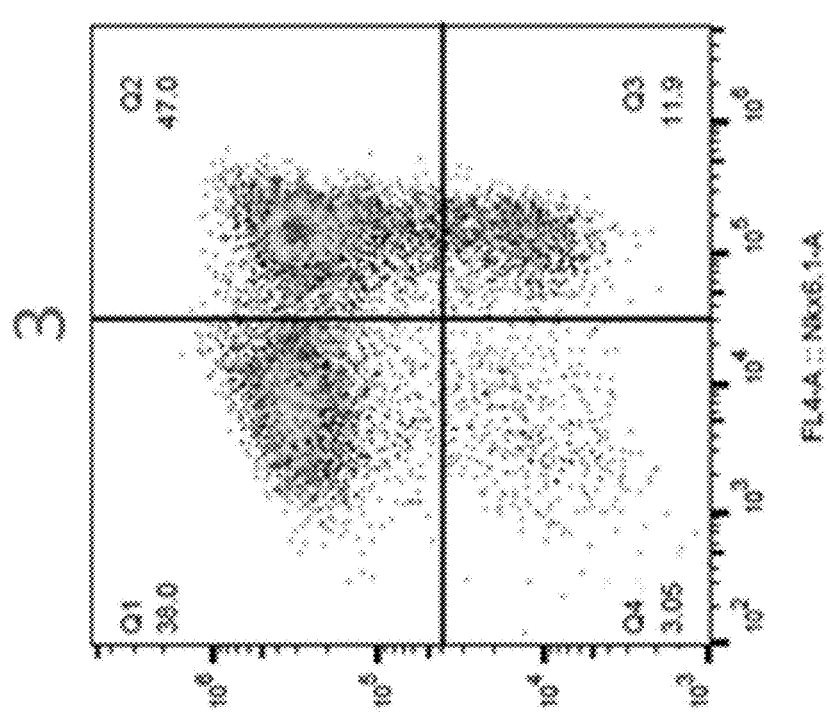
Figure 16F:
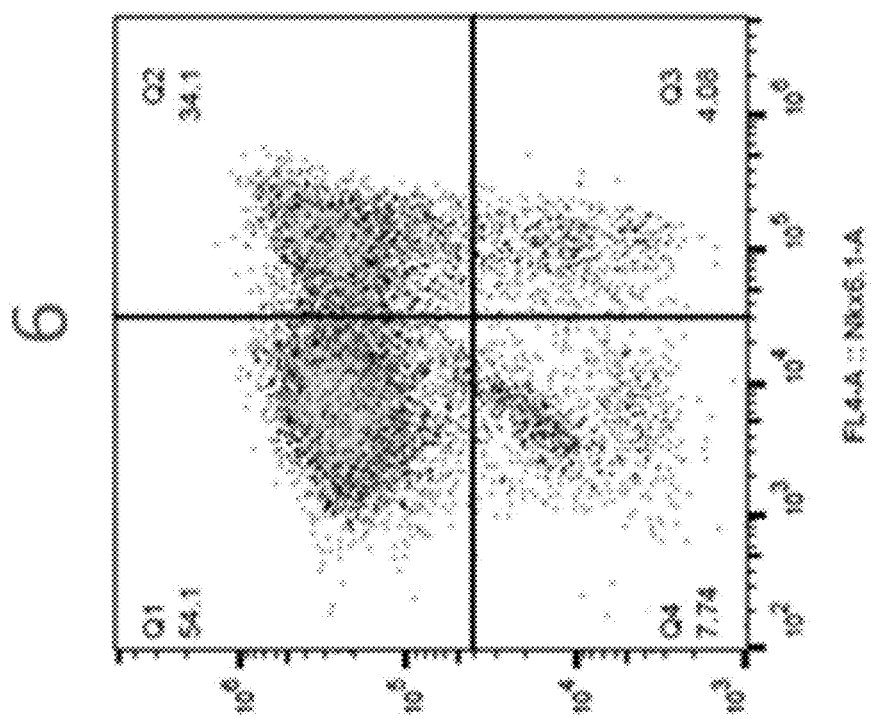
Figure 16E:
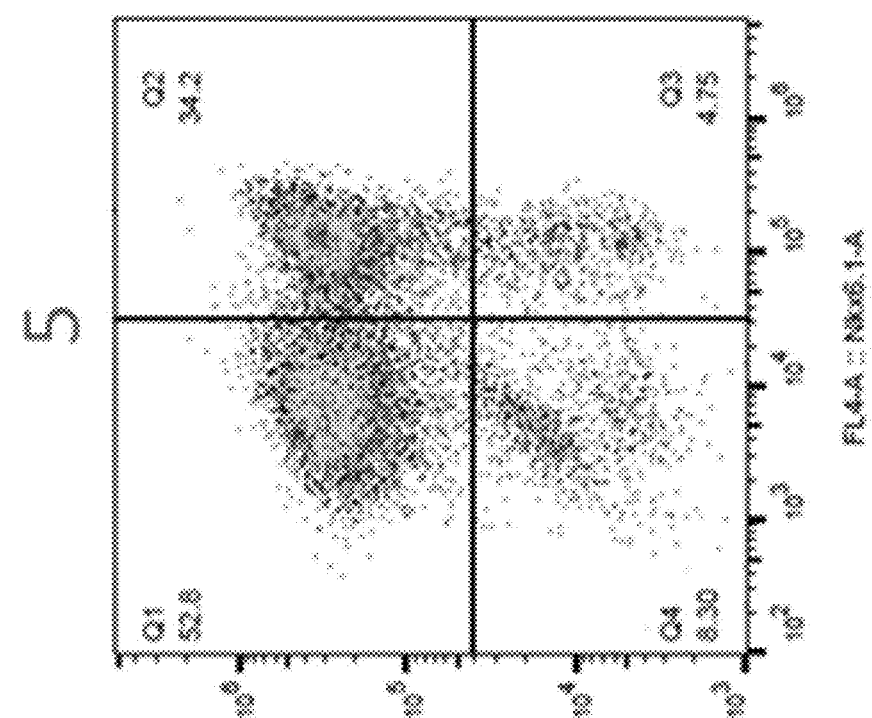
Figure 16H:
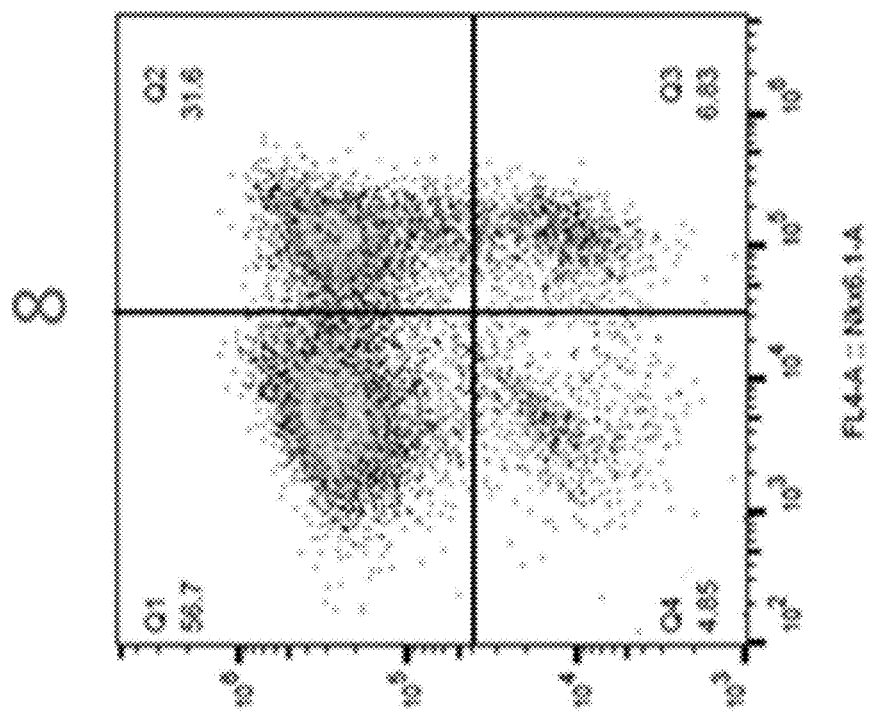
Figure 16G:
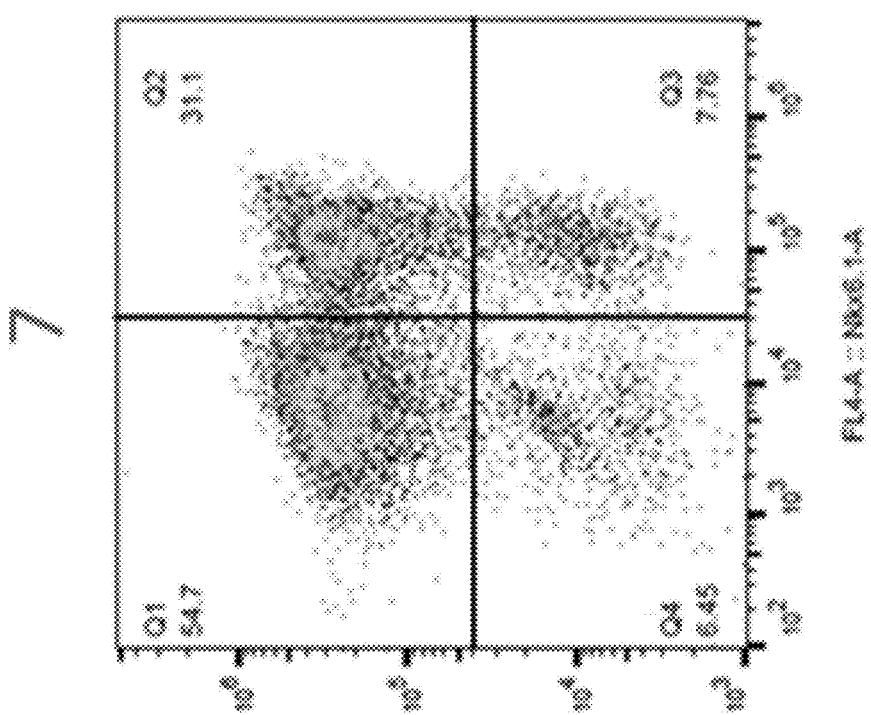
Figure 17A:
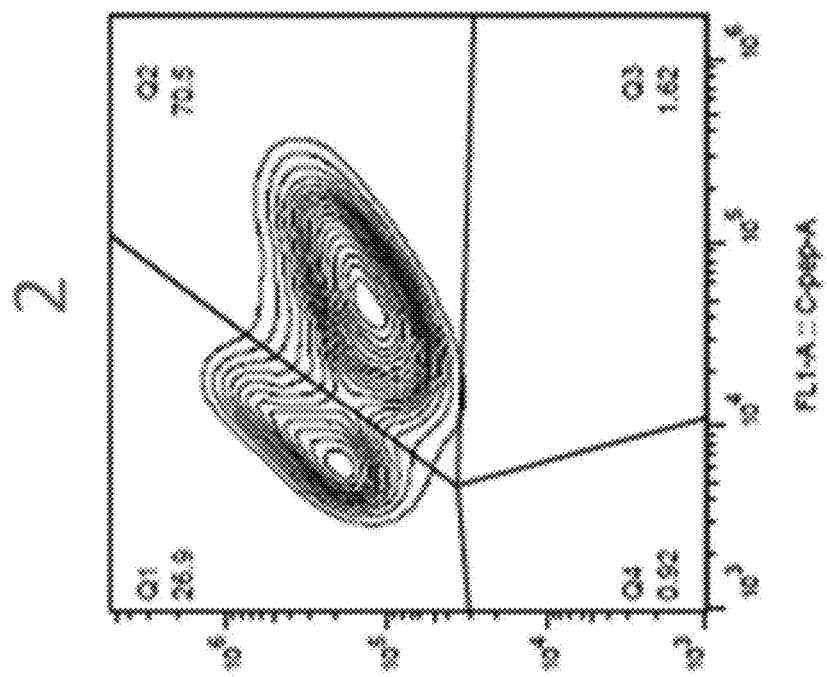
FIGS. 17A-17H are flow cytometry graphs showing Chromogranin A (CHGA)/C-Peptide expression on S6D4 in SC-islet cells differentiated using the methods described in Table 6.
Figure 17B:
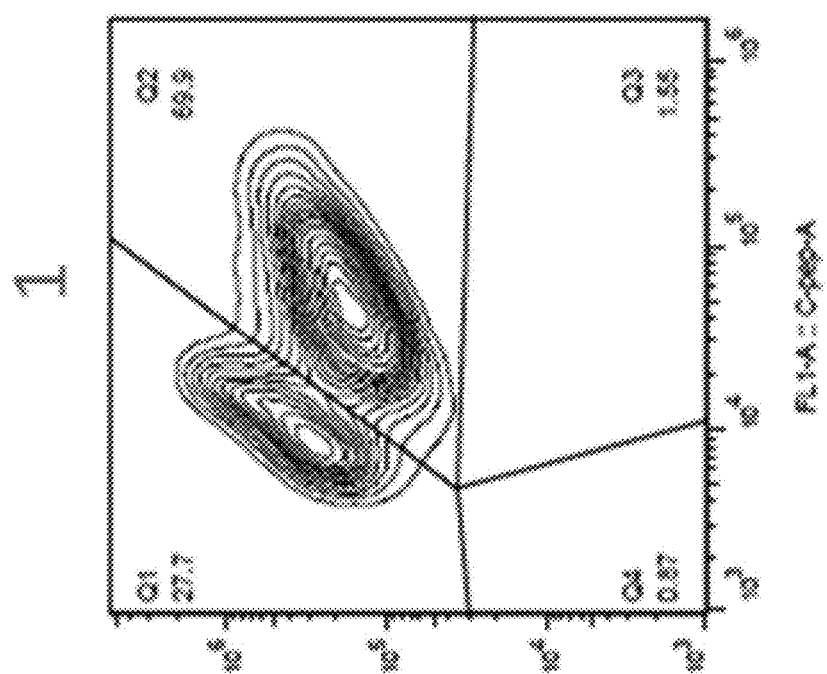
Figure 17D:
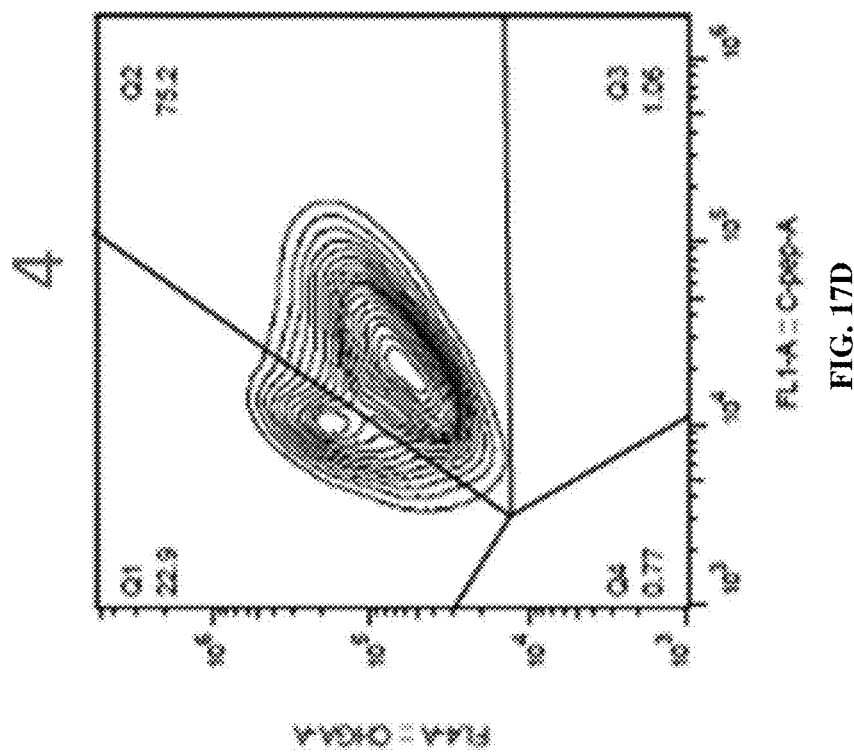
Figure 17C:
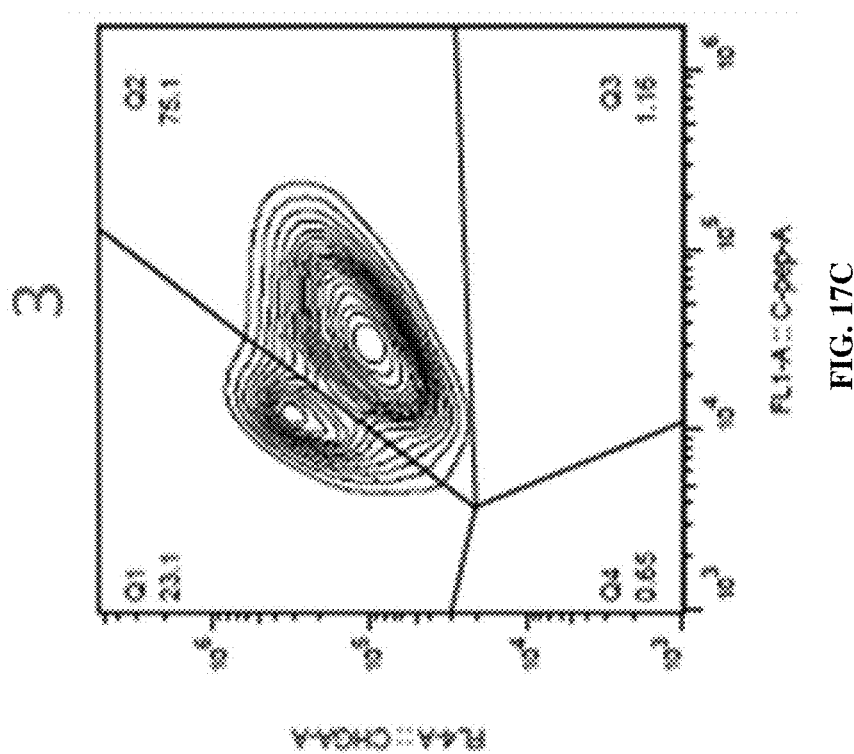
Figure 17F:
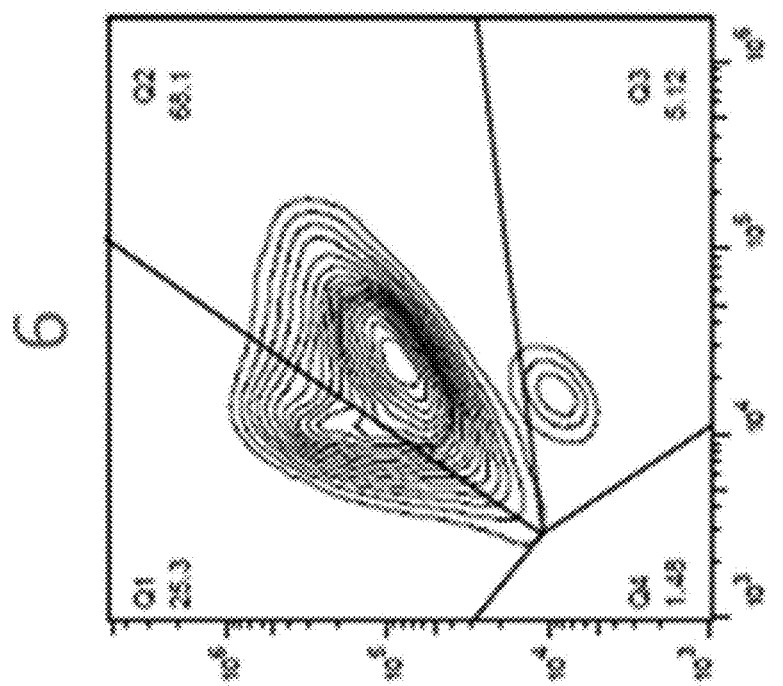
Figure 17E:
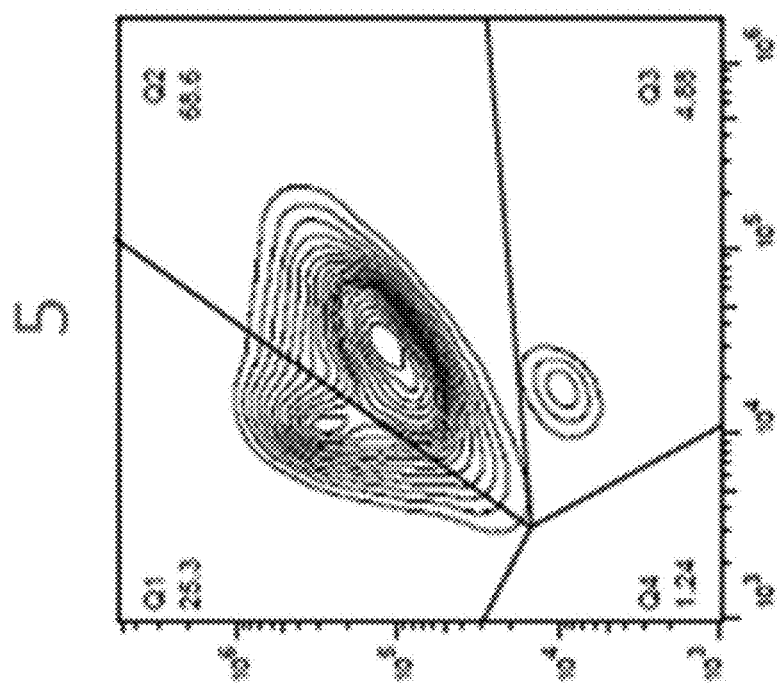
Figure 17H:
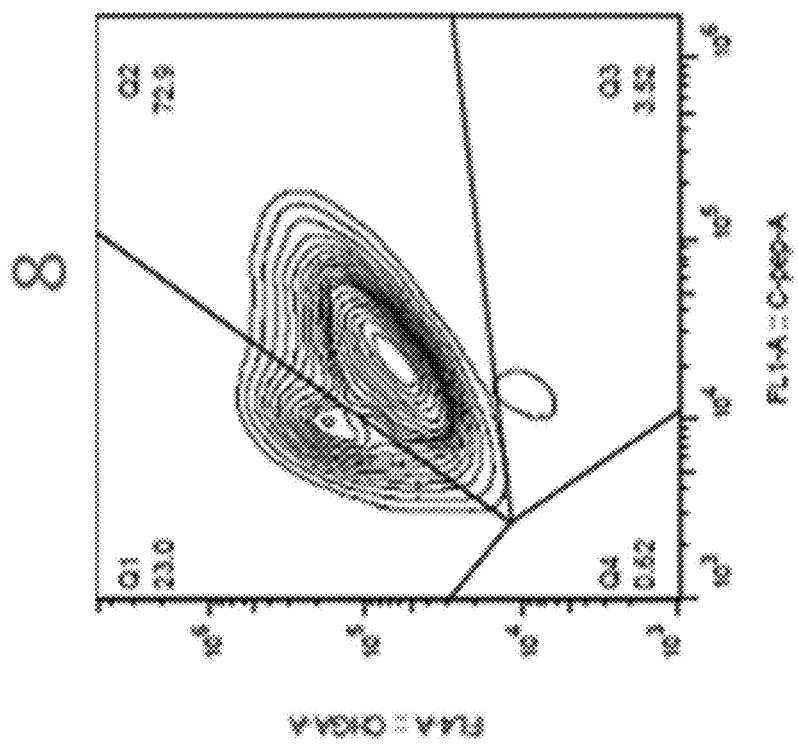
Figure 17G:
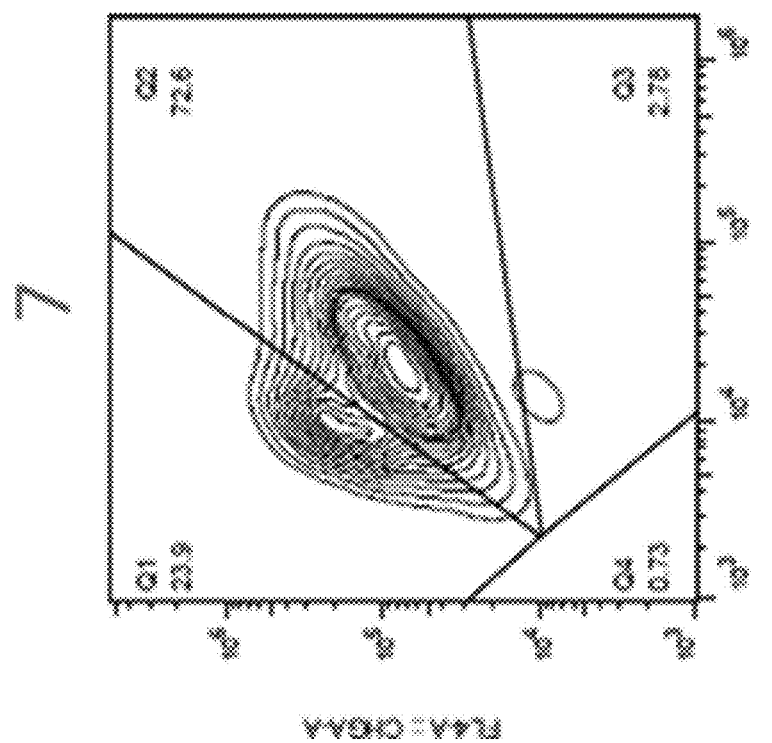
Figure 18B:
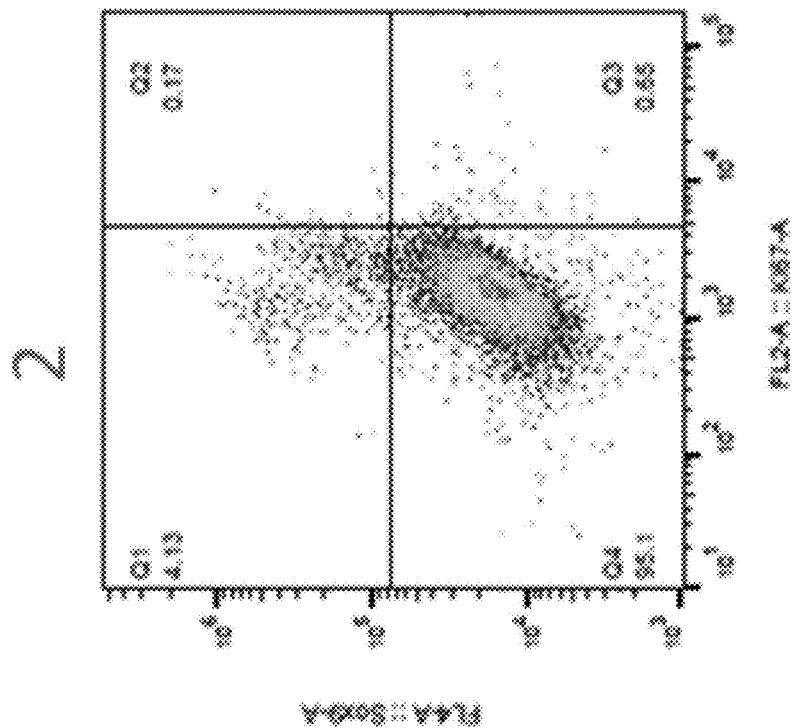
FIGS. 18A-18H are flow cytometry graphs showing SOX9/Ki67 expression on S6D4 in SC-islet cells differentiated using the methods described in Table 6.
Figure 18A:
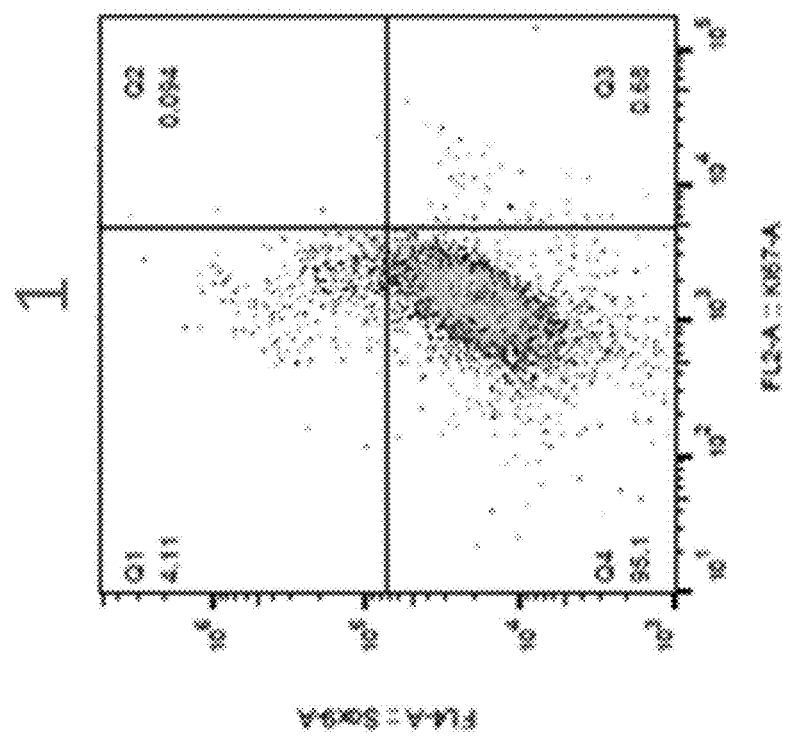
Figure 18D:
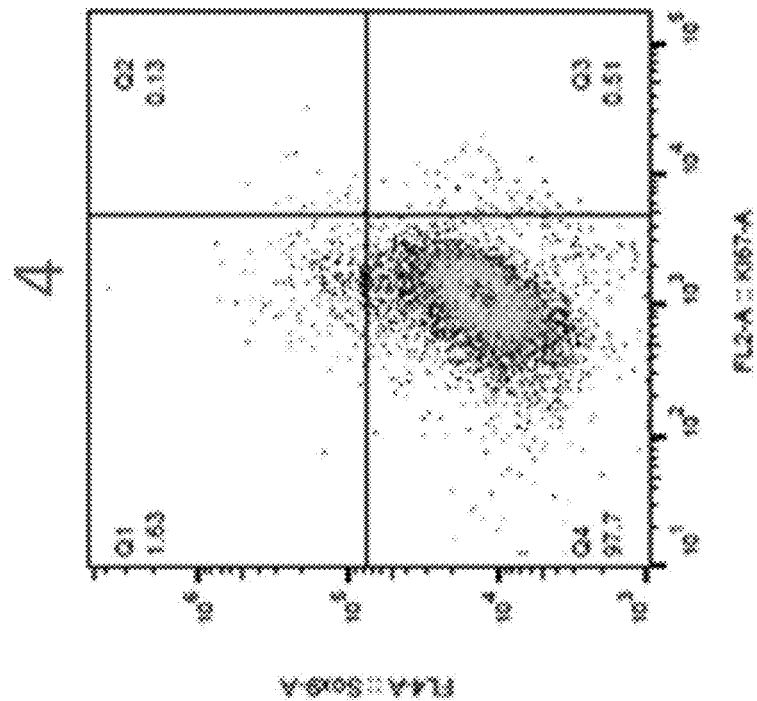
Figure 18C:
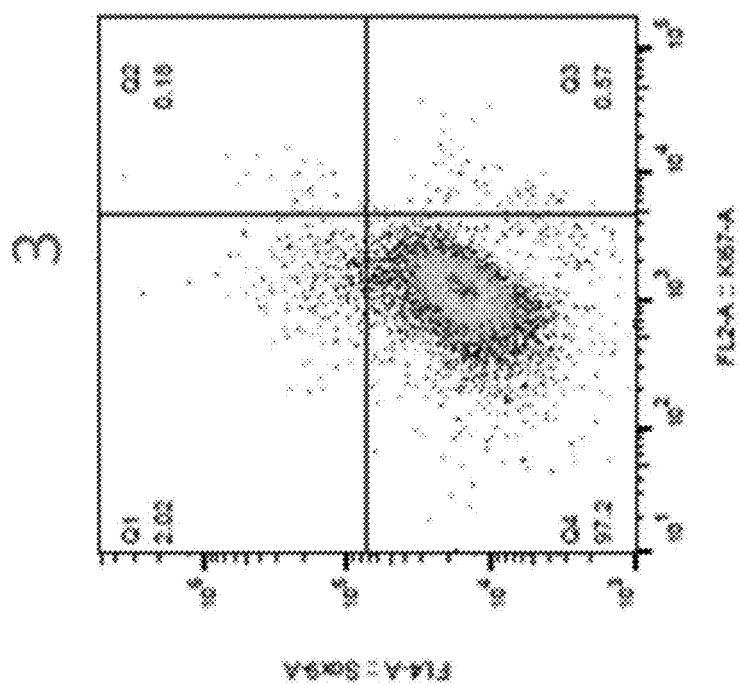
Figure 18F:
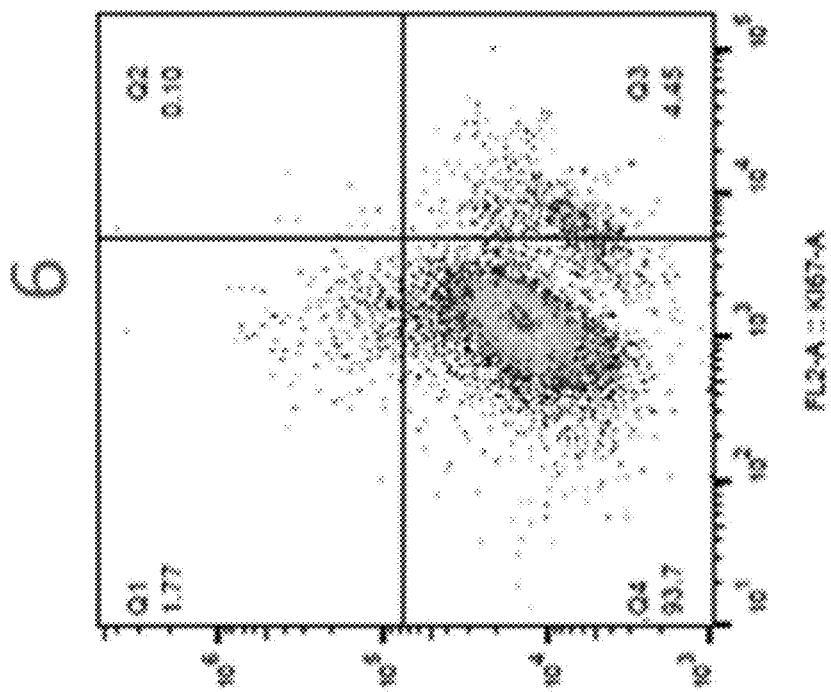
Figure 18E:
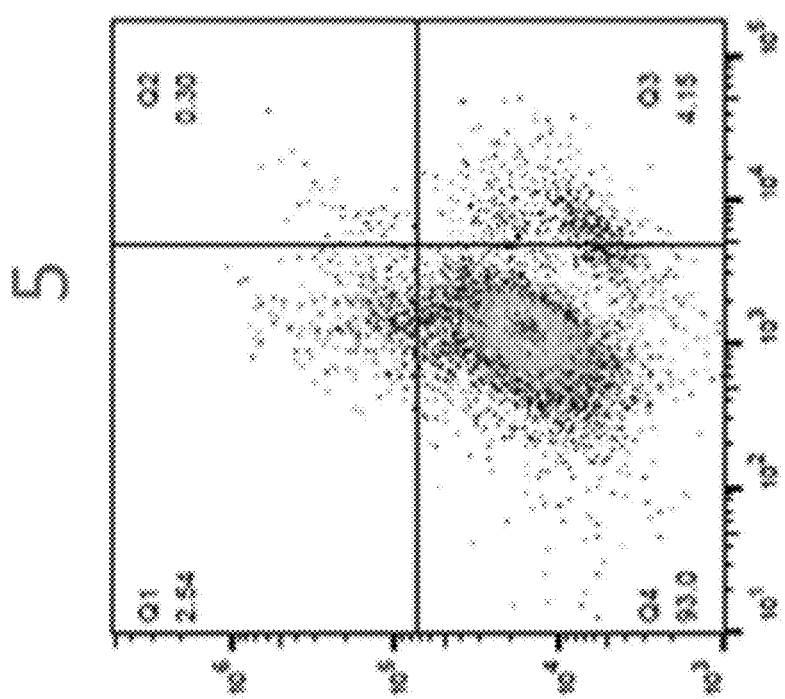
Figure 18G:
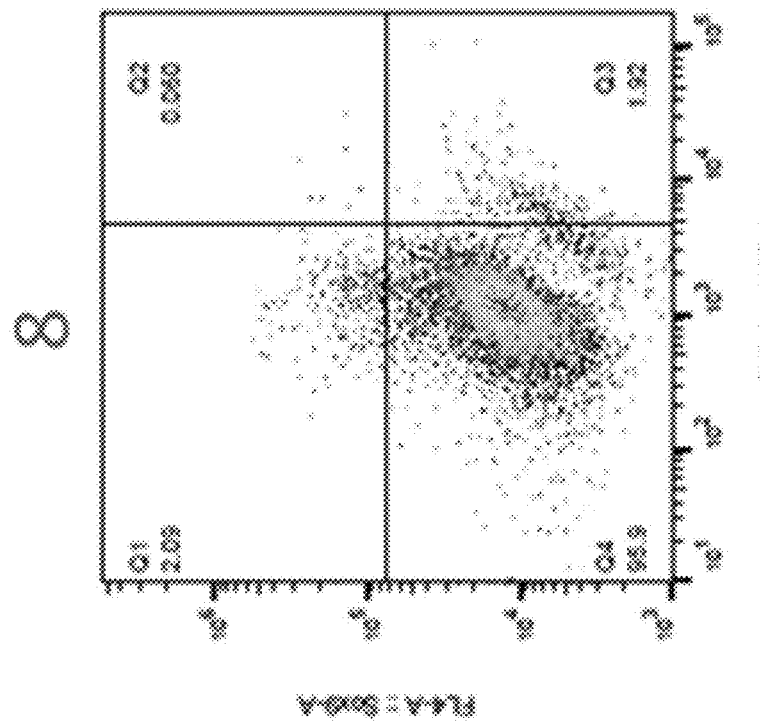
Figure 18H:
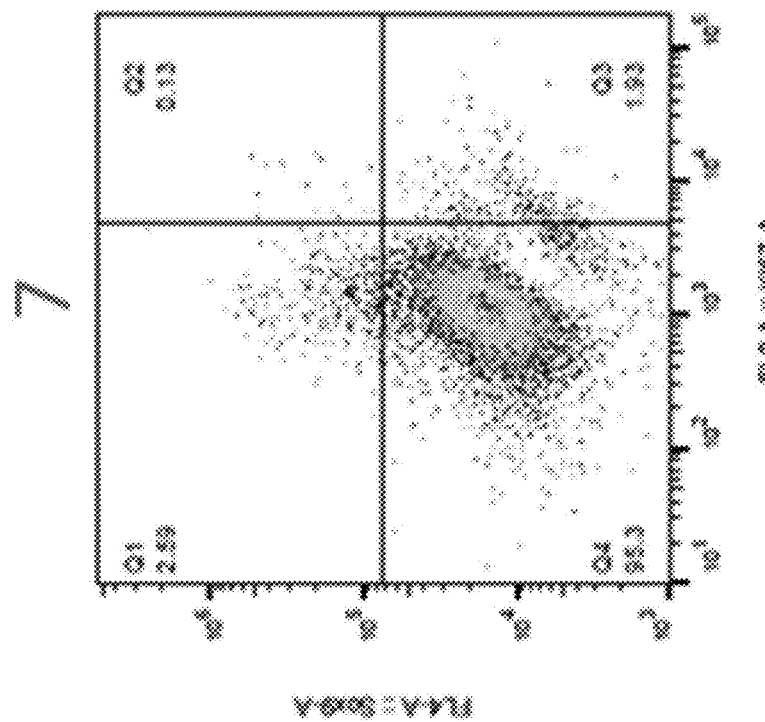
Figure 19A:
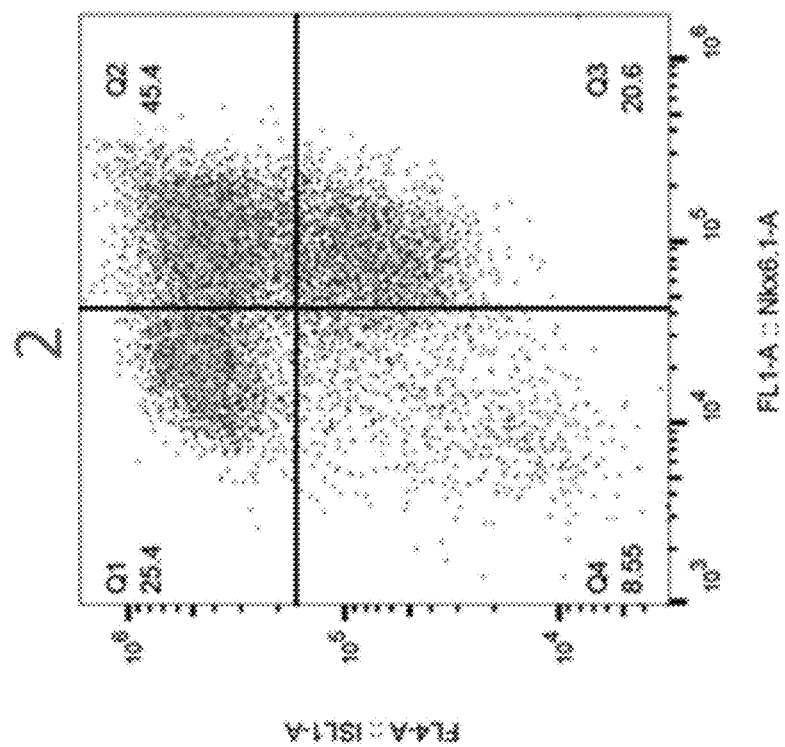
FIGS. 19A-19H are flow cytometry graphs showing ISL1/ NKX6.1 expression on S6D7 in SC-islet cells differentiated using the methods described in Table 6.
Figure 19B:
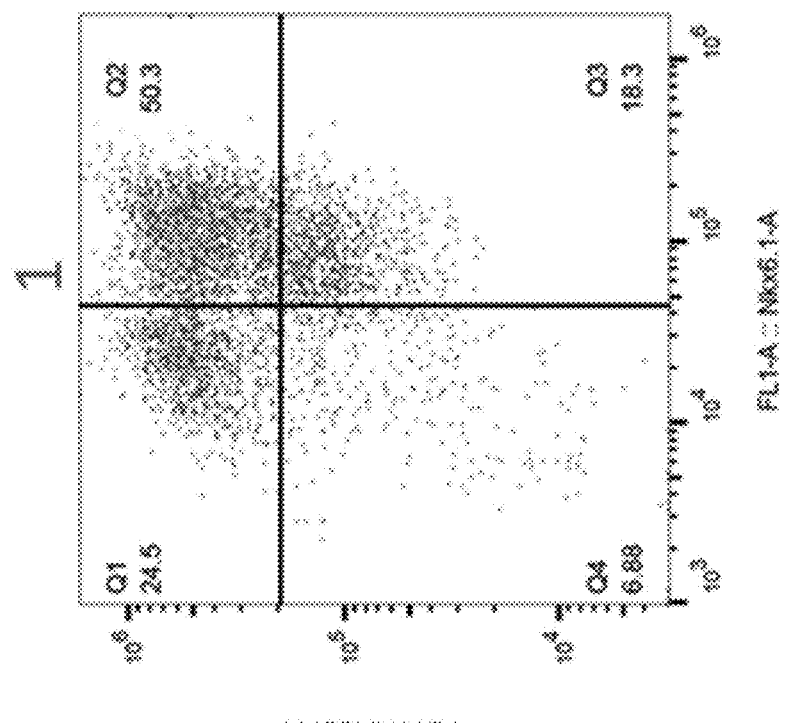
Figure 19D:
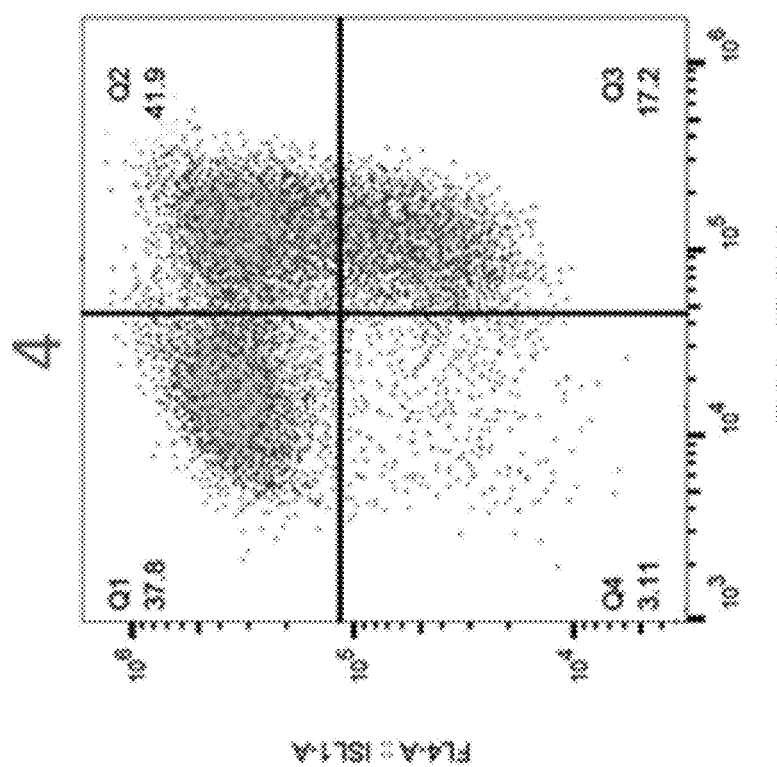
Figure 19C:
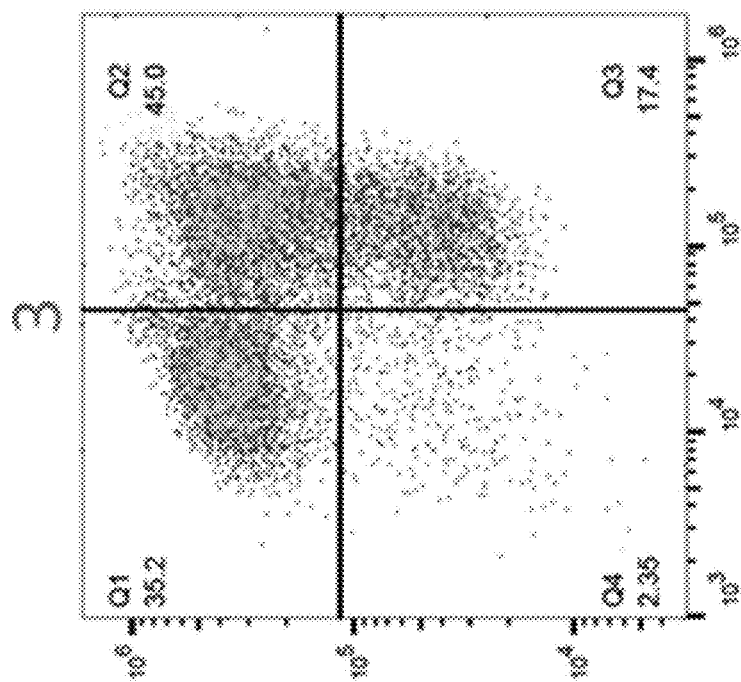
Figure 19F:
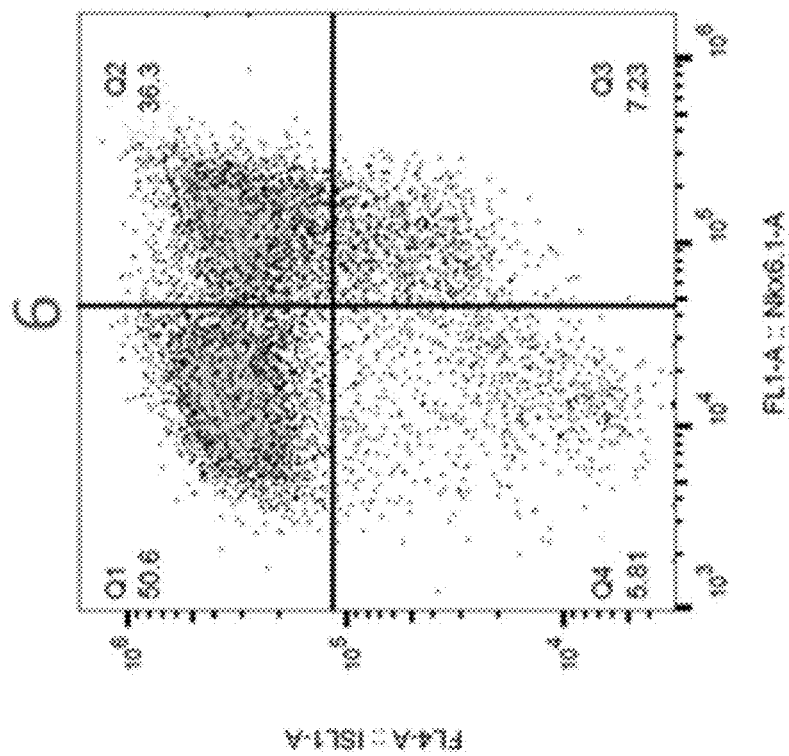
Figure 19E:
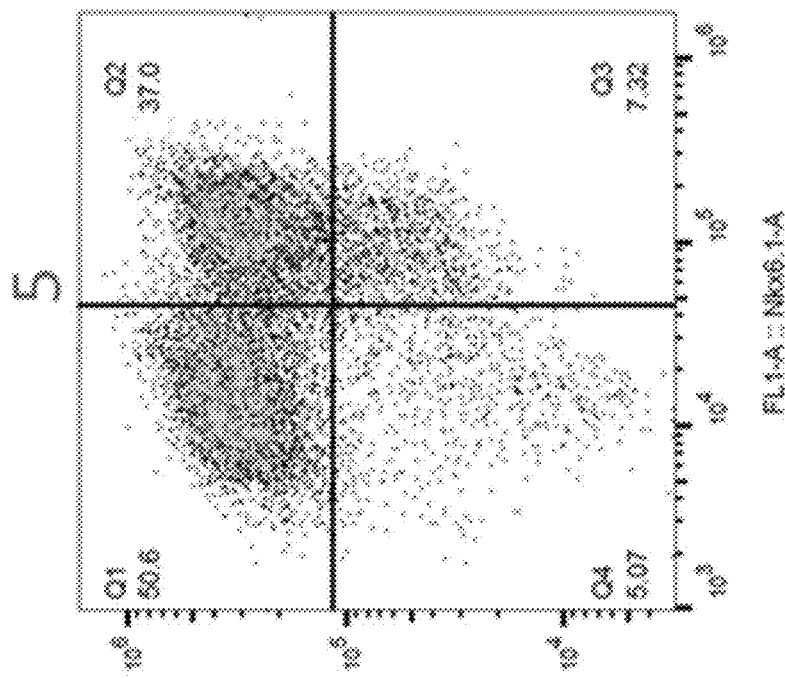
Figure 19H:
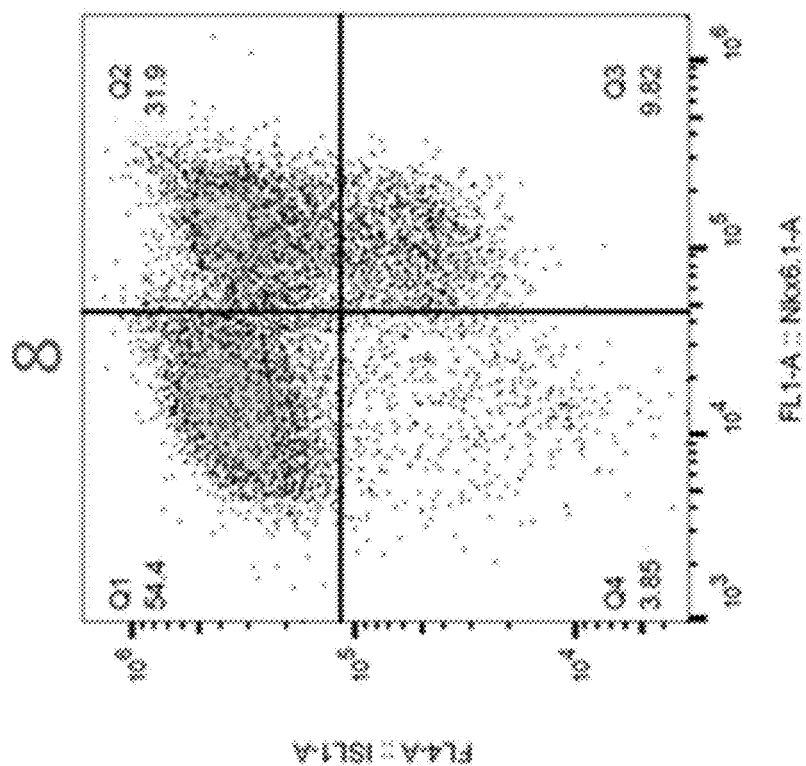
Figure 19G:
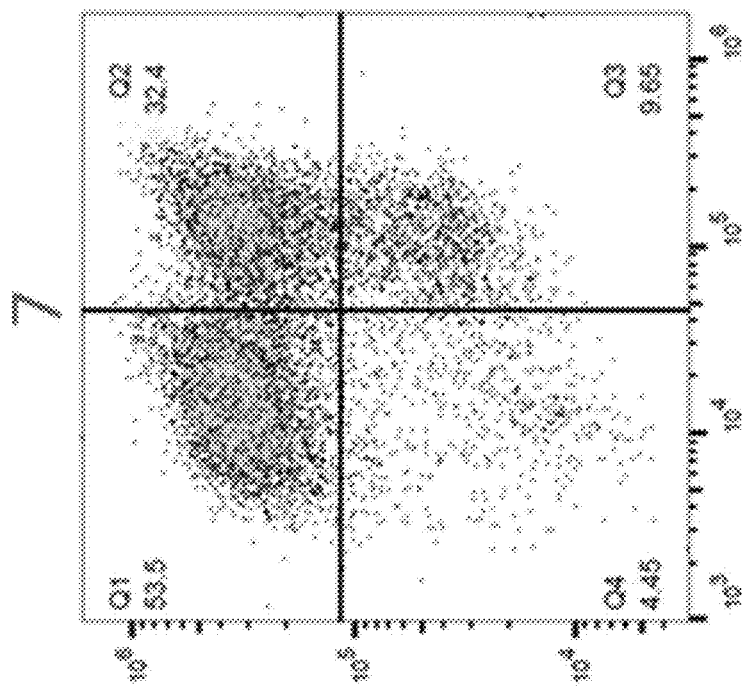
Figure 20A:
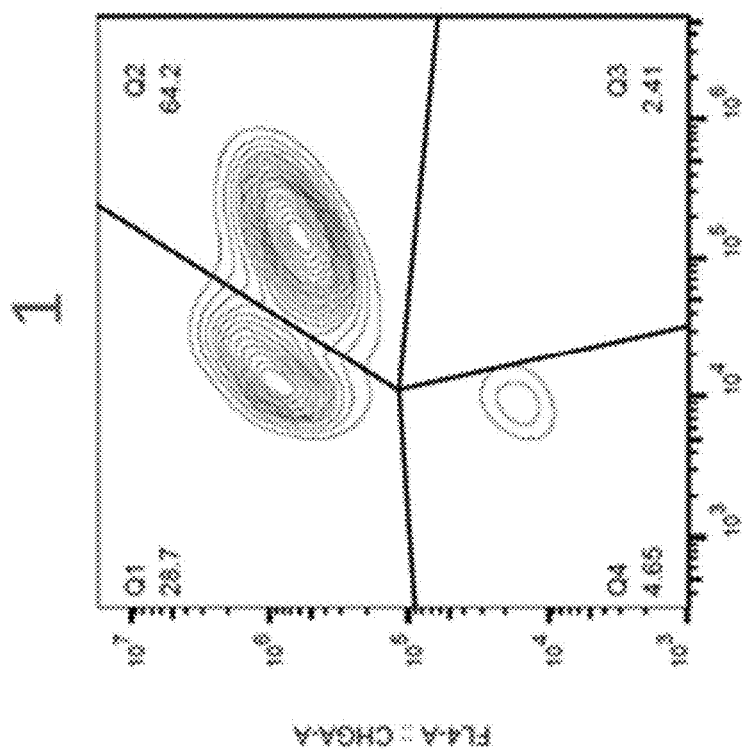
FIGS. 20A-20H are flow cytometry graphs showing Chromogranin A (CHGA)/C-Peptide expression on S6D7 in SC-islet cells differentiated using the methods described in Table 6.
Figure 20B:
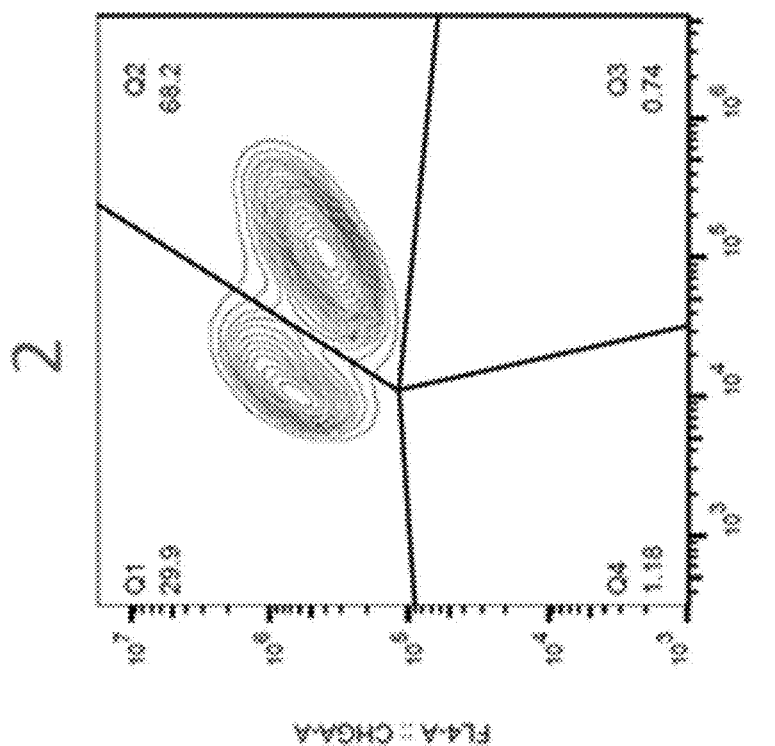
Figure 20D:
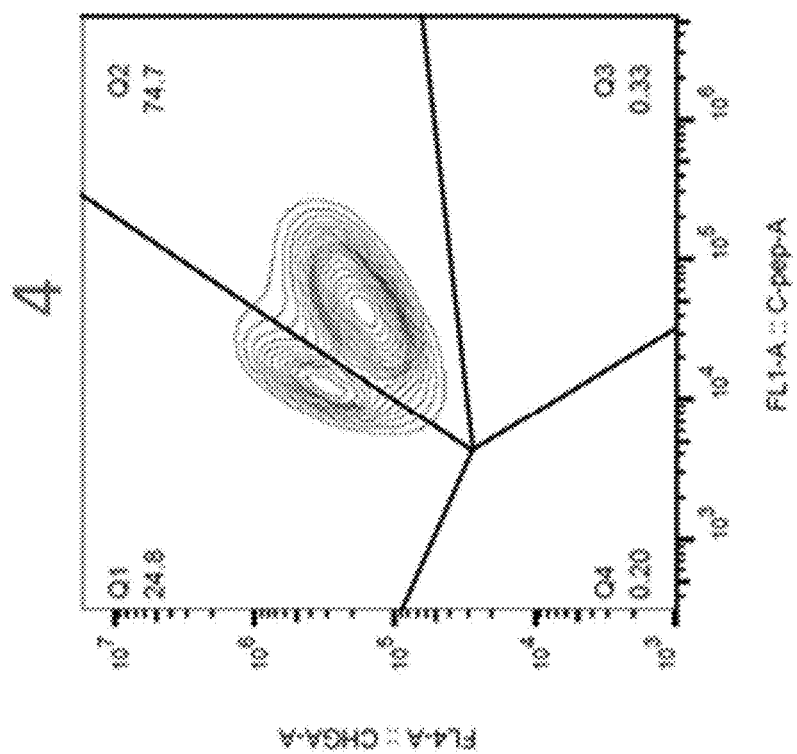
Figure 20C:
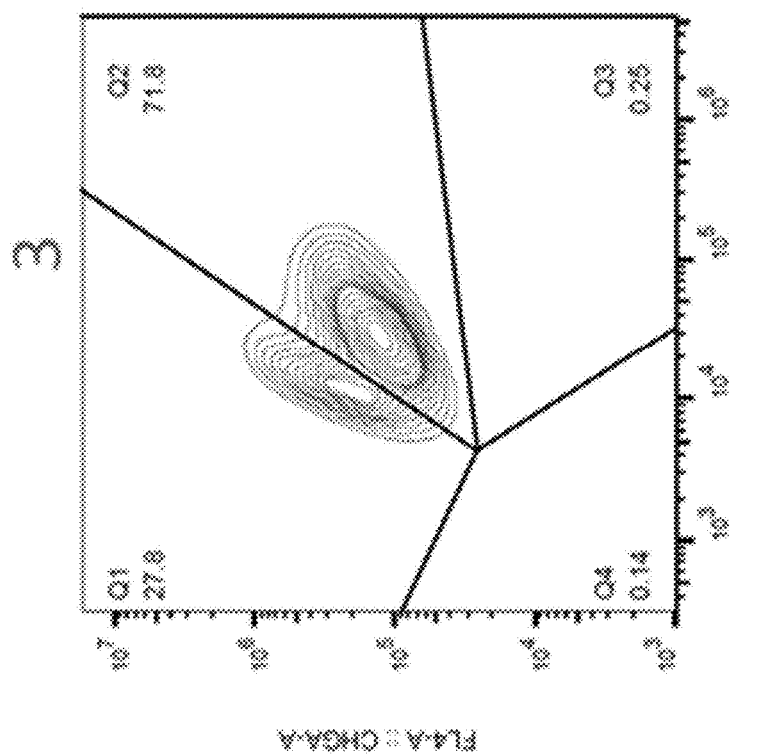
Figure 20F:
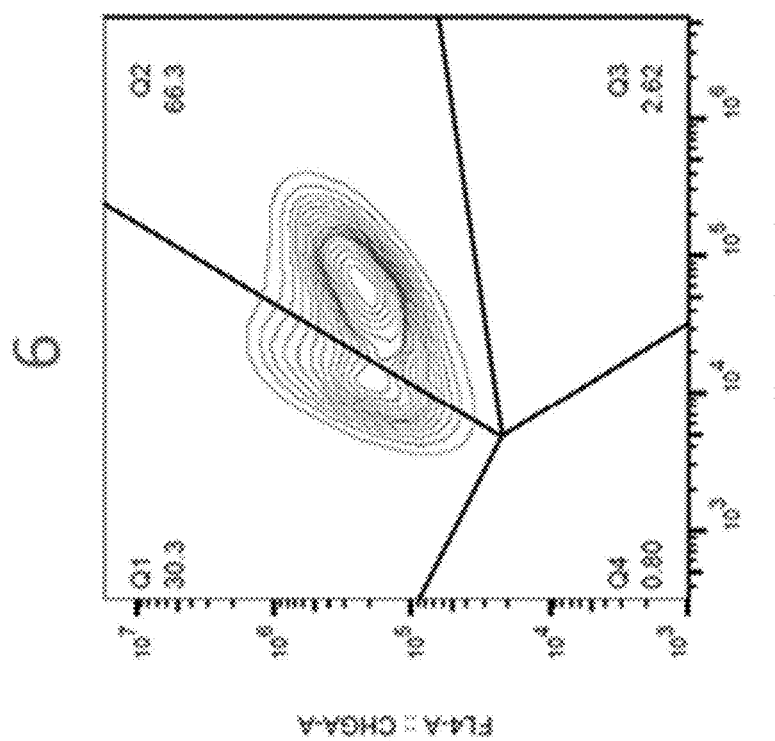
Figure 20E:
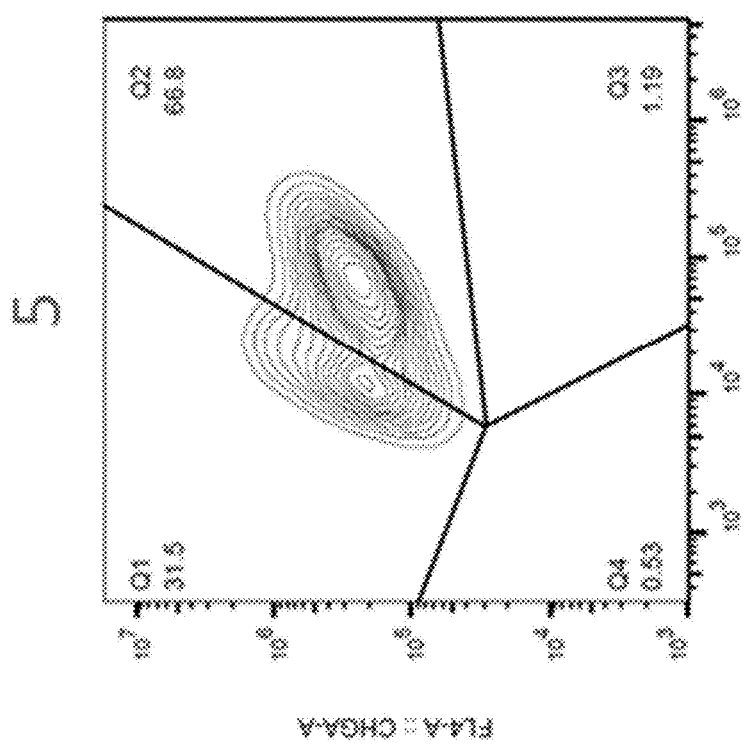
Figure 20H:
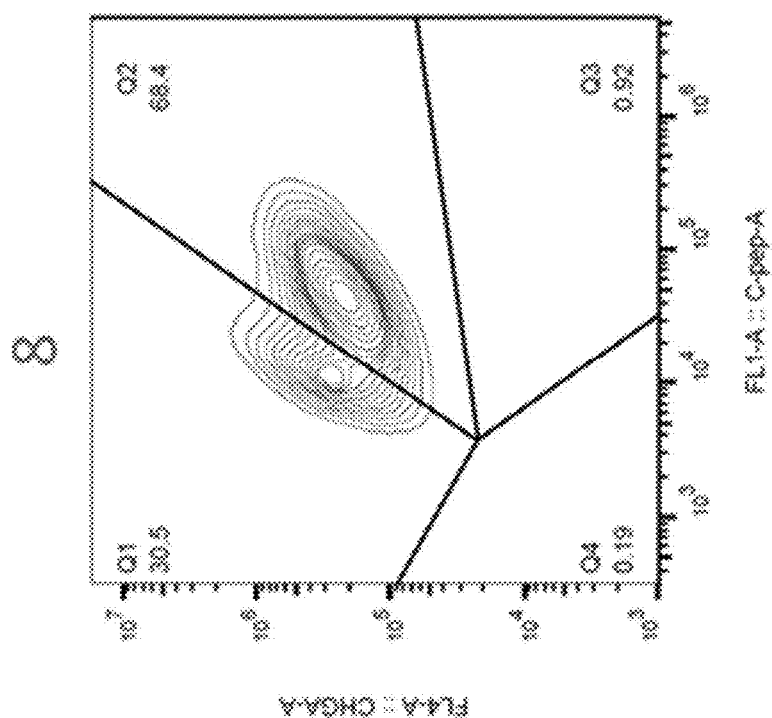
Figure 20G:
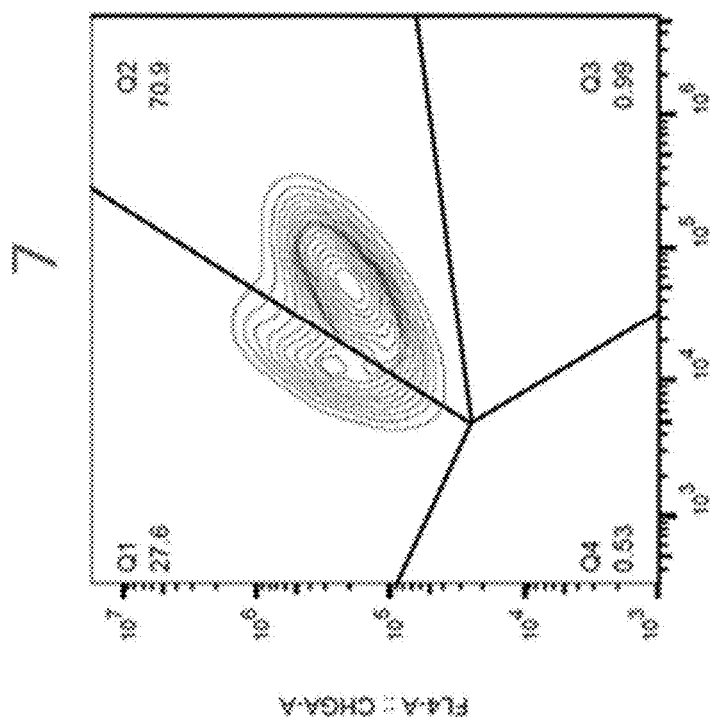
Figure 21B:
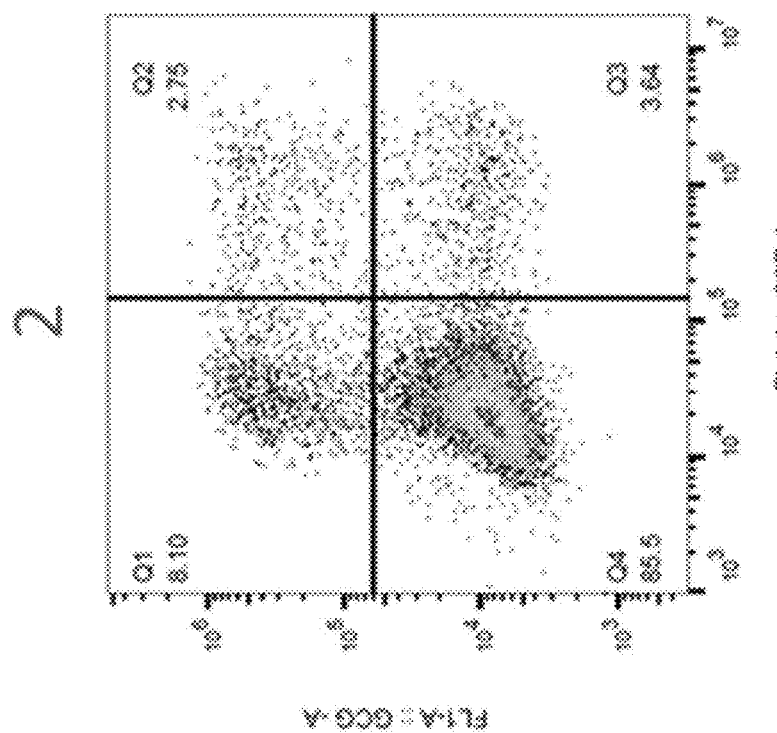
FIGS. 21A-21H are flow cytometry graphs showing Glucagon (GCG)/Somatostatin (SST) expression on S6D7 in SC-islet cells differentiated using the methods described in Table 6.
Figure 21A:
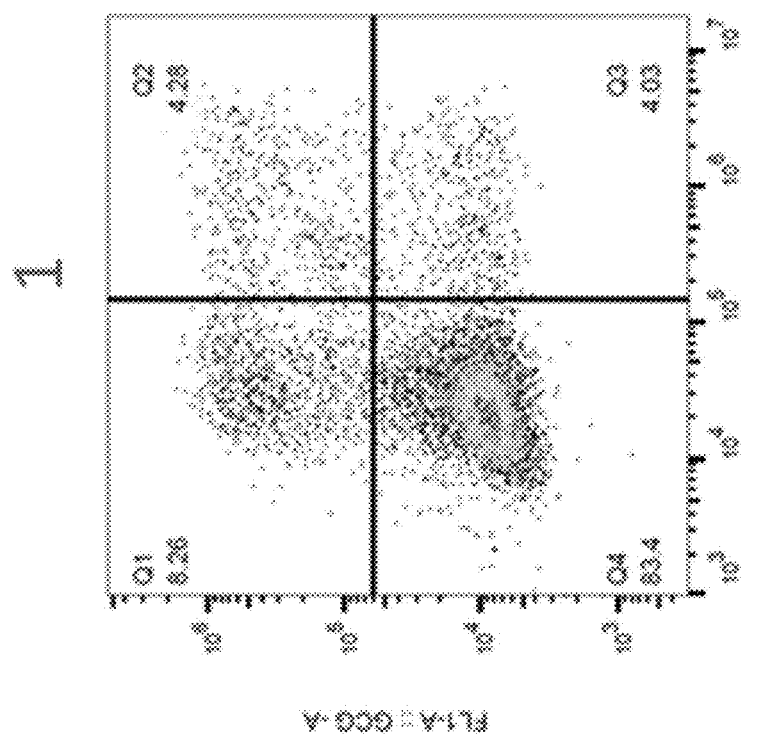
Figure 21D:
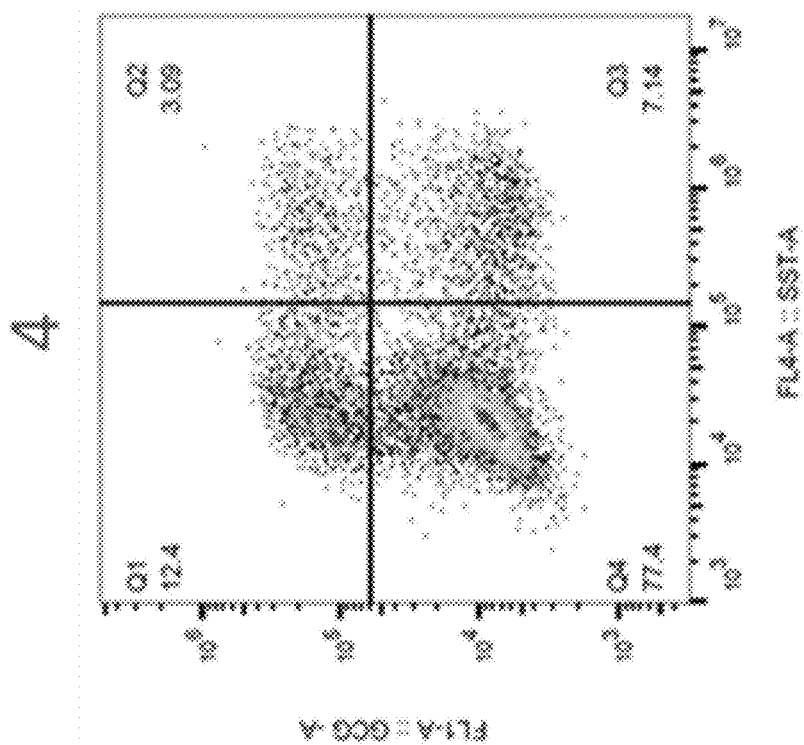
Figure 21C:
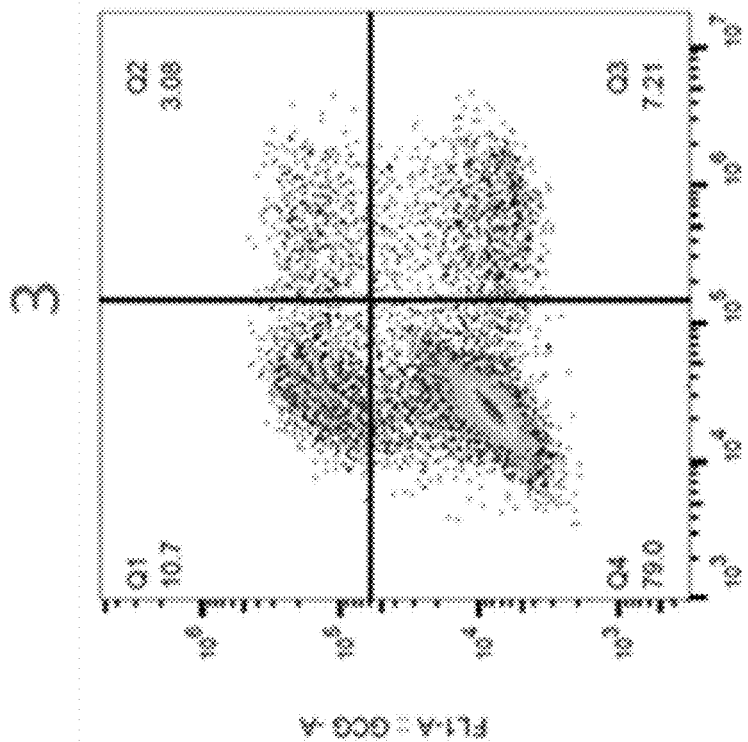
Figure 21F:
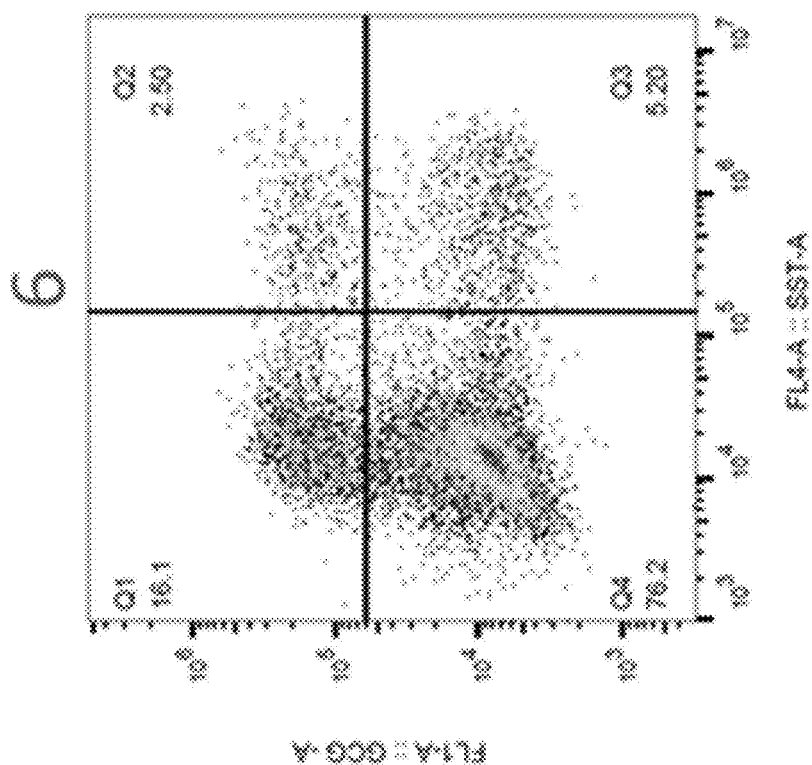
Figure 21E:
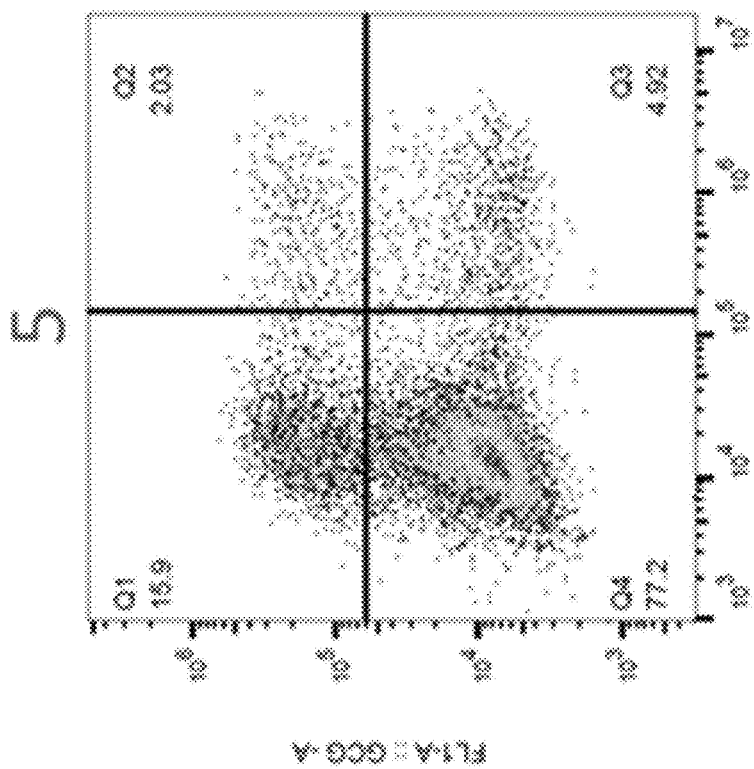
Figure 21H:
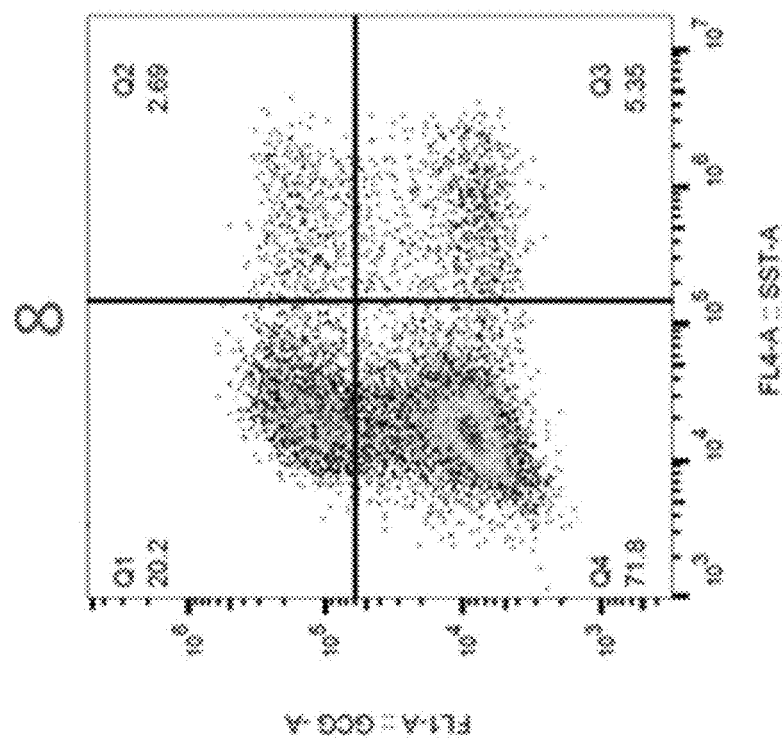
Figure 21G:
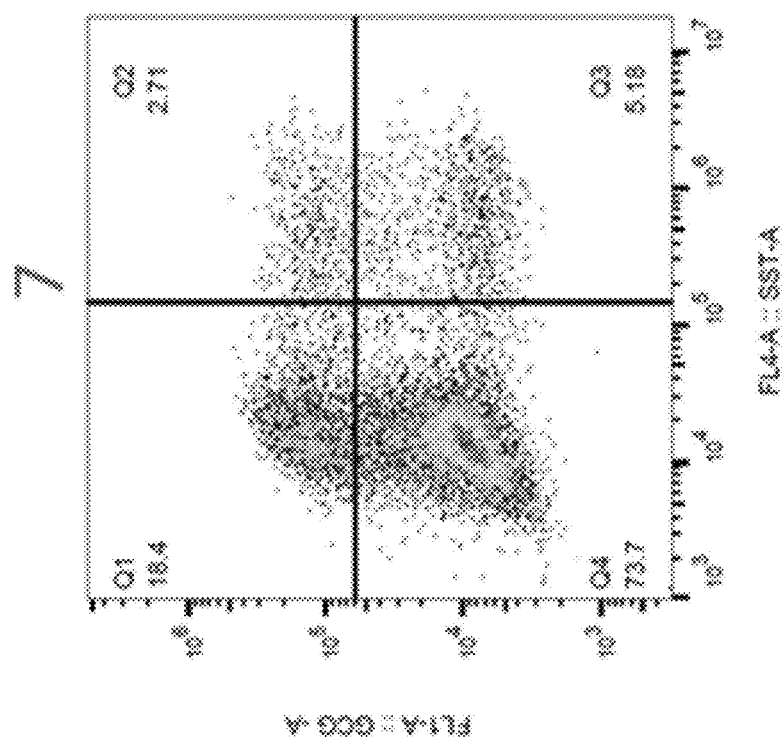
Figure 22A:
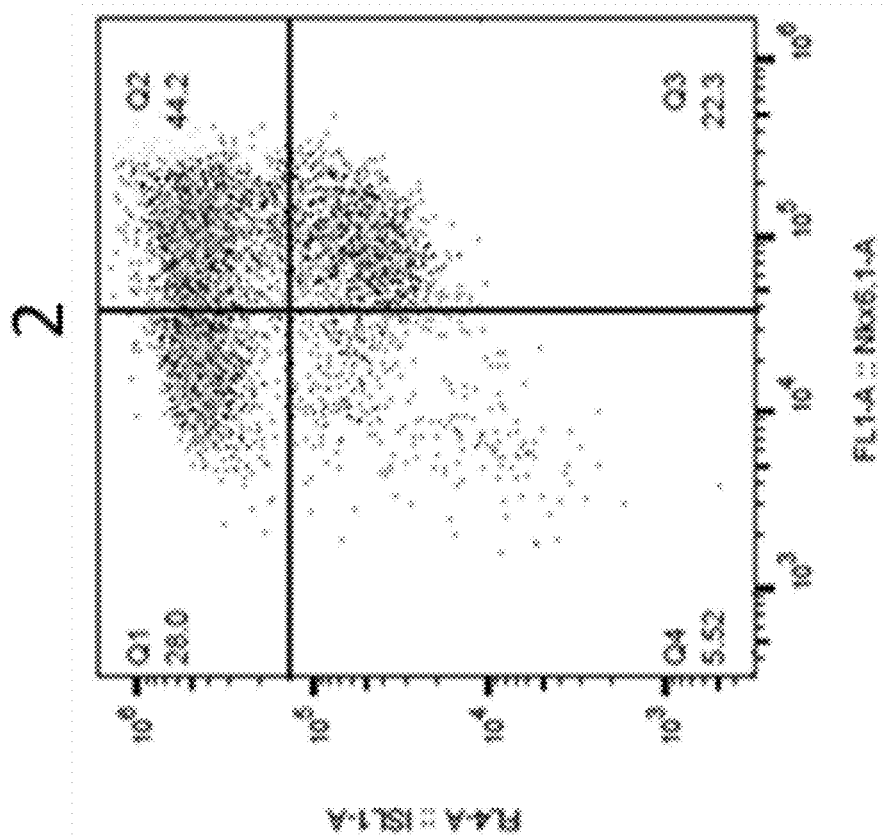
FIGS. 22A-22H are flow cytometry graphs showing ISL1/ NKX6.1 expression on S6D12 in SC-islet cells differentiated using the methods described in Table 6.
Figure 22B:
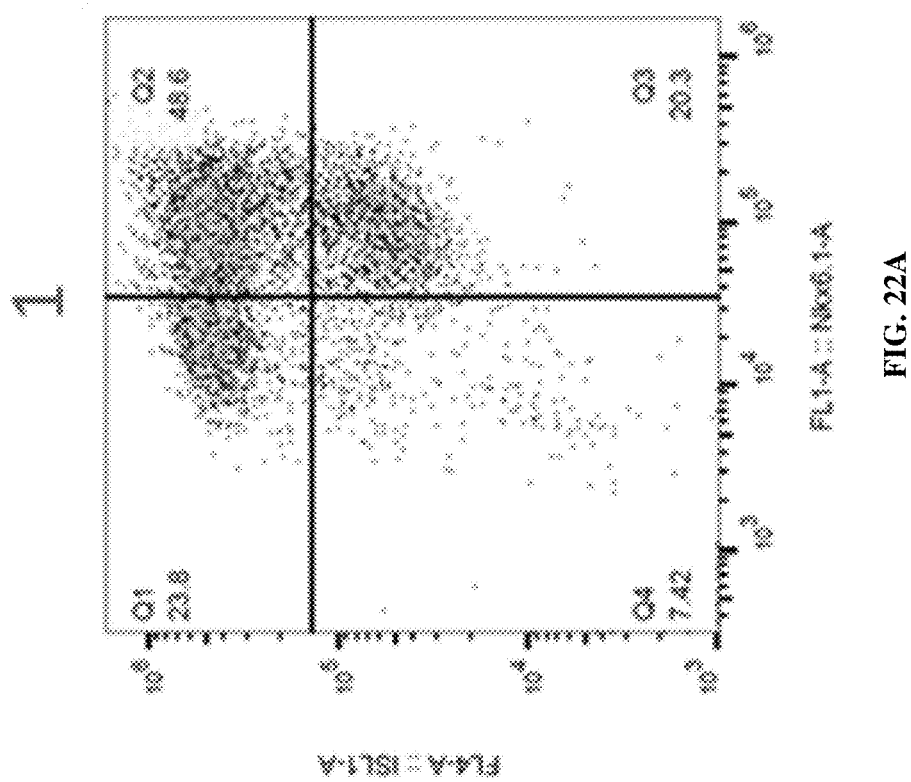
Figure 22D:
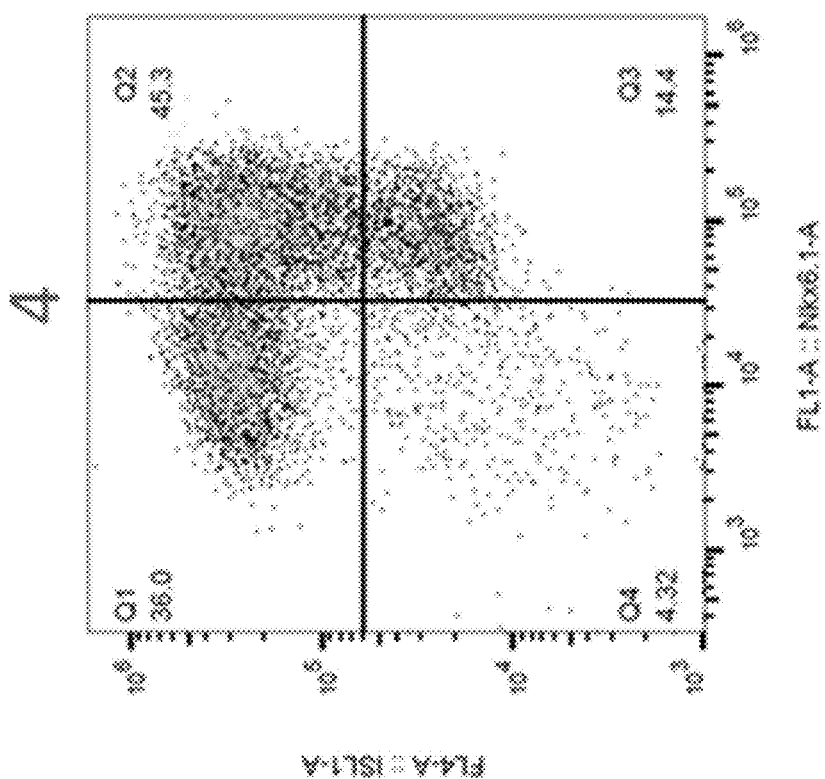
Figure 22C:
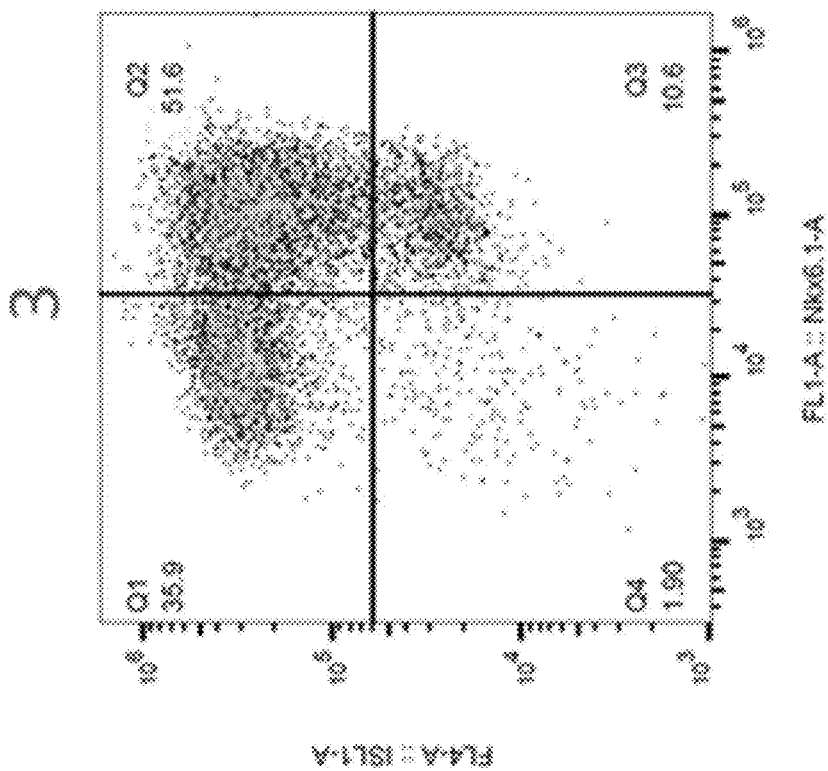
Figure 22F:
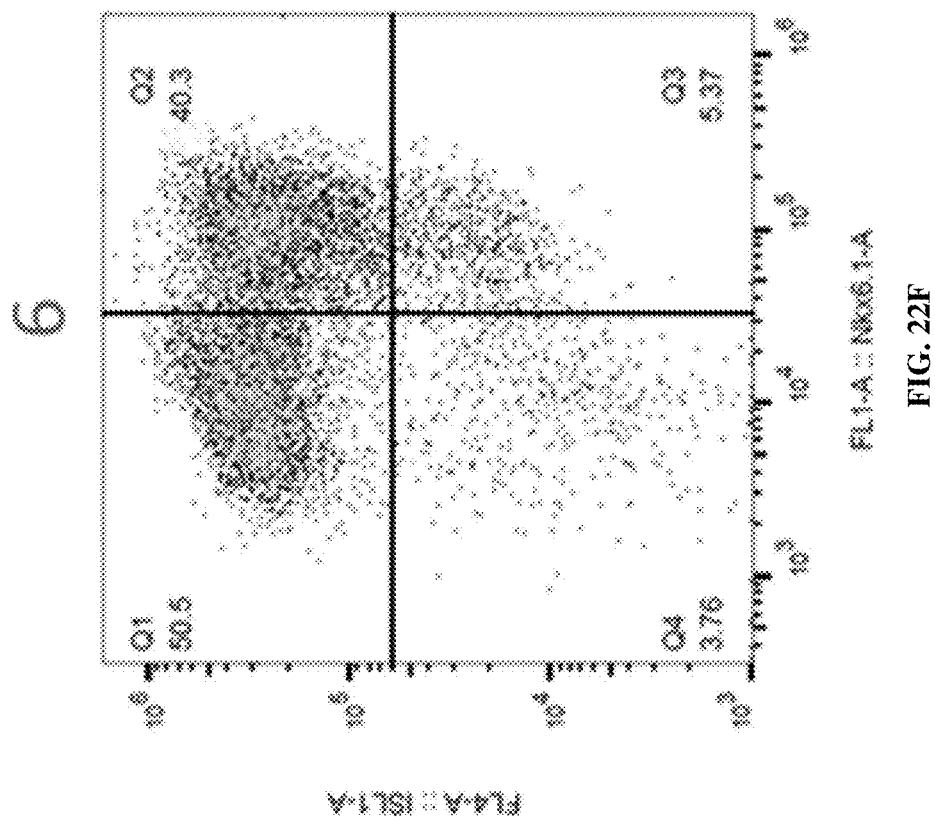
Figure 22E:
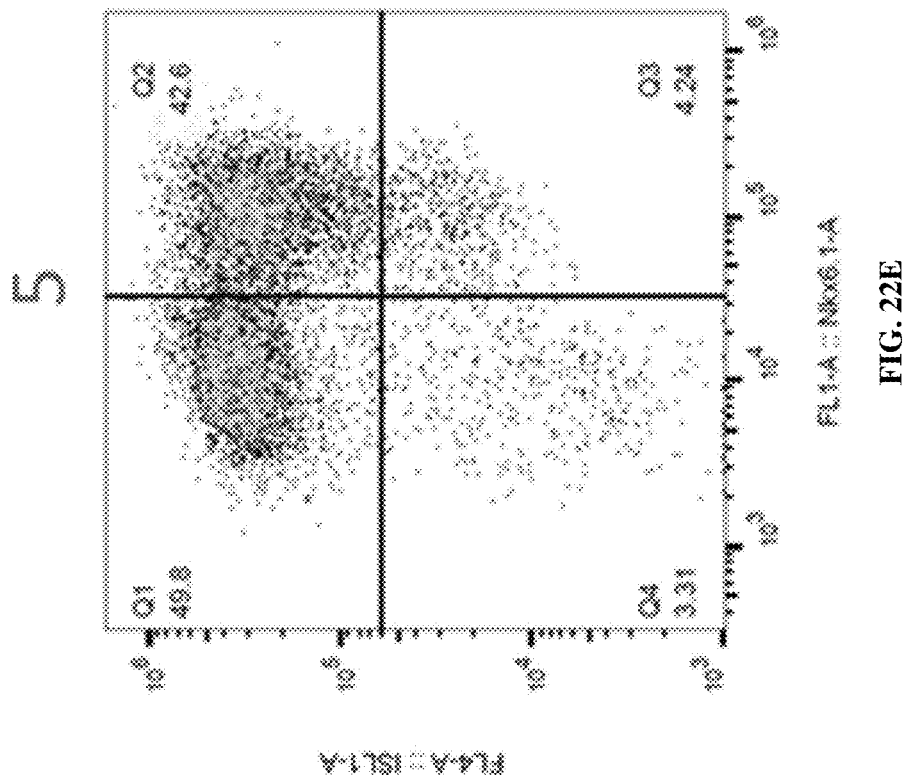
Figure 22H:
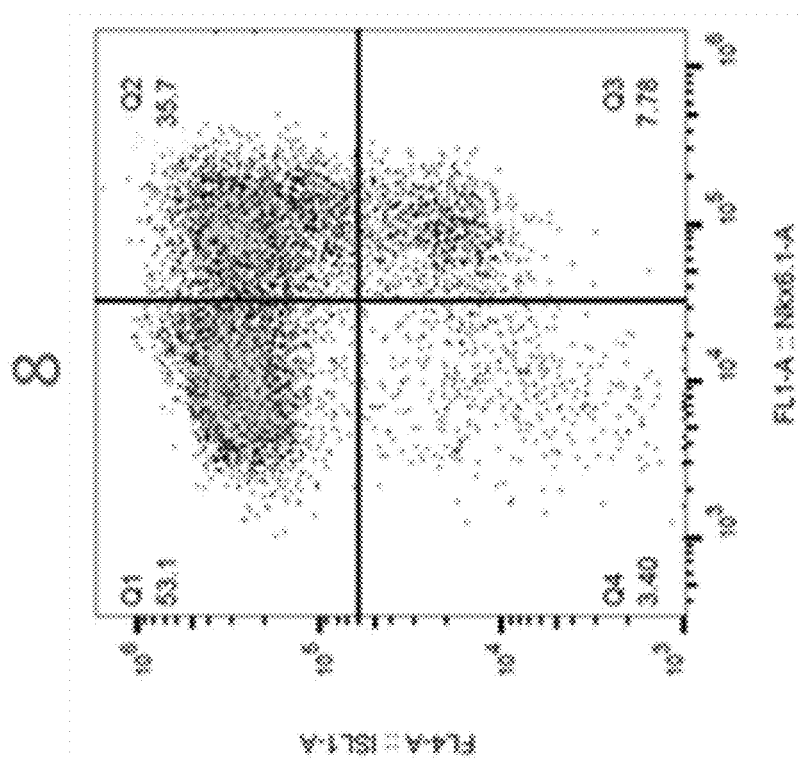
Figure 22G:
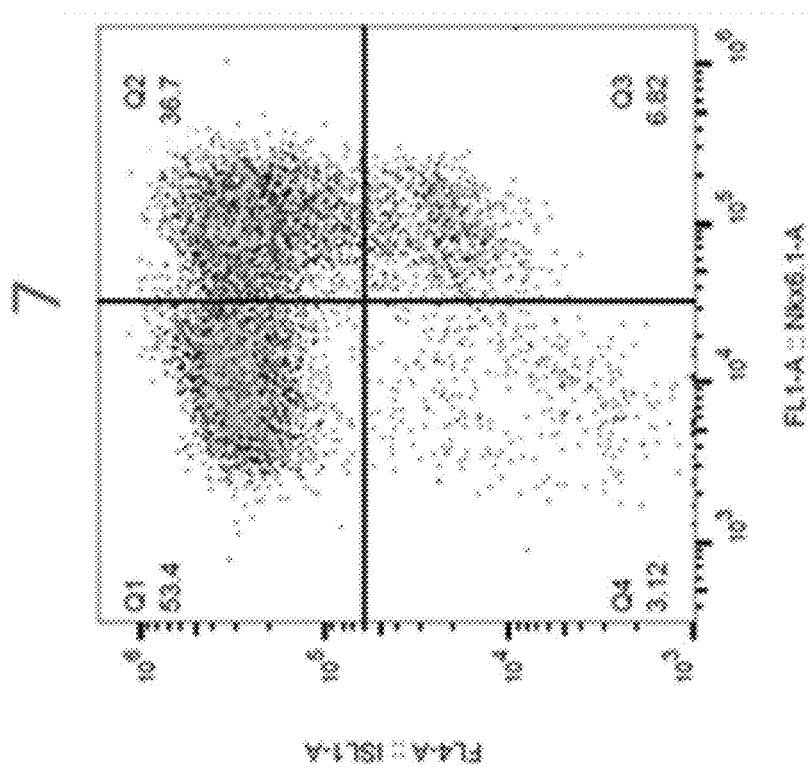
Figure 23A:
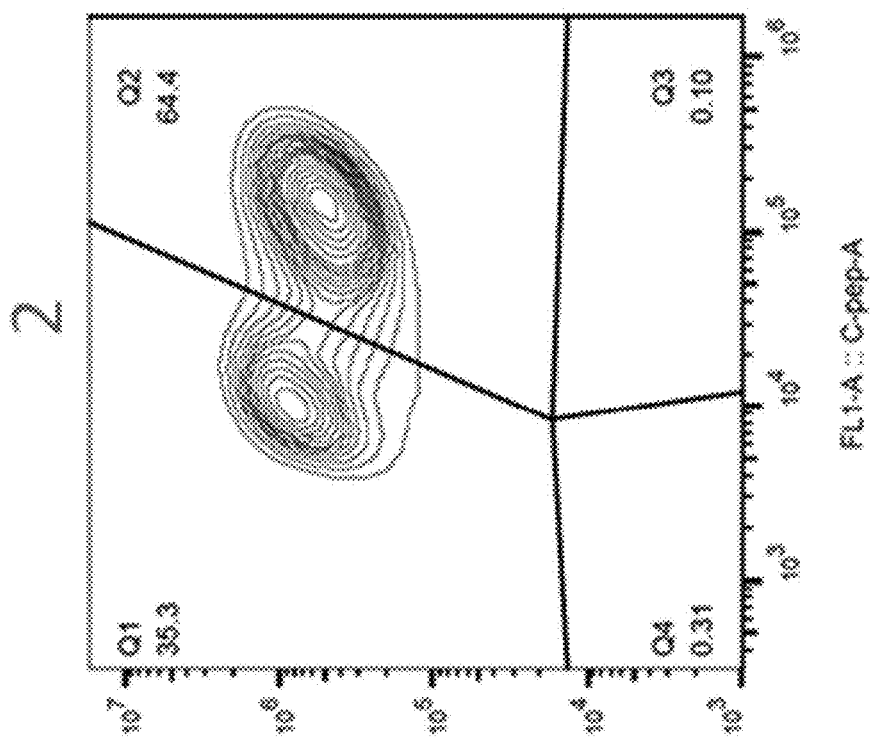
FIGS. 23A-23H are flow cytometry graphs showing Chromogranin A (CHGA)/C-Peptide expression on S6D12 in SC-islet cells differentiated using the methods described in Table 6.
Figure 23B:
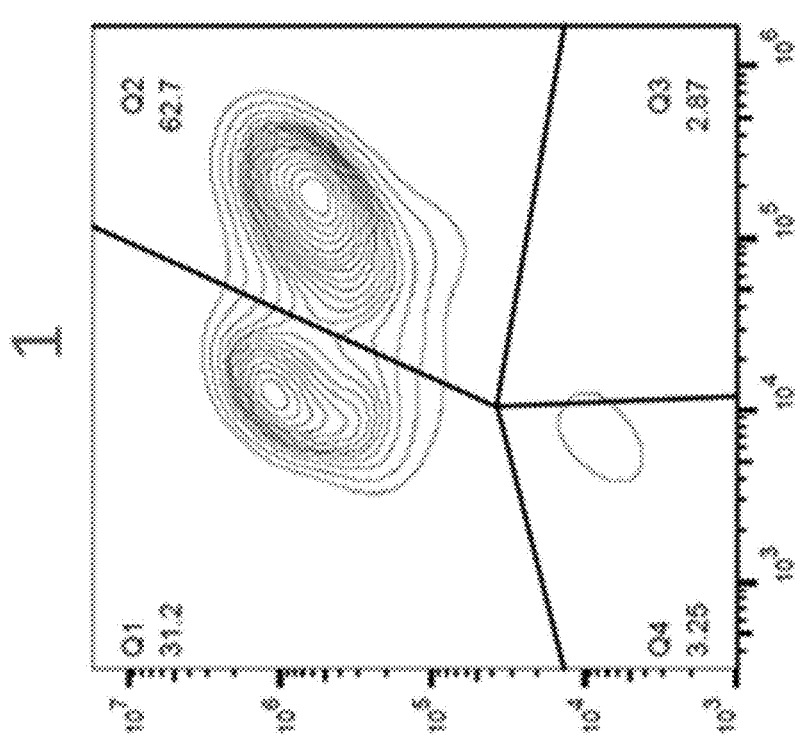
Figure 23D:
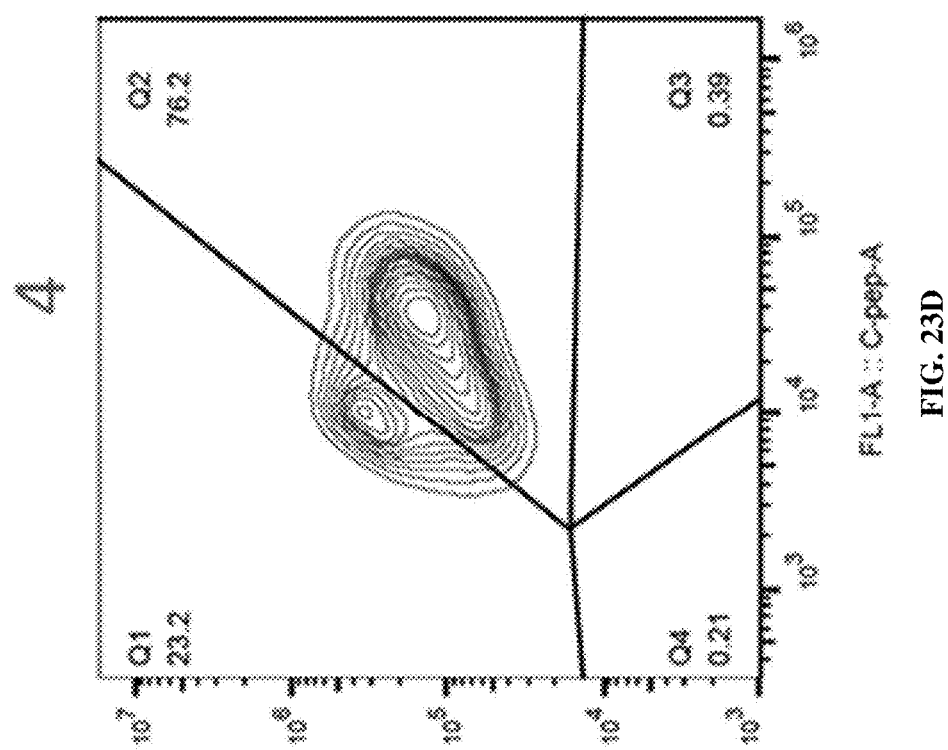
Figure 23C:
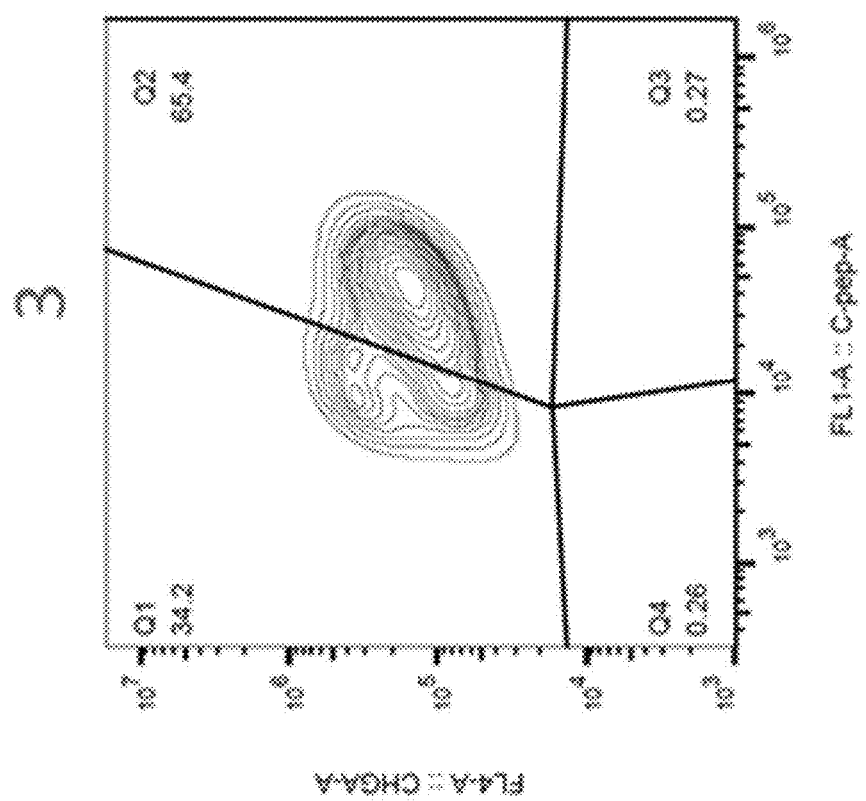
Figure 23F:
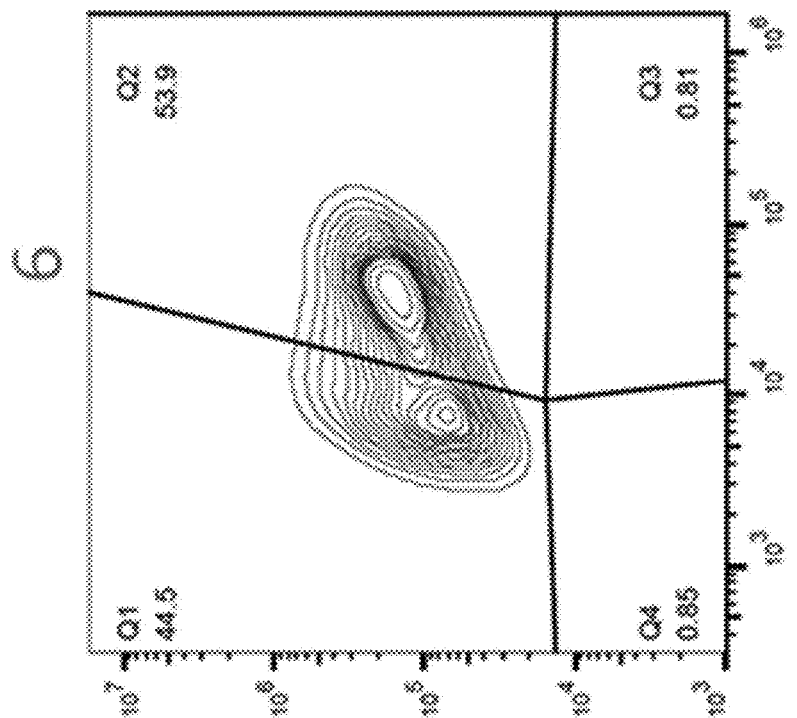
Figure 23E:
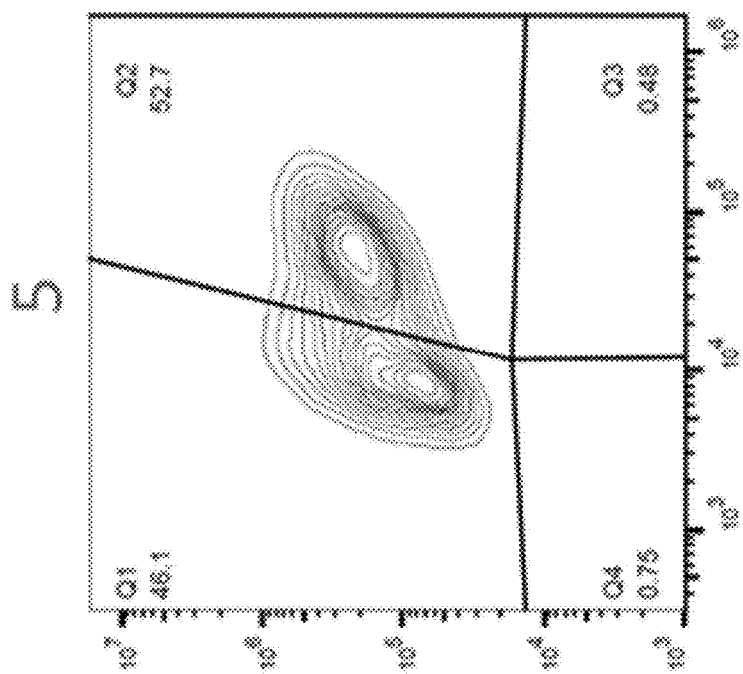
Figure 23H:
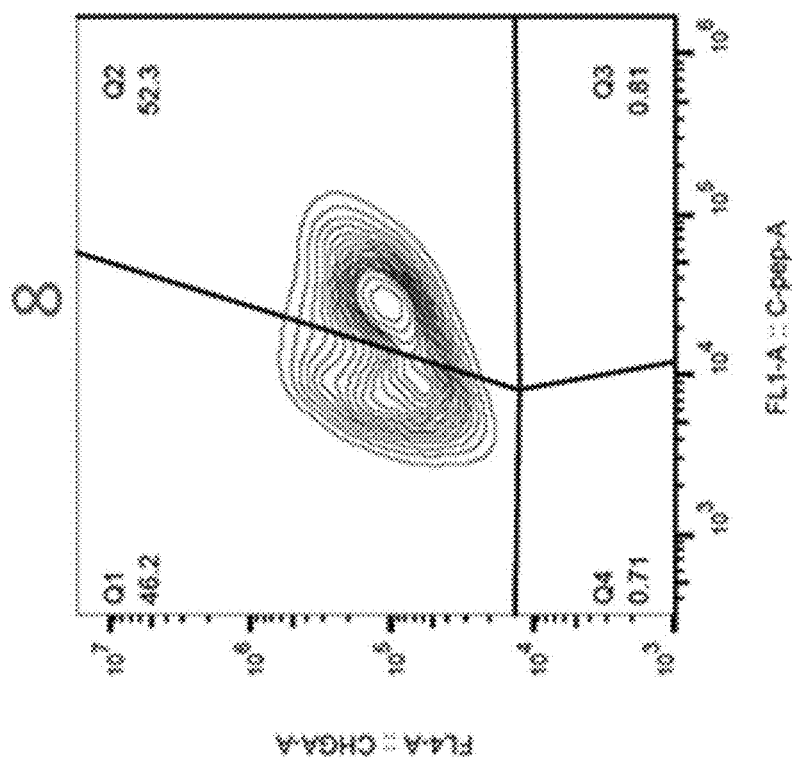
Figure 23G:
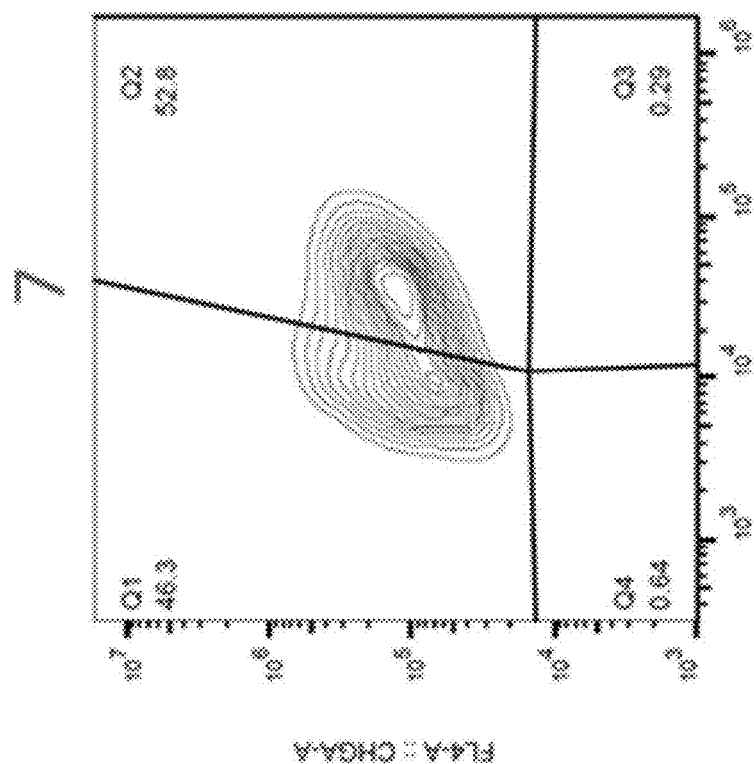
Figure 24D:
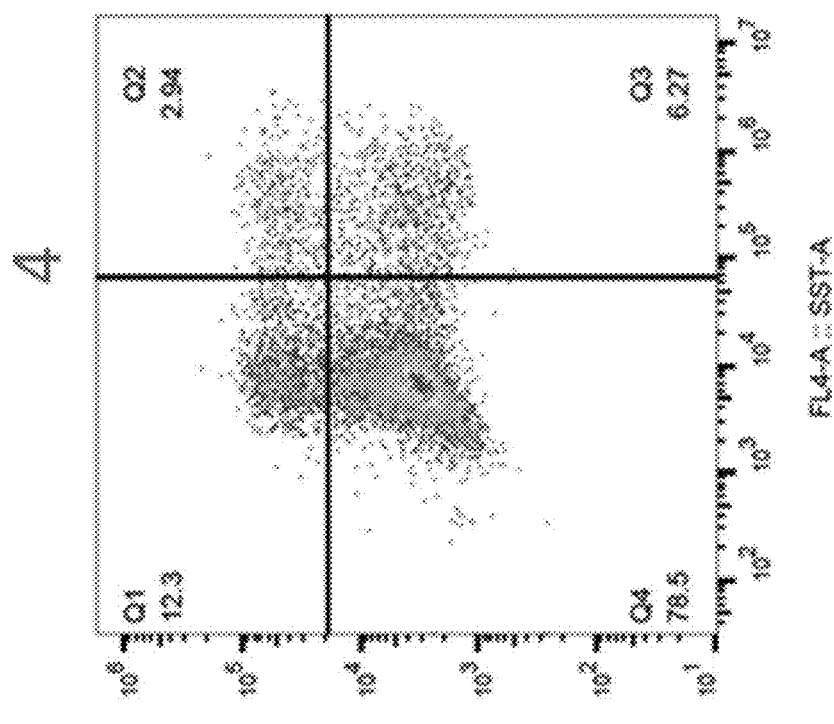
Figure 24C:
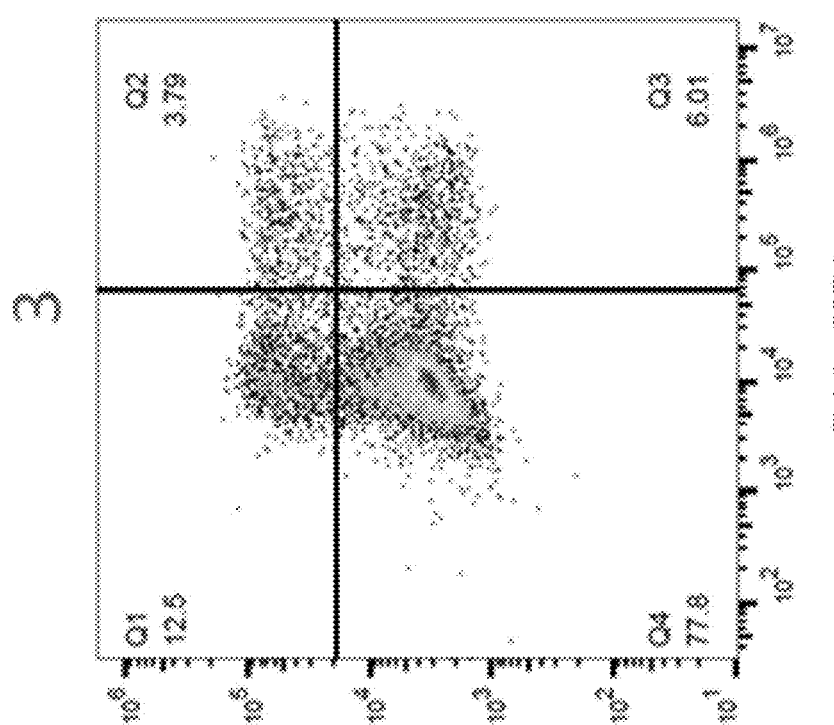
Figure 24F:
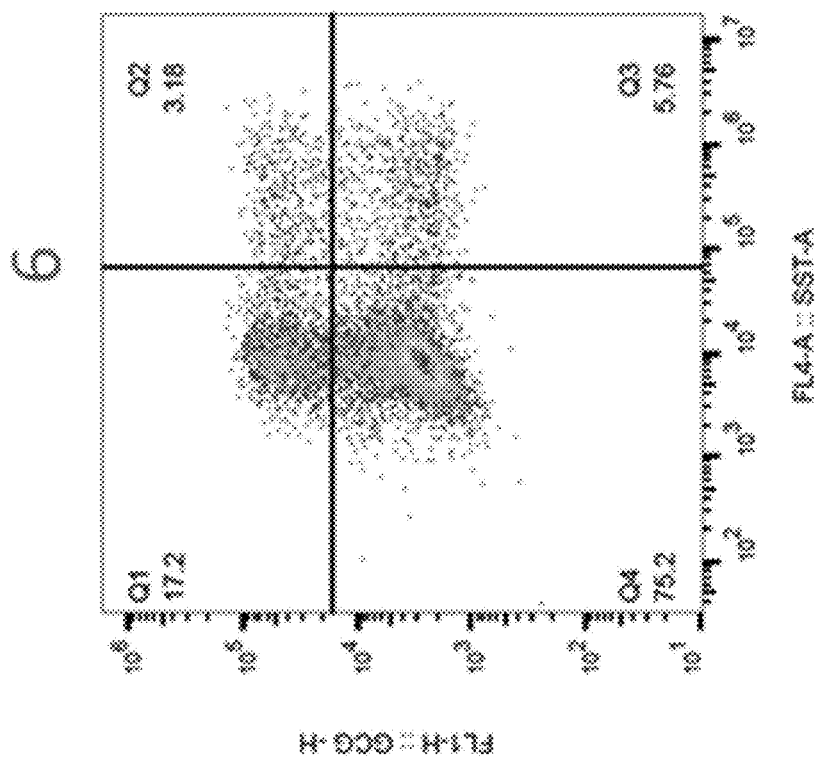
Figure 24E:
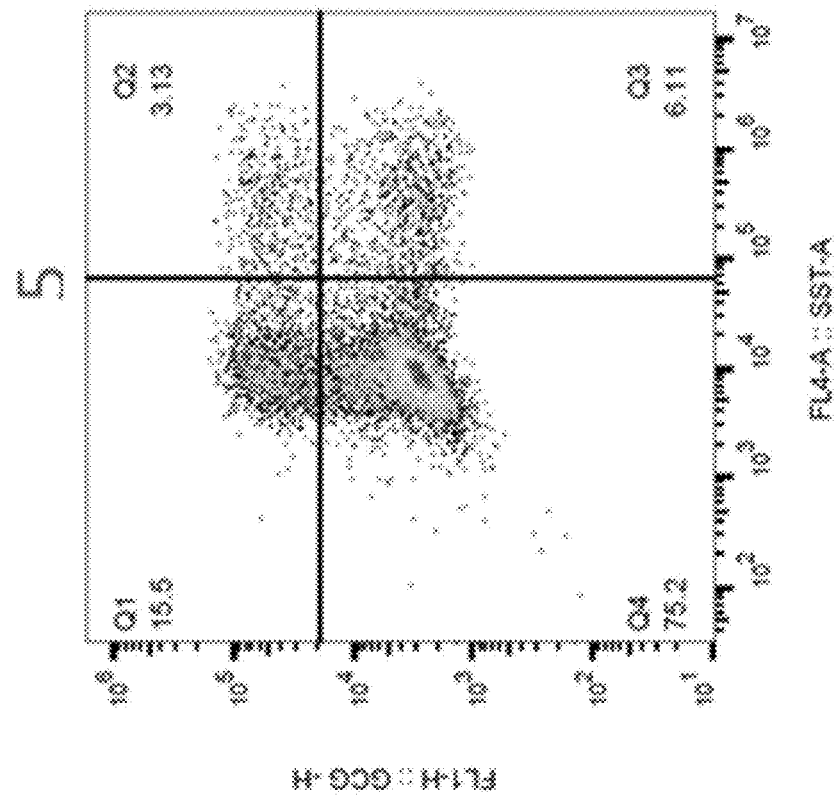
Figure 24H:
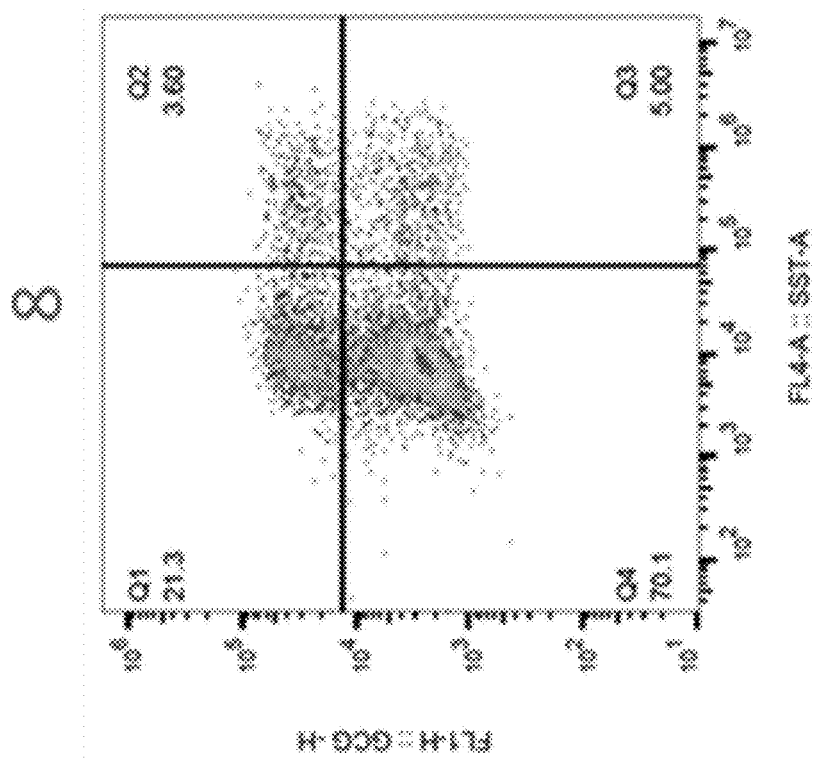
Figure 24G:
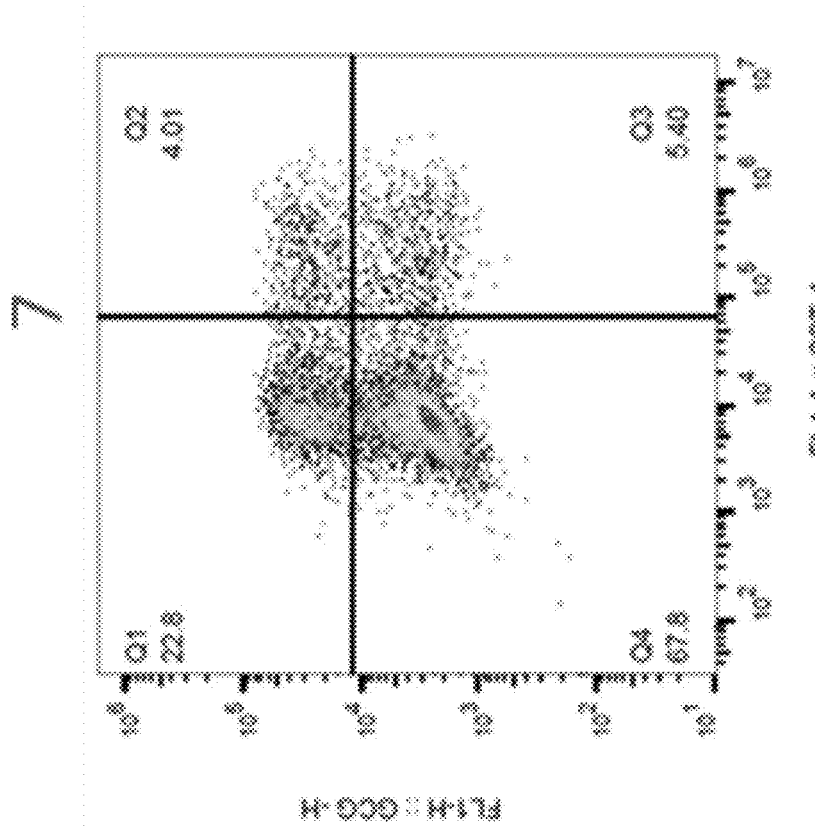

| Corresponding Figure | S4D5 | S5D1 | S5D2 | % of beta cells in S5D6 cell population |
|---|---|---|---|---|
| FIG. 9A | — | — | — | 29.8% |
| FIG. 9B | FOXOi (1 µM) | — | — | 13% |
| FIG. 10A | — | — | — | 8.3% |
| FIG. 10B | — | XAV* (2 µM) | XAV* (2 µM) | 5% |
| FIG 11A | FOXOi (1 µM) | — | — | 19% |
| FIG 11B | FOXOi (1 µM) | XAV* (2 µM) | XAV* (2 µM) | 10% |
| FIG. 12A | — | — | — | 9% |
| FIG. 12B | TPB (0.5 µM) | TPB (0.5 µM) | TPB (0.5 µM) | 17% |
| FIG. 13A | — | — | — | 9% |
| FIG. 13B | TPB (0.5 µM), XXI | TPB (0.5 µM) | TPB (0.5 µM) | 30% |
| FIG 14A | FOXOi (1 µM), TPB (0.5 µM), XXI (2 µM) | TPB (0.5 µM) | TPB (0.5 µM) | 37% |
| FIG. 14B | FOXOi (1 µM), PDBU (0.5 µM), XXI (2 µM) | TPB (0.5 µM), XAV* (2 µM) | TPB (0.5 µM), XAV* (2 µM) | 20.7% |
| FIG 15A | PDBU (0.5 µM) | PDBU (0.5 µM) | PDBU (0.5 µM) | 28% |
| FIG. 15B | FOXOi (1 µM), PDBU (0.5 µM), XXI (2 µM) | PDBU (0.5 µM) | PDBU (0.5 µM) | 33.6% |
| FIG. 15C | FOXOi (1 µM), PDBU (0.5 µM), XXI (2 µM) | PDBU (0.5 µM), XAV* | PDBU (0.5 µM), XAV* | 47.7% |

*XAV was present in the medium on S5D1-4 for the results shown in FIGS. 10B, 11B, 14B, and 15C.

First, inhibition of FoxO1 alone on S4D5 did not result in increased beta cell production (FIGS. 9A-9B). Inhibiting Wnt alone on S5D1 and S5D2 did not increase beta cell production (FIGS. 10A-10B). FoxO1 inhibition on S5D4 followed by Wnt inhibition on days 1-4 S5 also did not enhance beta cell production (FIGS. 11A-11B). Activation of PKC using PKC activator TPB on S4D5 and S5 days 1 and 3 did not result in more beta cell production (FIGS. 12A-12B). However, when both TPB and a notch inhibitor XXI were used on S4D5, beta cell production was improved, though a substantial amount of EC cells were still observed in the differentiated cell population (FIGS. 13A-13B). FoxO inhibition in combination with TPB and XXI on S4D5 followed by TPB (FIG. 14A) or TPB and XAV (FIG. 14B) on S5 days 1 and 2 further improved beta cell production (FIGS. 14A-14B). FoxO1 inhibition in combination with PDBU and XXI on S4D5 followed by the use of PDBU and XAV on S5 days 1 and 2 resulted in increased alpha and beta cell production and reduced off-target population effects (FIGS. 15A-15C). The percentage of SC-β cells in the SC-islet cells produced using indicated differentiation agents are also summarized in Table 5.

Example 3. Stage 6 SC-Islet Cell Composition

In this study, SC-islet cells were differentiated using the differentiation Protocol 2 (see Table 2) as the base protocol with additional agents and/or modifications to media used in S4 and S5 as provided in Table 6. After S5, cells were cryopreserved. For S6 differentiation, cryopreserved SC-cells were thawed into Biotts at 2M/mL in either 30 mL of Media A (Table 7A) or 30 mL of Media B. The formulation for Media A is provided in Table 7A. The formulation for Media B is provided in Table 7B. The composition of the SC-islet cells were analyzed on S6D4 or S6D7.

In S6, cells were cultured in a humidified incubator at 37° C. at 5% $CO_2$ for 12 days. Cell clusters were then collected at days 4, 7, and 12 of S6 and prepared for flow cytometry. During collection, cell clusters were dispersed with TrypLE (Life Technologies) at 37° C. for 10 minutes, fixed with 4% PFA for 15 minutes at 4° C., blocked with FACS buffer (5% donkey serum and 0.05% Triton-100 in PBS) for 1 hour at room temperature, and stained with primary antibodies diluted in FACS buffer at 4° C. overnight. The following day, the cells were washed twice with FACS buffer, stained with secondary antibody diluted in FACS buffer for one hour, then washed twice again with FACS buffer. Stained cells were measured using an Accuri 6 flow cytometer (BD Biosciences) and analyzed using Flowjo software. The primary and

TABLE 6

Differentiation methods

| No.* | AS1842856 | XXI | PDBU | Wnt Inhibitor | PVA 80% | PVA 87-89% | Metabolites | S6 media |
|---|---|---|---|---|---|---|---|---|
| 1 | N/A | S5D1-6 | S4D5, S5D1-2 | N/A | S1-S4 | S5 | S5D1-6 | A |
| 2 | | | | | | | | B |
| 3 | S4D5 | S4D5, S5D1-6 | S4D5, S5D2 | NVP-TNKS656 S5D1-2 | | | | A |
| 4 | | | | | | | | B |
| 5 | | | S4D5, S5D4, 6 | XAV S5D1-2 | | | | A |
| 6 | | | | | | | | B |
| 7 | | | S4D5, S5D2 | | | | | A |
| 8 | | | | | | | | B |

*Differentiation method No. 1 corresponds to FIGS. 16A, 17A, 18A, 19A, 20A, 21A, 22A, 23A, and 24A
Differentiation method No. 2 corresponds to FIGS. 16B, 17B, 18B, 19B, 20B, 21B, 22B, 23B, and 24B
Differentiation method No. 3 corresponds to FIGS. 16C, 17C, 18C, 19C, 20C, 21C, 22C, 23C, and 24C
Differentiation method No. 4 corresponds to FIGS. 16D, 17D, 18D, 19D, 20D, 21D, 22D, 23D, and 24D
Differentiation method No. 5 corresponds to FIGS. 16E, 17E, 18E, 19E, 20E, 21E, 22E, 23E, and 24E
Differentiation method No. 6 corresponds to FIGS. 16F, 17F, 18F, 19F, 20F, 21F, 22F, 23F, and 24F
Differentiation method No. 7 corresponds to FIGS. 16G, 17G, 18G, 19G, 20G, 21G, 22G, 23G, and 24G
Differentiation method No. 8 corresponds to FIGS. 16H, 17H, 18H, 19H, 20H, 21H, 22H, 23H, and 24H

TABLE 7A

Stage 6 Media A

| Basal Media | S6D1-4 DMEM/F12 w/ glutamine | S6D4-7 DMEM/F12 w/ glutamine | S6D7-11 DMEM/F12 w/ glutamine |
|---|---|---|---|
| Media change | day 4 | day 7 | day 10 |
| Media Supplements | HSA (0.05%) ZnSO4 (10 μM) | HSA (0.05%) ZnSO4 (10pM) | HSA (0.05%) ZnSO4 (10 μM) |
| Small Molecules | ALK5i (10 μM) GC-1 (1 μM) LDN-193189 (100 nM) Thiazovivin (2.5 μM) Staurosporine (3 nM) DZNEP (100 nM) | N/A | N/A |
| Metabolites | L-glutamate (0.5 mM) L-carnitine (40 μM) Taurine (90 μM) Acetate (160 nM) β-hydroxybutyrate | L-glutamate (0.5 mM) L-carnitine (40 μM) Taurine (90 μM) Acetate (160 nM) β-hydroxybutyrate | L-glutamate (0.5 mM) L-carnitine (40 μM) Taurine (90 μM) Acetate (160 nM) β-hydroxybutyrate |

TABLE 7A-continued

| | Stage 6 Media A | | |
|---|---|---|---|
| Basal Media | S6D1-4 DMEM/F12 w/ glutamine | S6D4-7 DMEM/F12 w/ glutamine | S6D7-11 DMEM/F12 w/ glutamine |
| | (200 nM) Biotin (800 nM) Formate (50 μM) | (200 nM) Biotin (800 nM) Formate (50 μM) | (200 nM) Biotin (800 nM) Formate (50 μM) |

TABLE 7B

| | Stage 6 Media B | | |
|---|---|---|---|
| Basal Media | S6D1-4 DMEM/F12 w/ glutamine | S6D4-7 DMEM/F12 w/ glutamine | S6D7-11 DMEM/F12 w/ glutamine |
| Media change | day 4 | day 7 | day 10 |
| Media Supplements | HSA (0.05%) ZnSO4 (10 μM) | HSA (1%) | HSA (1%) |
| Small Molecules | ALK5i (10 μM) GC-1 (1 μM) LDN-193189 (100 nM) Thiazovivin (2.5 μM) Staurosporine (3 nM) DZNEP (100 nM) | | |
| Metabolites | L-glutamate (0.5 mM) L-carnitine (40 μM) Taurine (90 μM) Acetate (160 nM) β-hydroxybutyrate (200 nM) Biotin (800 nM) Formate (50 μM) | | |

TABLE 8

Antibodies used in FACS

| Primary Antibody | Company | Cat# | Primary Antibody Species | Secondary Antibody Species | Cat# |
|---|---|---|---|---|---|
| NKX6.1 | DSHB | FSSA12 | Mouse | anti-Mouse 488 | A21202 |
| IsL1 | abcam | ab178400 | Rabbit | anti-Rabbit-647 | A31573 |
| SST | Santa Cruz Biotechnology | SC-55565 AF647 | Anti-Somatostatin Antibody (G-10) Alexa Fluor ® 647 | AlexaFluor ® 647 | |
| Glu | R&D | IC 1249G | Human/Mouse Glucagon Alexa Fluor ® 488-conjugated | AlexaFluor ® 488 | |
| Sox9 | Epitomics | AC-0284RUOC | Rabbit | anti-Rabbit-647 | A31573 |
| Ki67 | Thermo Fisher | | Ki-67 Monoclonal Antibody (SolA15), PE | PE | |
| C-pep | DSHB | GN-1D4-S | Rat | anti-Rat-488 | A21208 |
| CHGA | abcam | ab15160 | Rabbit | anti-Rabbit-647 | A31573 |

Cells were stained and analyzed for ISL1/NKX6.1 expression on S6D4 (FIGS. 16A-611), S6D7 (FIGS. 19A-19H), or S6D12 (FIGS. 22A-22H); for chromogranin A (CHG)/C-peptide expression on S6D4 (FIGS. 17A-17H), S6D7 (FIGS. 20A-20H), or S6D12 (FIGS. 23A-23H); for Glucagon (GCG)/Somatostatin (SST) expression on S6D7 (FIGS. 21A-21H), or S6D12 (FIGS. 24A-24H), or for SOX9/Ki67 expression on S6D4 (FIGS. 18A-18H).

Example 4. Improved Differentiation Protocol

Figures 26A, 26B, 26C:
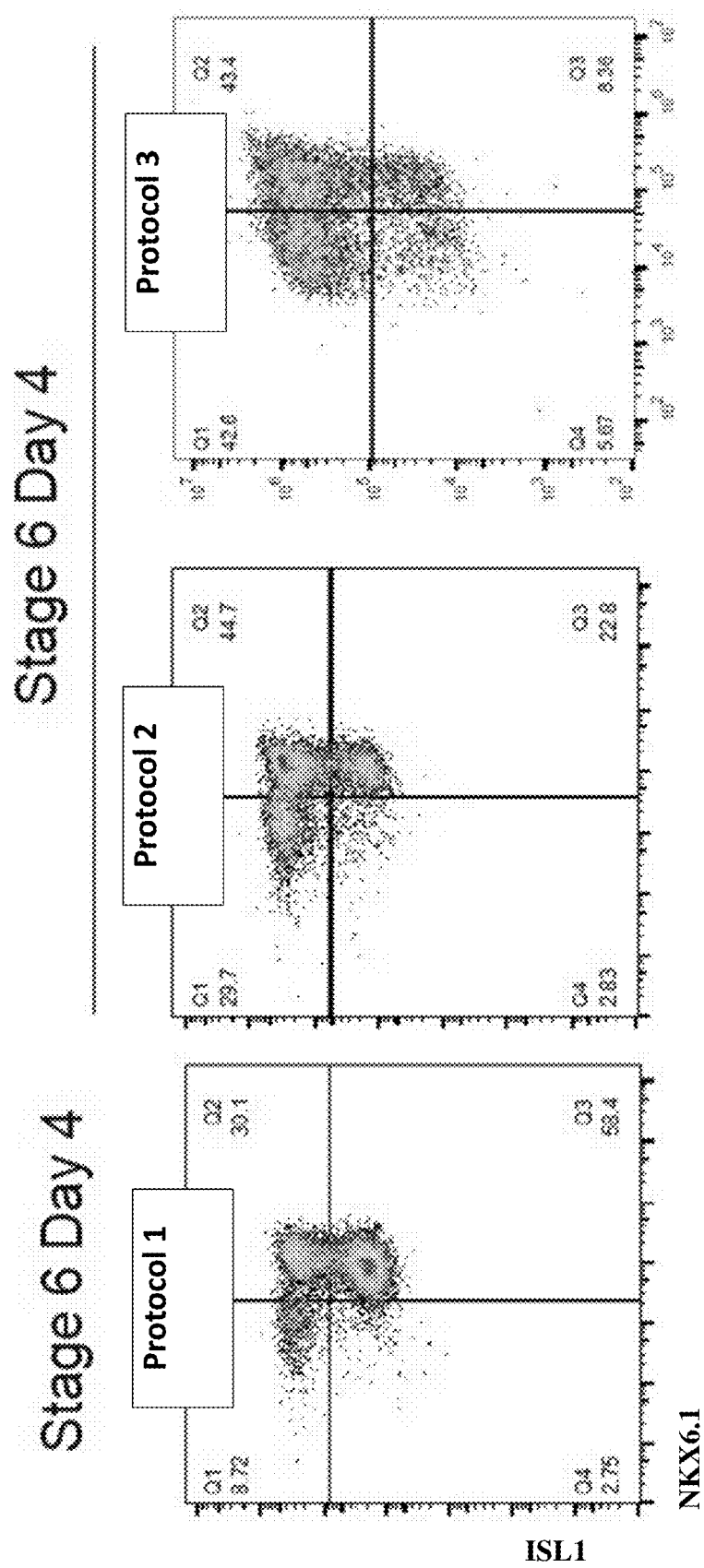
FIGS. 26A-26C are flow cytometry graphs showing ISL1/NKX6.1 expression on S6D4 in SC-islet cells differentiated using Protocol 1 (FIG. 26A), Protocol 2 (FIG. 26B), or Protocol 3 (FIG. 26C).
Figure 29B:
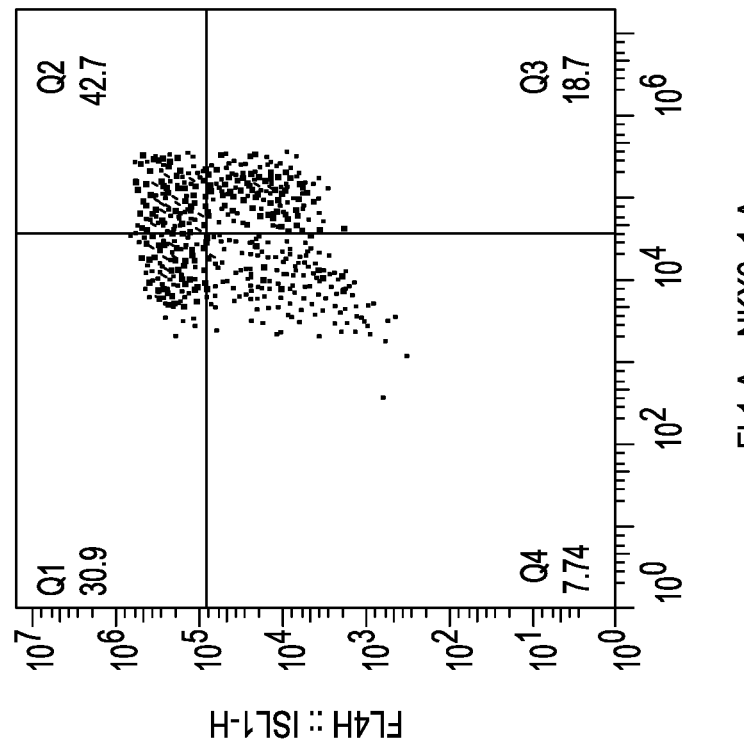
FIGS. 29A-29D are flow cytometry graphs showing ISL1/Nkx6.1 expression on S6D3 in SC-islet cells differentiated using Protocol 1 (FIG. 29A), Protocol 2 (FIG. 29B), Protocol 3 (FIG. 29C), or Protocol 3 with the addition of FGF2 (at 100 ng/ml) in stage 6 media (Media A shown in Table 7A) (FIG. 29D).
Figure 29A:
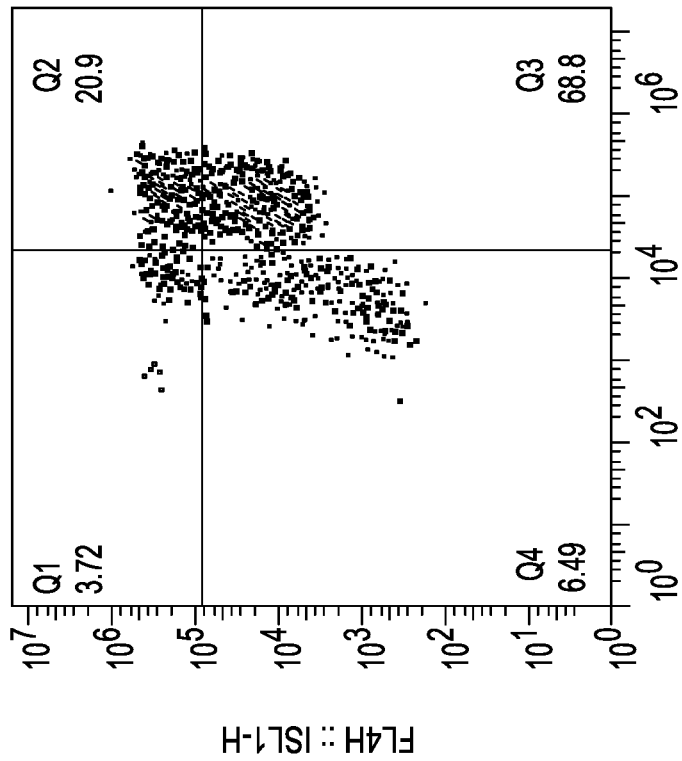
Figure 29D:
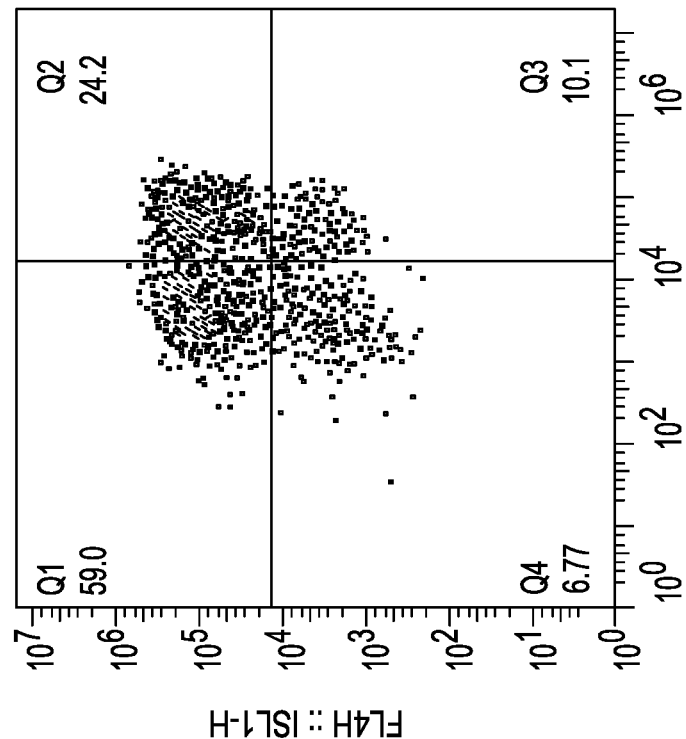
Figure 29C:
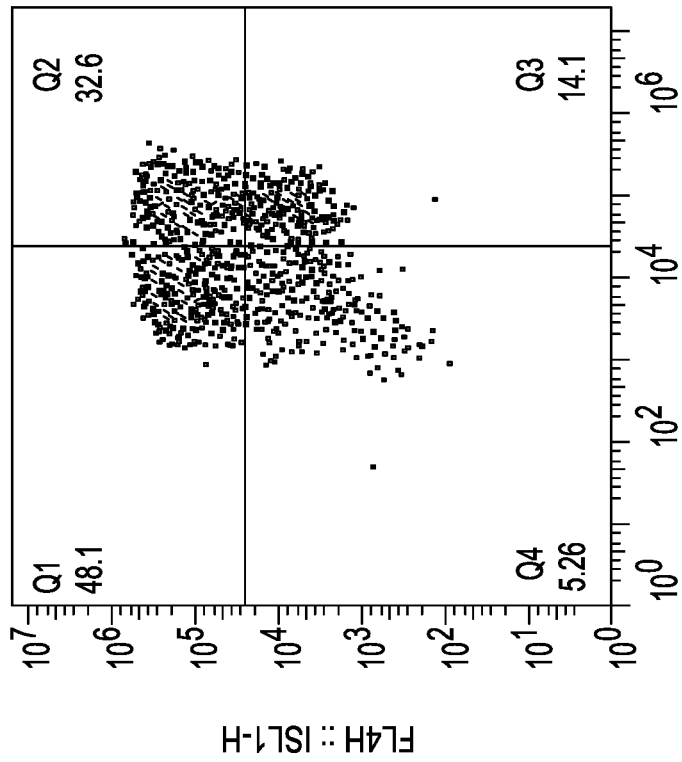
Figures 30A, 30B:
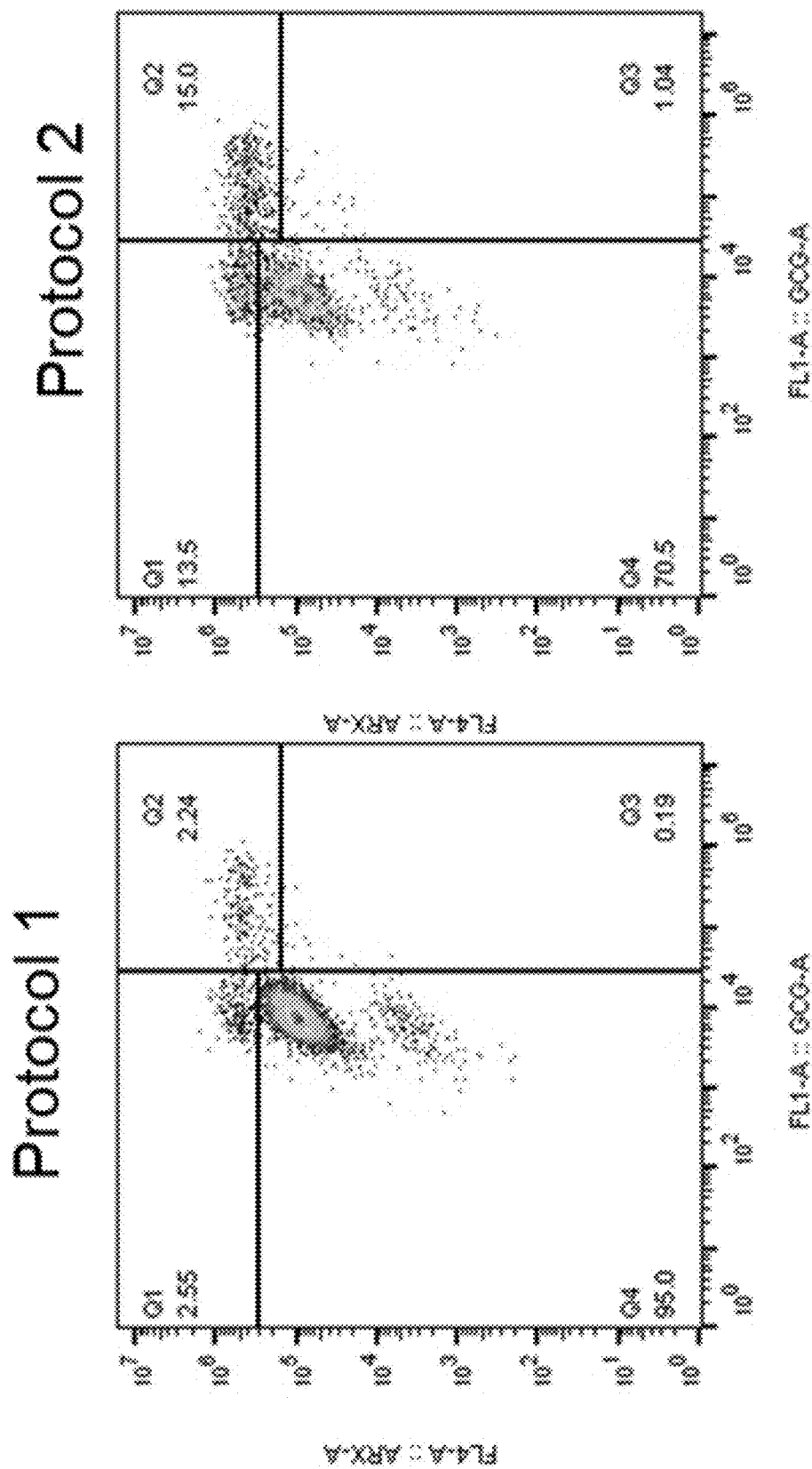
FIGS. 30A-30D are flow cytometry graphs showing Aristaless related homeobox (ARX)/Glucagon (GCG) expression on S6D3 in SC-islet cells differentiated using Protocol 1 (FIG. 30A), Protocol 2 (FIG. 30B), Protocol 3 (FIG. 30C), or Protocol 3 with the addition of FGF2 (at 100 ng/ml) in stage 6 media (Media A shown in Table 7A) (FIG. 30D).
Figure 30D:
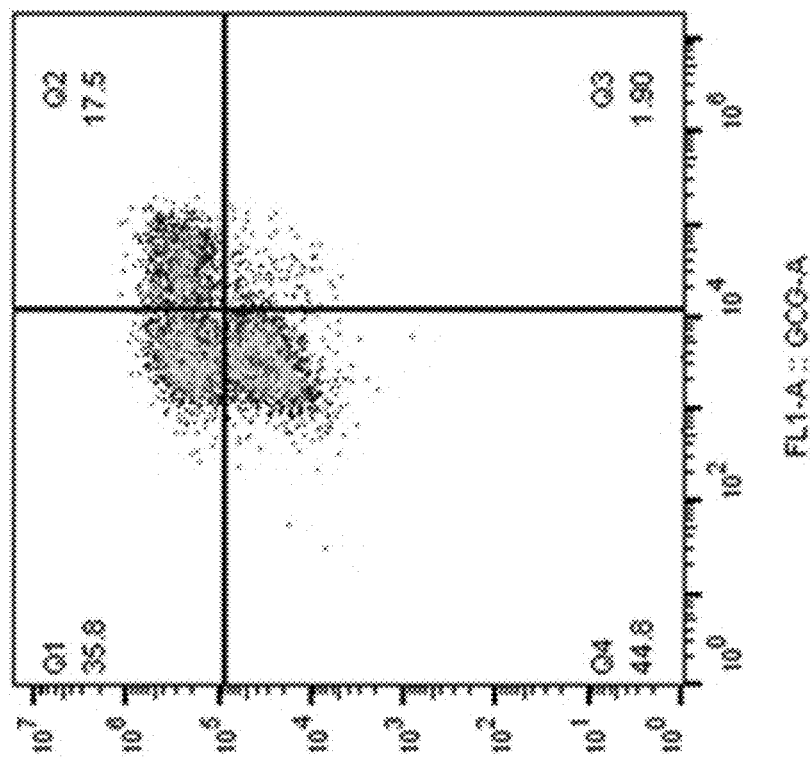
Figure 30C:
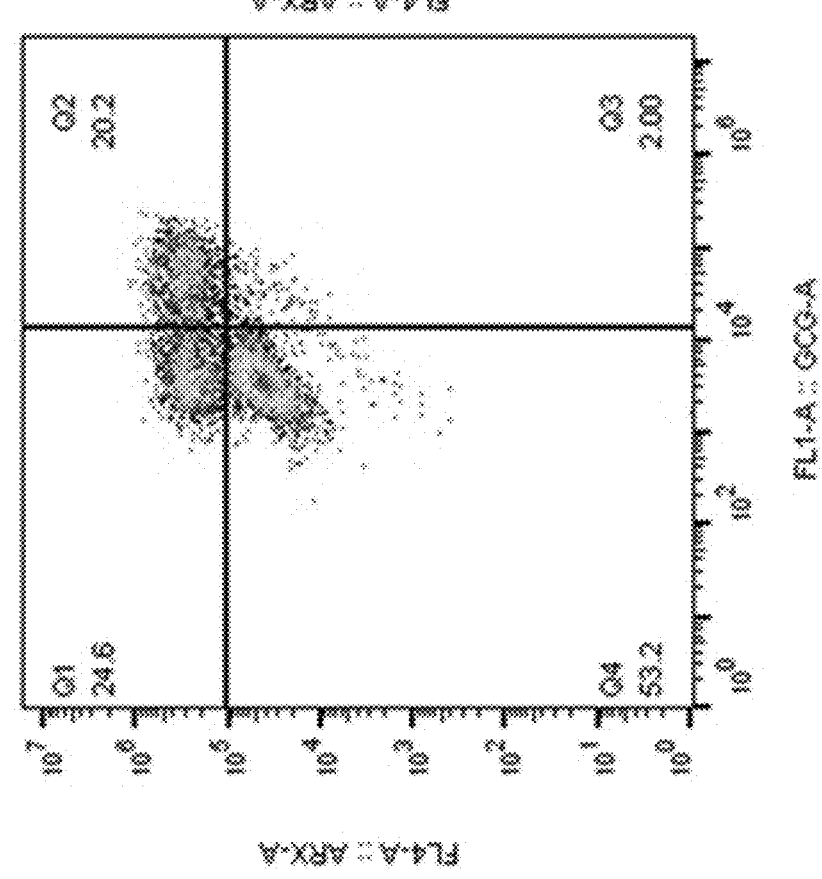
Figure 31B:
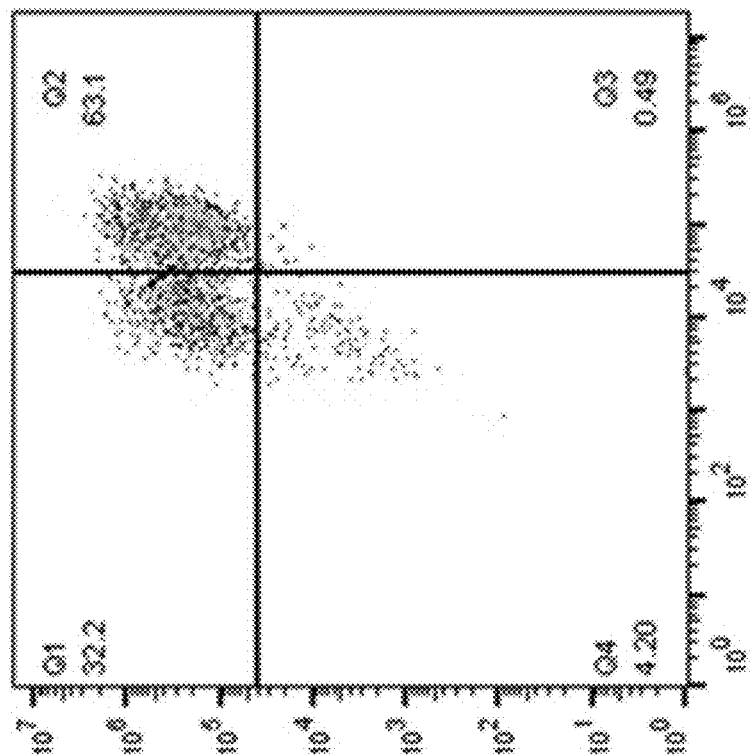
FIGS. 31A-31D are flow cytometry graphs showing Chromogranin A (CHGA)/Nkx6.1 expression on S6D3 in SC-islet cells differentiated using Protocol 1 (FIG. 31A), Protocol 2 (FIG. 31B), Protocol 3 (FIG. 31C), or Protocol 3 with the addition of FGF2 (at 100 ng/ml) in stage 6 media (Media A shown in Table 7A) (FIG. 31D).
Figure 31A:
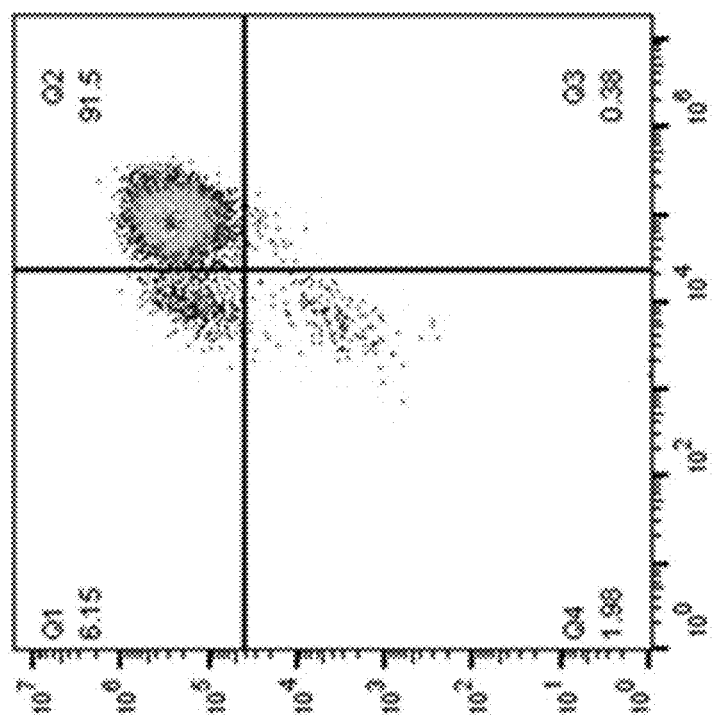
Figure 31D:
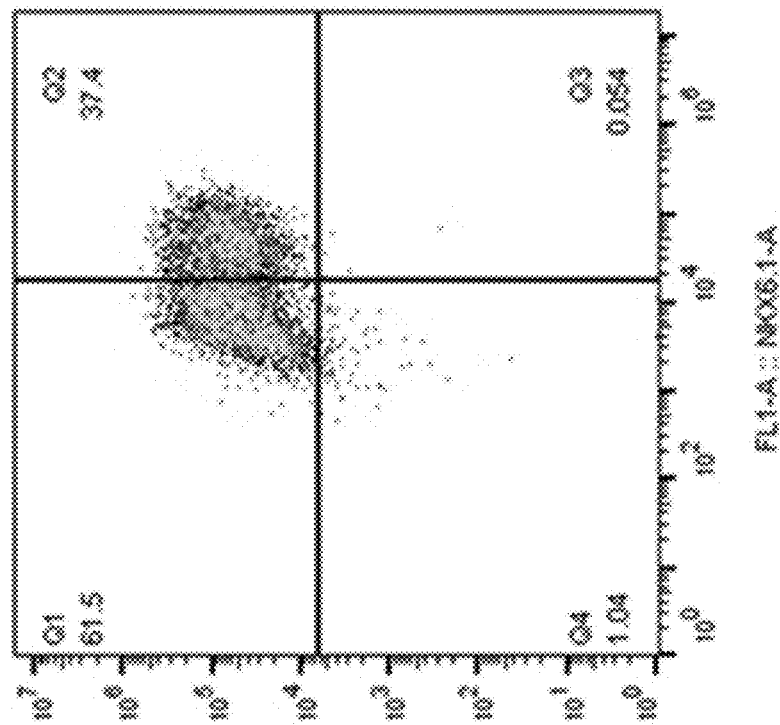
Figure 31C:
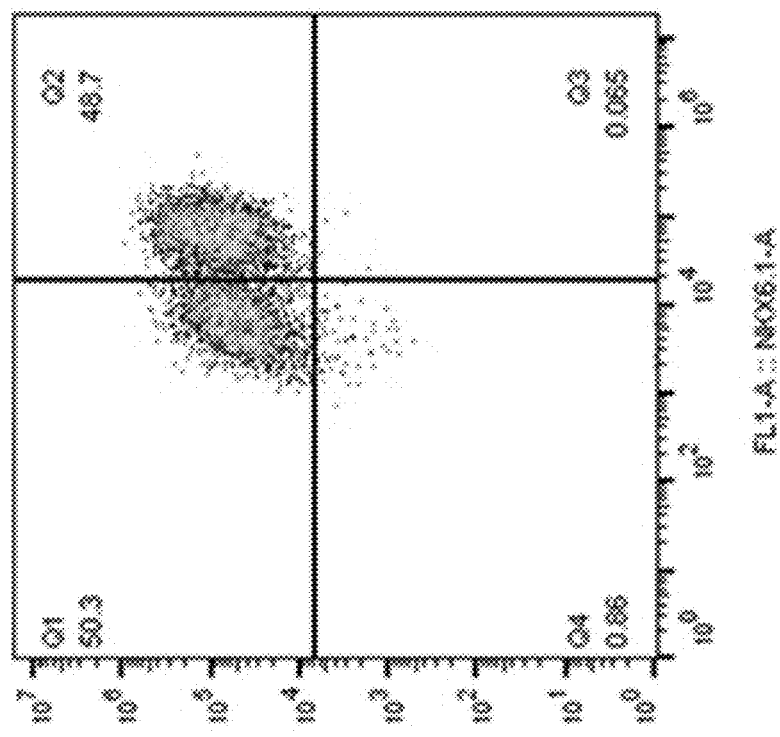
Figure 32B:
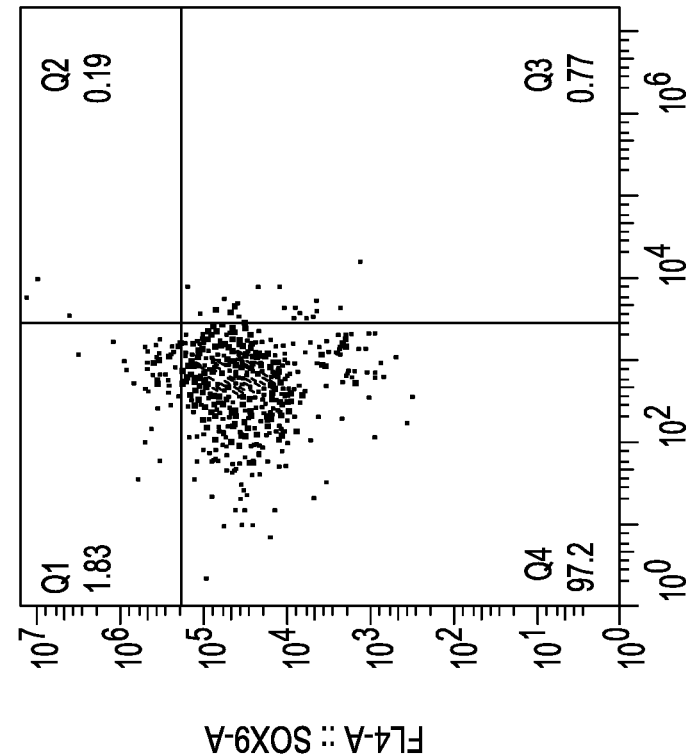
FIGS. 32A-32D are flow cytometry graphs showing SOX9/Ki67 expression on S6D3 in SC-islet cells differentiated using Protocol 1 (FIG. 32A), Protocol 2 (FIG. 32B), Protocol 3 (FIG. 32C), or Protocol 3 with the addition of FGF2 (at 100 ng/ml) in stage 6 media (Media A shown in Table 7A) (FIG. 32D).
Figure 32A:
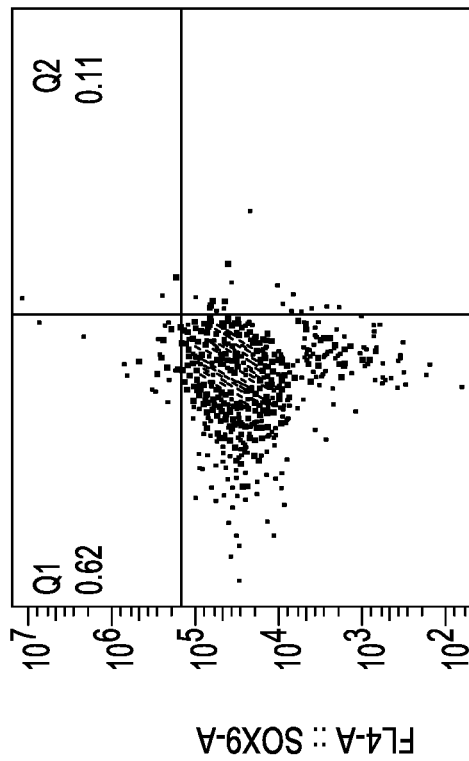
Figure 32D:
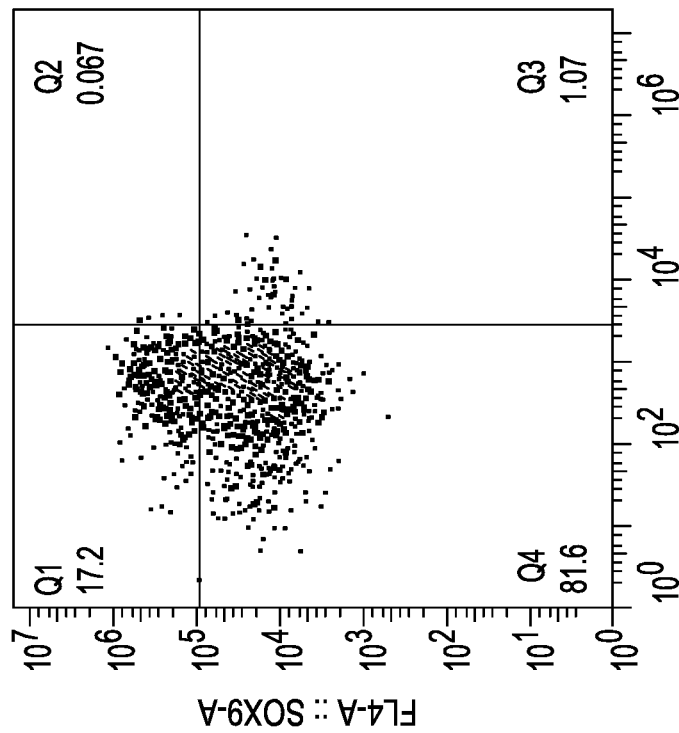
Figure 32C:
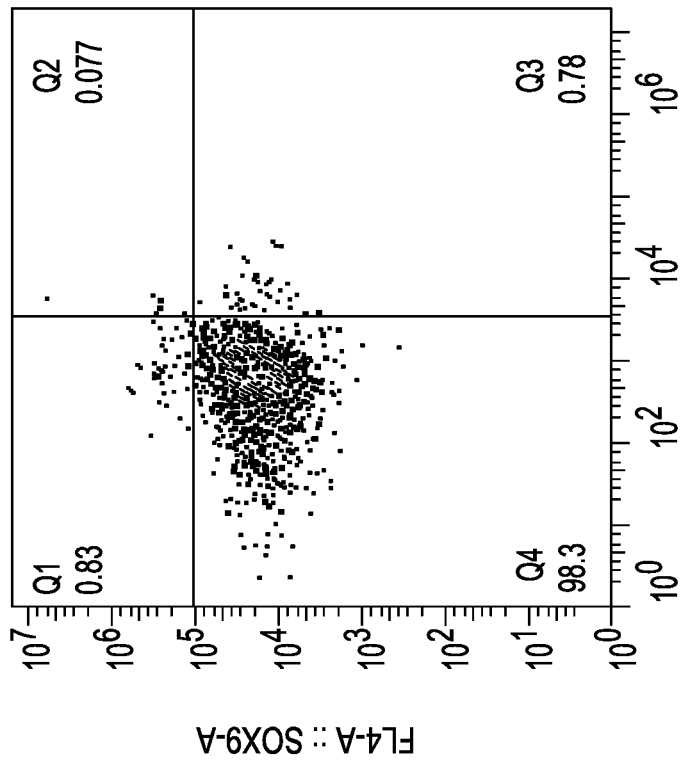
Figure 33B:
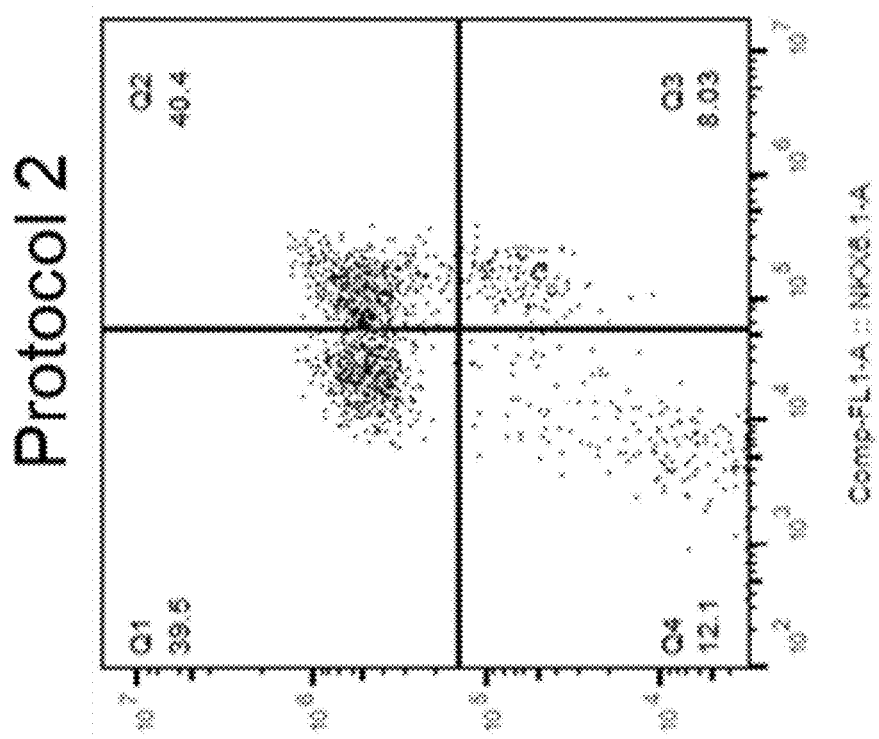
FIGS. 33A-33D are flow cytometry graphs showing ISL1/Nkx6.1 expression on S6D7 in SC-islet cells differentiated using Protocol 1 (FIG. 33A), Protocol 2 (FIG. 33B), Protocol 3 (FIG. 33C), or Protocol 3 with the addition of FGF2 (at 100 ng/ml) in stage 6 media (Media A shown in Table 7A) (FIG. 33D).
Figure 33A:
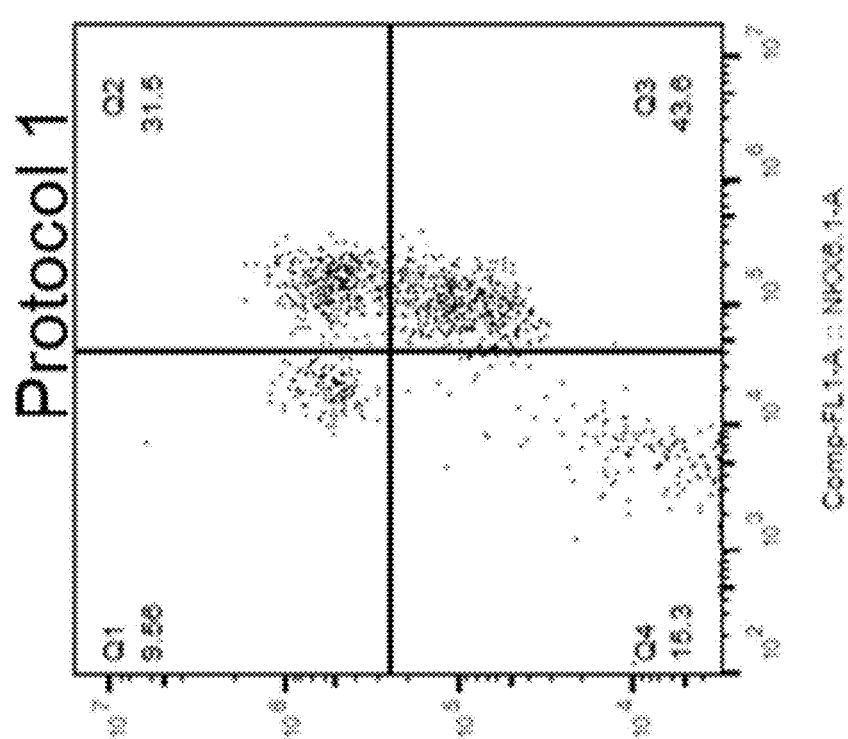
Figure 33D:
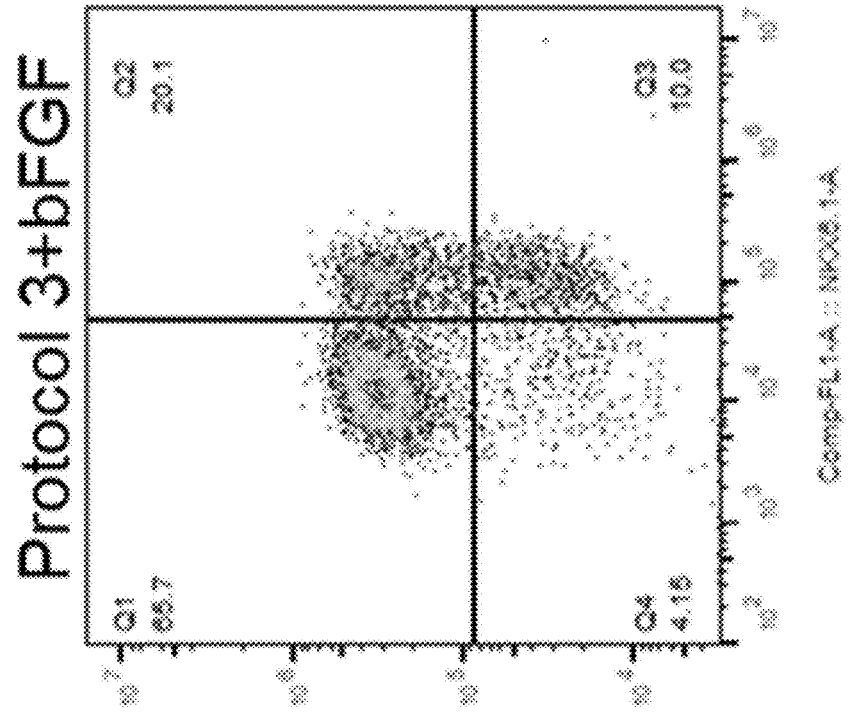
Figure 33C:
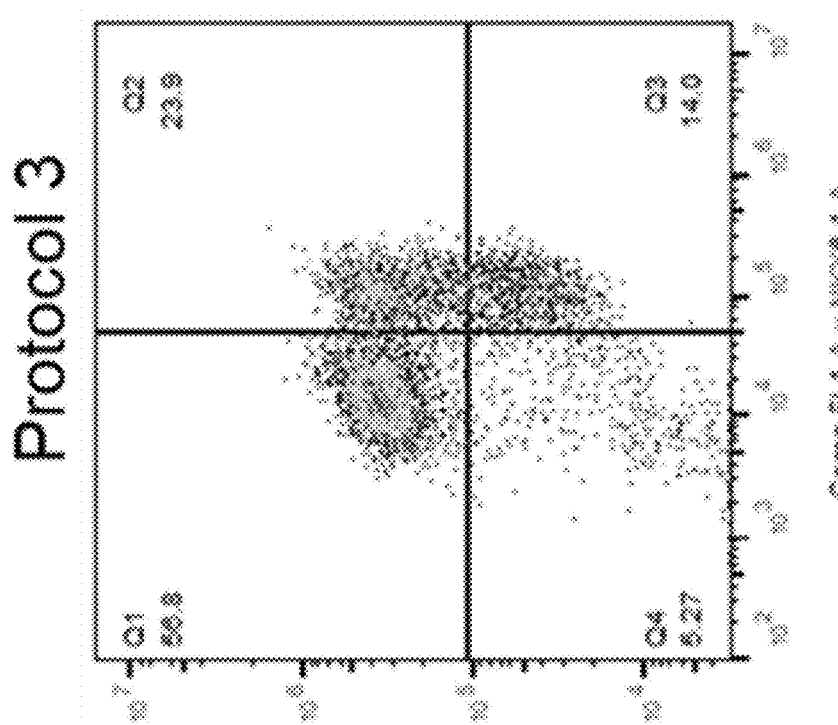
Figure 34D:
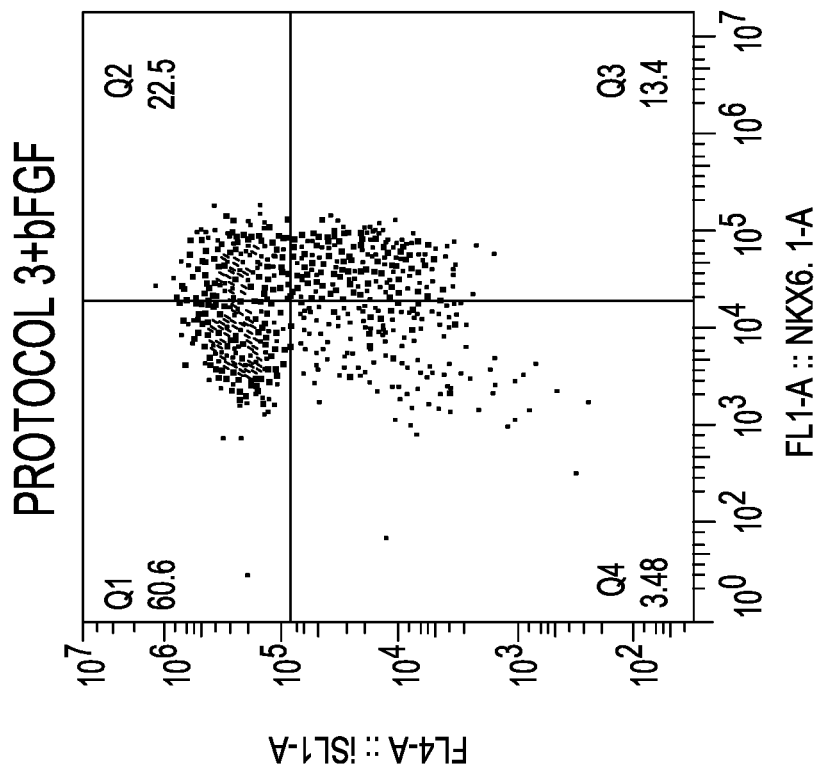
Figure 34C:
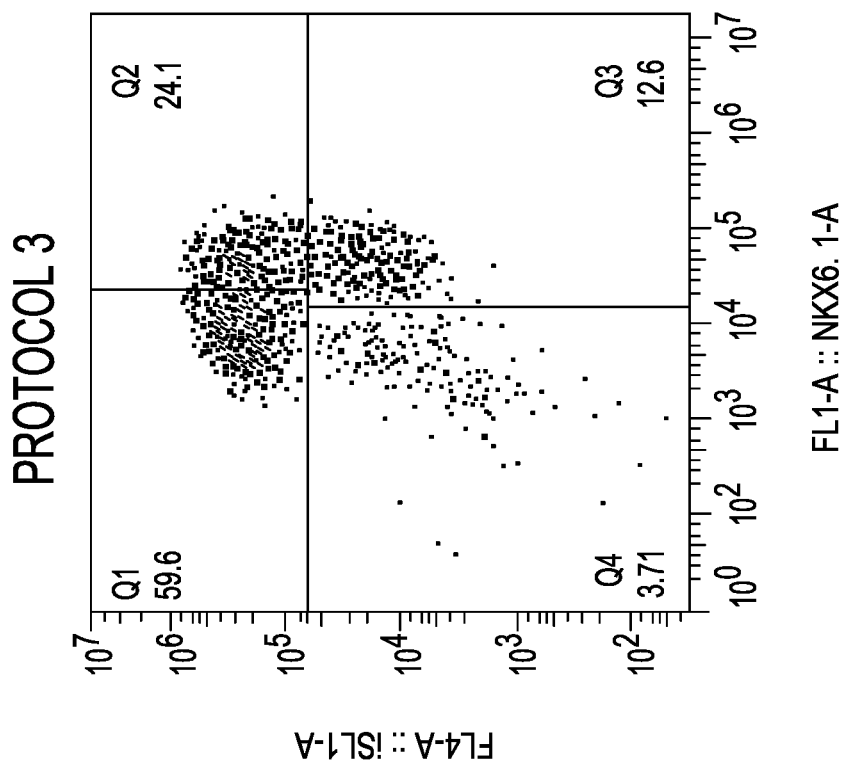

An additional differentiation protocol was developed (Protocol 3). SC-islet cells differentiated using Protocol 1 (Table 2), Protocol 2 (Table 2), or Protocol 3 (Table 9) were analyzed for islet cell yield and the percentage of ISL1+ and/or NKX6.1+ cells. Results show that differentiation Protocol 2 and Protocol 3 generated a higher yield of total ISL1-positive cells and reduced ISL1-negative (SC-EC) cells at stage 6 day 4 (FIGS. 25A-25B). Protocol 3 increases stage 5 cell yield by 2-fold (FIG. 27). ISL1/NKX6.1 expression in these SC-islet cells were analyzed by flow cytometry. Protocol 2 and Protocol 3 generated higher percentage of ISL1+/NKX6.1+ cells and ISL1+/NKX6.1− cells (FIGS. 26A-26C). Additionally, SC-islet cells differentiated using Protocol 2 or Protocol 3 also exhibited higher C-peptide (a marker for SC-β cells) and glucagon (a marker for SC-α cells) content (FIGS. 28A-28B).

TABLE 9

Differentiation Protocol 3

| | Protocol 3 |
|---|---|
| S0D1-2 | bFGF (100 ng/ml) |
| S1D1 | Activin- A (100 ng/ml)<br>CHIR99021 (3 µM)<br>PVA80 |
| S1D2-3 | Activin- A (100 ng/ml)<br>PVA80 |
| S2D1-3 | KGF (50 ng/ml)<br>PVA80 |
| S3D1 | KGF (50 ng/ml)<br>PDBU (500 nM)<br>Sant-1 (250 nM)<br>Retinoic Acid (2 µM)<br>Activin A (20 ng/ml)<br>Thiazovinin (2.5 µM)<br>DMH-1 (250 nM)<br>PVA80 |
| S3D2 | KGF (50 ng/ml)<br>PDBU (500 nM)<br>Sant-1 (250 nM)<br>Retinoic Acid (2 µM)<br>Activin A (20 ng/ml)<br>Thiazovinin (2.5 µM)<br>PVA80 |
| S4D1-4 | KGF (50 ng/ml)<br>Sant-1 (250 nM)<br>Thiazovinin (2.5 µM)<br>Activin A (5 ng/ml)<br>Retinoic Acid (100 nM)<br>PVA80 |
| S4D5-6 | KGF (50 ng/ml)<br>Sant-1 (250 nM)<br>Thiazovinin (2.5 µM)<br>Activin A (5 ng/ml)<br>Retinoic Acid (100 nM)<br>PDBU (500 nM)<br>AS 1842856 (1 µM)<br>XXI (2 µM)<br>PVA80 |
| S5D1-3 | Sant-1 (250 nM)<br>Betacellulin (20 ng/ml)<br>XXI (2 µM)<br>Alk5i (10 µM)<br>GC-1 (1 µM)<br>LDN-193189 (100 nM)<br>Thiazovinin (2.5 µM)<br>Staurosporine (3 nM)<br>DZNEP (100 nM)<br>Retinoic Acid (50 nM)<br>PDBU (500 nM)<br>NVP (2 µM)<br>L-glutamine (4 mM)<br>Formate (50 µM)<br>Taurine (90 µM)<br>Acetate (1 mM)<br>β-hydroxybutyrate (200 nM)<br>Biotin (800 nM)<br>PVA 87-89 |
| S5D4-7 | XXI (2 µM)<br>Alk5i (10 µM)<br>GC-1 (1 µM)<br>LDN-193189 (100 nM)<br>Thiazovinin (2.5 µM)<br>Staurosporine (3 nM)<br>DZNEP (100 nM)<br>L-glutamine (4 mM)<br>Formate (50 µM)<br>Taurine (90 µM)<br>Acetate (1 mM)<br>β-hydroxybutyrate (200 nM)<br>Biotin (800 nM)<br>PVA 87-89 |

Example 5. Effect of Additional FGF2 in Stage 6 of Differentiation

Figure 35A:
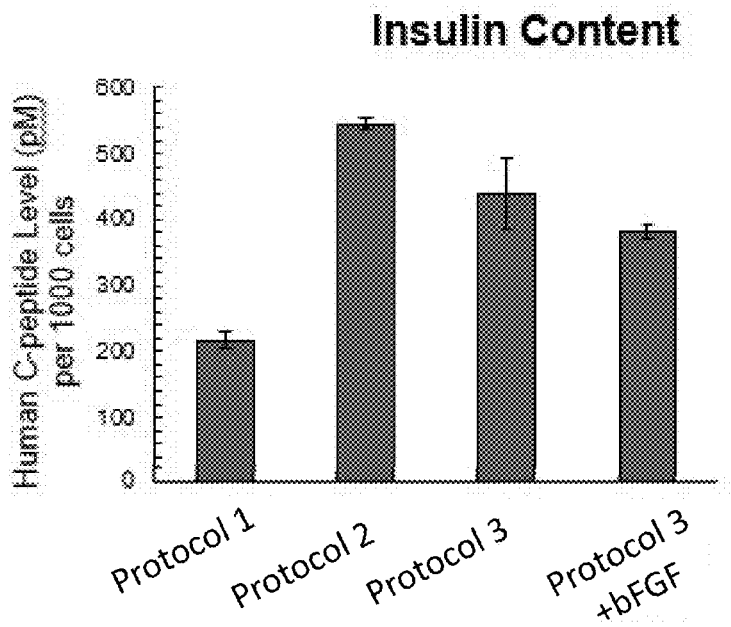
FIGS. 35A-35B are graphs showing human C-Peptide level (FIG. 35A) and human glucagon level (FIG. 35B) in SC-islet cells differentiated using Protocol 1, Protocol 2, Protocol 3, or Protocol 3 with the addition of FGF2 (at 100 ng/ml) in stage 6 media (Media A shown in Table 7A).
Figure 35B:
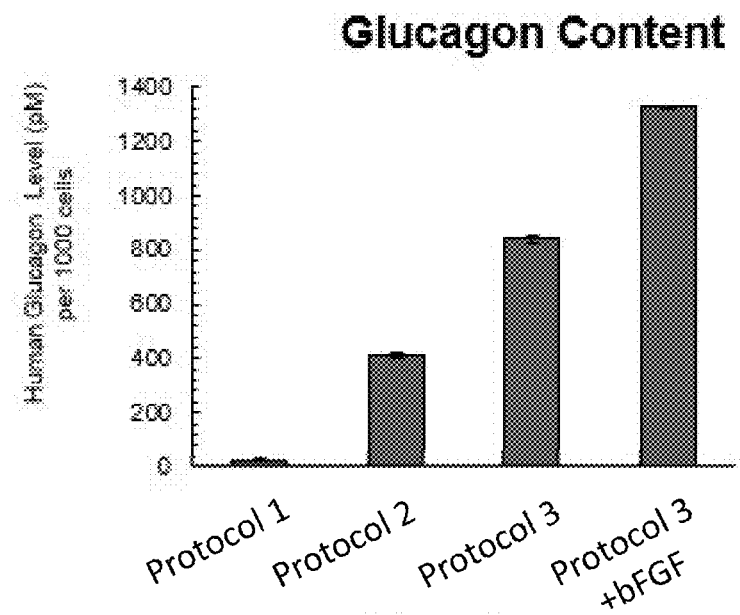

SC-islet cells were differentiated using Protocol 1, Protocol 2, Protocol 3, or Protocol 3 with the addition of FGF2 (at 100 ng/ml) in stage 6 media (Media A shown in Table 6). Cells were collected on S6D3, S6D7, and S6D111 for analysis. ISL1/NKX6.1 expression on S6D3 is shown in FIGS. 29A-29D, on S6D7 is shown in FIGS. 33A-33D, on S6D111 is shown in FIGS. 34A-34D. ARX/GCG expression on S6D3 is shown in FIGS. 30A-30D. CHGA/Nkx6.1 expression on S6D3 is shown in FIGS. 31A-31D. SOX9/Ki67 expression on S6D3 is shown in FIGS. 32A-32D. Cells were also tested for insulin content (FIG. 35A) and glucagon content (FIG. 35B). Results show that adding FGF in stage 6 of Protocol 3 increases glucagon-expressing cells (SC-alpha cells).

ADDITIONAL EMBODIMENTS

A1. An in vitro composition comprising a population of pancreatic progenitor cells and a medium comprising a Forkhead Box O1 (FoxO1) inhibitor and a notch signaling pathway inhibitor, wherein the population of pancreatic progenitor cells comprises cells that are PDX1-positive and NKX6.1-negative and cells that are PDX1-positive and NKX6.1-positive.

A2. The in vitro composition of embodiment A1, wherein the medium further comprises a PKC activator.

A3. The in vitro composition of embodiment A1 or embodiment A2, wherein the notch signaling pathway inhibitor is a γ-secretase inhibitor.

A4 The in vitro composition of embodiment A3, wherein the γ-secretase inhibitor is XXI, DAPT or derivatives thereof, optionally wherein the γ-secretase inhibitor is XXI.

A5. The in vitro composition of any one of embodiments A1-A4, wherein the FOXO1 inhibitor is of formula (I-B):

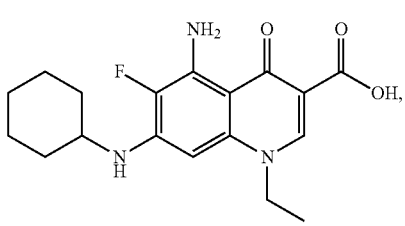

(I-B)

or a pharmaceutically acceptable salt, solvate, hydrate, polymorph, co-crystal, tautomer, stereoisomer, isotopically labeled derivative, prodrug, composition, or mixture thereof.

A6. The in vitro composition of any one of embodiments A1-A5, wherein the FoxO1 inhibitor is present in the medium at a concentration of 0.1-10 µM, optionally wherein the FoxO1 inhibitor is present in the medium at a concentration of 1 µM.

A7. The in vitro composition of any one of embodiments A2-A6, wherein the PKC activator is phorbol 12,13-dibutyrate (PdBU), TPB, phorbol 12-myristate 13-acetate, bryostatin 1, or derivatives thereof, optionally wherein the PKC activator is PdBU.

A8. The in vitro composition of any one of embodiments A1-A7, wherein medium does not comprise a Wnt inhibitor.

A9. The in vitro composition of any one of embodiments A1-A8, wherein at least 50% of the population of pancreatic progenitor cells are PDX1-positive and NKX6.1-negative, and/or no more than 50% of the population of pancreatic progenitor cells are PDX1-positive and NKX6.1-positive.

A10. The in vitro composition of any one of embodiments A1-A8, wherein no more than 50% of the population of pancreatic progenitor cells are PDX1-positive and NKX6.1-negative, and/or at least 50% of the population of pancreatic progenitor cells are PDX1-positive and NKX6.1-positive.

B1. An in vitro composition comprising a population of pancreatic progenitor cells comprising cells that are PDX1-positive, NKX6.1-positive, and insulin-negative; and a medium comprising a protein kinase C (PKC) activator and a Wnt signaling pathway inhibitor, wherein the medium does not comprise a FOXO1 inhibitor, and wherein the population of pancreatic progenitor cells had been previously cultured in a medium comprising a FOXO1 inhibitor.

B2. The in vitro composition embodiment B1, wherein the PKC activator is phorbol 12,13-dibutyrate (PdBU), phorbol 12-myristate 13-acetate, bryostatin 1, or derivatives thereof, optionally wherein the PKC activator is PdBU.

B3. The in vitro composition of embodiment B1 or embodiment B2, wherein the Wnt signaling pathway inhibitor is a tankyrase inhibitor, optionally wherein the tankyrase inhibitor is NVP-TNKS656.

B4. The in vitro composition of any one of embodiments B1-B3, wherein the Wnt signaling pathway inhibitor is present in the medium at a concentration of 0.2 µM-2.5 µM.

B5. The in vitro composition of any one of embodiments B1-B4, wherein the Wnt signaling pathway inhibitor is present in the medium at a concentration of about 2 µM.

B6. The in vitro composition of any one of embodiments B1-B5, further comprising pancreatic endocrine cells that are PDX1-positive, NKX6.1-positive, and insulin-positive.

B7. The in vitro composition of any one of embodiments B1-B6, wherein at least 50% of the population of pancreatic progenitor cells are PDX1-positive, NKX6.1-positive, and insulin-negative.

C1. A method comprising culturing a first population of cells in a first medium, wherein: the first population of cells comprises pancreatic progenitor cells that are PDX1-positive and NKX6.1 negative, and pancreatic progenitor cells that are PDX1-positive and NKX6.1 positive; and the first medium comprises a Forkhead Box O1 (FoxO1) inhibitor and a notch signaling pathway inhibitor.

C2. The method of embodiment C1, wherein the first medium further comprises a PKC activator.

C3. The method of embodiment C1 or embodiment C2, wherein the notch signaling pathway inhibitor is a γ-secretase inhibitor.

C4. The method of embodiment C3, wherein the γ-secretase inhibitor is XXI, DAPT or derivatives thereof, optionally wherein the γ-secretase inhibitor is XXI.

C5. The method of any one of embodiments C1-C4, wherein the FoxO1 inhibitor is of formula (I-B):

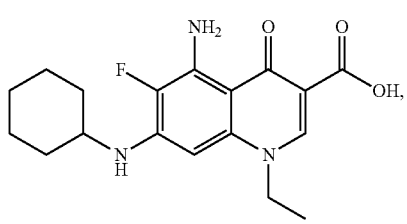

(I-B)

or a pharmaceutically acceptable salt, solvate, hydrate, polymorph, co-crystal, tautomer, stereoisomer, isotopically labeled derivative, prodrug, composition, or mixture thereof.

C6. The method of any one of embodiments C1 to C5, wherein the FoxO1 inhibitor is present in the first medium at a concentration of 0.1-10 µM, optionally wherein the FoxO1 inhibitor is present in the first medium at a concentration of 1 µM.

C7. The method of any one of embodiments C2-C6, wherein the PKC activator is phorbol 12,13-dibutyrate (PdBU), TPB, phorbol 12-myristate 13-acetate, bryostatin 1, or derivatives thereof, optionally wherein the PKC activator is PdBU.

C8. The method of any one of embodiments C1-C7, wherein the first medium does not comprise a Wnt signaling pathway inhibitor.

C9. The method of any one of embodiments C1-C8, wherein the first population of cells are cultured in the first medium for a period of 24-48 hours, resulting in a second population of cells.

C10. The method of embodiment C9, further comprising culturing the second population of cells with a second medium comprising a Wnt signaling pathway inhibitor and a PKC activator.

C11. The method of embodiment C10, wherein the Wnt signaling pathway inhibitor is a tankyrase inhibitor, optionally wherein the tankyrase inhibitor is NVP-TNKS656.

C12. The method of embodiment C10 or embodiment C11, wherein the PKC activator is phorbol 12,13-dibutyrate (PdBU), TPB, phorbol 12-myristate 13-acetate, bryostatin 1, or derivatives thereof, optionally wherein the PKC activator is PdBU.

C13. The method of any one of embodiments C10-C12, wherein the second medium does not comprise a FOXO1 inhibitor.

C14. The method of any one of embodiments C10-C13, wherein the Wnt signaling pathway inhibitor is present in the second medium at a concentration of 0.2 µM-2 µM.

C15. The method of any one of embodiments C10-C14, wherein the Wnt signaling pathway inhibitor is present in the second medium at a concentration of about 2 μM.

C16. The method of any one of embodiments C10-C15, wherein the second population of cells are cultured in the second medium for about 24-72 hours, resulting in a third population of cells.

C17. The method of embodiment C16, further comprising differentiating the third population of cells to obtain a fourth population of cells in which at least 30% of cells are insulin positive.

C18. The method of embodiment C17, further comprising differentiating the fourth population of cells to obtain a fifth population of cells in which at least 15% of the cells are NKX6.1-negative, ISL1-positive; and wherein less than 12% of the cells are NKX6.1-negative, ISL1-negative.

C19. A method comprising:
(i) culturing a first population of cells comprising pancreatic progenitor cells that are PDX1-positive and NKX6.1 negative, and pancreatic progenitor cells that are PDX1-positive and NKX6.1 positive in a first medium comprising a Forkhead Box O1 (FoxO1) inhibitor and a notch signaling pathway inhibitor to obtain a second population of cells;
(ii) culturing the second population of cells obtained in step (i) with a second medium comprising a Wnt signaling pathway inhibitor and a PKC activator to obtain a third population of cells;
(iii) differentiating the third population of cells obtained in step (ii) to obtain a fourth population of cells in which at least 30% of cells are insulin positive; and
(iv) differentiating the fourth population of cells obtained in step (iii) to obtain a fifth population of cells in which at least 15% of the cells are NKX6.1-negative, ISL1-positive; and wherein less than 12% of the cells are NKX6.1-negative, ISL1-negative.

C20. The method of any one of embodiments C1-C19, wherein the first population of cells are obtained by differentiation of human embryonic stem cells.

What is claimed is:

1. An in vitro composition comprising a plurality of non-native cells prepared in vitro; wherein:
   a) at least 30% of the cells in the composition are NKX6.1-positive, ISL1-positive cells;
   b) at least 25% of the cells in the composition are NKX6.1-negative, ISL1-positive cells;
   c) there are more NKX6.1-positive, ISL1-positive cells than NKX6.1-negative, ISL1-positive cells in the composition; and
   d)
      i) less than 6% of the cells in the composition are NKX6.1-negative, ISL1-negative cells; and/or
      ii) between 9-25% of the cells in the composition are NKX6.1-positive, ISL1-negative cells.

2. The composition of claim 1, wherein 30-60% of the cells in the plurality of cells are NKX6.1-positive, ISL1-positive cells, and wherein 20-50% of the cells in the plurality of cells are NKX6.1-negative, ISL1-positive cells.

3. The composition of claim 1, wherein 35-55% of the cells in the plurality of cells are NKX6.1-positive, ISL1-positive cells, and wherein 25-45% of the cells in the plurality of cells are NKX6.1-negative, ISL1-positive cells.

4. The composition of claim 1, wherein 1-6% of the cells in the plurality of cells are NKX6.1-negative, ISL1-negative cells.

5. The composition of claim 1, wherein between 2-25% of the cells in the plurality of cells are NKX6.1-positive, ISL1-negative cells, and wherein 1-6% of the cells in the plurality of cells are NKX6.1-negative, ISL1-negative cells.

6. The composition of claim 1, wherein between 9-25% of the cells in the plurality of cells are NKX6.1-positive, ISL1-negative cells.

7. The composition of claim 1, wherein 35-55% of the cells in the plurality of cells are NKX6.1-positive, ISL1-positive cells, wherein 25-45% of the cells in the plurality of cells are NKX6.1-negative, ISL1-positive cells; and wherein 1-6% of the cells in the plurality of cells are NKX6.1-negative, ISL1-negative cells.

8. The composition of claim 1, wherein the plurality of cells are in a cell cluster.

9. The composition of claim 1, wherein the plurality of cells are in a plurality of cell clusters.

10. The composition of claim 8, wherein the cell cluster comprises between 500-2500 cells.

11. The composition of claim 9, wherein the plurality of cell clusters each comprise between 500-2500 cells.

12. The composition of claim 8, wherein the cluster comprises between 500-2500 NKX6.1-positive, ISL1-positive cells.

13. The composition of claim 9, wherein the plurality of cell clusters each comprise between 500-2500 NKX6.1-positive, ISL1-positive cells.

14. The composition of claim 8, wherein the cell cluster has a diameter between 80-270 microns.

15. The composition of claim 9, wherein the plurality of cell clusters each have a diameter between 80-270 microns.

16. The composition of claim 1, wherein the composition comprises cells that have been genetically modified to reduce expression of any one or more of the following genes: B2M, CIITA, CXCL10, renalase, HLA-A, HLA-B, HLA-C, NLRC5, ABO, RHD, FUT1, KDMSD, PDGFRa, OLIG2, and/or GFAP as compared to a cell that has not been genetically modified.

17. The composition of claim 1, wherein the composition comprises cells that have been genetically modified to increase expression of any or more of the following genes: CD47, PDL1, PDL2, HLA-E, HLA-G, CD46, CD55, CD59 and CTLA, relative to cells that have not been genetically modified.

18. The composition of claim 1, wherein the composition further comprises a medium that comprises a sugar at a concentration of between about 0.05% and about 1.5%.

19. The composition of claim 1, wherein the composition further comprises a CMRL medium or a HypoThermosol® FRS Preservation Media.

20. The composition of claim 1, wherein the composition is in a device, wherein the device comprises a semipermeable membrane that is configured to retain the cells in the device and permit passage of insulin secreted by the cells out of the device.

21. The composition of claim 20, wherein the semipermeable membrane can be made of poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, polyortho esters, polyacetals, polycyanoacrylates, biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, or any combinations thereof.

22. The composition of claim 1, wherein at least 65-85% of the cells express ISL1.

23. The composition of claim 1, wherein the plurality of cells comprise 0.1-5% ghrelin-positive cells.

24. The composition of claim 1, wherein the plurality of cells comprise 2-10% somatostatin-positive cells.

25. The composition of claim 1, wherein the composition comprises NKX6.1-positive, ISL1-positive cells that display a glucose stimulated insulin secretion (GSIS) response similar or superior to that of an endogenous mature β cell if tested in vitro.

26. The composition of claim 1, wherein the composition comprises NKX6.1-positive, ISL1-positive cells that also express PC2, MNX1, or ABCC8.

27. The composition of claim 1, wherein the C-peptide content per 1,000 of the in vitro differentiated cells is at least 300 pM, optionally wherein the C-peptide content per 1,000 of the in vitro differentiated cells is at least 400 pM.

28. A method of treating a subject having Type 1 Diabetes comprising administering to the subject the composition of claim 1.

29. The method of claim 28, wherein the composition is administered in a device, wherein the device comprises a semipermeable membrane that is configured to retain the cells in the device and permit passage of insulin secreted by the cells out of the device.

30. The method of claim 28, wherein the composition is administered via the portal vein.

\* \* \* \* \*

SEQUENCE LISTING

```
Sequence total quantity: 32
SEQ ID NO: 1            moltype = AA  length = 116
FEATURE                 Location/Qualifiers
source                  1..116
                        mol_type = protein
                        organism = Homo sapiens
SEQUENCE: 1
GLECDGKVNI CCKKQFFVSF KDIGWNDWII APSGYHANYC EGECPSHIAG TSGSSLSFHS  60
TVINHYRMRG HSPFANLKSC CVPTKLRPMS MLYYDDGQNI IKKDIQNMIV EECGCS     116

SEQ ID NO: 2            moltype = DNA  length = 351
FEATURE                 Location/Qualifiers
source                  1..351
                        mol_type = genomic DNA
                        organism = Homo sapiens
SEQUENCE: 2
ggcttggagt gtgatggcaa ggtcaacatc tgctgtaaga aacagttctt tgtcagtttc   60
aaggacatcg gctggaatga ctggatcatt gctccctctg gctatcatgc caactactgc  120
gagggtgagt gcccgagcca tatagcaggc acgtccgggt cctcactgtc cttccactca  180
acagtcatca accactaccg catgcggggc catagccgct ttgccaacct caaatcgtgc  240
tgtgtgccca ccaagctgag acccatgtcc atgttgtact atgatgatgg tcaaaacatc  300
atcaaaaagg acattcagaa catgatcgtg gaggagtgtg ggtgctcata g           351

SEQ ID NO: 3            moltype = AA  length = 426
FEATURE                 Location/Qualifiers
source                  1..426
                        mol_type = protein
                        organism = Homo sapiens
SEQUENCE: 3
MPLLWLRGFL LASCWIIVRS SPTPGSEGHS AAPDCPSCAL AALPKDVPNS QPEMVEAVKK   60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAEEVGLKGE RSELLLSEKV VDARKSTWHV FPVSSSIQRL LDQGKSSLDV  240
RIACEQCQES GASLVLLGKK KKKEEEGEGK KKGGGEGGAG ADEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINHYRMRG HSPFANLKSC CVPTKLRPMS MLYYDDGQNI IKKDIQNMIV  420
EECGCS                                                            426

SEQ ID NO: 4            moltype = AA  length = 130
FEATURE                 Location/Qualifiers
source                  1..130
                        mol_type = protein
                        organism = Homo sapiens
SEQUENCE: 4
ARQSEDHPHR RRRRGLECDG KVNICCKKQF FVSFKDIGWN DWIIAPSGYH ANYCEGECPS   60
HIAGTSGSSL SFHSTVINHY RMRGHSPFAN LKSCCVPTKL RPMSMLYYDD GQNIIKKDIQ  120
NMIVEECGCS                                                        130

SEQ ID NO: 5            moltype = AA  length = 115
FEATURE                 Location/Qualifiers
source                  1..115
                        mol_type = protein
```

```
                          organism = Homo sapiens
SEQUENCE: 5
GLECDGKVNI CCKKQFFVSF KDIGWNDWII APSGYHANYC EGECPSHIAG TSGSSLSFHS     60
TVINHYACGH SPFANLKSCC VPTKLRPMSM LYYDDGQNII KKDIQNMIVE ECGCS         115

SEQ ID NO: 6              moltype = AA   length = 426
FEATURE                   Location/Qualifiers
source                    1..426
                          mol_type = protein
                          organism = Homo sapiens
SEQUENCE: 6
MPLLWLRGFL LASCWIIVRS SPTPGSEGHS AAPDCPSCAL AALPKDVPNS QPEMVEAVKK     60
HILNMLHLKK RPDVTQPVPK AALLNAIRKL HVGKVGENGY VEIEDDIGRR AEMNELMEQT    120
SEIITFAESG TARKTLHFEI SKEGSDLSVV ERAEVWLFLK VPKANRTRTK VTIRLFQQQK    180
HPQGSLDTGE EAEEVGLKGE RSELLLSEKV VDARKSTWHV FPVSSSIQRL LDQGKSSLDV    240
RIACEQCQES GASLVLLGKK KKKEEEGEGK KKGGGEGGAG ADEEKEQSHR PFLMLQARQS    300
EDHPHRRRRR GLECDGKVNI CCKKQFFVSF KDIGWNDWII APSGYHANYC EGECPSHIAG    360
TSGSSLSFHS TVINHYRMRG HSPFANLKSC CVPTKLRPMS MLYYDDGQNI IKKDIQNMIV    420
EECGCS                                                               426

SEQ ID NO: 7              moltype = AA   length = 424
FEATURE                   Location/Qualifiers
source                    1..424
                          mol_type = protein
                          organism = Mus musculus
SEQUENCE: 7
MPLLWLRGFL LASCWIIVRS SPTPGSEGHG SAPDCPSCAL ATLPKDGPNS QPEMVEAVKK     60
HILNMLHLKK RPDVTQPVPK AALLNAIRKL HVGKVGENGY VEIEDDIGRR AEMNELMEQT    120
SEIITFAESG TARKTLHFEI SKEGSDLSVV ERAEVWLFLK VPKANRTRTK VTIRLFQQQK    180
HPQGSLDTGD EAEEMGLKGE RSELLLSEKV VDARKSTWHI FPVSSSIQRL LDQGKSSLDV    240
RIACEQCQES GASLVLLGKK KKKEVDGDGK KKDGSDGGLE EEKEQSHRPF LMLQARQSED    300
HPHRRRRRGL ECDGKVNICC KKQFFVSFKD IGWNDWIIAP SGYHANYCEG ECPSHIAGTS    360
GSSLSFHSTV INHYRMRGHS PFANLKSCCV PTKLRPMSML YYDDGQNIIK KDIQNMIVEE    420
CGCS                                                                 424

SEQ ID NO: 8              moltype = AA   length = 424
FEATURE                   Location/Qualifiers
source                    1..424
                          mol_type = protein
                          organism = Rattus norvegicus
SEQUENCE: 8
MPLLWLRGFL LASCWIIVRS SPTPGSEGHG AAPDCPSCAL ATLPKDGPNS QPEMVEAVKK     60
HILNMLHLKK RPDVTQPVPK AALLNAIRKL HVGKVGENGY VEIEDDIGRR AEMNELMEQT    120
SEIITFAESG TARKTLHFEI SKEGSDLSVV ERAEVWLFLK VPKANRTRTK VTIRLFQQQK    180
HPQGSLDMGD EAEEMGLKGE RSELLLSEKV VDARKSTWHI FPVSSSIQRL LDQGKSSLDV    240
RIACEQCQES GASLVLLGKK KKKEVDGDGK KKDGSDGGLE EEKEQSHRPF LMLQARQSED    300
HPHRRRRRGL ECDGKVNICC KKQFFVSFKD IGWNDWIIAP SGYHANYCEG ECPSHIAGTS    360
GSSLSFHSTV INHYRMRGHS PFANLKSCCV PTKLRPMSML YYDDGQNIIK KDIQNMIVEE    420
CGCS                                                                 424

SEQ ID NO: 9              moltype = AA   length = 424
FEATURE                   Location/Qualifiers
source                    1..424
                          mol_type = protein
                          organism = Gallus gallus
SEQUENCE: 9
MPLLWKRGFL LVICWIIVRS SPTPGSEGHS SVADCPSCAL TTLSKDVPSS QPEMVEAVKK     60
HILNMLHLRD RPNITQPVPK AALLNATKKL HVGKVGDDGY VEIEDDVGRR AEMNEVVEQT    120
SEIITFAESG TPKKTLHFEI SKEGSELSVV EHAEVFLFLK VSKANRSRTK VTIRLFQQQR    180
QPKGNSEAAE DMEDMGLKGE RSETLISEKA VDARKSTWHI FPISSSVQRL LDQGQSSLDV    240
RIACDLCQET GASLVLLGKK KKKEDDGEGK EKDGGELTGE EEKEQSHRPF LMMLARHSED    300
RQHRRRERGL ECDGKVNICC KKQFFVSFKD IGWSDWIIAP TGYHANYCEE ECPSHIAGTS    360
GSSLSFHSTV INHYRMRGHS PFANLKSCCV PTKLRPMSML YYDDGQNIIK KDIQNMIVEE    420
CGCS                                                                 424

SEQ ID NO: 10             moltype = AA   length = 425
FEATURE                   Location/Qualifiers
source                    1..425
                          mol_type = protein
                          organism = Bos taurus
SEQUENCE: 10
MPLLWLRGFL LASCWIIVRS SPTPGSEGHS AAPDCPSCAL ATLPKDVPNS QPEMVEAVKK     60
HILNMLHLKK RPDVTQPVPK AALLNAIRKL HVGKVGENGY VEIEDDIGRR AEMNELMEQT    120
SEIITFAESG TARKTLHFEI SKEGSDLSVV ERAEIWLFLK VPKANRTRSK VTIRLFQQQK    180
HLQGSLDAGE EAEEVGLKGE KSEMLISEKV VDARKSTWHI FPVSSCIQRL LDQGKSSLDI    240
RIACEQCQET GASLVLLGKK KKKEEEGEGK KRDGEGGAGG DEEKEQSHRP FLMLQARQSE    300
DHPHRRRRRG LECDGKVNIC CKKQFFVSFK DIGWNDWIIA PSGYHANYCE GECPSHIAGT    360
SGSSLSFHST VINHYRMRGH SPFANLKSCC VPTKLRPMSM LYYDDGQNII KKDIQNMIVE    420
ECGCS                                                                425
```

```
SEQ ID NO: 11              moltype = AA   length = 426
FEATURE                    Location/Qualifiers
source                     1..426
                           mol_type = protein
                           organism = Equus caballus
SEQUENCE: 11
MPLLWLRGFL LASCWIIVKS SPTPGSEGHS AAPNCPSCAL ATLPKDVPNA QPEMVEAVKK    60
HILNMLHLKK RPDVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRSK VTIRLLQQQK   180
HPQGSSDTRE EAEEADLMEE RSEQLISEKV VDARKSTWHI FPVSSSIQRL LDQGKSSLDI   240
RIACDQCHET GASLVLLGKK KKKEEEGEGK KKDGGEAGAG VDEEKEQSHR PFLMLQARQS   300
EDHPHRRRRR GLECDGKVNI CCKKQFFVSF KDIGWNDWII APSGYHANYC EGECPSHIAG   360
TSGSSLSFHS TVINQYRLRG HNPFANLKSC CVPTKLRPMS MLYYDDGQNI IKKDIQNMIV   420
EECGCS                                                              426

SEQ ID NO: 12              moltype = AA   length = 424
FEATURE                    Location/Qualifiers
source                     1..424
                           mol_type = protein
                           organism = Sus scrofa
SEQUENCE: 12
MPLLWLRGFL LASCWIIVRS SPTPGSGGHS AAPDCPSCAL ATLPKDVPNS QPEMVEAVKK    60
HILNMLHLKK RPDVTQPVPK AALLNAIRKL HVGKVGENGY VELEDDIGRR AEMNELMEQT   120
SEIITFAEAG TARKTLRFEI SKEGSDLSVV ERAEIWLFLK VPKANRTRTK VSIRLFQQQR   180
RPQGSADAGE EAEDVGFPEE KSEVLISEKV VDARKSTWHI FPVSSSIQRL LDQGKSALDI   240
RTACEQCHET GASLVLLGKK KKKEEEAEGR KRDGEGAGVD EEKEQSHRPF LMLQARQSEE   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                                424

SEQ ID NO: 13              moltype = AA   length = 425
FEATURE                    Location/Qualifiers
source                     1..425
                           mol_type = protein
                           organism = Ovis aries
SEQUENCE: 13
MPLLWLRGFL LASCWIIVRS SPTPGSEGHS AAPDCPSCAL ATLPKDVPNS QPEMVEAVKK    60
HILNMLHLKK RPDVTQPVPK AALLNAIRKL HVGKVGENGY VEIEDDIGRR AEMNELMEQT   120
SEIITFAESG TARKTLHFEI SQEGSDLSVV ERAEIWLFLK VPKANRTRSK VTIRLFQQQK   180
HLQGSLDAGE EAEEVGLKGE KSEMLISEKV VDARKSTWHI FPVSSCIQRL LDQGKSSLDI   240
RIACEQCQET GASLVLLGKK KRKEEEGEGK KRDGEGGAGG DEEKEQSHRP FLMLQARQSE   300
DHPHRRRRRG LECDGKVNIC CKKQFYVSFK DIGWNDWIIA PSGYHANYCE GECPSHIAGT   360
SGSSLSFHST VINHYRMRGH SPFANLKSCC VPTKLRPMSM LYYDDGQNII KKDIQNMIVE   420
ECGCS                                                               425

SEQ ID NO: 14              moltype = AA   length = 424
FEATURE                    Location/Qualifiers
source                     1..424
                           mol_type = protein
                           organism = Felis catus
SEQUENCE: 14
MPLLWLRGFL LASCWIIVRS SPTPGSEGPG AAPDCPSCAL ATLPKDVPNS QPEMVEAVKK    60
HILNMLHLKK RPEVTQPVPK AALLNAIRKL HVGKVGENGY VEIEDDIGRR AEMNELMEQT   120
SEIITFAESG TARKTLHFEI SKEGSDLSVV ERAEVWLFLK VPKANRTRTK VTIQLLQQQK   180
QGGVDAGEEA EEMGLMEERN EVLISEKVVD ARKSTWHIFP VSSSIQRLLD QGKSSLDVRI   240
ACEQCHETGA SLVLLGKKKK KEEEGEGKKK DGDGGAGAD EDKEQSHRPF LMLQARQSED   300
HPHRRRRRGL ECDGKVNICC KKQFFVSFKD IGWNDWIIAP SGYHANYCEG ECPSHIAGTS   360
GSSLSFHSTV INHYRMRGHS PFANLKSCCV PTKLRPMSML YYDDGQNIIK KDIQNMIVEE   420
CGCS                                                                424

SEQ ID NO: 15              moltype = AA   length = 395
FEATURE                    Location/Qualifiers
source                     1..395
                           mol_type = protein
                           organism = Danio rerio
SEQUENCE: 15
MSPLPLLSGI LLLLIRSCSL SAMVTKGSLP MSEQQAGATV CPSCALARFR KGVSESEDEG    60
AQQDVVEAVK RHILNMLHLQ ERPNITHPVP RAALLNAIRK VHVGRVAKDG SVLIEDEASN   120
RAETEQAEQT EIITFAETGE APGIVNFLIS KEGGEMSVVD QANVWIFLRL PKGNRTRANV   180
NIRLLLQQGA GEKILAEKSV DTRRSGWHTF PASESVQSLL QRGGSTLSLR VSCPLCADAR   240
ATPVLVSPGG SEREQSHRPF LMAVVRQMDE LSLRRRRKRG LECDGKARVC CKRQFYVNFK   300
DIGWNDWIIA PSGYHANYCE GDCASNVASI TGNSLSFHST VISHYRIRGY SPFTNIKSCC   360
VPTRLRAMSM LYYNEEQKIV KKDIQNMIVE ECGCS                              395

SEQ ID NO: 16              moltype = AA   length = 404
FEATURE                    Location/Qualifiers
source                     1..404
                           mol_type = protein
```

```
                            organism = Carassius auratus
SEQUENCE: 16
MSSLTLVNRG TAALRLFVRG LLTHSSREWL SGDGEPDDPV TPCPSCALAQ RQKDSEEQTD    60
MVEAVKRHIL NMLHLNTRPN VTHPVPRAAL LNAIRRLHVG RVGEDGTVEM EEDGGGLGEH   120
REQSEEQPFE IITFAEPGDA PDIMKFDISM EGNTLSVVEQ ANVWLLLKVA KGSRGKGKVS   180
VQLLQHGKAD PGSADGPQEA VVSEKTVDTR RSGWHTLPVS RTVQTLLDGD SSMLSLRVSC   240
PMCAEAGAVP ILVPTESNKG KEREQSHRPF LMVVLKPAEE HPHRRSKRGL ECDGKIRVCC   300
KRQFYVNFKD IGWSDWIIAP SGYHANYCEG DCPSHVASIT GSALSFHSTV INHYRMRGYS   360
PFNNIKSCCV PTRLRAMSML YYNEEQKIIK KDIQNMIVEE CGCS                   404

SEQ ID NO: 17               moltype = DNA   length = 425
FEATURE                     Location/Qualifiers
misc_feature                1..425
                            note = Synthetic
source                      1..425
                            mol_type = other DNA
                            organism = synthetic construct
SEQUENCE: 17
gcccggcagt ctgaagacca ccctcatcgc cggcgtcggc ggggcttgga gtgtgatggc    60
aaggtcaaca tctgctgtaa gaaacagttc tttgtcagtt tcaaggacat cggctggaat   120
gactggatca ttgctccctc tggctatcat gccaactact gcgagggtga gtgcccgagc   180
catatagcag gcacgtccgg gtcctcactg tccttccact caacagtcat caaccactac   240
cgcatgcggg gccatagccc ctttgccaac ctcaaatcgt gctgtgtgcc caccaagctg   300
agacccatgt ccatgttgta ctatgatgat ggtcaaaaca tcatcaaaaa ggacattcag   360
aacatgatcg tggaggagtg tgggtgctca tagagttgcc cagcccaggg ggaaagggag   420
caaga                                                              425

SEQ ID NO: 18               moltype = DNA   length = 348
FEATURE                     Location/Qualifiers
source                      1..348
                            mol_type = genomic DNA
                            organism = Homo sapiens
SEQUENCE: 18
ggcctggagt gcgacggcaa ggtcaacatc tgctgtaaga aacagttctt tgtcagtttc    60
aaggacatcg gctggaatga ctggatcatt gctccctctg gctatcatgc caactactgc   120
gagggtgagt gcccgagcca tatagcaggc acgtccgggt cctcactgtc cttccactca   180
acagtcatca accactacgc atgcggccat agcccctttg ccaacctcaa atcgtgctgt   240
gtgcccacca agctgagacc catgtccatg ttgtactatg atgatggtca aaacatcatc   300
aaaaaggaca ttcagaacat gatcgtggag gagtgcgggt gctcctaa                348

SEQ ID NO: 19               moltype = AA   length = 194
FEATURE                     Location/Qualifiers
source                      1..194
                            mol_type = protein
                            organism = Homo sapiens
SEQUENCE: 19
MHKWILTWIL PTLLYRSCFH IICLVGTISL ACNDMTPEQM ATNVNCSSPE RHTRSYDYME    60
GGDIRVRRLF CRTQWYLRID KRGKVKGTQE MKNNYNIMEI RTVAVGIVAI KGVESEFYLA   120
MNKEGKLYAK KECNEDCNFK ELILENHYNT YASAKWTHNG GEMFVALNQK GIPVRGKKTK   180
KEQKTAHFLP MAIT                                                    194

SEQ ID NO: 20               moltype = AA   length = 176
FEATURE                     Location/Qualifiers
source                      1..176
                            mol_type = protein
                            organism = Homo sapiens
SEQUENCE: 20
MDRAARCSGA SSLPLLLALA LGLVILHCVV ADGNSTRSPE TNGLLCGDPE ENCAATTTQS    60
KRKGHFSRCP KQYKHYCIKG RCRFVVAEQT PSCVCDEGYI GARCERVDLF YLRGDRGQIL   120
VICLIAVMVV FIILVIGVCT CCHPLRKRRK RKKKEEEMET LGKDITPINE DIEETN       176

SEQ ID NO: 21               moltype = AA   length = 53
FEATURE                     Location/Qualifiers
source                      1..53
                            mol_type = protein
                            organism = Homo sapiens
SEQUENCE: 21
NSDSECPLSH DGYCLHDGVC MYIEALDKYA CNCVVGYIGE RCQYRDLKWW ELR            53

SEQ ID NO: 22               moltype = AA   length = 53
FEATURE                     Location/Qualifiers
REGION                      1..53
                            note = Synthetic
source                      1..53
                            mol_type = protein
                            organism = synthetic construct
SEQUENCE: 22
NSDSECPLSH DGYCLHGGVC MYIKAVDRYA CNCVVGYIGE RCQYRDLTWW GPR            53
```

```
SEQ ID NO: 23              moltype = AA   length = 53
FEATURE                    Location/Qualifiers
REGION                     1..53
                           note = Synthetic
source                     1..53
                           mol_type = protein
                           organism = synthetic construct
SEQUENCE: 23
NSDSECPLSH DGYCLHDGVC MYIKALDKYA CNCVVGYTGE RCQYRDLRWW GRR       53

SEQ ID NO: 24              moltype = AA   length = 53
FEATURE                    Location/Qualifiers
REGION                     1..53
                           note = Synthetic
source                     1..53
                           mol_type = protein
                           organism = synthetic construct
SEQUENCE: 24
NSNSECPLSH DGYCLHDGVC RYIEALDRYA CNCVVGYIGE RCQYGDLRWW GRR       53

SEQ ID NO: 25              moltype = AA   length = 53
FEATURE                    Location/Qualifiers
REGION                     1..53
                           note = Synthetic
source                     1..53
                           mol_type = protein
                           organism = synthetic construct
SEQUENCE: 25
NSDSGCPLSH SGYCLHDGVC MYIKALDRYA CNCVVGYAGE RCQYRDLRWW ARR       53

SEQ ID NO: 26              moltype = AA   length = 53
FEATURE                    Location/Qualifiers
REGION                     1..53
                           note = Synthetic
source                     1..53
                           mol_type = protein
                           organism = synthetic construct
SEQUENCE: 26
TRGSECPLSH DGYCLHDGVC MYIGALDRYA CNCVVGYTGE RCQYRDLRWW ARR       53

SEQ ID NO: 27              moltype = AA   length = 53
FEATURE                    Location/Qualifiers
REGION                     1..53
                           note = Synthetic
source                     1..53
                           mol_type = protein
                           organism = synthetic construct
SEQUENCE: 27
NSDFGCPLSY DGYCLHDGVC MYIKALDKYA CNCVVGYAGE RCQYRDLRWW GRR       53

SEQ ID NO: 28              moltype = AA   length = 53
FEATURE                    Location/Qualifiers
REGION                     1..53
                           note = Synthetic
source                     1..53
                           mol_type = protein
                           organism = synthetic construct
SEQUENCE: 28
SRGSKCPPSH DGYCLHDGVC MYIEALDRYA CNCVVGYAGE RCQYRDLRWW ARR       53

SEQ ID NO: 29              moltype = AA   length = 53
FEATURE                    Location/Qualifiers
REGION                     1..53
                           note = Synthetic
source                     1..53
                           mol_type = protein
                           organism = synthetic construct
SEQUENCE: 29
SSGSECPSSH DGYCLHDGAC MYIEALDRYA CNCAVGYAGE RCQYRDLRWW GRR       53

SEQ ID NO: 30              moltype = AA   length = 53
FEATURE                    Location/Qualifiers
REGION                     1..53
                           note = Synthetic
source                     1..53
                           mol_type = protein
                           organism = synthetic construct
SEQUENCE: 30
SSNSECPPSH DGYCLHDGVC MYIEALDRYA CNCVVGYAGE RCQYRDLRWW ARR       53
```

```
SEQ ID NO: 31          moltype = AA  length = 53
FEATURE                Location/Qualifiers
REGION                 1..53
                       note = Synthetic
source                 1..53
                       mol_type = protein
                       organism = synthetic construct
SEQUENCE: 31
NSYSECPPSY DGYCLHDGVC RYIEALDSYA CNCVVGYAGE RCQYRDLRWW GRR        53

SEQ ID NO: 32          moltype = AA  length = 53
FEATURE                Location/Qualifiers
REGION                 1..53
                       note = Synthetic
source                 1..53
                       mol_type = protein
                       organism = synthetic construct
SEQUENCE: 32
SSGSECPLSH DGYCLNDGVC MYIEALDKYA CNCVVGYVGE RCQYRDLRWW ARR        53
```